United States Patent
Hennequin et al.

(10) Patent No.: US 7,498,335 B2
(45) Date of Patent: Mar. 3, 2009

(54) METHOD OF PRODUCING AN ANTIANGIOGENIC OR VASCULAR PERMEABILITY REDUCING EFFECT

(75) Inventors: Laurent Francois Andre Hennequin, Reims Cedex (FR); Graham Charles Crawley, Macclesfield (GB); Darren McKerrecher, Macclesfield (GB); Patrick Ple, Reims Cedex (FR); Jeffrey Philip Poyser, Macclesfield (GB); Christine Marie Paul Lambert, Reims Cedex (FR)

(73) Assignee: AstraZeneca AB, Sodertalje (CH)

( * ) Notice: Subject to any disclaimer, the term of this patent is extended or adjusted under 35 U.S.C. 154(b) by 1091 days.

(21) Appl. No.: 10/220,140

(22) PCT Filed: Mar. 1, 2001

(86) PCT No.: PCT/GB01/00863

§ 371 (c)(1),
(2), (4) Date: Aug. 28, 2002

(87) PCT Pub. No.: WO01/66099

PCT Pub. Date: Sep. 13, 2001

(65) Prior Publication Data

US 2003/0225111 A1    Dec. 4, 2003

(30) Foreign Application Priority Data

Mar. 6, 2000    (EP) .................................. 00400595

(51) Int. Cl.
*A61K 31/517* (2006.01)
(52) U.S. Cl. .................... 514/266.2; 514/266.4
(58) Field of Classification Search .............. 514/266.2, 514/266.4
See application file for complete search history.

(56) References Cited

U.S. PATENT DOCUMENTS

| | | | |
|---|---|---|---|
| 5,962,458 A | 10/1999 | Lohmann et al. | |
| 6,071,921 A | 6/2000 | Lohmann et al. | |
| 6,184,225 B1 | 2/2001 | Thomas et al. | |
| 6,258,951 B1 | 7/2001 | Lohmann et al. | |
| 6,265,411 B1 | 7/2001 | Thomas et al. | |
| 6,291,455 B1 | 9/2001 | Thomas et al. | |
| 6,294,532 B1 | 9/2001 | Thomas et al. | |
| 6,362,336 B1 | 3/2002 | Lohmann et al. | |
| 6,414,148 B1 | 7/2002 | Thomas et al. | |
| 6,514,971 B1 | 2/2003 | Thomas et al. | |
| 6,806,274 B1 * | 10/2004 | Crawley et al. .......... | 514/266.2 |

FOREIGN PATENT DOCUMENTS

| | | |
|---|---|---|
| WO | WO 97/03069 | 1/1997 |
| WO | 97/22596 A | 6/1997 |
| WO | 97/30035 A | 8/1997 |
| WO | 97/32856 | 9/1997 |
| WO | 97/34876 | 9/1997 |
| WO | 97/42187 | 11/1997 |
| WO | 98/13350 A | 4/1998 |
| WO | 98/13354 | 4/1998 |
| WO | WO 98/38984 | 9/1998 |
| WO | WO 98/50047 | 11/1998 |
| WO | WO 98/50370 | 11/1998 |
| WO | WO 99/09024 | 2/1999 |
| WO | 99/10349 A | 3/1999 |
| WO | 00/21955 A | 4/2000 |
| WO | 00/47212 A | 8/2000 |
| WO | 01/04102 A1 | 1/2001 |
| WO | 01/74360 A1 | 10/2001 |
| WO | 01/77085 A1 | 10/2001 |
| WO | 02/02534 A1 | 1/2002 |
| WO | 02/12226 A1 | 2/2002 |
| WO | 02/12227 A2 | 2/2002 |
| WO | 02/12228 A1 | 2/2002 |
| WO | 02/16348 A1 | 2/2002 |

OTHER PUBLICATIONS

U.S. Appl. No. 10/310,074, filed Dec. 5, 2002, Thomas et al., WO 97/34876, Sep. 12, 1997.
U.S. Appl. No. 10/080,716, filed Feb. 25, 2002, Thomas et al., WO 98/13354, Apr. 2, 1998.
U.S. Appl. No. 09,254,440, filed Mar. 9, 1999, Thomas et al., WO 98/13350, Apr. 2, 1998.

(Continued)

*Primary Examiner*—Kevin E Weddington
(74) *Attorney, Agent, or Firm*—Morgan, Lewis & Bockius LLP

(57) ABSTRACT

The invention concerns the use of a quinazoline derivative of Formula (I) wherein $Q^1$ includes a quinazoline ring optionally substituted with a group such as halogeno, trifluoromethyl and cyano, or a group of the formula: $Q^3$—$X^1$— wherein $X^1$ includes a direct bond and O and $Q^3$ includes aryl, aryl-(1-6C)alkyl, heterocyclyl and heterocyclyl-(1-6C)alkyl; each of $R^2$ and $R^3$ is hydrogen or (1-6C)alkyl; Z includes O, S and NH; and $Q^2$ includes aryl and aryl-(1-3C)alkyl or a pharmaceutically-acceptable salt thereof, in the manufacture of a medicament for use in the production of an antiangiogenic and/or vascular permeability reducing effect in a warm-blooded animal such as a human.

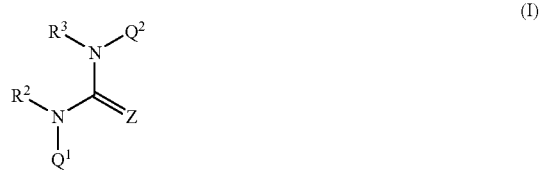

(I)

4 Claims, No Drawings

OTHER PUBLICATIONS

U.S. Appl. No. 09/806,836, filed Jun. 12, 2001, Hennequin et al., WO 00/21955, Apr. 20, 2000.
U.S. Appl. No. 09/913,020, filed May 6, 2002, Stokes et al., WO 00/47212, Aug. 17, 2000.
U.S. Appl. No. 10/019,945, filed Jan. 7, 2002, Crawley et al., WO 01/04102, Jan. 18, 2001.
U.S. Appl. No. 10/129,336, May 3, 2002, Thomas et al., WO 01/32651, May 10, 2001.
U.S. Appl. No. 10/240,413, filed Oct. 1, 2002, Curwen et al., WO 01/74360, Oct. 11, 2001.
U.S. Appl. No. 10/240,658, filed Oct. 3, 2002, Hennequin et al., WO 01/77085, Oct. 18, 2001.
U.S. Appl. No. 10/333,592, filed Jan. 22, 2003, Hennequin, WO 02/12228, Feb. 14, 2002.
U.S. Appl. No. 10/332,274, filed Jan. 7, 2003, Hennequin, WO 02/12226, Feb. 14, 2002.
U.S. Appl. No. 10/343,236, filed Jan. 30, 2003, Hennequin, WO 02/12227, Feb. 14, 2002.

Hennequin et al., "Design and Structure-Activity Relationship of a New Class of Potent VEGF Receptor Tyrosine Kinase Inhibitors", Journal of Medicinal Chemistry, vol. 42, No. 26, 1999, pp. 5369-5389, XP002134973.
Gibson et al.; "Epidermal Growth Factor Receptor Tyrosine Kinase: Structure-Activity Relationships and Antitumour Activity of Novel Quinazolines"; Bioorganic & Medicinal Chemistry Letters, 1997, vol. 7, No. 21, pp. 2723-2728.
Hong et al.; "Synthesis and Billogical Activities of Some $N^4$-Substituted 4-Aminopyrazolo[3,4-$d$-pyrimidines"; Journal of Medicinal Chemistry, 1976, vol. 19, No. 4, pp. 555-558.
Myers et al.; "The Preparation and SAR of 4-(Anilino), 4-(Phenoxy), and 4-(Thiophenoxy)-Quinazolines: Inhibitors of $p56^{lck}$ and EGF-R Tyrosine Kinase Activity"; Bioorganic & Medicinal Chemistry Letters, 1997, vol. 7, No. 4, pp. 417-420.
van Muijtwijk-Koezen et al.; "Isoquinoline and Quinazoline Urea Analogues as Antagonists for the Human Adenosine $A_3$ Receptor"; J. Med. Chem., 2000, vol. 43, pp. 2227-2238.

* cited by examiner

METHOD OF PRODUCING AN ANTIANGIOGENIC OR VASCULAR PERMEABILITY REDUCING EFFECT

The present invention relates to a new use for certain quinazoline derivatives in the treatment of disease states associated with angiogenesis and/or increased vascular permeability, to their use in the manufacture of medicaments for use in the production of antiangiogenic and/or vascular permeability reducing effects in warm-blooded animals such as humans.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (an et al, 1995, Trends Pharmacol. Sci. 16: 57-66; Folkman, 1995, Nature Medicine 1: 27-31). Alteration of vascular permeability is thought to play a role in both normal and pathological physiological processes (Cullinan-Bove et al, 1993, Endocrinology 133: 829-837; Senger et al, 1993, Cancer and Metastasis Reviews, 12: 303-324). Several polypeptides with in vitro endothelial cell growth promoting activity have been identified including, acidic and basic fibroblast growth factors (aFGF & bFGF) and vascular endothelial growth factor (VEGF). By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848-859; Kolch et al, 1995, Breast Cancer Research and Treatment, 36:139-155) and vascular permeability (Connolly et al, 1989, J. Biol. Chem. 264: 20017-20024). Antagonism of VEGF action by sequestration of VEGF with antibody can result in inhibition of tumour growth (Kim et al, 1993, Nature 362: 841-844).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity which leads to phosphorylation of tyrosine residues on both the receptor and other intracellular molecules. These changes in tyrosine phosphorylation initiate a signalling cascade leading to a variety of cellular responses. To date, at least nineteen distinct RTK subfamilies, defined by amino acid sequence homology, have been identified. One of these subfamilies is presently comprised by the fms-like tyrosine kinase receptor, Flt or Flt1, the kinase insert domain-containing receptor, KDR (also referred to as Flk-1), and another fms-like tyrosine kinase receptor, Flt4. Two of these related RTKs, Flt and KDR, have been shown to bind VEGF with high affinity (De Vries et al, 1992, Science 255: 989-991; Terman et al, 1992, Biochem. Biophys. Res. Comm 1992, 187: 1579-1586). Binding of VEGF to these receptors expressed in heterologous cells has been associated with changes in the tyrosine phosphorylation status of cellular proteins and calcium fluxes.

International Patent Application Publication No. WO 2001/004102 decribes the compounds of the present invention as modulators of T cell activation, for example by way of inhibition of the non-receptor tyrosine kinase p56[lck] tyrosine kinase, but nowhere does it mention VEGF, VEGF receptor tyrosine kinase, angiogenesis or vascular permeability.

Compounds of the present invention inhibit the effects of VEGF, a property of value in the treatment of disease states associated with angiogenesis and/or increased vascular permeability such as cancer, diabetes, psoriasis, rheumatoid arthritis, Kaposi's sarcoma, haemangioma, acute and chronic nephropathies, atheroma, arterial restenosis, autoimmune diseases, acute inflammation, excessive scar formation and adhesions, endometriosis, dysfunctional uterine bleeding and ocular diseases with retinal vessel proliferation.

Compounds of the present invention possess good activity against VEGF receptor tyrosine kinase whilst possessing some activity against EGF receptor tyrosine kinase. Furthermore, some compounds of the present invention, possess substantially higher potency against VEGF receptor tyrosine kinase than against EGF receptor tyrosine kinase or FGF R1 receptor tyrosine kinase. While we do not wish to be bound by theoretical considerations such compounds may for example be of interest in treating tumours which are associated with VEGF, especially those tumours which are dependent on VEGF for their growth.

According to one aspect of the invention there is provided a method of treating disease states associated with angiogenesis and/or increased vascular permeability comprising administering to a patient a quinazoline derivative of the Formula I

wherein $Q^1$ is a quinazoline-like ring such as a group of the formula Ia, Ib or Ic,

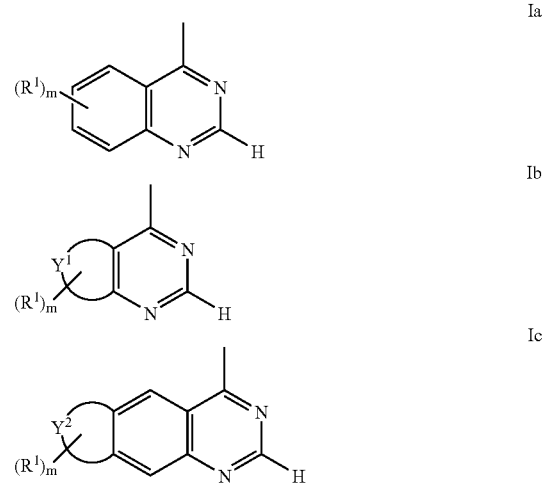

wherein:

$Y^1$ together with the carbon atoms to which it is attached forms a 5- or 6-membered aromatic or partially unsaturated ring comprising 1 to 3 heteroatoms selected from O, N and S provided that the group of formula Ib so formed is not a purine ring;

Y² together with the carbon atoms to which it is attached forms a 5- or 6-membered aromatic or partially unsaturated ring comprising 1 to 3 heteroatoms selected from O, N and S;

m is ,1, 2, 3or 4;

each $R^1$ group, which may be the same or different, is selected from halogeno, trifluoromethyl, cyano, isocyano, nitro, hydroxy, mercapto, amino, formyl, carboxy, carbamoyl, (1-6C)alkyl, (2-8C)alkenyl, (2-8C)alkynyl, (1-6C)alkoxy, (2-6C)alkenylox (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino,
N-(1-6C)alkylsulphamoyl,                     N,
N-di-[(1-6C)alkyl]sulphamoyl, (1-6C)alkanesulphonylamino and N-(1-6C)alkyl-(1-6C)alkanesulphonylamino, or from a group of the formula:

$$Q^3—X^1—$$

wherein $X^1$ is a direct bond or is selected from O, S, SO, SO₂, N(R⁴), CO, CH(OR⁴), CON(R⁴), N(R⁴)CO, SO₂N(R⁴), N(R⁴)SO₂, OC(R⁴)₂, SC(R⁴)₂ and N(R⁴)C(R⁴)₂, wherein $R^4$ is hydrogen or (1-6C)alkyl, and $Q^3$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, or $(R^1)_m$ is (1-3C)alkylenedioxy, and wherein adjacent carbon atoms in any (2-6C)alkylene chain within a $R^1$ substituent are optionally separated by the insertion into the chain of a group selected from O, S, SO, SO₂, N(R⁵), CO, CH(OR⁵), CON(R⁵), N(R⁵)CO, SO₂N(R⁵), N(R⁵)SO₂, CH=CH and C≡C wherein $R^5$ is hydrogen or (1-6C)alkyl, and wherein any CH₂=CH— or HC≡C— group within a $R^1$ substituent optionally bears at the terminal CH₂= or HC≡ position a substituent selected from halogeno, carboxy, carbamoyl, (1-6C)alkoxycarbonyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino(1-6C)alkylamino-(1-6C)alkyl or from a group of the formula:

$$Q^4—X^2—$$

wherein $X^2$ is a direct bond or is selected from CO and N(R⁶)CO, wherein $R^6$ is hydrogen or (1-6C)alkyl, and $Q^4$ is aryl, aryl-(1-6C)alkyl, heteroaryl, heteroaryl-(1-6C)alkyl, heterocyclyl or heterocyclyl-(1-6C)alkyl, and wherein any CH₂ or CH₃ group within a $R^1$ substituent optionally bears on each said CH₂or CH₃ group one or more halogeno substituents or a substituent selected from hydroxy, cyano, amino, carboxy, carbamoyl, (1-6C)alkyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N, N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino,
N-(1-6C)alkylsulphamoyl,                     N,
N-di-[(1-6C)alkyl]sulphamoyl, (1-6C)alkanesulphonylamino and N-(1-6C)alkyl-(1-6C)alkanesulphonylamino, or from a group of the formula:

$$—X^3—Q^5$$

wherein $X^3$ is a direct bond or is selected from O, S, SO, SO₂, N(R⁷), CO, CH(OR⁷), CON(R⁷), N(R⁷)CO, SO₂N(R⁷), N(R⁷)SO₂, C(R⁷)₂O, C(R⁷)₂S and N(R⁷)C (R⁷)₂, wherein $R^7$ is hydrogen or (1-6C)alkyl, and $Q^5$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, and wherein any aryl, heteroaryl or heterocyclyl group within a substituent on $R^1$ optionally bears 1, 2 or 3 substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N, N-di-[(1-6C)alkyl]carbamoyl, (2-6C)alkanoyl, (2-6C)alkanoyloxy,               (2-6C)alkanoylamino, N-(1-6C)alkyl-(2-6C)alkanoylamino,
N-(1-6C)alkylsulphamoyl,                     N,
N-di-[(1-6C)alkyl]sulphamoyl, (1-6C)alkanesulphonylamino and N-(1-6C)alkyl-(1-6C)alkanesulphonylamino, or from a group of the formula:

$$—X^4—R^8$$

wherein $X^4$ is a direct bond or is selected from O and N(R⁹), wherein $R^9$ is hydrogen or (1-6C)alkyl, and $R^8$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl, (2-6C)alkanoylamino-(1-6C)alkyl or (1-6C)alkoxycarbonylamino-(1-6C)alkyl, or from a group of the formula:

$$—X^5—Q^6$$

wherein $X^5$ is a direct bond or is selected from O and N(R¹⁰), wherein $R^{10}$ is hydrogen or (1-6C)alkyl, and $Q^6$ is aryl, aryl-(1-6C)alkyl, heteroaryl, heteroaryl-(1-6C)alkyl, heterocyclyl or heterocyclyl-(1-6C)alkyl, and any $Q^6$ group optionally bears 1 or 2 substituents, which may be the same or different, selected from halogeno, (1-6C)alkyl and (1-6C)alkoxy, and wherein any heterocyclyl group within a substituent on $R^1$ optionally bears 1 or 2 oxo or thioxo substituents;

$R^2$ is hydrogen or (1-6C)alkyl and $R^3$ is hydrogen or (1-6C)alkyl, or $R^2$ and $R^3$ together form a CH₂, (CH₂)₂ or (CH₂)₃ group;

Z is O, S, N(C≡N) or N(R¹¹), wherein $R^{11}$ is hydrogen or (1-6C)alkyl; and $Q^2$ is aryl, aryl-(1-3C)alkyl, aryl-(3-7C)cycloalkyl, heteroaryl, heteroaryl-(1-3C)alkyl or heteroaryl-(3-7C)cycloalkyl wherein each aryl group is phenyl or naphthyl and each heteroaryl group is a 5- or 6-membered monocyclic or a 9- or 10-membered bicyclic heteroaryl ring containing 1 or 2 nitrogen heteroatoms and optionally containing a further heteroatom selected from nitrogen, oxygen and sulphur, and $Q^2$ is optionally substituted with 1, 2, 3 or 4 substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino,
N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—$X^6$—$R^{12}$ wherein $X^6$ is a direct bond or is selected from O and $N(R^{13})$, wherein $R^{13}$ is hydrogen or (1-6C)alkyl, and $R^{12}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl, or from a group of the formula:

—$X^7$—$Q^7$ wherein $X^7$ is a direct bond or is selected from O, S, SO, $SO_2$, $N(R^{14})$, CO, $CH(OR^{14})$, $CON(R^{14})$, $N(R^{14})CO$, $SO_2N(R^{14})$, $N(R^{14})SO_2$, $C(R^{14})_2O$, $C(R^{14})_2S$ and $C(R^{14})_2N(R^{14})$, wherein each $R^{14}$ is hydrogen or (1-6C)alkyl, and $Q^7$ is aryl, aryl-(1-6C)alkyl, heteroaryl, heteroaryl-(1-6C)alkyl, heterocyclyl or heterocyclyl-(1-6C)alkyl, or $Q^2$ is optionally substituted with a (1-3C)alkylenedioxy group, and wherein any aryl, heteroaryl or heterocyclyl group within a substituent on $Q^2$ optionally bears 1, 2 or 3 substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—$X^8$—$R^{15}$ wherein $X^8$ is a direct bond or is selected from O and $N(R^{16})$, wherein $R^{16}$ is hydrogen or (1-6C)alkyl, and $R^{15}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl, and wherein any heterocyclyl group within a substituent on $Q^2$ optionally bears 1 or 2 oxo or thioxo substituents;

or a pharmaceutically-acceptable salt thereof.

According to another aspect of the invention there is provided a method of treating disease states associated with angiogenesis and/or increased vascular permeability comprising administering to a patient a quinazoline derivative of the Formula I

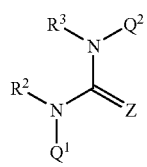

I wherein $Q^1$ is a quinazoline-like ring such as a group of the formula Ia, Ib or Ic,

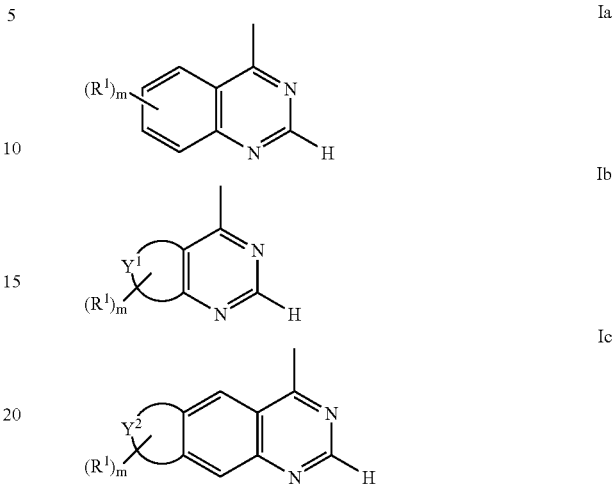

wherein:

$Y^1$ together with the carbon atoms to which it is attached forms a 5- or 6-membered aromatic or partially unsaturated ring comprising 1 to 3 heteroatoms selected from O, N and S provided that the group of formula Ib so formed is not a purine ring;

$Y^2$ together with the carbon atoms to which it is attached forms a 5- or 6-membered aromatic or partially unsaturated ring comprising 1 to 3 heteroatoms selected from O, N and S;

m is 0, 1, 2, 3 or 4;

each $R^1$ group, which may be the same or different, is selected from halogeno, trifluoromethyl, cyano, isocyano, nitro, hydroxy, mercapto, amino, formyl, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl(3-6C)alkynoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$Q^3$—$X^1$— wherein $X^1$ is a direct bond or is selected from O, S, SO, $SO_2$, $N(R^4)$, CO, $CH(OR^4)$, $CON(R^4)$, $N(R^4)CO$, $SO_2N(R^4)$, $N(R^4)SO_2$, $OC(R^4)_2$, $SC(R^4)_2$ and $N(R^4)C(R^4)_2$, wherein $R^4$ is hydrogen or (1-6C)alkyl, and $Q^3$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, or $(R^1)_m$ is (1-3C)alkylenedioxy, and wherein adjacent carbon atoms in any (2-6C)alkylene chain within a $R^1$ substituent are optionally separated by the insertion into the chain of a group selected from O S, SO, $SO_2$, $N(R^5)$, CO, $CH(OR^5)$, $CON(R^5)$, $N(R^5)CO$, $SO_2N(R^5)$, $N(R^5)SO_2$, CH=CH and C≡C wherein $R^5$ is hydrogen or (1-6C)alkyl, and wherein any CH$_2$=C— or HC≡C— group within a R$^1$ substituent optionally bears at the terminal CH$_2$= or HC≡ position a substituent selected from halogeno, carboxy, carbamoyl, (1-6C)alkoxycarbonyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

Q$^4$·X$^2$— wherein X$^2$ is a direct bond or is selected from CO and N(R$^6$)CO, wherein R$^6$ is hydrogen or (1-6C)alkyl, and Q$^4$ is aryl, aryl-(1-6C)alkyl, heteroaryl, heteroaryl1-6C)alkyl, heterocyclyl or heterocyclyl-(1-6C)alkyl, and wherein any CH$_2$ or CH$_3$ group within a R$^1$ substituent optionally bears on each said CH$_2$or CH$_3$ group one or more halogeno substituents or a substituent selected from hydroxy, cyano, amino, carboxy, carbamoyl, (1-6C)alkyl, (1-6C) alkoxy, (1-6C)alkylthio, (1-6C)alkylsulphinyl, (1-6C)alkylsulphonyl, (1-6C)alkylamino, di-[(1-6C)alkyl]amino, (1-6C) alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—X$^3$—Q$^5$ wherein X$^3$ is a direct bond or is selected from O, S, SO, SO$_2$, N(R$^7$), CO, CH(OR$^7$), CON(R$^7$), N(R$^7$)CO, SO$_2$N(R$^7$), N(R$^7$)SO$_2$, C(R$^7$)$_2$O, C(R$^7$)$_2$S and N(R$^7$)C(R$^7$)$_2$, wherein R$^7$ is hydrogen or (1-6C)alkyl, and Q$^5$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C) alkyl, and wherein any aryl, heteroaryl or heterocyclyl group within a substituent on R$^1$ optionally bears 1, 2 or 3 substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—X$^4$—R$^8$ wherein X$^4$ is a direct bond or is selected from O and N(9), wherein R$^9$ is hydrogen or (1-6C)alkyl, and R$^{11}$ is halogeno-(1-6C)alkyl, hydroxyl-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl, or from a group of the formula:

—X$^5$—Q$^6$ wherein X$^5$ is a direct bond or is selected from O and N(R$^{10}$), wherein R$^{10}$ is hydrogen or (1-6C)alkyl, and Q$^6$ is aryl, aryl-(1-6C)alkyl, heteroaryl, heteroaryl-(1-6C)alkyl, heterocyclyl or heterocyclyl-(1-6C)alkyl, and wherein any heterocyclyl group within a substituent on R$^{11}$ optionally bears 1 or 2 oxo or thioxo substituents;

R$^2$ is hydrogen or (1-6C)alkyl and R$^3$ is hydrogen or (1-6C) alkyl, or R$^2$ and R$^3$ together form a CH$_2$, (CH$_2$), or (CH$_2$)$_3$ group;

Z is O, S, N(C≡N) or N(R$^{11}$), wherein R$^{11}$ is hydrogen or (1-6C)alkyl; and Q$^2$ is aryl, aryl-(1-3C)alkyl, aryl-(3-7C)cycloalkyl, heteroaryl, heteroaryl-(1-3C)alkyl or heteroaryl-(3-7C)cycloalkyl wherein each aryl group is phenyl or naphthyl and each heteroaryl group is a 5- or 6-membered monocyclic or a 9- or 10-membered bicyclic heteroaryl ring containing 1 or 2 nitrogen heteroatoms and optionally containing a further heteroatom selected from nitrogen, oxygen and sulphur, and Q$^2$ is optionally substituted with 1, 2, 3 or 4 substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C) alkoxy, (2-6C)alkenyloxy, (2-6C)alkynyloxy, (1-6C)alkylthio, (1-6C)alkylsulphinyl, (1-6C)alkylsulphonyl, (1-6C) alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—X$^6$—R$^{12}$ wherein X$^6$ is a direct bond or is selected from O and N(R3), wherein R$^{13}$ is hydrogen or (1-6C)alkyl, and R$^{12}$ is halogeno-(1-6C)alkyl, hydroxy-(1-6C)alkyl, (1-6C)alkoxy-(1-6C) alkyl, cyano-(1-6C)alkyl, amino-(1-6C)alkyl, (1-6C)alkylamino1-6C)alkyl or di-[(1-6C)alkyl]amino-(1-6C)alkyl, or from a group of the formula:

—X$^7$—Q$^7$ wherein X$^7$ is a direct bond or is selected from O, S, SO, SO$_2$, N(R$^4$), CO, CH(OR$^{14}$), CON(R$^{14}$), N(R$^4$)CO, SO$_2$N(R$^{14}$), N(R$^{14}$)SO$_2$, C(R$^{14}$)$_2$O, C(R$^{14}$)$_2$S and C(R$^{14}$)$_2$N(R$^{14}$), wherein each R$^{14}$ is hydrogen or (1-6C)alkyl, and Q$^7$ is aryl, aryl-1-6C)alkyl, heteroaryl, heteroaryl-(1-6C)alkyl, heterocyclyl or heterocyclyl-(1-6C)alkyl, or Q$^2$ is optionally substituted with a (1-3C)alkylenedioxy group, and wherein any aryl, heteroaryl or heterocyclyl group within a substituent on Q$^2$ optionally bears 1, 2 or 3 substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C) alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N, N-di-[(1-6C)alkyl]sulphamoyl, (1-6C)alkanesulphonylamino and N-(1-6C)alkyl-(1-6C)alkanesulphonylamino, or from a group of the formula:

—X$^8$—R$^{15}$ wherein X$^8$ is a direct bond or is selected from O and N(R$^{16}$), wherein R$^{16}$ is hydrogen or (1-6C)alkyl, and R$^{15}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl, and wherein any heterocyclyl group within a substituent on Q$^2$ optionally bears 1 or 2 oxo or thioxo substituents;

or a pharmaceutically-acceptable salt thereof

In another aspect the invention relates to a method of producing an antiangiogenic and/or vascular permeability reducing effect in a warm-blooded animal in need of such treatment which comprises administering to the animal an effective amount of a compound of the formula (1) or a pharmaceutically-acceptable salt thereof.

In yet another aspect the invention relates to a method of producing an antiangiogenic and/or vascular permeability reducing effect mediated alone or in part by VEGF receptor tyrosine kinase in a warm-blooded animal in need of such treatment which comprises administering to the animal an effective amount of a compound of the formula (I) or a pharmaceutically-acceptable salt thereof.

In yet another aspect the invention relates to a method of producing VEGF receptor tyrosine kinase inhibitory effect in a warm-blooded animal in need of such treatment which comprises administering to the animal an effective amount of a compound of the formula (1) or a pharmaceutically-acceptable salt thereof.

In yet another aspect the invention relates to a method of treating in a warm-blooded animal a disease or medical condition mediated alone or in part by VEGF receptor tyrosine kinase which comprises administering to the animal an effective amount of a compound of the formula (I) or a pharmaceutically-acceptable salt thereof.

In yet another aspect the invention relates to the use of a compound of the formula (I) or a pharmaceutically-acceptable salt thereof in the manufacture of a medicament for treating disease states associated with angiogenesis and/or increased vascular permeability in warm-blooded animals.

In yet another aspect the invention relates to the use of a compound of the formula (I) or a pharmaceutically-acceptable salt thereof in the manufacture of a medicament for use in the production of antiangiogenic and/or vascular permeability reducing effects in warm-blooded animals.

In yet another aspect the invention relates to the use of a compound of the formula (I) or a pharmaceutically-acceptable salt thereof in the manufacture of a medicament for use in producing an antiangiogenic and/or vascular permeability reducing effect mediated alone or in part by VEGF receptor tyrosine kinase in a warm-blooded animal.

In yet another aspect the invention relates to the use of a compound of the formula (I) or a pharmaceutically-acceptable salt thereof in the manufacture of a medicament for producing a VEGF receptor tyrosine kinase inhibitory effect in warm-blooded animals.

In yet another aspect the invention relates to the use of a compound of the formula (I) or a pharmaceutically-acceptable salt thereof in the manufacture of a medicament for treating, in a warm-blooded animal, a disease or medical condition mediated alone or in part by VEGF receptor tyrosine kinase.

In particular the warm-blooded animal is a human.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of Formula I defined above may exist in optically active or racemic forms by virtue of one or more asymmetric carbon atoms, the invention includes in its definition any such optically active or racemic form which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

It is to be understood that the hydrogen atom which is shown at the 2-position in each of the part structures of the formulae Ia, Ib, and Ic indicates that that position remains unsubstituted by any R$^1$ group.

Suitable values for the generic radicals referred to above include those set out below.

A suitable value for any one of the 'Q' groups (Q$^2$ to Q$^7$) when it is aryl or for the aryl group within a 'Q' group is, for example, phenyl or naphthyl, preferably phenyl.

A suitable value for a (3-7C)cycloalkyl group within Q$^2$ or for Q$^3$ or Q$^4$ when it is (3-7C)cycloalkyl is, for example, cyclopropyl, cyclobutyl, cyclopentyl, cyclohexyl, cycloheptyl or bicyclo[2.2.1]heptyl and a suitable value for Q$^3$ or Q$^4$ when it is (3-7C)cycloalkenyl is, for example, cyclobutenyl, cyclopentenyl cyclohexenyl or cycloheptenyl.

A suitable value for Q$^2$ when it is a 5- or 6-membered monocyclic or a 9- or 10-membered bicyclic heteroaryl ring containing 1 or 2 nitrogen heteroatoms and optionally containing a further heteroatom selected from nitrogen, oxygen and sulphur is, for example, pyrrolyl, oxazolyl, isoxazolyl, imidazolyl, pyrazolyl, thiazolyl, isothiazolyl, oxadiazolyl, thiadiazolyl, triazolyl, pyridyl, pyridazinyl, pyrimidinyl, pyrazinyl, 1,3,5-triazenyl, indolyl, benzoxazolyl, benzimidazolyl, benzothiazolyl, indazolyl, benzofurazanyl, quinolyl, isoquinolyl, quinazolinyl, quinoxalinyl, cinnolinyl or naphthyridinyl, preferably isoxazolyl, 1,2,3-triazolyl, pyridyl, benzothiazolyl, quinolyl or quinazolinyl.

A suitable value for any one of the 'Q' groups, Q$^3$ to Q$^7$, when it is heteroaryl or for the heteroaryl group within a 'Q' group is, for example, an aromatic 5- or 6-membered monocyclic ring or a 9- or 10-membered bicyclic ring with up to five ring heteroatoms selected from oxygen, nitrogen and sulphur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl or naphthyridinyl, preferably thienyl, 1,2,3-triazolyl, pyridyl, quinolyl, quinazolinyl or quinoxalinyl.

A suitable value for any one of the 'Q' groups, $Q^3$ to $Q^7$, when it is heterocyclyl or for the heterocyclyl group within a 'Q' group is, for example, a non-aromatic saturated or partially saturated 3 to 10 membered monocyclic or bicyclic ring with up to five heteroatoms selected from oxygen, nitrogen and sulphur, for example oxiranyl, oxetanyl, tetrahydrofuranyl, tetrahydropyranyl, pyrrolinyl, pyrrolidinyl, morpholinyl, tetrahydro-1,4-thiazinyl, 1,1-dioxotetrahydro-1,4-thiazinyl, piperidinyl, homopiperidinyl, piperazinyl, homopiperazinyl, dihydropyridinyl, tetrahydropyridinyl, dihydropyrimidinyl or tetrahydropyrimidinyl, preferably pyrrolidin-1-yl, pyrrolidin-2-yl, morpholino, 1,1-dioxotetrahydro4$\underline{H}$-1,4-thiazin-4-yl, piperidino, piperidin-3-yl, piperidin-4-yl, homopiperidin-1-yl, piperazin-1-yl or homopiperazin-1-yl, more preferably piperidin-4-yl. A suitable value for such a group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl, or 2,6-dioxopiperidinyl.

A suitable value for a 'Q' group when it is heteroaryl-(1-6C)alkyl is, for example, heteroarylmethyl, 2-heteroarylethyl and 3-heteroarylpropyl. The invention comprises corresponding suitable values for 'Q' groups when, for example, rather than a heteroaryl-(1-6C)alkyl group, an aryl-(1-6C)alkyl, (3-7C)cycloalkyl(1-6C)alkyl, (3-7C)cycloalkenyl-(1-6C)alkyl or heterocyclyl-(1-6C)alkyl group is present.

When, as defined hereinbefore, $Y^1$ together with the carbon atoms to which it is attached forms a 5- or 6-membered aromatic or partially unsaturated ring comprising 1 to 3 heteroatoms selected from O, N and S (provided that the group of formula Ib so formed is not a purine ring), ring $Y^1$ is suitably unsaturated or partially unsaturated wherein a —$CH_2$— group can optionally be replaced by a —CO— group and a ring nitrogen atom may optionally bear a (1-6C)alkyl group. Diradicals of suitable fused $Y^1$ rings include thiendiyl, furandiyl, pyrazolediyl, oxazolediyl, isoxazolediyl, thiazolediyl, isothiazolediyl, 1,2,3-oxadiazolediyl, 1,2,3-triazolediyl, pyridinediyl, pyrimidinediyl, pyrazinediyl, pyridazinediyl and 1,3,4-triazinediyl. Examples of suitable bicyclic rings of formula Ib formed by the fusion of ring $Y^1$ to the adjacent pyrimidine ring include furopyrimidinyl, thienopyrimidinyl, pyrrolopyrimidinyl, pyrrolinopyrimidinyl, oxopyrrolinopyrimidinyl, oxazolopyrimidinyl, oxazolinopyrimidinyl, oxooxazolinopyrimidinyl, isoxazolopyrimidinyl, thiazolopyrimidinyl, thiazolinopyrimidinyl, oxothiazolinopyrimidinyl, isothiazolopyrimidinyl, oxoimidazolinopyrimidinyl, pyrazolopyrimidinyl, pyrazolinopyrimidinyl, oxopyrazolinopyrimidinyl, pyridopyrimidinyl, pyrimidopyrimidinyl and pteridinyl. Preferably the bicyclic ring of formula Ib is furo[3,2-d]pyrimidinyl, furo[2,3-d]pyrimidinyl, thieno[3,2-d]pyrimidinyl, thieno[2,3-d]pyrimidinyl, pyrrolo[3,2-d]pyrimidinyl, pyrrolo[2,3-d]pyrimidinyl, oxazolo[5,4-d]pyrimidinyl, oxazolo[4,5-d]pyrimidinyl, thiazolo[5,4-d]pyrimidinyl, thiazolo[4,5-d]pyrimidinyl, pyrido[2,3-d]pyrimidinyl, pyrido[3,4-d]pyrimidinyl, pyrido[4,3-d]pyrimidinyl, pyrido[3,2-d]pyrimidinyl, pyrimido[4,5-d]pyrimidinyl, pyrimido[5,6-d]pyrimidinyl or pteridinyl. More specifically the bicyclic ring of formula Ib is 6-oxopyrrolino[2,3-d]pyrimidin-4-yl, 6-oxopyrrolino[3,2-d]pyrimidin-4-yl, 2-oxooxazolino[5,4-d]pyrimidin-7-yl, 2-oxothiazolino[5,4-d]pyrimidin-7-yl, 2-oxooxazolino[4,5-d]pyrimidin-7-yl, 2-oxothiazolino[4,5-d]pyrimidin-7-yl, 2-oxoimidazolino[4,5-d]pyrimidin-7-yl, 3-oxopyrazolino[3,4-d]pyrimidin-4-yl or 3-oxopyrazolino[4,3-d]pyrimidin-7-yl. Further preferred bicyclic rings of formula Ib include thieno[3,2-d]pyrimidinyl, thieno[2,3-d]pyrimidinyl, thiazolo[5,4-d]pyrimidinyl, pyrido[2,3-d]pyrimidinyl, pyrido[3,4-d]pyrimidinyl, pyrido[4,3-d]pyrimidinyl, pyrido[3,2-d]pyrimidinyl and pteridinyl, more specifically thieno[3,2-d]pyrimidin, thieno[2,3-d]pyrimidin-4-yl, thiazolo[5,4-d]pyrimidin-7-yl, pyrido[2,3-d]pyrimidin-4-yl, pyrido[3,4-d]pyrimidin-4-yl, pyrido[4,3-d]pyrimidin, pyrido[3,2-d]pyrimidin-4-yl and pteridin-4-yl.

When, as defined hereinbefore, $Y^2$ together with the carbon atoms to which it is attached forms a 5- or 6-membered aromatic or partially unsaturated ring comprising 1 to 3 heteroatoms selected from O, N and S, ring $Y^2$ is suitably unsaturated or partially unsaturated wherein a —$CH_2$— group can optionally be replaced by a —CO— group and a ring nitrogen atom may optionally bear a (1-6C)alkyl group. Diradicals of suitable fused $Y^2$ rings include thiendiyl, furandiyl, imidazolediyl, pyrazolediyl, oxazolediyl, isoxazolediyl, thiazolediyl, isothiazolediyl, 1,2,3-oxadiazolediyl, 1,2,3-triazolediyl, pyridinediyl, pyrimidinediyl, pyrazinediyl, pyridazinediyl and 1,3,4-triazinediyl. Examples of suitable tricyclic rings of formula Ic formed by the fusion of ring $Y^2$ to the adjacent quinazoline ring include imidazoquinazolinyl, oxazoloquinazolinyl, thiazoloquinazolinyl, [1,2,3]triazoloquinazolinyl, pyrazoloquinazolinyl, pyrroloquinazolinyl, oxoimidazolinoquinazolinyl, oxooxazolinoquinazolinyl, oxothiazolinoquinazolinyl and oxopyrazolinoquinazolinyl. Preferably the tricyclic ring of formula Ic is 3$\underline{H}$-imidazo[4,5-g]quinazolinyl, oxazolo[4,5-g]quinazolinyl, thiazolo[4,5-g]quinazolinyl, 3$\underline{H}$-[1,2,3]triazolo[4,5-g]quinazolinyl, 1H-pyrazolo[3,4-g]quinazolinyl, 6$\underline{H}$-pyrrolo[2,3-g]quinazolinyl, 2-oxo-1,2-dihydro-3$\underline{H}$-imidazo[4,5-g]quinazolinyl, 2-oxo-1,2-dihydrooxazolo[4,5-g]quinazolinyl, 2-oxo-1,2-dihydrothiazolo[4,5-g]quinazolinyl, 3-oxo-2,3-dihydro-1$\underline{H}$-pyrazolo[3,4-g]quinazolinyl, pyrido[2,3-g]quinazolinyl, pyrimidino[4,5-g]cinnolinyl, pyrimidino[4,5-g]quinazolinyl, pyrazino[2,3-g]quinazolinyl, 7-oxo-6,7-dihydropyrido[2,3-g]quinazolinyl, pyrazino[2,3-g]quinazolinyl and 8-oxo-8,9-dihydropyrazino[2,3-g]quinazolinyl. More specifically the tricyclic ring of formula Ic is 3$\underline{H}$-imidazo[4,5-g]quinazolin-8-yl, oxazolo[4,5-g]quinazolin-8-yl, thiazolo[4,5-g]quinazolin-8-yl, 3$\underline{H}$-[1,2,3]triazolo[4,5-g]quinazolin-8-yl, 1$\underline{H}$-pyrazolo[3,4-g]quinazolin-8-yl, 6$\underline{H}$-pyrrolo[2,3-g]quinazolin-4-yl, 2-oxo-1,2-dihydro-3$\underline{H}$-imidazo[4,5-g]quinazolin-8-yl, 2-oxo-1,2-dihydrooxazolo[4,5-g]quinazolin-8-yl, 2-oxo-1,2-dihydrothiazolo[4,5-g]quinazolin-8yl, 3-oxo-2,3-dihydro-1H-pyrazolo[3,4g]quinazolin-8-yl, pyrido[2,3-g]quinazolin-4-yl, pyrimidino[4,5-g]cinnolin-9-yl, pyrimidino[4,5-g]quinazolin-4-yl, pyrazino[2,3-g]quinazolinyl, 7-oxo-6,7-dihydropyrido[2,3-g]quinazolin-4-yl, pyrazino[2,3-g]quinazolin-4-yl or 8-oxo-8,9-dihydropyrazino[2,3-g]quinazolin-4-yl. Further preferred tricyclic rings of formula Ic include 3-methyl-3$\underline{H}$-imidazo[4,5-g]quinazolin-8-yl, 3-methyl-3$\underline{H}$-[1,2,3]triazolo[4,5-g]quinazolin-8-yl, 3-methyl-2-oxo-1,2-dihydro-3$\underline{H}$-imidazo[4,5-g]quinazolin-8-yl, pyrazino[2,3-g]quinazolin-4-yl and 9-methyl-8-oxo-8,9-dihydropyrazino[2,3-g]quinazolin-4-yl.

Suitable values for any of the 'R' groups ($R^1$ to $R^{16}$), or for various groups within an $R^1$ substituent, or within a substituent on $Q^2$ include:

| | |
|---|---|
| for halogeno | fluoro, chloro, bromo and iodo; |
| for (1-6C)alkyl: | methyl, ethyl, propyl, isopropyl and tert-butyl; |
| for (2-8C)alkenyl: | vinyl, allyl and but-2-enyl; |
| for (2-8C)alkynyl: | ethynyl, 2-propynyl and but-2-ynyl; |
| for (1-6C)alkoxy: | methoxy, ethoxy, propoxy, isopropoxy and butoxy; |
| for (2-6C)alkenyloxy: | vinyloxy and allyloxy; |
| for (2-6C)alkynyloxy: | ethynyloxy and 2-propynyloxy; |
| for (1-6C)alkylthio: | methylthio, ethylthio and propylthio; |
| for (1-6C)alkylsulphinyl: | methylsulphinyl and ethylsulphinyl; |
| for (1-6C)alkylsulphonyl: | methylsulphonyl and ethylsulphonyl; |
| for (1-6C)alkylamino: | methylamino, ethylamino, propylamino, isopropylamino and butylamino; |
| for di-[(1-6C)alkyl]amino: | dimethylamino, diethylamino, N-ethyl-N-methylamino and diisopropylamino; |
| for (1-6C)alkoxycarbonyl: | methoxycarbonyl, ethoxycarbonyl, propoxycarbonyl and tert-butoxycarbonyl; |
| for N-(1-6C)alkylcarbamoyl: | N-methylcarbamoyl, N-ethylcarbamoyl and N-propylcarbamoyl; |
| for N,N-di-[(1-6C)alkyl]carbamoyl: | N,N-dimethylcarbamoyl, N-ethyl-N-methylcarbamoyl and N,N-diethylcarbamoyl; |
| for (2-6C)alkanoyl: | acetyl and propionyl; |
| for (2-6C)alkanoyloxy: | acetoxy and propionyloxy; |
| for (2-6C)alkanoylamino: | acetamido and propionamido; |
| for N-(1-6C)alkyl-(2-6C)alkanoylamino: | N-methylacetamido and N-methylpropionamido; |
| for N-(1-6C)alkylsulphamoyl: | N-methylsulphamoyl and N-ethylsulphamoyl; |
| for N,N-di-[(1-6C)alkyl]sulphamoyl: | N,N-dimethylsulphamoyl; |
| for (1-6C)alkanesulphonylamino: | methanesulphonylamino and ethanesulphonylamino; |
| for N-(1-6C)alkyl-(1-6C)alkanesulphonylamino: | N-methylmethanesulphonylamino and N-methylethanesulphonylamino; |
| for (3-6C)alkenoylamino: | acrylamido, methacrylamido and crotonamido; |
| for N-(1-6C)alkyl-(3-6C)alkenoylamino: | N-methylacrylamido and N-methylcrotonamido; |
| for (3-6C)alkynoylamino: | propiolamido; |
| for N-(1-6C)alkyl-(3-6C)alkynoylamino: | N-methylpropiolamido; |
| for amino-(1-6C)alkyl: | aminomethyl, 2-aminoethyl, 1-aminoethyl and 3-aminopropyl; |
| for (1-6C)alkylamino-(1-6C)alkyl: | methylaminomethyl, ethylaminomethyl, 1-methylaminoethyl, 2-methylaminoethyl, 2-ethylaminoethyl and 3-methylaminopropyl; |
| for di-[(1-6C)alkyl]amino-(1-6C)alkyl: | dimethylaminomethyl., diethylaminomethyl, 1-dimethylaminoethyl, 2-dimethylaminoethyl and 3-dimethylaminopropyl; |
| for halogeno-(1-6C)alkyl: | chloromethyl, 2-chloroethyl, 1-chloroethyl and 3-chloropropyl; |
| for hydroxy-(1-6C)alkyl: | hydroxymethyl, 2-hydroxyethyl, 1-hydroxyethyl and 3-hydroxypropyl; |
| for (1-6C)alkoxy-(1-6C)alkyl: | methoxymethyl, ethoxymethyl, 1-methoxyethyl, 2-methoxyethyl, 2-ethoxyethyl and 3-methoxypropyl; |
| for cyano-(1-6C)alkyl: | cyanomethyl, 2-cyanoethyl, 1-cyanoethyl and 3-cyanopropyl; |
| for (2-6C)alkanoylamino-(1-6C)alkyl: | acetamidomethyl, propionamidomethyl and 2-acetamidoethyl; and |
| for (1-6C)alkoxycarbonylamino-(1-6C)alkyl: | methoxycarbonylaminomethyl, ethoxycarbonylaminomethyl, tert-butoxycarbonylaminomethyl and 2-methoxycarbonylaminoethyl. |

A suitable value for $(R^1)_m$ or for a substituent on $Q^2$ when it is (1-3C)alkylenedioxy is, for example, methylenedioxy or ethylenedioxy and the oxygen atoms thereof occupy adjacent ring positions.

When, as defined hereinbefore, an $R^1$ group forms a group of the formula $Q^3$—$X^1$— and, for example, $X^1$ is a $OC(R^4)_2$ linking group, it is the carbon atom, not the oxygen atom, of the $OC(R^4)_2$ linking group which is attached to the quinazoline-like ring such as the ring of formula Ia and the oxygen atom is attached to the $Q^3$ group. Similarly, when, for example a $CH_3$ group within a $R^1$ substituent bears a group of the formula —$X^3$—$Q^5$ and, for example, $X^3$ is a $C(R^7)_2O$ linking group, it is the carbon atom, not the oxygen atom, of the $C(R^7)_2O$ linking group which is attached to the $CH_3$ group and the oxygen atom is linked to the $Q^5$ group. A similar convention applies to the attachment of the groups of the formulae $Q^4$—$X^2$— and —$X^7$—$Q^7$.

As defined hereinbefore, adjacent carbon atoms in any (2-6C)alkylene chain within a $R^1$ substituent may be optionally separated by the insertion into the chain of a group such as O, $CON(R^5)$ or C≡C. For example, insertion of a C≡C group into the ethylene chain within a 2-morpholinoethoxy group gives rise to a 4-morpholinobut-2-ynyloxy group and, for example, insertion of a CONH group into the ethylene chain within a 3-methoxypropoxy group gives rise to, for example, a 2-(2-methoxyacetamido)ethoxy group.

When, as defined hereinbefore, any $CH_2$=CH— or HC≡C— group within a $R^1$ substituent optionally bears at the terminal $CH_2$= or HC≡ position a substituent such as a group of the formula $Q^4$—$X^2$—wherein $X^2$ is, for example, NHCO and $Q^4$ is a heterocyclyl-(1-6C)alkyl group, suitable $R^1$ substituents so formed include, for example, N-[heterocyclyl-(1-6C)alkyl]carbamoylvinyl groups such as N-(2-pyrrolidin-1-ylethyl)carbamoylvinyl or N-[heterocyclyl-(1-6C)alkyl]carbamoylethynyl groups such as N-(2-pyrrolidin-1-ylethyl)carbamoylethynyl.

When, as defined hereinbefore, any $CH_2$ or $CH_3$ group within a $R^1$ substituent optionally bears on each said $CH_2$ or $CH_3$ group one or more halogeno substituents, there are suitably 1 or 2 halogeno substituents present on each said $CH_2$ group and there are suitably 1, 2 or 3 halogeno substituents present on each said $CH_3$ group.

When, as defined hereinbefore, any $CH_2$ or $CH_3$ group within a $R^1$ substituent optionally bears on each said $CH_2$ or $CH_3$ group a substituent as defined hereinbefore, suitable $R^1$ substituents so formed include, for example, hydroxy-substituted heterocyclyl-(1-6C)alkoxy groups such as 2-hydroxy-3-piperidinopropoxy and 2-hydroxy-3-morpholinopropoxy, hydroxy-substituted amino-(2-6C)alkoxy groups such as 3-amino-2-hydroxypropoxy, hydroxy-substituted (1-6C)alkylamino-(2-6C)alkoxy groups such as 2-hydroxy-3-methylaminopropoxy, hydroxy-substituted di-[(1-6C)alkyl]amino-(2-6C)alkoxy groups such as 3-dimethylamino-2-hydroxypropoxy, hydroxy-substituted heterocyclyl-(1-6C)alkylamino groups such as 2-hydroxy-3-piperidinopropylamino and 2-hydroxy-3-morpholinopropylamino, hydroxy-substituted amino-(2-6C)alkylamino groups such as 3-amino-2-hydroxypropylamino, hydroxy-substituted (1-6C)alkylamino-(2-6C)alkylamino groups such as 2-hydroxy-3-methylaminopropylamino, hydroxy-substituted di-[(1-6C)alkyl]amino-(2-6C)alkylamino groups such as 3-dimethylamino-2-hydroxypropylamino, hydroxy-substituted (1-6C)alkoxy groups such as 2-hydroxyethoxy, (1-6C)alkoxy-substituted (1-6C)alkoxy groups such as 2-methoxyethoxy and 3-ethoxypropoxy, (1-6C)alkylsulphonyl-substituted (1-6C)alkoxy groups such as 2-methylsulphonylethoxy and heterocyclyl-substituted (1-6C)alkylamino-(1-6C)alkyl groups such as 2-morpholinoethylaminomethyl, 2-piperazin-1-ylethylaminomethyl and 3-morpholinopropylaminomethyl.

A suitable pharmaceutically-acceptable salt of a compound of the Formula I is, for example, an acid-addition salt of a compound of the Formula I, for example an acid-addition salt with an inorganic or organic acid such as hydrochloric, hydrobromic, sulphuric, trifluoroacetic, citric or maleic acid; or, for example, a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris2-hydroxyethyl)amine.

Particular compounds of the formula I include, for example, (i) quinazoline derivatives of the Formula II:

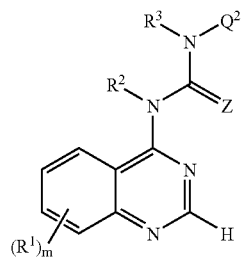

wherein each of m, $R^1$, $R^2$, $R^3$, Z and $Q^2$ has any of the meanings defined hereinbefore;

(ii) pyrimidine derivatives of the Formula III:

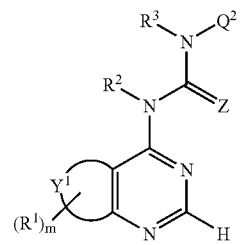

wherein each of m, $R^1$, $Y^1$, $R^2$, $R^3$, Z and $Q^2$ has any of the meanings defined hereinbefore; and (iii) quinazoline derivatives of the Formula IV:

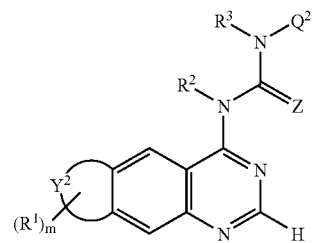

wherein each of m, $R^1$, $R^2$, $R^3$, Z and $Q^2$ has any of the meanings defined hereinbefore.

Compounds of formula I are preferably quinazoline derivatives of formula II or pyrimidine derivatives of formula m, especially quinazoline derivatives of formula II.

Subject to the provisos described hereinbefore, further particular compounds of the formula I include, for example, quinazoline derivatives of the Formula II, or pharmaceutically-acceptable salts thereof, wherein, unless otherwise stated, each of m, $R^1$, $R^2$, $R^3$, Z and $Q^2$ has any of the meanings defined hereinbefore or in paragraphs (a) to (o) hereinafter:

(a) m is 1, 2 or 3, and each $R^1$ group, which may be the same or different, is selected from halogeno, trifluoromethyl, hydroxy, amino, carbamoyl, (1-6C)alkyl, (2-8C)alkenyl, (2-8C)alkynyl, (1-6C)alkoxy, (1-6C)alkylamino, di-[(1-6C)alkyl]amino, N-(1-6C)alkylcarbamoyl, N,N-di-[(1-6C)alkyl]carbamoyl, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino and N-(1-6C)alkyl-(3-6C)alkynoylamino, or from a group of the formula:

$$Q^3-X^1-$$

wherein $X^1$ is a direct bond or is selected from O, N($R^4$), CON($R^4$), N($R^4$)CO and OC($R^4$)$_2$ wherein $R^4$ is hydrogen or (1-6C)alkyl, and $Q^3$ is aryl, aryl-(1-6C)alkyl, cycloalkyl-(1-6C)alkyl, heteroaryl, heteroaryl-(1-6C)alkyl, heterocyclyl or heterocyclyl-(1-6C)alkyl, and wherein adjacent carbon atoms in any (2-6C)alkylene chain within a substituent are optionally separated by the insertion into the chain of a group selected from O, N($R^5$), CON($R^5$), N($R^5$)CO, CH=CH and C≡C wherein $R^1$ is hydrogen or (1-6C)alkyl, and wherein any CH$_2$=CH— or HC≡C— group within a R$^1$ substituent optionally bears at the terminal CH$_2$= or HC≡ position a substituent selected from carbamoyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

$$Q^4—X^2—$$

wherein X$^2$ is a direct bond or is CO or N(R$^6$)CO, wherein R$^6$ is hydrogen or (1-6C)alkyl, and Q$^4$ is heteroaryl, heteroaryl-(1-6C)alkyl, heterocyclyl or heterocyclyl-(1-6C)alkyl, and wherein any CH$_2$ or CH$_3$ group within a R$^1$ substituent optionally bears on each said CH$_2$ or CH$_3$ group a substituent selected from hydroxy, amino, (1-6C)alkoxy, (1-6C)alkylsulphonyl, (1-6C)alkylamino and di-[(1-6C)alkyl]amino, or from a group of the formula:

$$—X^3—Q^5$$

wherein X$^3$ is a direct bond or is selected from O, N(R$^7$), CON(R$^7$), N(R$^7$)CO and C(R$^7$)$_2$O, wherein R$^7$ is hydrogen or (1-6C)alkyl, and Q$^5$ is heteroaryl, heteroaryl-(1-6C)alkyl, heterocyclyl or heterocyclyl-(1-6C)alkyl, and wherein any aryl, heteroaryl or heterocyclyl group within a substituent on R$^1$ optionally bears 1, 2 or 3 substituents, which may be the same or different, selected from halogeno, trifluoromethyl, hydroxy, amino, carbamoyl, (1-6C)alkyl, (1-6C)alkoxy, N-(1-6C)alkylcarbamoyl, N,N-di-[(1-6C)alkyl]arbamoyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl and (1-6C)alkoxycarbonylamino-(1-6C)alkyl, and wherein any heterocyclyl group within a substituent on R$^1$ optionally bears 1 or 2 oxo substituents;

(b) m is 1, 2 or 3, and each R$^1$ group, which may be the same or different, is selected from halogeno, trifluoromethyl, hydroxy, amino, carbamoyl, (1-6C)alkyl, (2-8C)alkenyl, (2-8C)alkynyl, (1-6C)alkoxy, (1-6C)alkylamino, di-[(1-6C)alkyl]amino, N-(1-6C)alkylcarbamoyl, N,N-di-[(-6C)alkyl]carbamoyl, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino and N-(1-6C)alkyl-(3-6C)alkynoylamino, or from a group of the formula:

wherein X$^1$ is a direct bond or is selected from O, N(R$^4$), CON(F$^4$), N(R$^4$)CO and OC(R$^4$)$_2$ wherein R$^4$ is hydrogen or (1-6C)alkyl, and Q$^3$ is aryl, aryl-(1-6C)alkyl, heteroaryl, heteroaryl-(1-6C)alkyl, heterocyclyl or heterocyclyl-(1-6C)alkyl, and wherein adjacent carbon atoms in any (2-6C)alkylene chain within a R$^1$ substituent are optionally separated by the insertion into the chain of a group selected from O, N(R$^5$), CON(R$^5$), N(R$^5$)CO, CH=CH and C≡C wherein R$^5$ is hydrogen or (1-6C)alkyl, and wherein any CH$_2$=CH— or HC≡C— group within a R$^1$ substituent optionally bears at the terminal CH$_2$= or HC≡ position a substituent selected from carbamoyl, N1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

$$—Q4—X^2—$$

wherein X$^2$ is a direct bond or is CO or N(R$^6$)CO, wherein R$^6$ is hydrogen or (1-6C)alkyl, and Q$^4$ is heteroaryl, heteroaryl-(1-6C)alkyl, heterocyclyl or heterocyclyl-(1-6C)alkyl, and wherein any CH$_2$ or CH$_3$ group within a R$^1$ substituent optionally bears on each said CH$_2$ or CH$_3$ group a substituent selected from hydroxy, amino, (1-6C)alkoxy, (1-6C)alkylsulphonyl, (1-6C)alkylamino and di-[(1-6C)alkyl]amino, or from a group of the formula:

$$—X^3—Q^5$$

wherein X$^3$ is a direct bond or is selected from O, N(F$^7$), CON(R$^7$), N(R$^7$)CO and C(R$^7$)$_2$O, wherein R$^7$ is hydrogen or (1-6C)alkyl, and Q$^5$ is heteroaryl, heteroaryl-(1-6C)alkyl, heterocyclyl or heterocyclyl-(1-6C)alkyl, and wherein any aryl, heteroaryl or heterocyclyl group within a substituent on R$^1$ optionally bears 1, 2 or 3 substituents, which may be the same or different, selected from halogeno, trifluoromethyl, hydroxy, amino, (1-6C)alkyl and (1-6C)alkoxy, and wherein any heterocyclyl group within a substituent on R$^1$ optionally bears 1 or 2 oxo substituents;

(c) m is 1, 2 or 3, and each R$^1$ group, which may be the same or different, is selected from fluoro, chloro, trifluoromethyl, hydroxy, amino, carbamoyl, methyl, ethyl, propyl, vinyl, ethynyl, methoxy, ethoxy, propoxy, methylamino, ethylamino, propylamino, dimethylamino, diethylamino, dipropylamino, N-methylcarbamoyl, N,N-dimethylcarbamoyl, acetamido, propionamido, acrylamido and propiolamido, or from a group of the formula:

$$Q^3—X^1—$$

wherein X$^1$ is a direct bond or is selected from O, NA CONK, NHCO and OCH$_2$ and Q$^3$ is phenyl, benzyl, cyclopropylmethyl, thienyl, 1-imidazolyl, 1,2,3-triazolyl, pyridyl, 2-imidazol-1-ylethyl, 3-imidazol-1-ylpropyl, 2-(1,2,3-triazolyl)ethyl, 3-(1,2,3-triazolyl)propyl, pyridylmethyl, 2-pyridylethyl, 3-pyridylpropyl, pyrrolidin-1-yl, pyrrolidin-2-yl, morpholino, 1,1-dioxotetrahydro4H-1,4-thiazin-4-yl, piperidino, piperidin-3-yl, piperidin-4-yl, homopiperidin-1-yl, piperazin-1-yl, homopiperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-(1,1-dioxotetrahydro-4H-1,4thiazin-4-yl)ethyl, -3-(1,1-dioxotetrahydro-4H-1,4-thiazin 4-yl)propyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-homopiperidin-1-ylethyl, 3-homopiperidin-1-ylpropyl, 2-piperazin-1-ylethyl, 3-piperazin-1-ylpropyl, 2-homopiperazin-1-ylethyl or 3-homopiperazin-1-ylpropyl, and wherein adjacent carbon atoms in any (2-6C)alkylene chain within a R$^1$ substituent are optionally separated by the insertion into the chain of a group selected from O, NH, CONK, NHCO, CH=CH and C≡C, and wherein any CH$_2$=CH$_2$— or HC≡C— group within a R$^1$ substituent optionally bears at the terminal CH$_2$= or HC≡ position a substituent selected from carbamoyl, N,-methylcarbamoyl, N,-ethylcarbamoyl, N,-propylcarbamoyl, N,N-dimethylcarbamoyl, aminomethyl, 2-aminoethyl, 3-aminopropyl, 4-aminobutyl, methylaminomethyl, 2-methylaminoethyl, 3-methylaminopropyl, 4-methylaminobutyl, dimethylaminomethyl, 2-dimethylaminoethyl, 3-dimethylaminopropyl or 4-dimethylaminobutyl, or from a group of the formula:

$$Q^4—X^2—$$

wherein X$^2$ is a direct bond or is CO, NHCO or N(Me)CO and Q$^4$ is pyridyl, pyridylmethyl, 2-pyridylethyl, pyrrolidin-1-yl, pyrrolidin-2-yl, morpholino, piperidino, piperidin-3-yl, piperidin-4-yl, piperazin-1-yl, pyrrolidin-1-ylmethyl, 2-pyrrolidin-1-ylethyl, 3-pyrrolidin-1-ylpropyl, 4-pyrrolidin-1-ylbutyl, pyrrolidin-2-ylmethyl, 2-pyrrolidin-2-ylethyl, 3-pyrrolidin-2-ylpropyl, morpholinomethyl, 2-morpholinoethyl, 3-morpholinopropyl, 4-morpholinobutyl, piperidinomethyl, 2-piperidinoethyl, 3-piperidinopropyl, 4-piperidinobutyl, piperidin-3-ylmethyl, 2-piperidin-3-ylethyl, piperidin-4-ylmethyl, 2-piperidin-4-ylethyl, piperazin-1-ylmethyl, 2-piperazin-1-ylethyl, 3-piperazin-1-ylpropyl or 4-piperazin-1-ylbutyl, and wherein any $CH_2$ or $CH_3$ group within a $R^1$ substituent optionally bears on each said $CH_2$ or—$CH_3$ group a substituent selected from hydroxy, amino, methoxy, methylsulphonyl, methylamino and dimethylamino, or from a group of the formula:

$$-X^3-Q^5$$

wherein $X^3$ is a direct bond or is selected from O, NH, CONK, NHCO and $CH_2O$ and $Q^5$ is pyridyl, pyridylmethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any aryl, heteroaryl or heterocyclyl group within a substituent on $R^1$ optionally bears 1, 2 or 3 substituents, which may be the same or different, selected from fluoro, chloro, trifluoromethyl, hydroxy, amino, carbamoyl, methyl, ethyl, methoxy, aminomethyl, methylaminomethyl, dimethylaminomethyl, acetamidomethyl, methoxycarbonylaminomethyl, ethoxycarbonylaminomethyl and tert-butoxycarbonylaminomethyl, and wherein any heterocyclyl group within a substituent on $R^1$ optionally bears 1 or 2 oxo substituents;

(d) m is 1, 2 or 3, and each $R^1$ group, which may be the same or different, is selected from fluoro, chloro, trifluoromethyl, hydroxy, amino, carbamoyl, methyl, ethyl, propyl, vinyl, ethynyl, methoxy, ethoxy, propoxy, methylamino, ethylamino, propylamino, dimethylamino, diethylamino, dipropylamino, N,-methylcarbamoyl, N,N-dimethylcarbamoyl, acetamido, propionamido, acrylamido and propiolamido, or from a group of the formula:

$$Q^3-X^1-$$

wherein $X^1$ is a direct bond or is selected from O, NH, CONH, NHCO and $OCH_2$ and $Q^3$ is phenyl, benzyl, thienyl, 1,2,3-triazolyl, pyridyl, 2-(1,2,3-triazolyl)ethyl, 3-(1,2,3-triazolyl)propyl, pyridylmethyl, 2-pyridylethyl, 3-pyridylpropyl, pyrrolidin-1-yl, pyrrolidin-2-yl, morpholino, 1,1-dioxotetrahydro-4H-1,4-thiazin-4-yl, piperidino, piperidin-3-yl, piperidin-4-yl, homopiperidin-1-yl, piperazin-1-yl, homopiperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-(1,1-dioxotetrahydro-4H-1,4-thiazin-4-yl)ethyl, 3-(1,1dioxotetrahydro4H-1,4-thiazin-4-yl)propyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-homopiperidin-1-ylmethyl, 3-homopiperidin-1-ylpropyl, 2-piperazin-1-ylethyl, 3-piperazin-1-ylpropyl, 2-homopiperazin-1-ylethyl or 3-homopiperazin-1-ylpropyl, and wherein adjacent carbon atoms in any (2-6C)alkylene chain within a substituent are optionally separated by the insertion into the chain of a group selected from O. NH, CONK, NHCO, CH=CH and C≡C, and wherein any $CH_2$=CH— or HC≡C— group within a $R^1$ substituent optionally bears at the terminal $CH_2$= or HC≡ position a substituent selected from carbamoyl, N,-methylcarbamoyl, N,-ethylcarbamoyl, N,-propylcarbamoyl, N,N-dimethylcarbamoyl, aminomethyl, 2-aminoethyl, methylaminomethyl, 2-methylaminoethyl, dimethylaminomethyl or 2-dimethylaminoethyl, or from a group of the formula:

$$Q^4-X^2-$$

wherein $X^2$ is a direct bond or is CO, NHCO or N(Me)CO and $Q^4$ is pyridyl, pyridylmethyl, 2-pyridylethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino and dimethylamino, or from a group of the formula:

$$-X^3-Q^5$$

wherein $X^3$ is a direct bond or is selected from O, NH CONH, NHCO and $CH_2O$ and $Q^5$ is pyridyl, pyridylmethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any aryl, heteroaryl or heterocyclyl group within a substituent on $R^1$ optionally bears 1, 2 or 3 substituents, which may be the same or different, selected from fluoro, chloro, trifluoromethyl hydroxy, amino, methyl, ethyl and methoxy, and wherein any heterocyclyl group within a substituent on $R^1$ optionally bears 1 or 2 oxo substituents;

(e) m is 1 or 2 and the $R^1$ groups, which may be the same or different, are located at the 6- and/or 7-positions and are selected from hydroxy, amino, methyl, ethyl, propyl, vinyl, ethynyl, methoxy, ethoxy, propoxy, methylamino, ethylamino, dimethylamino, diethylamino, acetamido, propionamido, benzyloxy, cyclopropylmethoxy, 2-imidazol-1-ylethoxy, 3-imidazol-1-ylpropoxy, 2-(1,2,3-triazol-1-yl)ethoxy, 3-(1,2,3-triazol-1-yl)propoxy, pyrid-2-ylmethoxy, pyrid-3-ylmethoxy, 2-pyrid-2-ylethoxy, 2-pyrid-3-ylethoxy, 2-pyrid4-ylethoxy, 3-pyrid-2-ylpropoxy, 3-pyrid-3-ylpropoxy, 3-pyrid-4-ylpropoxy, pyrrolidin-1-yl, morpholino, piperidino, piperazin-1-yl, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-1-ylpropoxy, 2-morpholinoethoxy, 3-morpholinopropoxy, 2-(1,1-dioxotetrahydro4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-yl methoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy, 3-homopiperazin-1-ylpropoxy, 2-pyrrolidin-1-ylethylamino, 3-pyrrolidin-1-ylpropylamino, pyrrolidin-3-ylamino, pyrrolidin-2-ylmethylamino, 2-pyrrolidin-2-ylethylamino, 3-pyrrolidin-2-ylpropylamino, 2-morpholinoethylamino, 3-morpholinopropylamino, 2l1,1-dioxotetrahydro-4$\underline{H}$-1,4-thiazin-4-yl)ethylamino, 3-(1,1-dioxotetrahydro4$\underline{H}$-1,4-thiazin-4-yl)propylamino, 2-piperidinoethylamino, 3-piperidinopropylamino, piperidin-3-ylamino, piperidin-4-ylamino, piperidin-3-ylmethylamino, 2-piperidin-3-ylethylamino, piperidin-4-ylmethylamino, 2-piperidin-4-ylethylamino, 2-homopiperidin-1-ylethylamino, 3-homopiperidin-1-ylpropylamino, 2-piperazin-1-ylethylamino, 3-piperazin-1-ylpropylamino, 2-homopiperazin-1-ylethylamino or 3-homopiperazin-1-ylpropylamino, and wherein adjacent carbon atoms in any (2-6C)alkylene chain within a $R^1$ substituent are optionally separated by the insertion into the chain of a group selected from O, NH, CH=CH and C≡C, and when $R^1$ is a vinyl or ethynyl group, the $R^1$ substituent optionally bears at the terminal $CH_2$= or HC≡ position a substituent selected from $\underline{N}$,-(2dimethylaminoethyl)carbamoyl, $\underline{N}$,-(3-dimethylaminopropyl)carbamoyl, methylaminomethyl, 2-methylaminoethyl, 3-methylaminopropyl, 4-methylaminobutyl, dimethylaminomethyl, 2-dimethylaminoethyl, 3-dimethylaminopropyl and 4-dimethylaminobutyl, or from a group of the formula:

$$Q^4\text{—}X^2\text{—}$$

wherein $X^2$ is a direct bond or is NHCO or N(Me)CO and $Q^4$ is imidazolylmethyl, 2-imidazolylethyl, 3-imidazolylpropyl, pyridylmethyl, 2-pyridylethyl, 3-pyridylpropyl, pyrrolidin-1-ylmethyl, 2-pyrrolidin-1-ylethyl, 3-pyrrolidin-1-ylpropyl, 4-pyrrolidin-1-ylbutyl, pyrrolidin-2-ylmethyl, 2-pyrrolidin-2-ylethyl, 3-pyrrolidin-2-ylpropyl, morpholinomethyl, 2-morpholinoethyl, 3-morpholinopropyl, 4-morpholinobutyl, piperidinomethyl, 2-piperidinoethyl, 3-piperidinopropyl, 4-piperidinobutyl, piperidin-3-ylmethyl, 2-piperidin-3-ylethyl, piperidin-4-ylmethyl, 2-piperidin-4-ylethyl, piperazin-1-ylmethyl, 2-piperazin-1-ylethyl, 3-piperazin-1-ylpropyl or 4-piperazin-1-ylbutyl, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino and dimethylamino, and wherein any phenyl, pyridyl or heterocyclyl group within a substituent on optionally bears 1 or 2 substituents, which may be the same or different, selected from fluoro, chloro, trifluoromethyl, hydroxy, amino, carbamoyl, methyl, ethyl, methoxy, aminomethyl, acetamidomethyl and tert-butoxycarbonylaminomethyl, and wherein any heterocyclyl group within a substituent on $R^1$ optionally bears 1 or 2 oxo substituents;

(f) m is 1 or 2 and the $R^1$ groups, which may be the same or different, are located at the 6- and/or 7-positions and are selected from hydroxy, amino, methyl, ethyl, propyl, vinyl, ethynyl, methoxy, ethoxy, propoxy, methylamino, ethylamino, dimethylamino, diethylamino, acetamido, propionamido, benzyloxy, 2-(1,2,3-triazol-1-yl)ethoxy, 3-(1,2,3-triazol-1-yl)propoxy, pyrid-2-ylmethoxy, pyrid-3-ylmethoxy, 2-pyrid-2-ylethoxy, 2-pyrid-3-ylethoxy, 2-pyrid4-ylethoxy, 3-pyrid-2-ylpropoxy, 3-pyrid-3-ylpropoxy, 3-pyrid4-ylpropoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4$\underline{H}$-1,4-thiazin-4-yl)ethoxy, 3-(1,1-dioxotetrahydro-4$\underline{H}$-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy or 3-homopiperazin-1-ylpropoxy, and wherein adjacent carbon atoms in any (2-6C)alkylene chain within a $R^1$ substituent are optionally separated by the insertion into the chain of a group selected from O, NH, CH=CH and C≡C, and when $R^1$ is a vinyl or ethynyl group, the $R^1$ substituent optionally bears at the terminal $CH_2$= or HC≡ position a substituent selected from $\underline{N}$,-(2-dimethylaminoethyl)carbamoyl or $\underline{N}$,-(3-dimethylaminopropyl)carbamoyl, or from a group of the formula:

$$Q^4\text{—}X^2\text{—}$$

wherein $X^2$ is NHCO or N(Me)CO and $Q^4$ is imidazolylmethyl, 2-imidazolylethyl, 3-imidazolylpropyl, pyridylmethyl, 2-pyridylethyl, 3-pyridylpropyl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino and dimethylamino, and wherein any phenyl, pyridyl or heterocyclyl group within a substituent on $R^1$ optionally bears 1 or 2 substituents, which may be the same or different, selected from fluoro, chloro, trifluoromethyl, hydroxy, amino, methyl, ethyl and methoxy, and wherein any heterocyclyl group within a substituent on $R^1$ optionally bears 1 or 2 oxo substituents;

(g) each of $R^2$ and $R^3$ is hydrogen or methyl;

(H) each of $R^2$ and $R^3$ is hydrogen;

(i) Z is O, S or $N(CR^{11})$, wherein $R^{11}$ is hydrogen or (1-6C)alkyl;

(J) Z is O, S, $N(R^{11})$, wherein $R^{11}$ is hydrogen, methyl, ethyl or propyl;

(k) Z is O;

(l) $Q^2$ is phenyl, benzyl, α-methylbenzyl, phenethyl, naphthyl, 1-(1-naphthyl)ethyl or 2-phenylcyclopropyl which is optionally substituted with 1, 2 or 3 substituents, which may be the same or different, selected from halogeno, trifluoromethyl, cyano, nitro, hydroxy, amino, carbamoyl, (1-6C)alkyl, (2-8C)alkenyl, (2-8C)alkynyl, (1-6C)alkoxy, (1-6C)alkylamino, di-[(1-6C)alkyl]amino, $\underline{N}$,-(1-6C)alkylcarbamoyl, $\underline{N}$,$\underline{N}$-di-[(1-6C)alkyl]carbamoyl, (2-6C)alkanoylamino, or from a group of the formula:

$$\text{—}X^7\text{—}Q^7$$

wherein x is a direct bond or is selected from O and $N(R^{13})$, wherein $R^3$ is hydrogen or (1-6C)alkyl, and $R^{12}$ is hydroxy- (1-6C)alkyl, (1-6C)alkoxy-(1-6C)alkyl, amino-(1-6C)alkyl, (1-6C)alkylamino-(1-6C)alkyl or di-[(1-6C)alkyl]amino-(1-6C)alkyl, or from a group of the formula:

$$-X^7-Q^7$$

wherein $X^7$ is a direct bond or is selected from O, N(W$^4$), CO, CON(R$^{14}$), N(R$^{14}$)CO and C(R$^{24}$)$_2$O, wherein each R$^{14}$ is hydrogen or (1-6C)alkyl, and Q$^7$ is phenyl, benzyl, heteroaryl or heteroaryl-(1-6C)alkyl, and wherein any phenyl or heteroaryl group within a substituent on Q$^2$ optionally bears 1, 2 or 3 substituents, which may be the same or different, selected from halogeno, trifluoromethyl, hydroxy, amino, (1-6C)alkyl and (1-6C)alkoxy;

(m) Q$^2$ is phenyl, benzyl, α-methylbenzyl or phenethyl which is optionally substituted with 1, 2 or 3. substituents, which may be the same or different, selected from fluoro, chloro, bromo, trifluoromethyl, cyano, nitro, hydroxy, methyl, ethyl, propyl, tert-butyl, vinyl, ethynyl and methoxy, or from a group of the formula:

$$-X^7-Q^7$$

wherein $X^7$ is a direct bond or is selected from O and CO, and Q$^7$ is phenyl, benzyl, pyridyl or pyridylmethyl, and wherein any phenyl or pyridyl group within a substituent on Q$^2$ optionally bears 1 or 2 substituents, which may be the same or different selected from fluoro, chloro, trifluoromethyl, hydroxy, amino, methyl and methoxy;

(n) Q$^2$ is phenyl, benzyl or phenethyl which is substituted with 1, 2 or 3 substituents, which may be the same or different, selected from fluoro, chloro, bromo, trifluoromethyl, cyano, nitro, hydroxy, methyl, ethyl, propyl, tert-butyl, vinyl, ethynyl and methoxy provided that at least one substituent is located at an ortho position (for example the 2-position on a phenyl group); and (o) Q$^2$ is phenyl, benzyl or phenethyl which is substituted with 2 or 3 substituents, which may be the same or different, selected from fluoro, chloro, bromo, trifluoromethyl, cyano, nitro, hydroxy, methyl, ethyl, propyl, tert-butyl, vinyl, ethynyl and methoxy provided that two substituents are located at ortho positions (for example the 2- and 6-positions on a phenyl group).

According to another aspect of the present invention and subject to the provisos described hereinbefore, further particular compounds of the formula I include, for example, quinazoline derivatives of the Formula II, or pharmaceutically acceptable salts thereof, wherein, unless otherwise stated, each of m, R$^1$, R$^2$, R$^3$, Z and Q$^2$ has any of the meanings defined hereinbefore or in paragraphs (aa) to (hh) hereinafter:

(aa) m is 1, 2 or 3, and each R$^1$ group, which may be the same or different, is selected from halogeno, trifluoromethyl, hydroxy, amino, carbamoyl, (1-6C)alkyl, (2-8C)alkenyl, (2-8C)alkynyl, (1-6C)alkoxy, (1-6C)alkylamino, di-[(1-6C)alkyl]amino, $\underline{N}$-(1-6C)alkylcarbamoyl, $\underline{N},\underline{N}$-di-[(1-6C)alkyl]carbamoyl, (2-6C)alkanoylamino, $\underline{N}$,-(1-6C)alkyl-(2-6C)alkanoylamino, (3-6C)alkenoylamino, $\underline{N}$,-(1-6C)alkyl-(3-6C)alkenoylamino, (3-6C)alkynoylamino and $\underline{N}$,-(1-6C)alkyl-(3-6C)alkynoylamino, or from a group of the formula:

$$Q^3-X^1-$$

wherein $X^1$ is a direct bond or is selected from O, N(R$^4$), CON(R$^4$), N(R$^4$)CO and OC(R$^4$)$_2$ wherein R$^4$ is hydrogen or (1-6C)alkyl, and Q$^3$ is aryl, aryl-(1-6C)alkyl, heteroaryl, heteroaryl-(1-6C)alkyl, heterocyclyl or heterocyclyl-(1-6C)alkyl, and wherein adjacent carbon atoms in any (2-6C)alkylene chain within a R$^1$ substituent are optionally separated by the insertion into the chain of a group selected from O, N(R$^5$), CON(R$^5$), N(R$^5$)CO, CH=CH and C≡C wherein R$^5$ is hydrogen or (1-6C)alkyl, and wherein any CH$_2$=CH— or HC≡C— group within a R$^1$ substituent optionally bears at the terminal CH$_2$= or HC≡ position a substituent selected from carbamoyl, $\underline{N}$,-(1-6C)alkylcarbamoyl, $\underline{N},\underline{N}$-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

$$Q^4-X^2-$$

wherein $X^2$ is a direct bond or is CO or N(R$^6$)CO, wherein R$^6$ is hydrogen or (1-6C)alkyl, and Q$^4$ is heteroaryl, heteroaryl-(1-6C)alkyl, heterocyclyl or heterocyclyl-(1-6C)alkyl, and wherein any CH$_2$ or CH$_3$ group within a R$^1$ substituent optionally bears on each said CH$_2$ or CH$_3$ group a substituent selected from hydroxy, amino, (1-6C)alkoxy, (1-6C)alkylsulphonyl, (1-6C)alkylamino and di-[(1-6C)alkyl]amino, or from a group of the formula:

$$-X^3-Q^5$$

wherein $X^3$ is a direct bond or is selected from O, N(R$^7$), CON(R$^7$), N(R$^7$)CO and C(R$^7$)$_2$O, wherein R$^7$ is hydrogen or (1-6C)alkyl, and Q$^5$ is heteroaryl, heteroaryl-(1-6C)alkyl, heterocyclyl or heterocyclyl-(1-6C)alkyl, and wherein any aryl, heteroaryl or heterocyclyl group within a substituent on R$^1$ optionally bears 1, 2 or 3 substituents, which may be the same or different, selected from halogeno, trifluoromethyl, hydroxy, amino, (1-6C)alkyl and (1-6C)alkoxy, and wherein any heterocyclyl group within a substituent on R$^1$ optionally bears 1 or 2 oxo substituents;

(bb) m is 1, 2 or 3, and each R$^1$ group, which may be the same or different, is selected from fluoro, chloro, trifluoromethyl, hydroxy, amino, carbamoyl, methyl, ethyl, propyl, vinyl, ethynyl, methoxy, ethoxy, propoxy, methylamino, ethylamino, propylamino, dimethylamino, diethylamino, dipropylamino, $\underline{N}$-methylcarbamoyl, $\underline{N}$,$\underline{N}$-dimethylcarbamoyl, acetamido, propionamido, acrylamido and propiolamido, or from a group of the formula:

$$Q^3-X^1-$$

wherein $X^1$ is a direct bond or is selected from O, NH, CONH NHCO and OCH$_2$ and Q$^3$ is phenyl, benzyl, thienyl, 1,2,3-triazolyl, pyridyl, 2-(1,2,3-triazolyl)ethyl, 3-(1,2,3-triazolyl) propyl, pyridylmethyl, 2-pyridylethyl, 3-pyridylpropyl, pyrrolidin-1-yl, pyrrolidin-2-yl, morpholino, 1,1-dioxotetrahydro-4$\underline{H}$-1,4-thiazin-4-yl, piperidino, piperidin-3-yl, piperidin-4-yl, homopiperidin-1-yl, piperazin-1-yl, homopiperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-1-ylpropyl, 2-morpholinoethyl, 3-morpholinopropyl, 2-(1,1-dioxotetrahydro-4$\underline{H}$-1,4-thiazin-4-yl)ethyl, 3-(1,1-dioxotetrahydro-4$\underline{H}$-1,4-thiazin-4-yl)propyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-homopiperidin-1-ylethyl, 3-homopiperidin-1-ylpropyl, 2-piperazin-1-ylethyl, 3-piperazin-1-ylpropyl, 2-homopiperazin-1-ylethyl or 3-homopiperazin-1-ylpropyl, and wherein adjacent carbon atoms in any (2-6C)alkylene chain within a R$^1$ substituent are optionally separated by the insertion into the chain of a group selected from O, NH, CONH, NHCO, CH=CH and C≡C, and wherein any CH$_2$=CH— or HC≡C— group within a R$^1$ substituent optionally bears at the terminal CH$_2$= or HC≡ position a substituent selected from carbamoyl, N-methylcarbamoyl, N-ethylcarbamoyl, N-propylcarbamoyl, N,N-dimethylcarbamoyl, aminomethyl, 2-aminoethyl, methylaminomethyl, 2-methylaminoethyl, dimethylaminomethyl or 2-dimethylaminoethyl, or from a group of the formula:

Q$^4$—X$^2$— wherein X$^2$ is a direct bond or is CO, NHCO or N(Me)CO and Q$^4$ is pyridyl, pyridylmethyl, 2-pyridylethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-1-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any CH$_2$ or CH$_3$ group within a R$^1$ substituent optionally bears on each said CH$_2$ or CH$_3$ group a substituent selected from hydroxy, amino, methoxy, methylsulphonyl, methylamino and dimethylamino, or from a group of the formula:

—X$^3$—Q$^5$ wherein X$^3$ is a direct bond or is selected from O, NH CONH, NHCO and CH$_2$O and Q$^5$ is pyridyl, pyridylmethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-1-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any aryl, heteroaryl or heterocyclyl group within a substituent on R$^1$ optionally bears 1, 2 or 3 substituents, which may be the same or different, selected from fluoro, chloro, trifluoromethyl, hydroxy, amino, methyl, ethyl and methoxy, and wherein any heterocyclyl group within a substituent on R$^1$ optionally bears 1 or 2 oxo substituents;

(cc) m is 1 or 2 and the R$^1$ groups, which may be the same or different, are located at the 6- and/or 7-positions and are selected from hydroxy, amino, methyl, ethyl, propyl, vinyl, ethynyl, methoxy, ethoxy, propoxy, methylamino, ethylamino, dimethylamino, diethylamino, acetamido, propionamido, benzyloxy, 2-(1,2,3-triazol-1-yl)ethoxy, 3-(1,2,3-triazol-1-yl)propoxy, pyrid-2-ylmethoxy, pyrid-3-ylmethoxy, 2-pyrid-2-ylethoxy, 2-pyrid-3-ylethoxy, 2-pyrid-4-ylethoxy, 3-pyrid-2-ylpropoxy, 3-pyrid-3-ylpropoxy, 3-pyrid-4-ylpropoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(2-morpholinoethoxy)ethoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy or 3-homopiperazin-1-ylpropoxy, and wherein adjacent carbon atoms in any (2-6C)alkylene chain within a R$^1$ substituent are optionally separated by the insertion into the chain of a group selected from O, NH CH=CH and C≡C, and when R$^1$ is a vinyl or ethynyl group, the R$^1$ substituent optionally bears at the terminal CH$_2$= or HC≡ position a substituent selected from N-(2-dimethylaminoethyl)carbamoyl or N-(3-dimethylaminopropyl)carbamoyl, or from a group of the formula:

Q$^4$—X$^2$— wherein X$^2$ is NHCO or N(Me)CO and Q$^4$ is imidazolylmethyl, 2-imidazolylethyl, 3-imidazolylpropyl, pyridylmethyl, 2-pyridylethyl, 3-pyridylpropyl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any CH$_2$ or CH$_3$ group within a R$^1$ substituent optionally bears on each said CH$_2$ or CH$_3$ group a substituent selected from hydroxy, amino, methoxy, methylsulphonyl, methylamino and dimethylamino, and wherein any phenyl, pyridyl or heterocyclyl group within a substituent on R$_1$ optionally bears 1 or 2 substituents, which may be the same or different, selected from fluoro, chloro, trifluoromethyl, hydroxy, amino, methyl, ethyl and methoxy, and wherein any heterocyclyl group within a substituent on R$^1$ optionally bears 1 or 2 oxo substituents;

(dd) each of R$^2$ and R$^3$ is hydrogen or methyl;

(ee) Z is O;

(ff) Q$^2$ is phenyl, benzyl, α-methylbenzyl, phenethyl, naphthyl, 1-(1-naphthyl)ethyl or 2-phenylcyclopropyl which is optionally substituted. with 1, 2 or 3 substituents, which may be the same or different, selected from halogeno, trifluoromethyl, cyano, nitro, hydroxy, amino, carbamoyl, (1-6C)alkyl, (2-8C)alkenyl, (2-8C)alkynyl, (1-6C)alkoxy, (1-6C)alkylamino di-[(1-6C)alkyl]amino, N1-6C)alkylcarbamoyl, N,N-di-[(1-6C)alkyl]carbamoyl, (2-6C)alkanoylamino, or from a group of the formula:

—X$^6$—R$^{12}$ wherein X$^6$ is a direct bond or is selected from O and N(R$^{13}$), wherein R$^{13}$ is hydrogen or (1-6C)alkyl, and R$^{12}$ is hydroxy-(1-6C)alkyl, (1-6C)alkoxy-(1-6C)alkyl, amino-(1-6)alkyl, (1-6C)alkylamino-(1-6C)alkyl or di-[(1-6C)alkyl]amino-(1-6C)alkyl, or from a group of the formula:

—X$^7$—Q$^7$ wherein X$^7$ is a direct bond or is selected from O, N(R$^{14}$), CO, CON(R$^{14}$), N(R$^{14}$)CO and C(R$^{14}$)$_2$O, wherein each R$^{14}$ is hydrogen or (1-6C)alkyl, and Q$^7$ is phenyl, benzyl, heteroaryl or heteroaryl-(1-6C)alkyl, and wherein any phenyl or heteroaryl group within a substituent on Q$^2$ optionally bears 1, 2 or 3 substituents, which may be the same or different, selected from halogeno, trifluoromethyl, hydroxy, amino, (1-6C)alkyl and (1-6C)alkoxy;

(gg) Q$^2$ is phenyl, benzyl, α-methylbenzyl or phenethyl which is optionally substituted with 1, 2 or 3 substituents, which may be the same or different, selected from fluoro, chloro, bromo, trifluoromethyl, cyano, nitro, hydroxy, methyl, ethyl, propyl, tert-butyl, vinyl, ethynyl and methoxy, or from a group of the formula:

wherein $X^7$ is a direct bond or is selected from O and CO, and $Q^7$ is phenyl, benzyl, pyridyl or pyridylmethyl, and wherein any phenyl or pyridyl group within a substituent on $Q^2$ optionally bears 1 or 2 substituents, which may be the same or different, selected from fluoro, chloro, trifluoromethyl, hydroxy, amino, methyl and methoxy; and (hh) $Q^2$ is phenyl, benzyl or phenethyl which is substituted with 1, 2 or 3 substituents, which may be the same or different, selected from fluoro, chloro, bromo, trifluoromethyl, cyano, nitro, hydroxy, methyl, ethyl, propyl, tert-butyl, vinyl, ethynyl and methoxy provided that at least one substituent is located at an ortho position (for example the 2-position on a phenyl group).

Further particular compounds of the formula I include, for example, pyrimidine derivatives of the Formula III, or pharmaceutically-acceptable salts thereof, wherein, unless otherwise stated, each of m, $R^1$, $R^2$, $R^3$, Z and $Q^2$ has any of the meanings defined hereinbefore or in any of the paragraphs (a) to (o) or (aa) to (hh) immediately hereinbefore and $Y^1$ has any of the meanings defined hereinbefore or in paragraphs (a) to (c) hereinafter (a) bicyclic rings formed by the fusion of ring $Y^1$ to the adjacent pyrimidine ring include thieno[3,2-d]pyrimidin-4-yl, thieno[2,3-d]pyrimidin-4-yl, thiazolo[5,4-d]pyrimidin-7-yl, pyrido[2,3-d]pyrimidin-4-yl, pyrido[3,4-d]pyrimidin-4-yl, pyrido[4,3-d]pyrimidin-4-yl and pyrido[3,2-d]pyrimidin-4-yl;

(b) bicyclic rings formed by the fusion of ring $Y^1$ to the adjacent pyrimidine ring include thieno[3,2-d]pyrimidin-4-yl, pyrido[3,4-d]pyrimidin-4-yl, pyrido[4,3-d]pyrimidin-4yl and pyrido[3,2-d]pyrimidin-4-yl; and (c) the bicyclic ring formed by the fusion of ring $Y^1$ to the adjacent pyrimidine ring is thieno[3,2-d]pyrimidin-4yl.

Further particular compounds of the formula I include, for example, quinazoline derivatives of the Formula IV or pharmaceutically-acceptable salts thereof, wherein, unless otherwise stated, each of m, $R^1$, $R^2$, $R^3$, Z and $Q^2$ has any of the meanings defined hereinbefore or in any of the paragraphs (a) to (o) or (aa) to (hh) immediately hereinbefore and $Y^2$ has any of the meanings defined hereinbefore or in paragraphs (a) and (b) hereinafter:

(a) tricyclic rings formed by the fusion of ring $Y^2$ to the adjacent quinazoline ring include 3H-imidazo[4,5-g]quinazolin-8-yl and 2-oxo-1,2-dihydro-3H-imidazo[4,5-g]quinazolin-8-yl and (b) tricyclic rings formed by the fusion of ring $Y^2$ to the adjacent quinazoline ring include 3-methyl-3H-imidazo[4,5-g]quinazolin-8-yl and 3-methyl-2-oxo-1,2-dihydro-3H-imidazo[4,5-g]quinazolin-8-yl.

A preferred compound of the invention is a quinazoline derivative of the Formula II wherein:

m is 1 and the $R^1$ group is located at the 6- or 7-position and is selected from methoxy, benzyloxy, cyclopropylmethoxy, 2-aminoethylamino, 3-methoxypropylamino, 2-dimethylaminoethoxy, 2-diethylaminoethoxy, 3-dimethylaminopropoxy, 3-diethylaminopropoxy, 2-(1,2,3-triazol-1-yl)ethoxy, 3-(1,2,3-triazol-1-yl)propoxy, pyrid-2-ylmethoxy, pyrid-3-ylmethoxy, 2-pyrid-2-ylethoxy, 2-pyrid-3-ylethoxy, 2-pyrid4-ylethoxy, 3-pyrid-2-ylpropoxy, 3-pyrid-3-ylpropoxy, 3-pyrid4-ylpropoxy, N-[3-(imidazol-1-yl)propyl]carbamoyl, 2-pyrrolidin-1-ylethoxy, 3-pyrrolidin-1-ylpropoxy, 3-pyrrolidin-1-ylpropyl, 3(pyrrolidin-1-yl)-1-propenyl, pyrrolidin-3-yloxy, N-methylpyrrolidin-3-yloxy, pyrrolidin-2-ylmethoxy, N-methylpyrrolidin-2-ylmethoxy, 2-pyrrolidin-2-ylethoxy, 2-(N-methylpyrrolidin-2-yl)ethoxy, 3-pyrrolidin-2-ylpropoxy, 3-(N-methylpyrrolidin-2-yl)propoxy, 4-(pyrrolidin-1-yl)but-2-en-1-yloxy, 2-(2-oxoimidazolidin-1-yl) ethoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, N-methylpiperidin-4-yloxy, piperidin-3-ylmethoxy, N-methylpiperidin-3-ylmethoxy, 2-piperidin-3-ylethoxy, 2-(N-methylpiperidin-3-yl)ethoxy, piperidinylmethoxy, N-methylpiperidin-4-ylmethoxy, 2-piperidin-4-ylethoxy, 2-(N-methylpiperidin-4-yl)ethoxy, 3-(4-aminomethylpiperidin-1-yl)propoxy, 3-(4-tert-butoxycarbonylaminopiperidin-1-yl)propoxy, 3-(4-tert-butoxycarbonylaminomethylpiperidin-1-yl)propoxy, 4-tert-butoxycarbonylpiperazin-1-yl, 3-(4-carbamoylpiperidin-1-yl)propoxy, 2-piperazin-1-ylethoxy, 3-piperazin-1-ylpropoxy, 2-(4-methylpiperazin-1-yl)ethoxy, 3-(4-methylpiperazin-1-yl)propoxy, N-[3-(4-methylpiperazin-1-yl)propyl]carbamoyl, 4-morpholinobut-2-en-1-yloxy, 4-morpholinobut-2-yn-1-yloxy, 2-(2-morpholinoethoxy) ethoxy, 3-morpholinopropylcarbamoyl, 2-methylsulphonylethoxy, 3-methylsulphonylpropoxy, N-(2-diethylaminoethyl)-N-methylamino, 2-[N-(2-methoxyethyl)-N-methylamino]ethoxy, 3-[N-(2-methoxyethyl)-N-methylamino]propoxy, 2-(2-methoxyethoxy)ethoxy, 3-methylamino-1-propynyl, 3-dimethylamino-1-propynyl, 3-diethylamino-1-propynyl, 6-methylamino-1-hexynyl, 6-dimethylamino-1-hexynyl, 3-(pyrrolidin-1-yl)-1-propynyl, 3-(piperidino)-1-propynyl, 3-(morpholino)-1-propynyl, 3-(4-methylpiperazin-1-yl)-1-propynyl, 6-(2-methylimidazol-1-yl)-1-hexynyl, 6-(pyrrolidin-1-yl)-1-hexynyl, 6-(piperidino)-1-hexynyl, 6-(morpholino)-1-hexynyl, 6-(4methylpiperazin-1-yl)-1-hexynyl piperazin-1-yl, 4-methylpiperazin-1-yl, 3-imidazol-1-ylpropylamino, 3-pyrrolidin-1-ylpropylamino, 3-morpholinopropylamino, 3-piperidinopropylamino and 3-piperazin-1-ylpropylamino, 6-(4-methylpiperazin-1-yl)hexyl, or m is 2 and the $R^1$ groups are located at the 6- and 7-positions, one $R^1$ group is located at the 6- or 7-position and is selected from the groups defined immediately hereinbefore and the other $R^1$ group is a methoxy group;

$R^2$ is hydrogen or methyl;

$R^3$ is hydrogen;

Z is O, S, NH or N(Et); and $Q^2$ is phenyl, benzyl or phenethyl which optionally bears 1, 2 or 3 substituents, which may be the same or different, selected from fluoro, chloro, bromo, trifluoromethyl, nitro, methyl, ethyl and methoxy provided that at least one substituent is located at an ortho position;

or a pharmaceutically-acceptable acid-addition salt thereof.

A preferred compound of the invention is a quinazoline derivative of the Formula II wherein:

m is 1 and the $R^1$ group is located at the 6- or 7-position and is selected from methoxy, cyclopropylmethoxy, 2-aminoethylamino, 2-dimethylaminoethoxy, 3-(1,2,3-triazol-1-yl) propoxy, 2-pyrid-4-ylethoxy, N-[3-(imidazol-1-yl)propyl]carbamoyl, 2-pyrrolidin-1-ylethoxy, 3-pyrrolidin-1-ylpropoxy, 3pyrrolidin-1-ylpropyl, 3-(pyrrolidin-1-yl)-1-propenyl, 4-(pyrrolidin-1-yl)but-2-en-1-yloxy, 2-(2-oxoimidazolidin-1-yl)ethoxy, 2-morpholinoethoxy, 3-morpholinopropoxy, 3-(1,1-dioxotetrahydro-4H-1,4-thiazin-4-yl)propoxy, 2-piperidinoethoxy, 3-piperidinopropoxy, N-methylpiperidin-3-ylmethoxy, N-methylpiperidin-4-ylmethoxy, 3-(4-aminomethylpiperidin-1-yl)propoxy, 3-(4-tert-butoxycarbonylaminomethylpiperidin-1-yl)propoxy, 4-tert-butoxycarbonylpiperazin-1-yl, 3-(4-carbamoylpiperidin-1-yl)propoxy, 2-(4-methylpiperazin-1-yl)

ethoxy, 3-(4-methylpiperazin-1-yl)propoxy, N-[3-(4-methylpiperazin-1-yl)propyl]carbamoyl, 4-morpholinobut-2-en-1-yloxy, 4-morpholinobut-2-yn-1-yloxy, 3-methylsulphonylpropoxy, N-(2-diethylaminoethyl)-N-methylamino, 2-[N-(2-methoxyethyl)-N-methylamino]ethoxy, 2-(2-methoxyethoxy)ethoxy, 6-methylamino-1-hexynyl, 3-(pyrrolidin-1-yl)-1-propynyl, 6-(2-methylimidazol-1-yl)-1-hexynyl, 6-(morpholino)-1-hexynyl, 4-methylpiperazin-1-yl, 3-imidazol-1-ylpropylamino, 3-morpholinopropylamino, and 6-(4-methylpiperazin-1-yl)hexyl, or m is 2 and the $R^1$ groups are located at the 6- and 7-positions, one $R^1$ group is located at the 6- or 7-position and is selected from the groups defined immediately hereinbefore and the other $R^1$ group is a methoxy group;

$R^2$ is hydrogen;
$R^3$ is hydrogen;
Z is O, S, NH or N(Et); and
$Q^2$ is phenyl, benzyl or phenethyl which optionally bears 1, 2 or 3 substituents, which may be the same or different, selected from fluoro, chloro, bromo, methyl and ethyl provided that at least one substituent is located at an <u>ortho</u> position;

or a pharmaceutically-acceptable acid-addition salt thereof.

A preferred compound of the invention is a quinazoline derivative of the Formula II wherein:

m is 1 or 2 and the $R^1$ groups, which may be the same or different, are located at the 6- and/or 7-positions and are selected from methoxy, benzyloxy, 2-(1,2,3-triazol-1-yl)ethoxy, 3-(1,2,3-triazol-1-yl)propoxy, pyrid-2-ylmethoxy, pyrid-3-ylmethoxy, 2-pyrid-2-ylethoxy, 2-pyrid-3-ylethoxy, 2-pyrid-4-ylethoxy, 3-pyrid-2-ylpropoxy, 3-pyrid-3-ylpropoxy, 3-pyrid-4-ylpropoxy, 2-pyrrolidin-1-ylethoxy, 3-pyrrolidin-1-ylpropoxy, pyrrolidin-3-yloxy, 1-methylpyrrolidin-3-yloxy, pyrrolidin-2-ylmethoxy, 1-methylpyrrolidin-2-ylmethoxy, 2-pyrrolidin-2-ylethoxy, 2-(1-methylpyrrolidin-2-yl)ethoxy, 3-pyrrolidin-2-ylpropoxy, 3-(1-methylpyrrolidin-2-yl)propoxy, 2-morpholinoethoxy, 3-morpholinopropoxy, 2-(2-morpholinoethoxy)ethoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, 1-methylpiperidin-4-yloxy, piperidin-3-ylmethoxy, 1-methylpiperidin-3-ylmethoxy, 2-piperidin-3-ylethoxy, 2-(1-methylpiperidin-3-yl)ethoxy, piperidin-4-ylmethoxy, N-methylpiperidin-4-ylmethoxy, 2-piperidin-4-ylethoxy, 2-(N-methylpiperidin-4-yl)ethoxy, 2-piperazin-1-ylethoxy, 3-piperazin-1-ylpropoxy, 2-(4-methylpiperazin-1-yl)ethoxy, 3-(4-methylpiperazin-1-yl)propoxy, 4-morpholinobut-2-en-1-yloxy, 4-morpholinobut-2-yn-1-yloxy, 2-methylsulphonylethoxy, 3-methylsulphonylpropoxy, 2-[N-(2-methoxyethyl)-N-methylamino]ethoxy and 3-[N-(2-methoxyethyl)-N-methylamino]propoxy;

$R^2$ is hydrogen or methyl;
$R^3$ is hydrogen;
Z is O; and
$Q^2$ is phenyl, benzyl or phenethyl which optionally bears 1, 2 or 3 substituents, which may be the same or different, selected from fluoro, chloro, bromo, trifluoromethyl and methyl;

or a pharmaceutically-acceptable acid-addition salt thereof.

A further preferred compound of the invention is a quinazoline derivative of the Formula II wherein:

m is 1 or 2; $R^1$ group is located at the 7-position and is selected from methoxy, 3-(1,2,3-triazol-1-yl)propoxy, 2-pyridylethoxy, 3-pyrrolidin-1-ylpropoxy, 3-morpholinopropoxy, 3-(1,1-dioxotetrahydro-4H-1,4-thiazin-4-yl)propoxy, 2-piperidinoethoxy, 3-piperidinopropoxy, N-methylpiperidin-4-ylmethoxy, 3-(4-methylpiperazin-1-yl)propoxy, 4-morpholinobut-2-en-1-yloxy, 4-morpholinobut-2-yn-1-yloxy, 2-(2-morpholinoethoxy)ethoxy, 3-methylsulphonylpropoxy and 2-[N-(2-methoxyethyl)-N-methylamino]ethoxy;

$R^2$ is hydrogen or methyl;
$R^3$ is hydrogen;
Z is O; and
$Q^2$ is phenyl which bears 1, 2 or 3 substituents, which may be the same or different, selected from fluoro, chloro, bromo and trifluoromethyl provided that at least one substituent is located at the ortho position;

or a pharmaceutically-acceptable acid-addition salt thereof.

A particular preferred compound of the invention is, for example, a quinazoline derivative of the Formula II selected from:

1-(2,6-dichlorophenyl)-3-[7-(3-morpholinopropoxy)quinazolin-4-yl]urea and 1-(2,6-dichlorophenyl)-3-{7-[3-(1,1-dioxotetrahydro-4H-1,4-thiazin-4-yl)propoxy]quinazolin-4-yl}urea;

or a pharmaceutically-acceptable acid-addition salt thereof.

A further particular preferred compound of the invention is, for example, a quinazoline derivative of the Formula II selected from:

1-benzyl-3-[6-methoxy-7-(1-methylpiperidin-4-ylmethoxy)quinazolin-4-yl]urea and 1-phenethyl-3-[6-methoxy-7-(1-methylpiperidin-4-ylmethoxy)quinazolin-4-yl]urea, or a pharmaceutically-acceptable acid-addition salt thereof.

A further particular preferred compound of the invention is, for example, a quinazoline derivative of the Formula II selected from:

1-(2,6-dichlorophenyl)-3-[6-methoxy-7-(1-methylpiperidin-4-ylmethoxy)quinazolin-4-yl]urea and 1-(2,6-difluorophenyl)-3-[6-methoxy-7-(1-methylpiperidin-4-ylmethoxy)quinazolin-4-yl]urea;

or a pharmaceutically-acceptable acid-addition salt thereof.

A further particular preferred compound of the invention is, for example, a quinazoline derivative of the Formula II selected from any one of Examples:

1, 2.1, 2.3, 2.4, 2.5, 2.6, 2.8, 2.9, 2.11, 2.12, 2.13, 2.14, 2.15, 2.16, 2.17, 2.18,2.19, 2.20, 2.21, 2.22,2.23, 2.24, 2.25, 2.31, 2.32, 2.34, 2.35, 2.36, 2.37, 2.38, 2.39, 2.40, 2.41, 2.42, 2.43, 2.45, 2.48, 2.50, 2.51, 2.52, 2.53, 2.55, 2.56, 2.57, 2.58, 2.59, 2.60, 2.61, 2.62, 2.63, 2.64, 2.65, 2.66, 2.67, 2.68, 2.69, 2.70, 2.72, 2.74, 275, 2.77, 2.78, 2.80, 2.81, 2.82, 2.83, 2.84, 2.85, 2.86, 2.87, 2.89, 2.90, 2.91, 2.92, 2.94, 2.95, 2.96, 2.98, 2.99, 2.100, 2.101, 2.102, 2.104, 2.105, 2.106, 2.108, 2.109, 2.110, 2.111, 2.112, 2.113, 2.114, 2.115, 2.116, 2.117, 2.119, 2.122, 2.123, 2.129, 2.134, 2.136, 2.137, 2.139, 2.140, 2.141, 2.142, 2.143, 2.144, 2.145, 2.146, 2.147, 2.149, 2.151, 2.152, 4, 11, 12, 13.1, 13.4, 20.1, 20.2, 20.3, 20.4, 21, 22, 23, 24, 25.2, 25.4, 25.11, 26, 27, 28.1, 28.2, 28.3, 28.4, 28.5, 28.6, 28.7, 28.8, 28.9, 28.10, 28.11, 28.12, 28.13, 28.14, 28.15, 28.16, 29, 30.2, 30.3, 30.5, 30.6, 30.7, 30.8, 30.9, 30.10, 30.11, 30.12, 30.13, 33, 34.1 and 34.4 or a pharmaceutically-acceptable acid-addition salt thereof.

A further preferred compound of the invention is a pyrimidine derivative of the Formula III wherein the fusion of ring $Y^1$ to the adjacent pyrimidine ring forms a thieno[3,2-d]pyrimidin-4-yl group;

m is 0, or m is 1 and the $R^1$ group is a methyl, ethyl, vinyl or ethynyl group which is located at the 6-position and bears a substituent selected from carboxy, carbamoyl, N-(2-methylaminoethyl)carbamoyl, N-(2-dimethylaminoethyl)carbamoyl, N-(3-methylaminopropyl)carbamoyl or N-(3-dimethylaminopropyl)carbamoyl, or from a group of the formula:

wherein $X^2$ is NHCO or N(Me)CO and $Q^4$ is 2-imidazol-1-ylethyl 3-imidazol-1-ylpropyl, 2-pyridylmethyl, 3-pyridylmethyl, 4-pyridylmethyl, 2-pyrid-2-ylethyl, 2-pyrrolidin-1-ylethyl, 2-(2-oxopyrrolidin-1-yl)ethyl, 3-pyrrolidin-1-ylpropyl, 3-(2-oxopyrrolidin-1-yl)propyl, pyrrolidin-2-ylmethyl, 1-methylpyrrolidin-2-ylmethyl, 2-pyrrolidin-2-ylethyl, 2-(1-methylpyrrolidin-2-yl)ethyl, 3-pyrrolidin-2-ylpropyl, 3-(1-methylpyrrolidin-2-yl)propyl, 2-morpholinoethyl, 3-morpholinopropyl, 2-piperidinoethyl, 3-piperidinopropyl, piperidin-3-ylmethyl, 1-methylpiperidin-3-ylmethyl, 2-piperidin-3-ylethyl, 2-(1-methylpiperidin-3-yl)ethyl, piperidin-4-ylmethyl, 1-methylpiperidin-4-ylmethyl, 2-piperidin-4-ylethyl, 2-(1-methylpiperidin-4-yl)ethyl, 2-piperazin-1-ylethyl, 2-(4-methylpiperazin-1-yl)ethyl, 3-piperazin-1-ylpropyl or 3-(4-methylpiperazin-1-yl)propyl, $R^2$ is hydrogen or methyl;
$R^3$ is hydrogen;
Z is O; and
$Q^2$ is phenyl, benzyl or phenethyl which optionally bears 1, 2 or 3 substituents, which may be the same or different, selected from fluoro, chloro, bromo, trifluoromethyl and methyl;

or a pharmaceutically-acceptable acid-addition salt thereof.

A further preferred compound of the invention is a pyrimidine derivative of the Formula III wherein the fusion of ring $Y^1$ to the adjacent pyrimidine ring forms a thieno[3,2-d]pyrimidin-4-yl group;

m is 0, or m is 1 and the $R^1$ group is a vinyl group located at the 6-position which bears at the terminal $CH_2$= position a substituent selected from carboxy N-(2-dimethylaminoethyl)carbamoyl or N-(3-dimethylaminopropyl)carbamoyl, or from a group of the formula:

wherein $X^2$ is NHCO or N(Me)CO and $Q^4$ is 2-pyridylmethyl, 3-pyridylmethyl, 4-pyridylmethyl, 2-pyrid-2-ylethyl, 3-imidazol-1-ylpropyl, 2-pyrrolidin-1-ylethyl, 3-(2-oxopyrrolidin-1-yl)propyl, 3-morpholinopropyl, 2-piperidinoethyl or 3-(4-methylpiperazin-1-yl)propyl, $R^2$ is hydrogen or methyl;
$R^3$ is hydrogen;
Z is O; and
$Q^2$ is phenyl which bears 1, 2 or 3 substituents, which may be the same or different, selected from fluoro, chloro, bromo and trifluoromethyl provided that at least one substituent is located at the ortho position;

or a pharmaceutically-acceptable acid-addition salt thereof.

A further preferred compound of the invention is a pyrimidine derivative of the Formula III wherein the fusion of ring $Y^1$ to the adjacent pyrimidine ring forms a thieno[3,2-d]pyrimidin-4-yl group;

m is 0, or m is 1 and the $R^1$ group is a vinyl group located at the 6-position which bears at the terminal $CH_2$= position a substituent selected from N-(2-dimethylaminoethyl)carbamoyl or N-(3-dimethylaminopropyl)carbamoyl, or from a group of the formula:

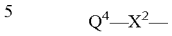

wherein $X^2$ is NHCO or N(Me)CO and $Q^4$ is 2-pyridylmethyl, 3-pyridylmethyl, 4-pyridylmethyl, 2-pyrid-2-ylethyl, 2-pyrrolidin-1-ylethyl, 3-(2-oxopyrrolidin-1-yl)propyl, 3-morpholinopropyl, 2-piperidinoethyl or 3-(4-methylpiperazin-1-yl)propyl, $R^2$ is hydrogen or methyl;
$R^3$ is hydrogen;
Z is O; and
$Q^2$ is phenyl which bears 1, 2 or 3 substituents, which may be the same or different, selected from fluoro, chloro, bromo and trifluoromethyl provided that at least one substituent is located at the ortho position;

or a pharmaceutically-acceptable acid-addition salt thereof.

A further particular preferred compound of the invention is, for example, a pyrimidine derivative of the Formula III selected from any one of Examples:
8, 9, 10.1, 10.2, 10.3, 10.4, 10.5, 10.6, 10.7 and 10.8 or a pharmaceutically-acceptable acid-addition salt thereof.

A quinazoline derivative of the Formula I, or a pharmaceutically-acceptable salt thereof, may be prepared by any process known to be applicable to the preparation of chemically-related compounds. Such processes, when used to prepare a quinazoline derivative of the Formula I are illustrated by the following representative process variants in which,unless otherwise stated, $Q^1$, $R^2$, Z, $R^3$ and $Q^2$ have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which. are within the ordinary skill of an organic chemist For the avoidance of doubt Formula V is not used herein.

(a) For those compounds of the Formula I wherein $R^3$ is hydrogen and Z is oxygen, the reaction, conveniently in the presence of a suitable base, of an amine of the Formula VI

    VI wherein $Q^1$ and $R^2$ have any of the meanings defined hereinbefore except that any functional group is protected if necessary, with an isocyanate of the Formula VII, or a conventional chemical equivalent thereof or a conventional chemical precusor thereof,

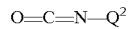    VII wherein $Q^2$ has any of the meanings defined hereinbefore except that any functional group is protected if necessary, whereafter any protecting group that is present is removed by conventional means.

A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate, alkoxide or hydroxide, for example sodium carbonate, potassium carbonate, calcium carbonate, sodium ethoxide, potassium tert-butoxide, sodium hydroxide or potassium hydroxide, or, for example, an alkali metal hydride, for example sodium hydride or potassium hydride, or an organometallic base such as an alkyl-lithium, for example n-butyl-lithium or a dialkylamino-lithium, for example lithium di-isopropylamide.

The reaction is conveniently carried out in the presence of a suitable inert solvent or diluent, for example a halogenated solvent such as methylene chloride, chloroform or carbon tetrachloride, an ether such as tetrahydrofuran or 1,4-dioxan, or a dipolar aprotic solvent such as acetonitrile, N,N-dimethylformamide, N,N-dimethylacetamide, N-methylpyrrolidin-2-one or dimethylsulphoxide. The reaction is conveniently carried out at a temperature in the range, for example, 10 to 150° C., preferably in the range 20 to 75° C.

A suitable conventional chemical equivalent of an isocyanate of the Formula VII is, for example, a compound of the Formula VIII

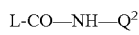          VIII wherein $Q^2$ has any of the meanings defined hereinbefore except that any functional group is protected if necessary, and L is a suitable displaceable or leaving group. On treatment with a suitable base as defined hereinbefore, the compound of the Formula VIII reacts to form the desired isocyanate of the Formula VII.

A suitable displaceable or leaving group L is, for example, a halogeno, alkoxy, aryloxy or sulphonyloxy group, for example a chloro, bromo, methoxy, phenoxy, methanesulphonyloxy or toluene-4-sulphonyloxy group.

A suitable conventional chemical precursor of an isocyanate of the Formula VII is, for example, an acyl azide of the Formula IX

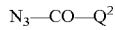          IX wherein $Q^2$ has any of the meanings defined hereinbefore except that any functional group is protected if necessary. On thermal or photolytic treatment the acyl azide of the Formula IX decomposes and rearranges to form the desired isocyanate of the Formula VII.

Protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned are, of course, within the scope of the invention.

A carboxy protecting group may be the residue of an ester-forming aliphatic or arylaliphatic alcohol or of an ester-forming silanol (the said alcohol or silanol preferably containing 1-20 carbon atoms). Examples of carboxy protecting groups include straight or branched chain (1-12C)alkyl groups (for example isopropyl, and tert-butyl); lower alkoxy-lower alkyl groups (for example methoxymethyl, ethoxymethyl and isobutoxymethyl); lower acyloxy-lower alkyl groups, (for example acetoxymethyl, propionyloxymethyl, butyryloxymethyl and pivaloyloxymethyl); lower alkoxycarbonyloxy-lower alkyl groups (for example 1-methoxycarbonyloxyethyl and 1-ethoxycarbonyloxyethyl); aryl-lower alkyl groups (for example benzyl, 4-methoxybenzyl, 2-nitrobenzyl, 4-nitrobenzyl, benzhydryl and phthalidyl); tri(lower alkyl)silyl groups (for example trimethylsilyl and tert-butyldimethylsilyl); tri(lower alkyl)silyl-lower alkyl groups (for example trimethylsilylethyl); and (2-6C)alkenyl groups (for example alkyl). Methods particularly appropriate for the removal of carboxyl protecting groups include for example acid-, base-, metal- or enzymically-catalysed cleavage.

Examples of hydroxy protecting groups include lower alkyl groups (for example tert-butyl), lower alkenyl groups (for example alkyl); lower alkanoyl groups (for example acetyl); lower alkoxycarbonyl groups (for example tert-butoxycarbonyl); lower alkenyloxycarbonyl groups (for example alkyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); tri(lower alkyl)silyl (for example trimethylsilyl and tert-butyldimethylsilyl) and aryl-lower alkyl (for example benzyl) groups.

Examples of amino protecting groups include formyl, aryl-lower alkyl groups (for example benzyl and substituted benzyl, 4-methoxybenzyl, 2-nitrobenzyl and 2,4-dimethoxybenzyl, and triphenylmethyl); di-4-anisylmethyl and furylmethyl groups; lower alkoxycarbonyl (for example tert-butoxycarbonyl); lower alkenyloxycarbonyl (for example alkyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); trialkylsilyl (for example trimethylsilyl and tert-butyldimethylsilyl); alkylidene (for example methylidene) and benzylidene and substituted benzylidene groups.

Methods appropriate for removal of hydroxy and amino protecting groups include, for example, acid-, base-, metal- or enzymically-catalysed hydrolysis for groups such as 2-nitrobenzyloxycarbonyl, hydrogenation for groups such as benzyl and photolytically for groups such as 2-nitrobenzyloxycarbonyl.

The reader is referred to Advanced Organic Chemistry, 4th Edition, by J. March, published by John Wiley & Sons 1992, for general guidance on reaction conditions and reagents and to Protective Groups in Organic Synthesis, $2^{nd}$ Edition, by T. Green et al., also published by John Wiley & Son, for general guidance on protecting groups.

When L is, for example, a chloro group, the compound of the Formula VIII may be prepared by, for example, the reaction, conveniently in the presence of a suitable base as defined hereinbefore, of phosgene with an amine of the Formula X.

          X

The compound of the Formula IX may be prepared by, for example, the reaction of a metal azide such as sodium azide with a compound of the Formula XI.

          XI (b) For those compounds of the Formula I wherein $R^3$ is hydrogen and Z is sulphur, the reaction, conveniently in the presence of a suitable base as defined hereinbefore, of an amine of the Formula VI

          VI wherein $Q^1$ and $R^2$ have any of the meanings defined hereinbefore except that any functional group is protected if necessary, with an isothiocyanate of the Formula XII, or a conventional chemical equivalent thereof or a conventional chemical precursor thereof, $$S{=}C{=}N{-}Q^2 \qquad \text{XI}$$

wherein $Q^2$ has any of the meanings defined hereinbefore except that any functional group is protected if necessary, whereafter any protecting group that is present is removed by conventional means.

A suitable conventional chemical equivalent of an isothiocyanate of the Formula XI is, for example, a compound of the Formula XIII $$L{-}CS{-}NH{-}Q^2 \qquad \text{XIII}$$

wherein $Q^2$ has any of the meanings defined hereinbefore except that any functional group is protected if necessary, and L is a suitable displaceable group as defined hereinbefore. On treatment with a suitable base as defined hereinbefore, the compound of the Formula XIII reacts to form the desired isothiocyanate of the Formula XII.

A suitable conventional chemical precursor of an isothiocyanate of the Formula XII is, for example, an acyl azide of the Formula XIV $$N_3{-}CS{-}Q^2 \qquad \text{XIV}$$

wherein $Q^1$ has any of the meanings defined hereinbefore except that any functional group is protected if necessary. On thermal or photolytic treatment the thioacyl azide of the Formula XIV decomposes and rearranges to form the desired isothiocyanate of the Formula XII.

When L is, for example, a chloro group, the compound of the Formula XIII may be prepared by, for example, the reaction, conveniently in the presence of a suitable base as defined hereinbefore, of thiophosgene with an amine of the Formula X.

$$H_2N{-}Q^2 \qquad \text{X}$$

The compound of the Formula XIV may be prepared by, for example, the reaction of a metal azide such as sodium azide with a compound of the Formula XV.

$$L{-}CS{-}Q^2 \qquad \text{XV}$$

(c) For those compounds of the Formula I wherein $R^2$ is hydrogen and Z is oxygen, the reaction, conveniently in the presence of a suitable base, of an amine of the Formula XVI $$R^3NH{-}Q^2 \qquad \text{XVI}$$

wherein $Q^2$ and $R^3$ have any of the meanings defined hereinbefore except that any functional group is protected if necessary, with an isocyanate of the Formula XVII, or a conventional chemical equivalent thereof or a conventional chemical precursor thereof, $$Q^1{-}N{=}C{=}O \qquad \text{XVII}$$

wherein $Q^1$ has any of the meanings defined hereinbefore except that any functional group is protected if necessary, whereafter any protecting group that is present is removed by conventional means.

A suitable conventional chemical equivalent of an isocyanate of the Formula XVII is, for example, a compound of the Formula XVIII $$Q^1{-}NH{-}CO{-}L \qquad \text{XVIII}$$

wherein $Q^1$ has any of the meanings defined hereinbefore except that any functional group is protected if necessary, and L is a suitable displaceable group as defined hereinbefore. On treatment with a suitable base as defined hereinbefore, the compound of the Formula XVIII reacts to form the desired isocyanate of the Formula XVII.

A suitable conventional chemical precursor of an isocyanate of the Formula XVII is, for example, an acyl azide of the Formula XIX $$Q^1{-}CO{-}N_3 \qquad \text{XIX}$$

wherein $Q^1$ has any of the meanings defined hereinbefore except that any functional group is protected if necessary. On thermal or photolytic treatment the thioacyl azide of the Formula XIX decomposes and rearranges to form the desired isocyanate of the Formula XVII.

When L is, for example, a chloro group, the compound of the Formula XVIII may be prepared by, for example, the reaction, conveniently in the presence of a suitable base as defined hereinbefore, of phosgene with an amine of the Formula XX.

$$Q^1{-}NH_2 \qquad \text{XX}$$

The compound of the Formula XIX may be prepared by, for example, the reaction of a metal azide such as sodium azide with a compound of the Formula XXI.

$$Q^1{-}CO{-}Z \qquad \text{XXI}$$

(d) For those compounds of the Formula I wherein $R^2$ is hydrogen and Z is sulphur, the reaction, conveniently in the presence of a suitable base, of an amine of the Formula XVI $$R^3NH{-}Q^2 \qquad \text{XVI}$$

wherein $Q^2$ and $R^3$ have any of the meanings defined hereinbefore except that any functional group is protected if necessary, with an isothiocyanate of the Formula XXII, or a conventional chemical equivalent thereof or a conventional chemical precursor thereof, $$Q^1{-}N{=}C{=}S \qquad \text{XXII}$$

wherein $Q^1$ has any of the meanings defined hereinbefore except that any functional group is protected if necessary, whereafter any protecting group that is present is removed by conventional means.

A suitable conventional chemical equivalent of an isothiocyanate of the Formula XXII is, for example, a compound of the Formula XXIII $$Q^1{-}NH{-}CS{-}L \qquad \text{XXIII}$$

wherein $Q^1$ has any of the meanings defined hereinbefore except that any functional group is protected if necessary, and L is a suitable displaceable group as defined hereinbefore. On treatment with a suitable base as defined hereinbefore, the compound of the Formula XXII reacts to form the desired isothiocyanate of the Formula XXII.

A suitable conventional chemical precursor of an isothiocyanate of the Formula XXII is, for example, an acyl azide of the Formula XXIV $$Q^1{-}CS{-}N_3 \qquad \text{XXIV}$$

wherein $Q^1$ has any of the meanings defined hereinbefore except that any functional group is protected if necessary. On thermal or photolytic treatment the thioacyl azide of the Formula XXIV decomposes and rearranges to form the desired isothiocyanate of the Formula XXII.

When L is, for example, a chloro group, the compound of the Formula XXIII may be prepared by, for example, the reaction, conveniently in the presence of a suitable base as defined hereinbefore, of thiophosgene with an amine of the Formula XX.

XX

The compound of the Formula XXIV may be prepared by, for example, the reaction of a metal azide such as sodium azide with a compound of the Formula XXV.

XXV (e) For those compounds of the Formula I wherein a substituent on $Q^1$ or $Q^2$ contains an alkylcarbamoyl group or a substituted alkylcarbamoyl group, the reaction of the corresponding compound of Formula I wherein a substituent on $Q^1$ or $Q^2$ is a carboxy group, or a reactive derivative thereof, with an amine or substituted amine as appropriate.

A suitable reactive derivative of a compound of Formula I wherein a substituent on $Q^1$ or $Q^2$ is a carboxy group is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol, an ester formed by the reaction of the acid and an ester such as pentafluorophenyl trifluoroacetate or an ester formed by the reaction of the acid and an alcohol such as N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide or 1-(3-dimethylaminopropyl)-3-ethylcarbodiimide.

The reaction is conveniently carried out in the presence of a suitable base as defined hereinbefore and in the presence of a suitable inert solvent or diluent as defined hereinbefore.

Typically a carbodiimide coupling reagent is used in the presence of an organic solvent (preferably an anhydrous polar aprotic organic solvent) at a non-extreme temperature, for example in the region −10 to 40° C., typically at ambient temperature of about 20° C.

A compound of Formula I wherein a substituent on $Q^1$ or $Q^2$ is a carboxy group may conveniently be prepared by the cleavage of the corresponding ester such as a (1-12C)alkyl ester, for example by acid-, base- metal- or enzymatically-catalysed cleavage.

(f) For those compounds of the Formula I wherein a substituent on $Q^1$ or $Q^2$ contains an amino-(1-6C)alkyl group, the cleavage of the corresponding compound of Formula I wherein a substituent on $Q^1$ or $Q^2$ is a protected amino-(1-6C)alkyl group.

Suitable protecting groups for an amino-(1-6C)alkyl group are, for example, any of the protecting groups disclosed hereinbefore for an amino group. Suitable methods for the cleavage of such amino protecting groups are also disclosed hereinbefore. In particular, a suitable protecting group is a lower alkoxycarbonyl group such as a tert-butoxycarbonyl group which may be cleaved under conventional reaction conditions such as under acid-catalysed hydrolysis.

(g) For those compounds of the Formula I wherein Z is a $N(R^{11})$ group wherein $R^{11}$ is hydrogen or (1-6C)alkyl, the reaction, conveniently in the presence of a suitable metallic salt catalyst, of a thiourea of the Formula I wherein $Q^1$, $Q^2$, $R^2$ and $R^3$ have any of the meanings defined hereinbefore except that any functional group is protected if necessary and Z is sulphur, with an amine of formula $R^{11}NH_2$, whereafter any protecting group that is present is removed by conventional means.

A suitable metallic salt catalyst is, for example, a mercuric salt such as mercuric(II) oxide and the reaction is conveniently carried out in the presence of a suitable inert solvent or diluent as defined hereinbefore.

(h) For those compounds of the Formula I wherein a substituent on $Q^1$ or $Q^2$ contains an amino group, the reduction of a corresponding compound of Formula I wherein a substituent on $Q^1$ or $Q^2$ contains a nitro group.

Typical reaction conditions include the use of ammonium formate or hydrogen gas in the presence of a catalyst, for example a metallic catalyst such as palladium-on-carbon. Alternatively a dissolving metal reduction may be carried out, for example using iron in the presence of an acid, for example an inorganic or organic acid such as hydrochloric, hydrobromic, sulphuric or acetic acid. The reaction is conveniently carried out in the presence of an organic solvent (preferably a polar protic solvent) and preferably with heating, for example to about 60° C. Any functional groups are protected and deprotected as necessary.

When a pharmaceutically-acceptable salt of a quinazoline derivative of the Formula I is required, for example an acid-addition salt, it may be obtained by, for example, reaction of said quinazoline derivative with a suitable acid using a conventional procedure.

Biological Assays

Compounds which potently inhibit the tyrosine kinase activity associated with the VEGF receptors such as Flt and/or KDR and which inhibit angiogenesis and/or increased vascular permeability may be identified and assessed by, for example, using one or more of the procedures set out below:

(a) In Vitro Receptor Tyrosine Kinase Inhibition Test

This assay determines the ability of a test compound to inhibit tyrosine kinase activity. DNA encoding VEGF or epidermal growth factor (EGF) receptor cytoplasmic domains may be obtained by total gene synthesis (Edwards M, International Biotechnology Lab 5(3), 19-25, 1987) or by cloning. These may then be expressed in a suitable expression system to obtain polypeptide with tyrosine kinase activity. For example VEGF and EGF receptor cytoplasmic domains, which were obtained by expression of recombinant protein in insect cells, were found to display intrinsic tyrosine kinase activity. In the case of the VEGF receptor Flt (Genbank accession number X51602), a 1.7 kb DNA fragment encoding most of the cytoplasmic domain, commencing with methionine 783 and including the termination codon, described by Shibuya et al (Oncogene, 1990, 5: 519-524), was isolated from cDNA and cloned into a baculovirus transplacement vector (for example pAcYM1 (see The Baculovirus Expression System: A Laboratory Guide, L. A King and R. D. Possee, Chapman and Hall, 1992) or pAc360 or pBlueBacHis (available from Invitrogen Corporation)). This recombinant construct was co-transfected into insect cells (for example Spodoptera frugiperda 21(Sf21)) with viral DNA (eg Pharmingen BaculoGold) to prepare recombinant baculovirus. (Details of the methods for the assembly of recombinant DNA molecules and the preparation and use of recombinant baculovirus can be found in standard texts for example Sambrook et al, 1989, Molecular cloning—A Laboratory Manual, 2nd edition, Cold Spring Harbour Laboratory Press and O'Reilly et al, 1992, Baculovirus Expression Vectors—A Laboratory Manual, W. H. Freeman and Co, New York). For other tyrosine linases for use in assays, cytoplasmic fragments starting from methionine 806 (KDR, Genbank accession number L04947) and methionine 668 (EGF receptor, Genbank accession number X00588) may be cloned and expressed in a similar manner.

For expression of cFlt tyrosine kinase activity, Sf21 cells were infected with plaque-pure cFlt recombinant virus at a multiplicity of infection of 3 and harvested 48 hours later. Harvested cells were washed with ice cold phosphate buffered saline solution (PBS) (10 mM sodium phosphate pH7.4, 138 mM sodium chloride, 2.7 mM potassium chloride) then resuspended in ice cold HNTG/PMSF (20 mM Hepes pH7.5, 150 mM sodium chloride, 10% v/v glycerol, 1% v/v Triton X100, 1.5 mM magnesium chloride, 1 mM ethylene glycol-bis(βaminoethyl ether) N,N,N',N'-tetraacetic acid (EGTA), 1 mM PMSF (phenylmethylsulphonyl fluoride); the PMSF is added just before use from a freshly-prepared 100 mM solution in methanol) using 1 ml HNTG/PMSF per 10 million cells. The suspension was centrifuged for 10 minutes at 13,000 rpm at 4° C., the supernatant (enzyme stock) was removed and stored in aliquots at −70° C. Each new batch of stock enzyme was titrated in the assay by dilution with enzyme diluent (100 mM Hepes pH 7.4, 0.2 mM sodium orthovanadate, 0.1% v/v Triton X100, 0.2 mM dithiothreitol). For a typical batch, stock enzyme is diluted 1 in 2000 with enzyme diluent and 50 μl of dilute enzyme is used for each assay well.

A stock of substrate solution was prepared from a random copolymer containing tyrosine, for example Poly (Glu, Ala, Tyr) 6:3:1 (Sigma P3899), stored as 1 mg/ml stock in PBS at −20° C. and diluted 1 in 500 with PBS for plate coating.

On the day before the assay 100 μl of diluted substrate solution was dispensed into all wells of assay plates (Nunc maxisorp 96-well immunoplates) which were sealed and left overnight at 4° C.

On the day of the assay the substrate solution was discarded and the assay plate wells were washed once with PBST (PBS containing 0.05% v/v Tween 20) and once with 50 mM Hepes pH7.4.

Test compounds were diluted with 10% dimethylsulphoxide (DMSO) and 25 μl of diluted compound was transferred to wells in the washed assay plates. "Total" control wells contained 10% DMSO instead of compound. Twenty five microlitres of 40 mM manganese(II)chloride containing 8 μM adenosine-5'-triphosphate (ATP) was added to all test wells except "blank" control wells which contained manganese(II)chloride without ATP. To start the reactions 50 μl of freshly diluted enzyme was added to each well and the plates were incubated at room temperature for 20 minutes. The liquid was then discarded and the wells were washed twice with PBST. One hundred microlitres of mouse IgG anti-phosphotyrosine antibody (Upstate Biotechnology Inc. product 05-321), diluted 1 in 6000 with PBST containing 0.5% w/v bovine serum albumin (BSA), was added to each well and the plates were incubated for 1 hour at room temperature before discarding the liquid and washing the wells twice with PBST. One hundred microlitres of horse radish peroxidase (HRP)-inked sheep anti-mouse Ig antibody (Amersham product NXA 931), diluted 1 in 500 with PBST containing 0.5% w/v BSA, was added and the plates were incubated for 1 hour at room temperature before discarding the liquid and washing the wells twice with PBST. One hundred microlitres of 2,2'-azino-bis(3-ethylbenzthiazoline-6-sulphonic acid) (ABTS) solution, freshly prepared using one 50 mg ABTS tablet (Boehringer 1204 521) in 50 ml freshly prepared 50 mM phosphate-citrate buffer pH5.0+0.03% sodium perborate (made with 1 phosphate citrate buffer with sodium perborate (PCSB) capsule (Sigma P4922) per 100 ml distilled water), was added to each well. Plates were then incubated for 20-60 minutes at room temperature until the optical density value of the "total" control wells, measured at 405 nm using a plate reading spectrophotometer, was approximately 1.0. "Blank" (no ATP) and "total" (no compound) control values were used to determine the dilution range of test compound which gave 50% inhibtion of enzyme activity.

(b) In Vitro HUVEC Proliferation Assay

This assay determines the ability of a test compound to inhibit the growth factor-stimulated proliferation of human umbilical vein endothelial cells (HUVEC).

HUVEC cells were isolated in MCDB 131 (Gibco BRL) +7.5% v/v foetal calf serum (FCS) and were plated out (at passage 2 to 8), in MCDB 131+2% v/v FCS+3 μg/ml heparin+1 μg/ml hydrocortisone, at a concentration of 1000 cells/well in 96 well plates. After a minimum of 4 hours they were dosed with the appropriate growth factor (i.e. VEGF 3 ng/ml, EGF 3 ng/ml or b-FGF 0.3 ng/ml) and compound. The cultures were then incubated for 4 days at 37° C. with 7.5% carbon dioxide. On day 4 the cultures were pulsed with 1 μCi/well of tritiated-thymidine (Amersham product TRA 61) and incubated for 4 hours. The cells were harvested using a 96-well plate harvester (Tomtek) and then assayed for incorporation of tritium with a Beta plate counter. Incorporation of radioactivity into cells, expressed as cpm, was used to measure inhibition of growth factor-stimulated cell proliferation by compounds.

(c) In Vivo Solid Tumour Disease Model

This test measures the capacity of compounds to inhibit solid tumour growth.

CaLu-6 tumour xenografts were established in the flank of female athymic Swiss nu/nu mice, by subcutaneous injection of $1\times10^6$ CaLu-6 cells/mouse in 100 μl of a 50% (v/v) solution of Matrigel in serum free culture medium. Ten days after cellular implant, mice were allocated to groups of 8-10, so as to achieve comparable group mean volumes. Tumours were measured using vernier calipers and volumes were calculated as: $(l\times w)\times\sqrt{(l\times w)}\times(\pi/6)$, where l is the longest diameter and w the diameter perpendicular to the longest diameter. Test compounds were administered orally once daily for a minimum of 21 days, and control animals received compound diluent. Tumours were measured twice weekly. The level of growth inhibition was calculated by comparison of the mean tumour volume of the control group versus the treatment group, and statistical significance determined using a Students' t-test and/or a Mann-Whitney Rank Sum Test. The inhibitory effect of compound treatment was considered significant when $p<0.05$.

Although the pharmacological properties of the compounds of Formula I vary with structural change, in general, activity possessed by compounds of the Formula I, may be demonstrated at the following concentrations or doses in one or more of the above tests (a), (b) and (c):

Test (a):—$IC_{50}$, in the range, for example, <5 μM

Test (b):—$IC_{50}$ in the range, for example, 0.001-5 μM;

Test (c):—activity in the range, for example, 0.1-100 mg/kg;

For example in test (a), Example 2.1 had an $IC_{50}$ of 0.4-1.2 μM using the Flt receptor and an $IC_{50}$ of 0.015-0.05 μM using the KDR receptor and Example 2.13 had an $IC_{50}$ of 0.002-0.05 μM using the Flt receptor and an $IC_{50}$ of <0.002 μM using the KDR receptor. In test (b) with VEGF as the growth factor, Example 2.1 had an $IC_{50}$ of 0.05 μM and Example 2.13 had an $IC_{50}$ of 0.1-0.5 μM.

A pharmaceutical composition for use in the treatment of disease states associated with angiogenesis and/or increased vascular permeability comprises a compound of the formula I as defined hereinbefore or a pharmaceutically acceptable salt thereof, in association with a pharmaceutically acceptable excipient or carrier.

The composition may be in a form suitable for oral administration, (for example as tablets, lozenges, hard or soft capsules, aqueous or oily suspensions, emulsions, dispersible powders or granules, syrups or elixirs), for administration by inhalation (for example as a finely divided powder or a liquid aerosol), for administration by insufflation (for example as a finely divided powder), for parenteral injection (for example as a sterile solution, suspension or emulsion for intravenous, subcutaneous, intramuscular, intravascular or infusion dosing), for topical administration (for example as creams, ointments, gels, or aqueous or oily solutions or suspensions), or for rectal administration (for example as a suppository). In general the above compositions may be prepared in a conventional manner using conventional excipients.

The compositions of the present invention are advantageously presented in unit dosage form. The compound will normally be administered to a warm-blooded animal at a unit dose within the range 5-5000 mg per square metre body area of the animal, i.e. approximately 0.1-100 mg/kg. A unit dose in the range, for example, 1-100 mg/kg, preferably 1-50 mg/kg is envisaged and this normally provides a therapeutically-effective dose. A unit dose form such as a tablet or capsule will usually contain, for example 1-250 mg of active ingredient.

We have found that compounds of the present invention inhibit VEGF receptor tyrosine kinase activity and are therefore of interest for their antiangiogenic effects and/or their ability to cause a reduction in vascular permeability.

As stated above the size of the dose required for the therapeutic or prophylactic treatment of a particular disease state will necessarily be varied depending on the host treated, the route of administration and the severity of the illness being treated. Preferably a daily dose in the range of 1-50 mg/kg is employed. However the daily dose will necessarily be varied depending upon the host treated, the particular route of administration, and the severity of the illness being treated. Accordingly the optimum dosage may be determined by the practitioner who is treating any particular patient.

The antiangiogenic and/or vascular permeability reducing treatment defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the antiangiogenic and/or vascular permeability reducing treatment defined hereinbefore may be: surgery, radiotherapy or chemotherapy. Such chemotherapy may cover five main categories of therapeutic agent:

(i) other antiangiogenic agents that work by different mechanisms from those defined hereinbefore (for example linomide, inhibitors of integrin αvβ3 function, angiostatin, endostatin, razoxin, thalidomide) and including vascular targeting agents (for example combretastatin phosphate and the vascular damaging agents described in International Patent Application Publication No. WO 99/02166 the entire disclosure of which document is incorporated herein by reference, (for example N-acetylcolchinol-O-phosphate));
(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LBRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor such inhibitors include growth factor antibodies, growth factor receptor antibodies, tyrosine kinase inhibitors and serine/threonine kinase inhibitors);
(iii) biological response modifiers (for example interferon);
(iv) antibodies (for example edrecolomab); and
(v) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincristine and taxoids like taxol, taxotere); enzymes (for example asparaginase); thymidylate synthase inhibitors (for example raltitrexed); topoisomerase inhibitors (for example epipodophyllotoxins like etoposide and teniposide, amsacrine, topotecan, irinotecan).

As stated above the compounds defined in the present invention are of interest for their antiangiogenic and/or vascular permeability reducing effects. Such compounds of the invention are expected to be useful in a wide range of disease states including cancer, diabetes, psoriasis, rheumatoid arthritis, Kaposi's sarcoma, haemangioma, acute and chronic nephropathies, atheroma, arterial restenosis, autoimmune diseases, acute inflammation, excessive scar formation and adhesions, endometriosis, dysfunctional uterine bleeding and ocular diseases with retinal vessel proliferation. In particular such compounds of the invention are expected to slow advantageously the growth of primary and recurrent solid tumours of, for example, the colon, breast, prostate, lungs and skin. More particularly such compounds of the invention are expected to inhibit the growth of those primary and recurrent solid tumours which are associated with VEGF especially those tumours which are significantly dependent on VEGF for their growth and spread, including for example, certain tumours of the colon, breast, prostate, lung, vulva and skin.

In addition to their use in therapeutic medicine, the compounds of formula I and their pharmaceutically acceptable salts are also useful as pharmacological tools in the development and standardisation of in vitro and in vivo test systems for the evaluation of the effects of inhibitors of VEGF receptor tyrosine kinase activity in laboratory animals such as cats, dogs, rabbits, monkeys, rats and mice, as part of the search for new therapeutic agents.

The invention will now be illustrated in the following non-limiting Examples in which, unless otherwise stated:

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (TLC) were performed on Merck Kieselgel silica (Art. 9385) or Merck Lichroprep RP-18 (Art. 9303) reversed-phase silica obtained from E. Merck, Darmstadt, Germany or high pressure liquid chromatography (HPLC) was performed on C18 reverse phase silica, for example on a Dynamax C-18 60 Å preparative reversed-phase column;

(iv) yields, where present, are given for illustration only and are not necessarily the maximum attainable;

(v) in general, the end-products of the Formula I have satisfactory microanalyses and their structures were confirmed by nuclear magnetic resonance N) and/or mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Jeol JNM EX 400 spectrometer operating at a field strength of 400 MHz, a Varian Gemini 2000 spectrometer operating at a field strength of 300 MHz or a Bruker AM300 spectrometer operating at a field strength of 300 MHz]; the following abbreviations have been used: s, singlet; d, doublet; t, triplet; q, quartet; m, multiplet; br, broad;

(vi) intermediates were not generally fully characterised and purity was assessed by thin layer chromatographic, HPLC, infra-red (IR) and/or NMR analysis;

(vii) melting points are uncorrected and were determined using a Mettler SP62 automatic melting point apparatus or an oil-bath apparatus; melting points for the end-products of the Formula I were determined after crystallisation from a conventional organic solvent such as ethanol, methanol, acetone, ether or hexane, alone or in admixture; and (viii) the following abbreviations have been used:
DMF N,N-dimethylformamide
DMSO dimethylsulphoxide
TBF tetrahydrofuran

EXAMPLE 1

1-(2,6-dichlorophenyl)-3-[6-methoxy-7-(N-methylpiperidin-4-ylmethoxy)quinazolin-4-yl]urea 2,6Dichlorophenyl isocyanate (0.075 g) was added to a solution of 4amino-6-methoxy-7-(N-methylpiperidin-4-ylmethoxy)quinazoline (0.093 g) in a mixture of methylene chloride (2 ml) and DMF (0.1 ml) and the reaction mixture was stirred at ambient temperature for 16 hours. The resultant solid was isolated, redissolved in a 20:1 mixture of methylene chloride and methanol and purified by column chromatography on silica using increasingly polar mixtures of methylene chloride, methanol and a 1% aqueous ammonium hydroxide solution as eluent. There was thus obtained the title compound as a white solid (0.029 g); NMR Spectrum: (DMSOd$_6$) 1.3-1.4 (m, 2H), 1.7-1.8 (m, 4H), 1.85 (t, 1H), 2.1 (s, 3H), 2.8 (d, 2H), 3.9 (s, 3H), 4.0 (br d, 2H), 7.3 (br s, 1H), 7.4 (d, 1H), 7.5 (s, 1H), 7.6 (s, 1H), 8.0 (br s, 1H), 8.7 (s, 1H); Mass Spectrum: M+H$^+$ 490, 492 and 494.

The 4-amino-6-methoxy-7-(N-methylpiperidin-4-ylmethoxy)quinazoline used as a starting material was prepared as follows:

A solution of di-tert-butyl dicarbonate (41.7 g) in ethyl acetate (75 ml) was added dropwise to a stirred solution of ethyl piperidine-4-carboxylate (30 g) in ethyl acetate (150 ml) which had been cooled to 0 to 5° C. in an ice-bath. The resultant mixture was stirred at ambient temperature for 48 hours. The mixture was poured into water (300 ml). The organic layer was separated, washed in turn with water (200 ml), 0.1N aqueous hydrochloric acid solution (200 ml), a saturated aqueous sodium bicarbonate solution (200 ml) and brine (200 ml), dried over magnesium sulphate and evaporated. There was thus obtained ethyl N-tert-butoxycarbonylpiperidine-4-carboxylate (48 g); NMR Spectrum: (CDCl$_3$) 1.25 (t, 3H), 1.45 (s, 9H), 1.55-1.7 (m, 2H), 1.8-2.0 (d, 2H), 2.35-2.5 (m, 1H), 2.7-2.95 (t, 2H), 3.9-4.1 (br s, 2H), 4.15 (q, 2H).

A solution of the material so obtained in THF (180 ml) was cooled at 0° C. and lithium aluminium hydride (1M solution in TBF; 133 ml) was added dropwise. The mixture was stirred at 0° C. for 2 hours. Water (30 ml) and 2N aqueous sodium hydroxide solution (10 ml) were added in turn and the mixture was stirred for 15 minutes. The resultant mixture was filtered through diatomaceous earth and the solids were washed with ethyl acetate. The filtrate was washed in turn with water and with brine, dried over magnesium sulphate and evaporated. There was thus obtained N-tert-butoxycarbonyl-4-hydroxymethylpiperidine (36.3 g); NMR Spectrum: (CDCl$_3$) 1.05-1.2 (m, 2H), 1.35-1.55 (m, 10H), 1.6-1.8 (m, 2H), 2.6-2.8 (t, 2H), 3.4-3.6 (t, 2H), 4.0-4.2 (br s, 2H).

1,4-Diazabicyclo[2.2.2]octane (42.4 g) was added to a solution of N-tert-butoxycarbonyl-4-hydroxymethylpiperidine (52.5 g) in tert-butyl methyl ether (525 ml) and the mixture was stirred at ambient temperature for 15 minutes. The mixture was then cooled in an ice-bath to 5° C. and a solution of 4-toluenesulphonyl chloride (62.8 g) in tert-butyl methyl ether (525 ml) was added dropwise over 2 hours while maintaining the reaction temperature at approximately 0° C. The resultant mixture was allowed to warm to ambient temperature and was stirred for 1 hour. Petroleum ether (b.p. 60-80° C., 1L) was added and the precipitate was removed by filtration. The filtrate was evaporated to give a solid residue which was dissolved in diethyl ether. The organic solution was washed in turn with 0.5N aqueous hydrochloric acid solution, water, a saturated aqueous sodium bicarbonate solution and brine, dried over magnesium sulphate and evaporated. There was thus obtained N-tert-butoxycarbonyl-4-(4-toluenesulphonyloxymethyl) piperidine (76.7 g), NMR Spectrum: (CDCl$_3$) 1.0-1.2 (m, 2H), 1.45 (s, 9H), 1.65 (d, 2H), 1.75-1.9 (m, 2H), 2.45 (s, 3H), 2.55-2.75 (m, 2H), 3.85 (d, 1H), 4.0-4.2 (br s, 2H), 7.35 (d, 2H), 7.8 (d, 2H).

A portion (40 g) of the material so obtained was added to a suspension of ethyl 4-hydroxy-3-methoxybenzoate (19.6 g) and potassium carbonate (28 g) in DMF (200 ml) and the resultant mixture was stirred and heated to 95° C. for 2.5 hours. The mixture was cooled to ambient temperature and partitioned between water and a mixture of ethyl acetate and diethyl ether. The organic layer was washed in turn with water and brine, dried over magnesium sulphate and evaporated. The resulting oil was crystallised from petroleum ether (b.p. 60-80° C.) and the suspension was stored overnight at 5° C. The resultant solid was collected by filtration, washed with petroleum ether and dried under vacuum. There was thus obtained ethyl 4-(N-tert-butoxycarbonylpiperidin-4-lmethoxy)-3-methoxy-benzoate (35 g), m.p. 81-83° C.; NMR Spectrum: (CDCl$_3$) 1.2-1.35 (m, 2H), 1.4 (t, 3H), 1.48 (s, 9H), 1.8-1.9 (d, 2H), 2.0-2.15 (m, 2H), 2.75 (t, 2H), 3.9 (d, 2H), 3.95 (s, 3H), 4.05-4.25 (br s, 2H), 4.35 (q, 2H), 6.85 (d, 1H), 7.55 (s, 1H), 7.65 (d, 1H).

The material so obtained was dissolved in formic acid (35 ml), formaldehyde (12M, 37% in water, 35 ml) was added and the mixture was stirred and heated to 95° C. for 3 hours. The resultant mixture was evaporated. The residue was dissolved in methylene chloride and hydrogen chloride (3M solution in diethyl ether; 40 ml) was added. The mixture was diluted with diethyl ether and the mixture was triturated until a solid was formed. The solid was collected, washed with diethyl ether and dried under vacuum overnight at 50° C. There was thus obtained ethyl 3-methoxy-4-(N-methylpiperidin-4-ylmethoxy)benzoate (30.6 g), NMR Spectrum: (DMSOd$_6$) 1.29 (t, 3H), 1.5-1.7 (m, 2H), 1.95 (d, 2H), 2.0-2.15 (br s, 1H), 2.72 (s, 3H), 2.9-3.1 (m, 2H), 3.35-3.5 (br s, 2H), 3.85 (s, 3H), 3.9-4.05 (br s, 2H), 4.3 (q, 2H), 7.1 (d, 1H), 7.48 (s, 1H), 7.6 (d, 1H).

The material so obtained was dissolved in methylene chloride (75 ml) and the solution was cooled in an ice-bath to 0-5° C. Trifluoroacetic acid (37.5 ml) was added followed by the dropwise addition over 15 minutes of a solution of fuming nitric acid (24M; 7.42 ml) in methylene chloride (15 ml). The resultant solution was allowed to warm to ambient temperature and was stirred for 2 hours. Volatile materials were evaporated. The residue was dissolved in methylene chloride (50 ml) and the solution was cooled in an ice-bath to 0-5° C. Diethyl ether was added and the resultant precipitate was collected and dried under vacuum at 50° C. The solid was dissolved in methylene chloride (500 ml) and hydrogen chloride (3M solution in diethyl ether, 30 ml) was added followed by diethyl ether (500 ml). The resultant solid was collected and dried under vacuum at 50° C. There was thus obtained ethyl 5-methoxy-4-(N-methylpiperidin-4-ylmethoxy)-2-nitrobenzoate (28.4 g), NMR Spectrum: (DMSOd$_6$) 1.3 (t, 3H), 1.45-1.65 (m, 2H), 1.75-2.1 (m, 3H), 2.75 (s, 3H), 2.9-3.05 (m, 2H), 3.4-3.5 (d, 2H), 3.95 (s, 3H), 4.05 (d, 2H), 4.3 (q, 2H), 7.32 (s, 1H), 7.66 (s, 1H).

A mixture of a portion (3.89 g) of the material so obtained, 10% platinum-on-activated carbon (50% wet, 0.389 g) and methanol (80 ml) was stirred under 1.8 atmospheres pressure of hydrogen until uptake of hydrogen ceased. The mixture was filtered and the filtrate was evaporated. The residue was dissolved in water (30 ml) and basified to pH10 by the addition of a saturated aqueous sodium bicarbonate solution. The mixture was diluted with a 1:1 mixture of ethyl acetate and diethyl ether and the organic layer was separated. The aqueous layer was further extracted with a 1:1 mixture of ethyl acetate and diethyl ether and the organic extracts were combined, washed in turn with water and brine, dried over magnesium sulphate and evaporated. The residue was triturated under a mixture of petroleum ether (b.p. 60-80° C.) and diethyl ether. The solid so obtained was isolated, washed with petroleum ether and dried under vacuum at 60° C. There was thus obtained ethyl 2-amino-5-methoxy-4-(N-methylpiperidin-4-ylmethoxy)benzoate (2.58 g), m.p. 111-112° C.; NMR Spectrum: (CDCl$_3$) 1.35 (t, 3H), 1.4-1.5 (m, 2H), 1.85 (m, 3H), 1.95 (t, 2H), 2.29 (s, 3H), 2.9 (d, 2H), 3.8 (s, 3H), 3.85 (d, 2H), 4.3 (q, 2H), 5.55 (br s, 2H), 6.13 (s, 1H), 7.33 (s, 1H).

A mixture of ethyl 2-amino-5-methoxy-4-(N-methylpiperidin-4-ylmethoxy)benzoate (16.1 g), formamidine acetic acid salt (5.2 g) and 2-methoxyethanol (160 ml) was stirred and heated at 115° C. for 2 hours. Further formamidine acetic acid salt (10.4 g) was added in portions every 30 minutes during 4 hours and heating was continued for 30 minutes after the last addition. The resultant mixture was evaporated. The solid residue was stirred under a mixture of methylene chloride (50 ml) and ethanol (100 ml). The precipitate was removed by filtration and the filtrate was concentrated to a final volume of 100 ml. The resultant suspension was cooled to 5° C. The solid so obtained was collected, washed with cold ethanol and with diethyl ether and dried under vacuum at 60° C. There was thus obtained 6-methoxy-7-(N-methylpiperidin-4-ylmethoxy)-3,4-dihydroquinazolin-4-one (12.7 g); NMR Spectrum: (DMSOd$_6$) 1.25-1.4 (m, 2H), 1.75 (d, 2H), 1.9 (t, 1H), 1.9 (s, 3H), 2.16 (s, 2H), 2.8 (d, 2H), 3.9 (s, 3H), 4.0 (d, 2H), 7.11 (s, 1H), 7.44 (s, 1H), 7.97 (s, 1H).

A mixture of a portion (2.8 g) of the material so obtained, thionyl chloride (28 ml) and DMF (0.28 ml) was heated to reflux for 1 hour. The mixture was evaporated and the precipitate was triturated under diethyl ether. The resultant solid was isolated and washed with diethyl ether. The solid was then dissolved in methylene chloride and the solution was washed with a saturated aqueous sodium bicarbonate solution. The organic layer was washed in turn-with water and brine, dried over magnesium sulphate and evaporated. There was thus obtained 4-chloro-6-methoxy-7-(N-methylpiperidin-4-ylmethoxy)quinazoline (2.9 g,), NMR Spectrum: (DMSOd$_6$) 1.3-1.5 (m, 2H), 1.75-1.9 (m, 4H), 2.0 (t, 1H), 2.25 (s, 3H), 2.85 (d, 2H), 4.02 (s, 3H), 4.12 (d, 2H), 7.41 (s, 1H), 7.46 (s, 1H), 8.9 (s, 1H).

A mixture of 4-chloro-6-methoxy-7-(N-methylpiperidin-4-ylmethoxy)quinazoline (11.17 g), 4-bromo-2-fluorophenol (4.57 ml), potassium carbonate (7.19 g) and DMF (110 ml) was stirred and heated at 100° C. for 2.5 hours. The mixture was allowed to cool to ambient temperature and was poured into a mixture (1L) of ice and water. The precipitate was collected, washed with water and dried. The solid was purified by column chromatography on silica using increasingly polar mixtures of methylene chloride, methanol and a 1% aqueous ammonium hydroxide solution (20:1:0 to 10:1:0 to 10:1:1) as eluent. There was thus obtained 4-(4-bromo-2-fluorophenoxy)-6-methoxy-7-(N-methylpiperidin-4-ylmethoxy)quinazoline (13.1 g), NMR Spectrum: (DMSOd$_6$) 1.3-1.4 (m, 2H), 1.7-1.8 (m, 4H), 1.9 (t, 1H), 2.15 (s, 3H), 2.5 (br s, 2H), 4.0 (s, 3H), 4.1 (d, 2H), 7.4 (s, 1H), 7.45-7.6 (m, 3H), 7.8 (d, 1H), 8.5 (s, 1H); Mass Spectrum: M+H$^+$ 476 and 478.

A portion (9.4 g) of the material so obtained was dissolved in a 2M solution of ammonia in isopropanol (150 ml). Liquid ammonia (10 ml) was added and the reaction mixture was sealed in a Carius tube. The reaction mixture was heated to 130° C. for 16 hours. The Carius tube was cooled and opened and the reaction mixture was evaporated. The residue was stirred under a 2N aqueous sodium hydroxide solution for 1 hour. The resultant solid was isolated and washed in turn with water and methyl tert-butyl ether. There was thus obtained 4-amino-6-methoxy-7-(N-methylpiperidin-4-ylmethoxy)quinazoline (5.55 g); NMR Spectrum: (DMSOd$_6$) 1.2-1.4 (m, 2H), 1.7-1.8 (m, 4H), 1.85 (t, 1H), 2.1 (s, 3H), 2.8 (d, 2H), 3.8 (s, 3H), 3.9 (d, 2H), 7.0 (s, 1H), 7.3 (br s, 2H), 7.5 (s, 1H), 8.2 (s, 1H), Mass Spectrum: M+H$^+$ 303.

EXAMPLE 2

Using an analogous procedure to that described in Example 1, except that, unless otherwise stated, chloroform was used in place of methylene chloride as the reaction solvent, the appropriate 4-aminoquinazoline was reacted with the appropriate isocyanate to give the compounds described in Table I. In general, unless otherwise stated, the appropriate isocyanates were commercially available. Alternatively appropriate isocyanates could be prepared by the reaction of the appropriate aniline with di-tert-butyl dicarbonate in the presence of 4-dimethylaminopyridine and a solvent such as methylene chloride.

TABLE I

| No. | R⁶ | R⁷ | (R²)ₙ | Note |
|---|---|---|---|---|
| 1 | methoxy | N-methylpiperidin-4-ylmethoxy | 2-chloro | [1] |
| 2 | methoxy | N-methylpiperidin-4-ylmethoxy | 2,3-dichloro | [2] |
| 3 | methoxy | N-methylpiperidin-4-ylmethoxy | 2,4-dichloro | [3] |
| 4 | methoxy | N-methylpiperidin-4-ylmethoxy | 2-fluoro | [4] |
| 5 | methoxy | N-methylpiperidin-4-ylmethoxy | 2,6-difluoro | [5] |
| 6 | methoxy | N-methylpiperidin-4-ylmethoxy | 2-bromo | [6] |
| 7 | methoxy | N-methylpiperidin-4-ylmethoxy | 2-trifluoromethyl | [7] |
| 8 | methoxy | N-methylpiperidin-4-ylmethoxy | 2-methyl | [8] |
| 9 | methoxy | N-methylpiperidin-4-ylmethoxy | 2,6-dimethyl | [9] |
| 10 | methoxy | N-methylpiperidin-4-ylmethoxy | 2-tert-butyl | [10] |
| 11 | methoxy | 3-piperidinopropoxy | 2,6-dimethyl | [11] |
| 12 | hydrogen | 3-morpholinopropoxy | 2,6-dichloro | [12] |
| 13 | hydrogen | 3-(1,1-dioxotetrahydro-4H-1,4-thiazin-4-yl)propoxy | 2,6-dichloro | [13] |
| 14 | hydrogen | 4-morpholinobut-2-ynyloxy | 2,6-dichloro | [14] |
| 15 | hydrogen | (E)-4-morpholinobut-2-enyloxy | 2,6-dichloro | [15] |
| 16 | methoxy | 2-pipeidinoethoxy | 2,6-dichloro | [16] |
| 17 | methoxy | 3-morpholinopropoxy | 2,6-dichloro | [17] |
| 18 | methoxy | 3-(4-methylpiperazin-1-yl)propoxy | 2,6-dichloro | [18] |
| 19 | methoxy | 3-pyrrolidin-1-ylpropoxy | 2,6-dichloro | [19] |
| 20 | methoxy | 3-(1,1-dioxotetrahydro-4H-1,4-thiazin-4-yl)propoxy | 2,6-dichloro | [20] |
| 21 | methoxy | 2-[N-(2-methoxyethyl)-N-methylamino]ethoxy | 2,6-dichloro | [21] |
| 22 | methoxy | 3-mesylpropoxy | 2,6-dichloro | [22] |
| 23 | methoxy | 3-(1,2,3-triazol-1-yl)propoxy | 2,6-dichloro | [23] |
| 24 | methoxy | 2-(4-pyridyl)ethoxy | 2,6-dichloro | [24] |
| 25 | methoxy | N-methylpiperidin-4-ylmethoxy | 2,4,6-trichloro | [25] |
| 26 | methoxy | N-methylpiperidin-4-ylmethoxy | 2,5-dichloro | [26] |
| 27 | methoxy | N-methylpiperidin-4-ylmethoxy | 2,4-difluoro | [27] |
| 28 | methoxy | N-methylpiperidin-4-ylmethoxy | 2,5-dimethoxy | [28] |
| 29 | methoxy | N-methylpiperidin-4-ylmethoxy | 2,4-dimethoxy | [29] |
| 30 | methoxy | N-methylpiperidin-4-ylmethoxy | 2,6-diisopropyl | [30] |
| 31 | methoxy | N-methylpiperidin-4-ylmethoxy | 2,4,6-trimethyl | [31] |
| 32 | methoxy | N-methylpiperidin-4-ylmethoxy | 2,5-dimethyl | [32] |
| 33 | methoxy | N-methylpiperidin-4-ylmethoxy | 2,5-diethyl | [33] |
| 34 | methoxy | N-methylpiperidin-4-ylmethoxy | 2-ethyl-6-methyl | [34] |
| 35 | methoxy | N-methylpiperidin-4-ylmethoxy | 4-bromo-2,6-dimethyl | [35] |
| 36 | methoxy | N-methylpiperidin-4-ylmethoxy | 2-chloro-6-methyl | [36] |
| 37 | methoxy | 3-pyrrolidin-1-ylpropoxy | 2,4,6-trichloro | [37] |
| 38 | methoxy | 3-(4-methylpiperazin-1-yl)propoxy | 2,4,6-trichloro | [38] |
| 39 | methoxy | 3-piperidinopropoxy | 2,6-dichloro | [39] |
| 40 | methoxy | 3-pyrrolidin-1-ylpropoxy | 2,6-difluoro | [40] |
| 41 | methoxy | 3-piperidinopropoxy | 2,6-difluoro | [41] |
| 42 | methoxy | 3-morpholinopropoxy | 2,6-difluoro | [42] |
| 43 | methoxy | 3-(4-methylpiperazin-1-yl)propoxy | 2,6-difluoro | [43] |
| 44 | methoxy | 2-piperidinoethoxy | 2,6-difluoro | [44] |
| 45 | methoxy | 2-piperidinoethoxy | 2,4,6-trichloro | [45] |
| 46 | methoxy | 3-pyrrolidin-1-ylpropoxy | 2-fluoro-6-trifluoromethyl | [46] |
| 47 | methoxy | 2-dimethylaminoethoxy | 2,6-difluoro | [47] |
| 48 | methoxy | 2-dimethylaminoethoxy | 2,6-dichloro | [48] |
| 49 | methoxy | 2-(2-oxoimidazolidin-1-yl)ethoxy | 2,6-difluoro | [49] |
| 50 | methoxy | 2-(2-oxoimidazolidin-1-yl)ethoxy | 2,6-dichloro | [50] |
| 51 | methoxy | 2-pyrrolidin-1-ylethoxy | 2,6-dichloro | [51] |
| 52 | methoxy | 2-pyrrolidin-1-ylethoxy | 2,6-difluoro | [52] |
| 53 | methoxy | 2-morpholinoethoxy | 2,6-dichloro | [53] |
| 54 | methoxy | 2-morpholinoethoxy | 2,6-difluoro | [54] |
| 55 | methoxy | 3-pyrrolidin-1-ylpropoxy | 2,6-dimethyl | [55] |
| 56 | methoxy | 3-morpholinopropoxy | 2,6-dimethyl | [56] |

TABLE I-continued

| No. | R⁶ | R⁷ | (R²)ₙ | Note |
|---|---|---|---|---|
| 57 | methoxy | 3-(4-methylpiperazin-1-yl)propoxy | 2,6-dimethyl | [57] |
| 58 | methoxy | 2-pyrrolidin-1-ylethoxy | 2,6-dimethyl | [58] |
| 59 | methoxy | 2-piperidinoethoxy | 2,6-dimethyl | [59] |
| 60 | methoxy | 2-morpholinoethoxy | 2,6-dimethyl | [60] |
| 61 | methoxy | 2-(2-oxoimidazolidin-1-yl)ethoxy | 2,6-dimethyl | [61] |
| 62 | methoxy | 2-dimethylaminoethoxy | 2,6-dimethyl | [62] |
| 63 | methoxy | 3-pyrrolidin-1-ylpropoxy | 4-bromo-2,6-dimethyl | [63] |
| 64 | methoxy | 3-piperidinopropoxy | 4-bromo-2,6-dimethyl | [64] |
| 65 | methoxy | 3-morpholinopropoxy | 4-bromo-2,6-dimethyl | [65] |
| 66 | methoxy | 3-(4-methylpiperazin-1-yl)propoxy | 4-bromo-2,6-dimethyl | [66] |
| 67 | methoxy | 2-piperidinoethoxy | 4-bromo-2,6-dimethyl | [67] |
| 68 | methoxy | 2-morpholinoethoxy | 4-bromo-2,6-dimethyl | [68] |
| 69 | methoxy | 2-(2-oxoimidazolidin-1-yl)ethoxy | 4-bromo-2,6-dimethyl | [69] |
| 70 | methoxy | 2-(2-methoxyethoxy)ethoxy | 2,6-dichloro | [70] |
| 71 | methoxy | 2-(2-methoxyethoxy)ethoxy | 2,6-difluoro | [71] |
| 72 | methoxy | 2-(2-methoxyethoxy)ethoxy | 2,6-dimethyl | [72] |
| 73 | methoxy | N-methylpiperidin-4-ylmethoxy | 2-fluoro-6-trifluoromethyl | [73] |
| 74 | hydrogen | 2-pyrrolidin-1-ylethoxy | 2,6-dichloro | [74] |
| 75 | hydrogen | 2-pyrrolidin-1-ylethoxy | 2-chloro-6-methyl | [75] |
| 76 | hydrogen | 2-pyrrolidin-1-ylethoxy | 2-chloro | [76] |
| 77 | hydrogen | 2-pyrrolidin-1-ylethoxy | 2,4,6-trichloro | [77] |
| 78 | hydrogen | 2-piperidinoethoxy | 2,6-dichloro | [78] |
| 79 | hydrogen | 2-piperidinoethoxy | 2,6-difluoro | [79] |
| 80 | hydrogen | 2-piperidinoethoxy | 2-chloro-6-methyl | [80] |
| 81 | hydrogen | 2-piperidinoethoxy | 2-chloro | [81] |
| 82 | hydrogen | 2-piperidinoethoxy | 2,4,6-trichloro | [82] |
| 83 | hydrogen | 2-(4-methylpiperazin-1-yl)ethoxy | 2,6-dichloro | [83] |
| 84 | hydrogen | 2-(4-methylpiperazin-1-yl)ethoxy | 2-chloro-6-methyl | [84] |
| 85 | hydrogen | 2-(4-methylpiperazin-1-yl)ethoxy | 2-chloro | [85] |
| 86 | hydrogen | 2-(4-methylpiperazin-1-yl)ethoxy | 2,4,6-trichloro | [86] |
| 87 | hydrogen | N-methylpiperidin-3-ylmethoxy | 2,6-dichloro | [87] |
| 88 | hydrogen | N-methylpiperidin-3-ylmethoxy | 2,6-difluoro | [88] |
| 89 | hydrogen | N-methylpiperidin-3-ylmethoxy | 2-chloro-6-methyl | [89] |
| 90 | hydrogen | N-methylpiperidin-3-yhmethoxy | 2-chloro | [90] |
| 91 | hydrogen | N-methylpiperidin-3-ylmethoxy | 2,4,6-trichloro | [91] |
| 92 | hydrogen | 3-pyrrolidin-1-ylpropoxy | 2,6-dichloro | [92] |
| 93 | hydrogen | 3-pyrrolidin-1-ylpropoxy | 2,6-difluoro | [93] |
| 94 | hydrogen | 3-pyrrolidin-1-ylpropoxy | 2-chloro-6-methyl | [94] |
| 95 | hydrogen | 3-pyrrolidin-1-ylpropoxy | 2-chloro | [95] |
| 96 | hydrogen | 3-pyrrolidin-1-ylpropoxy | 2,4,6-trichloro | [96] |
| 97 | hydrogen | 3-morpholinopropoxy | 2,6-difluoro | [97] |
| 98 | hydrogen | 3-morpholinopropoxy | 2-chloro-6-methyl | [98] |
| 99 | hydrogen | 3-morpholinopropoxy | 2,4,6-trichloro | [99] |
| 100 | hydrogen | 3-(4-methylpiperazin-1-yl)propoxy | 2,6-dichloro | [100] |
| 101 | hydrogen | 3-(4-methylpiperazin-1-yl)propoxy | 2-chloro | [101] |
| 102 | hydrogen | 3-(4-methylpiperazin-1-yl)propoxy | 2,4,6-trichloro | [102] |
| 103 | hydrogen | 3-(1,1-dioxotetrahydro-4H-1,4-thiazin-4-yl)propoxy | 2,6-difluoro | [103] |
| 104 | hydrogen | 3-(1,1-dioxotetrahydro-4H-1,4-thiazin-4-yl)propoxy | 2-chloro-6-methyl | [104] |
| 105 | hydrogen | 3-(1,1-dioxotetrahydro-4H-1,4-thiazin-4-yl)propoxy | 2,4,6-trichloro | [105] |
| 106 | hydrogen | 3-(1,2,3-triazol-1-yl)propoxy | 2,4,6-trichloro | [106] |
| 107 | hydrogen | (E)-4-pyrrolidin-1-ylbut-2-enyloxy | 2,6-difluoro | [107] |
| 108 | hydrogen | (E)-4-pyrrolidin-1-ylbut-2-enyloxy | 2-chloro-6-methyl | [108] |
| 109 | hydrogen | (E)-4-pyrrolidin-1-ylbut-2-enyloxy | 2-chloro | [109] |
| 110 | methoxy | 3-(4-carbamoylpiperidin-1-yl)propoxy | 2,6-dichloro | [110] |
| 111 | methoxy | 3-(4-carbamoylpiperidin-1-yl)propoxy | 2,6-difluoro | [111] |
| 112 | methoxy | 3-(4-carbamoylpiperidin-1-yl)propoxy | 2,6-dimethyl | [112] |
| 113 | methoxy | 3-(4-carbamoylpiperidin-1-yl)propoxy | 2-chloro-6-methyl | [113] |

TABLE I-continued

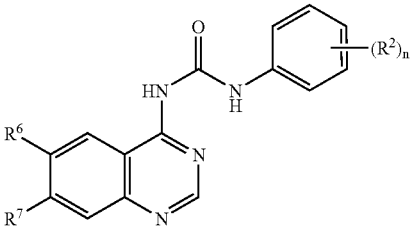

| No. | R⁶ | R⁷ | (R²)ₙ | Note |
|---|---|---|---|---|
| 114 | hydrogen | 3-(pyrrolidin-1-yl)-1-propynyl | 2,6-dichloro | [114] |
| 115 | methoxy | 3-(pyrrolidin-1-yl)-1-propynyl | 2,6-dichloro | [115] |
| 116 | methoxy | 6-morpholino-1-hexynyl | 2,6-dichloro | [116] |
| 117 | methoxy | 6-morpholino-1-hexynyl | 2,6-difluoro | [117] |
| 118 | methoxy | 6-(2-methylimidazol-1-yl)-1-hexynyl | 2,6-dichloro | [118] |
| 119 | methoxy | 6-(2-methylimidazol-1-yl)-1-hexynyl | 2,6-difluoro | [119] |
| 120 | methoxy | 3-dimethylamino-1-propynyl | 2,6-difluoro | [120] |
| 121 | methoxy | N-methylpiperidin-4-ylmethoxy | 2-nitro | [121] |
| 122 | methoxy | N-methylpiperidin-4-ylmethoxy | 2-methyl-3-fluoro | [122] |
| 123 | methoxy | N-methylpiperidin-4-ylmethoxy | 2,5-dichloro | [123] |
| 124 | methoxy | N-methylpiperidin-4-ylmethoxy | 2-methyl-5-nitro | [124] |
| 125 | methoxy | N-methylpiperidin-4-ylmethoxy | 2-chloro-5-trifluoromethyl | [125] |
| 126 | methoxy | N-methylpiperidin-4-ylmethoxy | 5-chloro-2-methoxy | [126] |
| 127 | methoxy | N-methylpiperidin-4-ylmethoxy | 2-methoxy-5-methyl | [127] |
| 128 | methoxy | N-methylpiperidin-4-ylmethoxy | 5-chloro-2-methyl | [128] |
| 129 | methoxy | N-methylpiperidin-4-ylmethoxy | 2-methyl-5-fluoro | [129] |
| 130 | methoxy | N-methylpiperidin-4-ylmethoxy | 2-chloro-5-methyl | [130] |
| 131 | methoxy | 3-pyrrolidin-1-ylpropoxy | 2,5-difluoro | [131] |
| 132 | methoxy | 3-pyrrolidin-1-ylpropoxy | 2,5-dichloro | [132] |
| 133 | methoxy | 3-pyrrolidin-1-ylpropoxy | 5-chloro-2-methyl | [133] |
| 134 | methoxy | 3-pyrrolidin-1-ylpropoxy | 5-fluoro-2-methyl | [134] |
| 135 | methoxy | 3-pyrrolidin-1-ylpropoxy | 2-methyl-5-nitro | [135] |
| 136 | methoxy | 3-pyrrolidin-1-ylpropoxy | 2-chloro-5-methyl | [136] |
| 137 | methoxy | 6-(N-methylpiperazin-1-yl)-1-hexynyl | 2,6-dichloro | [137] |
| 138 | methoxy | benzyloxy | 3-dimethylcarbamoyl-2,6-dimethyl | [138] |
| 139 | methoxy | cyclopropylmethoxy | 2,6-dimethyl | [139] |
| 140 | methoxy | 6-(N-methylpiperazin-1-yl)hexyl | 2,6-dichloro | [140] |
| 141 | methoxy | 3-(pyrrolidin-1-yl)propyl | 2,6-dichloro | [141] |
| 142 | methoxy | N-[3-(N-methylpiperazin-1-yl)propyl]carbamoyl | 2,6-dichloro | [142] |
| 143 | methoxy | N-[3-(imidazol-1-yl)propyl]carbamoyl | 2,6-dichloro | [143] |
| 144 | methoxy | N-methylpiperazin-1-yl | 2,6-dichloro | [144] |
| 145 | methoxy | N-(tert-butoxycarbonyl)piperazin-1-yl | 2,6-dichloro | [145] |
| 146 | methoxy | 3-morpholinopropylamino | 2,6-dichloro | [146] |
| 147 | methoxy | 3-imidazol-1-ylpropylamino | 2,6-dichloro | [147] |
| 148 | methoxy | N-methylpiperidin-4-ylmethoxy | 3-dimethylcarbamoyl-2,6-dimethyl | [148] |
| 149 | methoxy | 3-pyrrolidin-1-ylpropoxy | 2-chloro-6-methyl | [149] |
| 150 | methoxy | 3-methoxypropylamino | 2,6-dichloro | [150] |
| 151 | methoxy | 2-aminoethylamino | 2,6-dichloro | [151] |
| 152 | methoxy | N-(2-diethylaminoethyl)-N-methylamino | 2,6-dichloro | [152] |

Notes

[1] The product gave the following data: NMR Spectrum: (DMSOd₆) 1.36(m, 2H), 1.74(d, 3H), 1.86(t, 2H), 2.14(s, 3H), 2.87(d, 2H), 3.96(s, 3H), 4.03(d, 2H), 7.11(t, 1H), 7.29(s, 3H), 7.38(t, 1H), 7.56(d, 1H), 8.08(s, 1H), 8.41(d, 1H), 8.73(s, 1H), 10.59(s, 1H), 13.2(s, 1H); Mass Spectrum: M+H⁺ 456 and 458.

[2] The product gave the following data: NMR Spectrum: (CDCl₃) 1.87(m, 2H), 2.11(m, 3H), 2.78(m, 2H), 2.78(s, 3H), 3.68(d, 2H), 4.07(s, 3H), 4.1(s, 2H), 7.12(m, 2H), 7.43(s, 1H), 7.78(s, 1H), 8.28(m, 1H), 8.75(s, 1H), 13.2(s, 1H); Mass Spectrum: M+H⁺ 490 and 492.

[3] The product gave the following data: NMR Spectrum: (DMSOd₆) 1.83(m, 2H), 2.1(m, 3H), 2.63(m, 2H), 2.7(s, 3H), 3.6(d, 2H), 4.08(s, 3H), 4.1(d, 2H), 7.23(m, 1H), 7.33(s, 1H), 7.46(s, 1H), 7.72(s, 1H), 8.31(d, 1H), 8.74(s, 1H), 13.3(s, 1H); Mass Spectrum: M+H⁺ 490 and 492.

[4] Methylene chloride was used as the reaction solvent. The product gave the following data: NMR Spectrum: (DMSOd₆) 1.34(q, 2H), 1.74(d, 3H), 1.86(t, 2H), 2.15(s, 3H), 2.78(d, 2H), 3.96 (s, 3H), 4.02(d, 2H), 7.08-7.16(m, 1H), 7.19-7.36(m, 3H), 8.06(s, 1H), 8.27(s, 1H), 8.69(s, 1H), 10.56(s, 1H), 12.81(s, 1H); Mass Spectrum: M+H⁺ 440.

TABLE I-continued

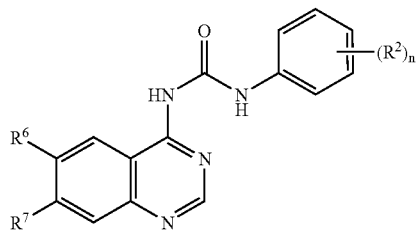

| No. | R⁶ | R⁷ | (R²)ₙ | Note |
|-----|----|----|-------|------|

[5] DMF was used as the reaction solvent. The product gave the following data: NMR Spectrum: (DMSOd$_6$) 1.35(m, 2H), 1.8(m, 5H), 2.15(s, 3H), 2.79(d, 2H), 2.94(s, 3H), 4.03(d, 2H), 7.1-7.35 (m, 5H), 8.03(s, 1H), 8.66(s, 1H), 10.6(s, 1H); Mass Spectrum: M+H⁺ 458.
[6] DMF was used as the reaction solvent. The product gave the following data: NMR Spectrum: (DMSOd$_6$) 1.3-1.5(m, 2H), 1.7-1.8(m, 4H), 1.85(t, 1H), 2.2(s, 3H), 2.8(d, 2H), 3.9(s, 3H), 4.1(br d, 2H), 7.0(t, 1H), 7.3(br s, 1H), 7.4(t, 1H), 7.7(d, 1H), 8.1(br s, 1H), 8.4(d, 1H), 8.8(s, 1H), 10.5 (br s, 1H); Mass Spectrum: M+H⁺ 500 and 502.
[7] The product gave the following data: NMR Spectrum: (CDCl$_3$) 1.47(m, 2H), 1.97(m, 5H), 2.3(s, 3H), 2.88(d, 2H), 3.61(s, 3H), 4.01(d, 2H), 7.24(s, partially obscured by CHCl$_3$ peak), 7.25 (t, partially obscured by CHCl$_3$ peak), 7.37(s, 1H), 7.56(t, 1H), 7.7(d, 1H), 8.17(d, 1H), 8.7(s, 1H), 9.36(s, 1H), 13.2(s, 1H); Mass Spectrum: M+H⁺ 490.
[8] The product gave the following data: NMR Spectrum: (CDCl$_3$) 1.38-1.55(m, 2H), 1.84-2.04 (m, 5H), 2.3(s, 3H), 2.47(s, 3H), 2.91(d, 2H), 3.66(s, 3H), 4.01(d, 2H), 7.05-7.14(m, 1H), 7.17-7.28(m, 4H), 7.4(s, 1H), 7.96(d, 1H), 8.7(s, 1H), 9.24(s, 1H), 12.34(s, 1H); Mass Spectrum: M+H⁺ 436.
[9] The product gave the following data: NMR Spectrum: (DMSOd$_6$ and CD$_3$COOH) 1.5-1.67(q, 2H), 1.93-2.17(m, 3H), 2.24(s, 6H), 2.71(s, 3H), 2.93(t, 2H), 3.37(d, 2H), 3.95(s, 3H), 4.09(d, 2H), 7.1(s, 3H), 7.31(s, 1H), 8.07(s, 1H), 8.66 (d, 1H); Mass Spectrum: M+H⁺ 450.
[10] The product gave the following data: NMR Spectrum: (CDCl$_3$) 1.43(m, 2H), 1.5(s, 9H), 1.82(m, 5H), 2.28(s, 3H), 2.89(d, 2H), 3.32(s, 3H), 4.0(d, 2H), 7.2(m, 3H), 7.5(m, 2H), 7.57(s, 1H), 8.62(s, 1H), 9.9(s, 1H). 12.35(s, 1H); Mass Spectrum: M+H⁺ 478.
[11] The product gave the following data: NMR Spectrum: (CDCl$_3$) 1.45(m, 2H), 1.59(m, 4H), 2.11(m, 2H), 2.33(s, 6H), 2.4(br s, 4H), 2.5(t, 2H), 3.23(s, 3H), 4.22(t, 2H), 7.14(m, 3H), 7.28(s, 1H), 7.62(s, 1H), 8.66(s, 1H), 10.16(s, 1H), 12.08(s, 1H); Mass Spectrum: M+H⁺ 513.

The 4-amino-6-methoxy-7-(3-piperidinopropoxy) quinazoline used as a starting material was prepared as follows:

Sodium hydride (60% suspension in mineral oil, 1.44 g) was added portionwise during 20 minutes to a solution of 7-benzyloxy-6-methoxy-3,4-dihydroquinazolin-4-one (International Patent Application WO 97/22596, Example 1 thereof; 8.46 g) in DMF (70 ml). The mixture was stirred at ambient temperature for 1.5 hours. Chloromethyl pivalate (5.65 g) was added dropwise and the mixture was stirred at ambient temperature for 2 hours. The mixture was diluted with ethyl acetate (100 ml) and poured onto a mixture (400 ml) of ice and water containing 2N aqueous hydrochloric acid (4 ml). The organic layer was separated and the aqueous layer was extracted with ethyl acetate. The combined extracts were washed with brine, dried over magnesium sulphate and evaporated. The residue was triturated under a mixture of diethyl ether and petroleum ether (b.p. 60-80° C.) and the resultant solid was collected and dried under vacuum. There was thus obtained 7-benzyloxy-6-methoxy -3-pivaloyloxymethyl-3,4-dihydroquinazolin-4-one (10 g); NMR Spectrum: (DMSOd$_6$) 1.11 (s, 9H), 3.89 (s, 3H), 5.3 (s, 2H), 5.9 (s, 2H), 7.27 (s, 1H), 7.35 (m, 1H), (m,1H), 7.47 (t,2H), 7.49 (d, 2H), 7.51 (s, 1H), 8.34 (s, 1H).

A mixture of a portion (7 g) of the material so obtained, 10% palladium-on-charcoal catalyst (0.7 g), DMF (50 ml), methanol (50 ml), acetic acid (0.7 ml) and ethyl acetate (250 ml) was stirred under an atmosphere pressure of hydrogen for 40 minutes. The catalyst was removed by filtration and the solvent was evaporated. The residue was triturated under diethyl ether and the resultant solid was collected and dried under vacuum. There was thus obtained 7-hydroxy-6-methoxy-3-pivaloyloxymethyl-3,4-dihydroquinazolin-4-one (4.36 g); NMR Spectrum: DMSOd$_6$) 1.1 (s, 9H), 3.89 (s, 3H), 5.89 (s, 2H), 7.0 (s, 1H), 7.48 (s,1H), 8.5 (s, 1H).

Diethyl azodicarboxylate (3.9 ml) was added dropwise to a stirred mixture of 7-hydroxy-6-methoxy-3-pivaloyloxymethyl-3,4-dihydroquinazolinone (5 g), 3-bromopropanol (2.21 ml), triphenylphosphine (6.42 g) and methylene chloride (50 ml) and the mixture was stirred at ambient temperature for 2 hours. The mixture was evaporated and the residue was purified by column chromatography on silica using a 19:1 mixture of methylene chloride and methanol as eluent. There was thus obtained 7-(3-bromopropoxy)-6-methoxy-3-pivaloyloxymethyl-3,4-dihydroquinazolin-4-one (6 g); NMR Spectrum: (DMSOd$_6$) 1.12 (s, 9H), 2.32 (t, 2H), 3.7 (t, 2H), 3.9 (s, 3H), 4.25 (t, 2H), 5.9 (s,2H), 7.20 (s, 1H), 7.61 (s, 1H), 8.36 (s, 1H).

A mixture of a portion (2.89 g) of the material so obtained and piperidine (10 ml) was stirred and heated to 100° C. for 1 hour. The mixture was evaporated and the residue was partitioned between methylene chloride and a saturated aqueous ammonium chloride solution. The organic phase was washed with brine, dried over magnesium sulphate and evaporated. There was thus obtained 6-methoxy-7-(3-piperidinopropoxy)3-pivaloyloxymethyl-3,4-dihydroquinazolin-4-one (2.4 g); NMR Spectrum: (DMSOd$_6$) 1.15 (s, 9H), 1.35-1.5 (m, 1H), 1.6-1.8 (m, 3H), 1.8-1.9 (d, 2H), 2.2-2.3 (m, 2H), 2.95 (t,2H), 3.25 (t, 2H), 3.55 (d, 2H), 3.95 (s, 3H), 4.25 (t, 2H), 5.94 (s, 2H), 7.24 (s, 1H), 7.56 (s, 1H), 8.35 (s, 1H).

A mixture of the material so obtained and a 7N solution of ammonia in methanol (50 ml) was stirred at ambient temperature for 16 hours. The mixture was evaporated and the residue was triturated under diethyl ether. The resultant solid was isolated, washed in turn with diethyl ether and a 1:1 mixture of diethyl ether and methylene chloride and dried under vacuum. There was thus obtained 6-methoxy-7-(3-piperidinopropoxy)-3,4-dihydroquinazolin-4-one (1.65 g); NMR Spectrum: (DMSOd$_6$) 1.3-1.4 (m, 2H), 1.4-1.55 (m, 4H), 1.85-1.95 (m, 2H), 2.35 (br s, 4H), 2.4 (t, 2H), 3.9 (s, 3H), 4.15 (t, 2H), 7.11 (s, 1H), 7.44 (s, 1H), 7.9 (s, 1H).

A mixture of the material so obtained, thionyl chloride (15 ml) and DMF (1.5 ml) was heated to reflux for 3 hours. The mixture was evaporated. Toluene was added and the mixture was again evaporated. The residue was partitioned between methylene chloride and a saturated aqueous sodium bicarbonate solution (the basicity of which was adjusted to pH10 by adding 6N aqueous sodium hydroxide). The organic layer was separated, washed with brine, dried over magnesium sulphate and evaporated. There was thus obtained 4-chloro-6-methoxy-7-(3-piperidinopropoxy)quinazoline (1.2 g); NMR Spectrum: (DMSOd$_6$) 1.35-1.45 (m, 2H), 1.5-1.6 (m, 4H), 1.9-2.05 (m, 2H), 2.4 (br s, 4H), 2.45 (t, 2H), 4.0 (s, 3H), 4.29 (t, 2H), 7.41 (s, 1H), 7.46 (s, 1H), 8.9 (s, 1H).

A portion (0.5 g) of the material so obtained was dissolved in a 1M solution of ammonia in isopropanol (10 ml). Liquid ammonia (1 ml) was added and the reaction mixture was sealed in a Carius tube. The reaction mixture was heated to 120° C. for 16 hours. The Carius tube was cooled and opened and the reaction mixture was evaporated. The residue was stirred under a 2N aqueous sodium hydroxide solution for 1 hour. The resultant solid was isolated and washed in turn with water and methyl tert-butyl ether. There was thus obtained 4-amino-6-methoxy-7-(3-piperidinopropoxy)quinazoline (0.225 g); NMR Spectrum: (DMSOd$_6$) 1.37 (d, 2H), 1.49 (t, 4H), 1.91 (m, 2H), 2.3 (s, 4H), 2.37 (t, 2H), 3.86 (s, 3H), 4.1 (t, 2H), 7.04 (s, 1H), 7.38 (s, 2H), 7.54 (s, 1H), 8.22 (s, 1H); Mass Spectrum: M+H$^+$ 317.

[12] Acetonitrile was used as the reaction solvent. The product gave the following data: NMR Spectrum: (CDCl$_3$) 2.1 (m, 2H), 2.5 (br s, 4H), 2.7 (t, 2H), 3.75 (t, 4H), 4.25 (t, 2H), 7.15 (d, 1H), 7.3 (m, 2H), 7.5 (d, 2H), 8.1 (d, 1H), 8.85 (s, 1H), 9.05 (s, 1H), 12.1 (s, 1H); Mass Spectrum: M+H$^+$ 476 and 478.

The 4-amino-7-(3-morpholinopropoxy)quinazoline used as a starting material was prepared as follows:

A solution of 2-amino-4-fluorobenzoic acid (3 g) in formamide (30 ml) was heated to 150° C. for 6 hours. The reaction mixture was poured onto a 1:1 mixture of ice and water (250 ml) and the precipitated solid was collected, washed with water and dried to give 7-fluoro-3,4-dihydroquinazolin-4-one (2.6 g)

Sodium metal (4.4 g) was added to benzyl alcohol (100 ml) and the resultant mixture was stirred at ambient temperature for 30 minutes and then and heated to 80° C. for 1 hour. The mixture was cooled to 40° C. and 7-fluoro-3,4-dihydroquinazolin-4-one (7.8 g) was added. The reaction mixture was stirred and heated to 130° C. for 4 hours. The mixture was allowed to cool to ambient temperature and was stirred for a further 18 hours. The solution was quenched with water (800 ml) and acidified to pH3 by the addition of concentrated hydrochloric acid. The resultant precipitate was collected, washed in turn with water and diethyl ether and dried under vacuum for 4 hours at 60° C. There was thus obtained 7-benzyloxy-3,4-dihydroquinazolin-4-one (7.02 g).

A mixture of the material so obtained, phosphorus pentasulphide (12.5 g) and pyridine (350 ml) was stirred and heated to reflux for 8 hours. After cooling, the mixture was poured into water (1 L). The precipitate was collected and washed with water. The solid so obtained was dissolved in 6N aqueous sodium hydroxide solution and the solution was filtered. The filtrate was acidified to pH2 by the addition of 6N aqueous hydrochloric acid. The resultant precipitate was collected, washed with water and dried under vacuum at 60° C. There was thus obtained 7-benzyloxy-3,4-dihydroquinazolin-4-thione (7.42 g); NMR Spectrum: (DMSOd$_6$) 5.32 (s, 2H), 7.25 (d, 1H), 7.32 (m, 1H), 7.4 (m, 1H), 7.45 (t, 2H), 7.55 (d, 2H), 8.15 (s, 1H), 8.5 (d, 1H).

A portion (3.45 g) of the material so obtained was dissolved in THF (13 ml) and 1N aqueous sodium hydroxide solution (25.7 ml) was added. Methyl iodide (0.97 ml) was added dropwise and the mixture was stirred at ambient temperature for 30 minutes. The mixture was neutralised by the addition of 2N aqueous hydrochloric acid and the mixture was diluted by the addition of water. The resultant solid was collected, washed with water and dried under vacuum to give 7-benzyloxy-4-methylthioquinazoline (3.3 g); NMR Spectrum: (DMSOd$_6$) 2.67 (s, 3H), 5.32 (s, 2H), 7.3-7.45 (m, 5H), 7.5 (d, 2H), 8.05 (d, 1H), 8.9 (s, 1H).

A mixture of a portion (3 g) of the material so obtained and trifluoroacetic acid (30 ml) was heated to reflux for 5 hours. The mixture was evaporated. The residue was suspended in water and solid sodium bicarbonate was added until complete dissolution. The solution was extracted with diethyl ether. The aqueous layer was acidified to pH12 by the addition of 2N aqueous hydrochloric acid and the resultant precipitate was collected, washed in turn with water and diethyl ether and dried under vacuum. There was thus obtained 7-hydroxy-4-methylthioquinazoline (2 g); NMR Spectrum: (DMSOd$_6$) 2.7 (s, 3H), 7.15 (d, 1H), 7.25 (m, 1H), 8.0 (d, 1H), 8.9 (s, 1H).

Diethyl azodicarboxylate (2.92 g) was added dropwise to a stirred mixture of 7-hydroxy-4-methylthioquinazoline (2.5 g), 4-(3-hydroxypropyl)morpholine (*Bull. Soc. Chim. Fr.* 1962, 1117; 2.47 g), triphenylphosphine (4.45 g) and methylene chloride (65 ml). The reaction mixture was stirred at ambient temperature for 1 hour. The mixture was evaporated and the residue was partitioned between a 1:1 mixture of ethyl acetate and diethyl ether and a 1N aqueous hydrochloric acid solution. The aqueous layer was separated, basified to pH9 by the addition of solid sodium bicarbonate and extracted with methylene chloride. The organic layer was separated, washed with water and brine, dried over magnesium sulphate and evaporated. The residue was purified by column chromatography on silica using increasingly polar mixtures of methylene chloride, ethyl acetate and methanol (from 6:3:1 to 5:3:2 to 75:0:25) as eluent. There was thus obtained 4-methylthio-7-(3-morpholinopropoxy)-quinazoline (2.03 g); NMR Spectrum: (DMSOd$_6$, and CF$_3$COOD) 2.2-2.3 (m, 2H), 2.7 (s, 3H), 3.05-3.25 (m, 2H), 3.35 (t, 2H), 3.55 (d, 2H), 3.7 (t, 2H), 4.05 (d, 2H), 4.32 (t, 2H), 7.38 (d, 1H), 7.4. (s, 1H), 8.1 (d, 1H), 9.05 (d, 1H); Mass Spectrum: M+H$^+$ 320.

A mixture of a portion (0.5 g) of the material so obtained and a solution of ammonia gas in methanol (7M; 50 ml) was sealed in a pressure vessel and heated to 120° C. for 16 hours. The mixture was cooled to ambient temperature and evaporated. The residue was purified by column chromatography on silica using increasingly polar mixtures of methylene chloride, methanol and a 1% aqueous ammonium hydroxide solution as eluent. The material so obtained was triturated under diethyl ether and the resultant solid was isolated, washed with diethyl ether and dried under vacuum. There was thus obtained 4-amino -7-(3-morpholinopropoxy)quinazoline (0.35 g); NMR Spectrum: (CDCl$_3$) 2.0-2.15 (m, 2H), 2.5 (br s, 4H), 2.6 (t, 2H), 3.75 (br s, 4H), 4.2 (t, 2H), 5.65 (br s, 2H), 7.1 (d, 1H), 7.2 (s, 1H), 7.65 (d, 1H), 8.55 (s, 1H); Mass Spectrum: M+H$^+$ 280.

[13] Acetonitrile was used as the reaction solvent. The product gave the following data: NMR Spectrum: (CDCl$_3$) 2.05 (m, 2H), 2.75 (t, 2H), 3.0-3.15 (m, 8H), 4.2 (t, 2H), 7.1 (d, 1H), 7.2-7.35 (m, 2H), 7.5 (d, 2H), 8.2 (d, 1H), 8.8 (s, 1H), 9.45 (s, 1H); Mass Spectrum: M+H$^+$ 524 and 526; Elemental Analysis: Found C, 50.0; H4.4; N, 13.3; $C_{22}H_{23}N_5O_4Cl_2S$ requires C, 50.39; H, 4.42; N, 13.35%.

The 4-amino-7-[3-(1,1-dioxotetrahydro-4H-1,4-thiazin-4-yl)propoxy]quinazoline used as a starting material was prepared as follows:

A mixture of 3-aminopropan-1-ol (0.650 ml) and divinyl sulphone (1 g) was heated to 110° C. for 45 minutes. The mixture was allowed to cool to ambient temperature and was purified by column chromatography on silica using a 19:1 mixture of methylene chloride and methanol as eluent. There was thus obtained 3-(1,1-dioxotetrahydro-4H-1,4-thiazin-4yl)propan-1-ol(0.8 g); NMR Spectrum: (CDCl$_3$) 1.7-1.8 (m, 2H), 2.73 (t, 2H), 3.06 (br s, 8H), 3.25 (s, 1H), 3.78 (t, 2H); Mass Spectrum: M+H$^+$ 194.

Diethyl azodicarboxylate (3.3 ml) was added dropwise to a stirred mixture of 7-hydroxy-4methylthioquinazoline (1.34 g), 3-(1,1-dioxotetrahydro4H-1,4-thiazin-4-yl)propan-1-ol (2.03 g), triphenylphosphine (5.51 g) and methylene chloride (100 ml). The reaction mixture was stirred at ambient temperature for 4 hours. The mixture was evaporated and the residue was purified by column chromatography on silica using initially ethyl acetate and then a 24:1 mixture of ethyl acetate and ethanol as eluent. There was thus obtained 7-[3-(1,1-dioxotetrahydro-4H-1,4-thiazin-4-yl)propoxy]-4-methylthioquinazoline (1.79 g); NMR Spectrum: (CDCl$_3$) 2.05 (m, 2H), 2.7 (s, 3H), 2.73 (t, 2H), 3.05 (m, 8H), 4.2 (t, 2H), 7.15 (m, 1H), 7.2 (d, 1H), 8.0 (d, 1H), 8-9 (s, 1H); Mass Spectrum: M+H$^+$ 368.

Using an analogous procedure to that described in the last paragraph of Note [12] immediately above, a portion (0.5 g) of the material so obtained was reacted with ammonia gas in methanol. The reaction product was purified by column chromatography on silica using increasingly polar mixtures of chloroform and methanol as eluent. There was thus obtained 4-amino-7-[3-(1,1-dioxotetrahydro-4H-1,4-thiazin-4yl)propoxy]quinazoline (0.45 g); NMR Spectrum (CDCl$_3$) 2.05 (m, 2H), 2.75 (t, 2H), 3.0-3.1 (m, 8H), 4.2 (t, 2H), 5.5 (br s, 2H), 7.15 (m, 1H), 7.2 (s, 1H), 7.65 (d, 1H), 8.6 (s, 1H); Mass Spectrum: M+H$^+$ 337.

[14] Acetonitrile was used as the reaction solvent. The product gave the following data: NMR Spectrum: (DMSOd$_6$ and CF$_3$COOD) 3.0-3.4 (m, 2H), 3.4 (br d, 2H), 3.6-3.7 (m, 2H), 3.95 (br d, 2H), 4.25 (s, 2H), 5.2 (s, 2H), 7.32 (t, 1H), 7.5 (d, 2H), 7.5-7.6 (m, 2H), 8.9 (d, 1H), 9.2 (s, 1H); Mass Spectrum: M+H$^+$ 486 and 488; Elemental Analysis: Found C, 55.4; H, 4.3; N, 14.1; $C_{23}H_{21}N_5O_3Cl_2$ 0.6 H$_2$O requires C, 55.57; H, 4.50; N, 14.09%

The 4-amino-7-(4-morpholinobut-2-yn-1-yloxy)quinazoline used as a starting material was prepared as follows:

Diethyl azodicarboxylate (2.46 ml) was added dropwise to a stirred mixture of 7-hydroxy-4-methylthioquinazoline (1.2 g), 4-morpholinobut-2-yn-1-ol (J. Amer. Chem. Soc. 1957, 79, 6184-1.26 g), triphenylphosphine (4.09 g) and methylene chloride (35 ml). The reaction mixture was stirred at ambient temperature for 3 hours. The mixture was evaporated and the residue was purified by column chromatography on silica using initially methylene chloride and then a 19:1 mixture of methylene chloride and methanol as eluent. The material so obtained was triturated under diethyl ether. The resultant solid was collected and dried under vacuum. There was thus obtained 4-methylthio-7-(4-morpholinobut-2-yn-1-yloxy)quinazoline (1.3 g); NMR Spectrum: (CDCl$_3$) 2.5 (t, 4H), 2.7 (s, 3H), 3.32 (t, 2H), 3.7 (t, 4H), 4.9 (t, 2H), 7.2 (d, 1H), 7.35 (d, 1H), 8.0 (d, 1H), 8.9 (s, 1H); Mass Spectrum: M+H$^{30}$ 330.

Using an analogous procedure to that described in the last paragraph of Note [12] above, a portion (0.5 g) of the material so obtained was reacted with a saturated solution of ammonia gas in methanol. The reaction product was purified by column chromatography on silica using increasingly polar mixtures of methylene chloride, methanol and a 1% aqueous ammonium hydroxide solution as eluent. There was thus obtained 4-amino-7-(4-morpholinobut-2-yn-1-yloxy)quinazoline (0.283 g); NMR Spectrum: (DMSOd6) 2.4 (m, 4H), 3.3 (t, 2H), 3.5 (m, 4H), 5.0 (s, 2H), 7.15 (m, 1H), 7.18 (d, 1H), (d, 1H), 7.6 (br s, 2H), 8.15 (d, 1H), 8.32 (s, 1H); Mass Spectrum: M+H$^+$ 321; Elemental Analysis: Found C, 63.8; H 6.1; N, 18.7; $C_{16}H_{18}N_4O_2$ 0.2 H$_2$O requires C, 63.65; H6.14; N, 18.55%.

[15] Acetonitrile was used as the reaction solvent. The product gave the following data: NMR Spectrum: (DMSOd$_6$ and CF$_3$COOD) 3.0-3.1 (m, 2H), 3.4 (d, 2H), 3.65 (t, 2H), 3.85 (d, 2H), 4.0 (d, 2H), 4.95 (br s, 2H), 6.0 (m, 1H), 6.3 (m, 1H), 7.4 (t, 1H), 7.45 (s, 1H), 7.55 (m, 1H), 7.6 (d, 2H), 8.85 (d, 1H), 9.17 (s, 1H); Mass Spectrum: M+Na$^+$ 510 and 512; Elemental Analysis: Found C, 56.2; H, 4.7; N, 14.2; $C_{23}H_{23}N_5O_3Cl_2$ requires C, 56.57; H. 4.75 N, 14.34%.

The 4-amino-7-[(E)-4morpholinobut-2-en-1-yloxy] quinazoline used as a staring material was prepared as follows:

Using an analogous procedure to that described in the second last paragraph of Note [12] above, (E)-4-morpholinobut-2-en-1-ol (J. Med. Chem., 1972, 15 110-112; 1.27 g), was reacted with 7-hydroxy-4-methylthioquinazoline (1.2 g) to give 4-methylthio -7-[(E)-4-morpholinobut-2-en-1-yloxy] quinazoline (1.15 g); NMR Spectrum: (CDCl$_3$) 2.45 (br s, 4H), 2.7 (s, 3H), 3.05 (d, 2H), 3.7 (t, 4H), 4.7 (d, 2H), 5.9 (m, 2H), 7.15-7.25 (m, 2H), 7.95 (d, 1H), 8.9 (d, 1H); Mass Spectrum: M+H$^+$ 332.

Using an analogous procedure to that described in the last paragraph of Note [12] above, 4-methylthio-7-[(E)-4-morpholinobut-2-en-1-yloxy]quinazoline (0.5 g) was reacted with a saturated solution of ammonia gas in methanol. The reaction product was purified by column chromatography on silica using increasingly polar mixtures of methylene chloride, methanol and a 1% aqueous ammonium hydroxide solution as eluent. There was thus obtained 4-amino-7-[(E)-4-morpholinobut-2-en-1-yloxy]quinazoline (0.372 g); NMR Spectrum: (DMSOd$_6$) 2.35 (br s, 4H), 3.0 (br s, 2H), 3.56 (t, 4H), 4.7 (br s, 2H), 5.9 (br s, 2H), 7.05 (s, 2H), 7.1 (m, 1H), 7.6 (br s, 2H), 8.12 (d, 1H), 8.3 (s, 1H), Mass Spectrum: M+Na$^+$ 323; Elemental Analysis: Found C, 63.1; H) 6.7; N, 18.4; $C_{16}H_{20}N_4O_2$0.2 H$_2$O requires C, 63.22; H. 6.76; N, 18.51%.

[16] Acetonitrile was used as the reaction solvent and the reaction mixture was heated to 35° C. for 7 hours and then to 50° C. for 5 hours. The resultant precipitate was collected, washed in turn with acetonitrile and diethyl ether and dried. The product gave the following data: NMR Spectrum: (DMSOd$_6$ and CF$_3$COOD) 1.4 (m, 1H), 1.7 (m, 3H), 1.9 (m, 2H), 3.1 (t, 2H), 3.65 (m, 4H), 4.05 (s, 3H), 4.65 (t, 2H), 7.45 (t, 1H), 7.52 (s, 1H), 7.62 (d, 2H), 8.3 (s, 1H), 9.05 (s, 1H); Mass Spectrum: M+H$^+$ 490 and 492.

The 4-amino-6-methoxy-7-(2-piperidinoethoxy)quinazoline used as a starting material was prepared as follows:

A mixture of 7-benzyloxy-6-methoxy-3,4-dihydroquinazolin-4-one (25.1 g), thionyl chloride (450 ml) and DMF (1 ml) was stirred and heated to reflux for 2 hours. The mixture was evaporated and the residue was dissolved in toluene and the solution was evaporated. The resultant solid was suspended in methylene chloride (500 ml), solid potassium carbonate (39 g) was added and the mixture was stirred for 10 minutes. Water (500 ml) was added and the mixture stirred for another 10 minutes. The methylene chloride layer was separated, dried over magnesium sulphate and evaporated. The residue was purified by column chromatography on silica using increasingly polar mixtures of methylene chloride and ethyl acetate as eluent. There was thus obtained 7-benzyloxy-4-chloro-6-methoxyquinazoline (21.54 g); NMR Spectrum: (DMSOd$_6$) 4.0 (s, 3H), 5.36 (s, 2H), 7.31-7.46 (m, 4H), 7.51 (d, 2H), 7.58 (s, 1H), 8.88 (s, 1H).

A portion (3 g) of the material so obtained was dissolved in a 1M solution of ammonia in isopropanol (50 ml). Liquid ammonia (5 ml) was added and the reaction mixture was sealed in a Carius tube. The reaction mixture was heated to 120° C. for 16 hours. The Carius tube was cooled and opened and the reaction mixture was evaporated. The residue was stirred under a 2N aqueous sodium hydroxide solution for 1 hour. The resultant solid was isolated and washed in turn with water and methyl tert-butyl ether. There was thus obtained 4-amino-7-benzyloxy-6-methoxyquinazoline (2.65 g); NMR Spectrum: (DMSOd$_6$) 3.88 (s, 3H), 3.9 (s, 3H), 7.2 (s, 1H), 7.63 (s, 2H), 7.69 (s, 1H), 8.38 (s, 1H); Mass Spectrum: M+H$^+$ 230.

A mixture of 4-amino-7-benzyloxy-6-methoxyquinazoline (4.15 g) and trifluoroacetic acid (35 ml) was stirred and heated to reflux for 1 hour. The solvent was evaporated, the residue was redissolved in a mixture of methylene chloride and toluene and the solvent was evaporated. The solid so obtained was suspended in water and basified to pH11 by the addition of 2N aqueous sodium hydroxide solution. The mixture was then neutralised to pH7 by the addition of 1N aqueous hydrochloric acid solution. The resultant solid was collected, washed in turn with water and acetonitrile and dried under vacuum over phosphorus pentoxide. There was thus obtained 4-amino-7-hydroxymethoxyquinazoline (2.55 g); NMR Spectrum: (DMSOd$_6$) 3.9 (s, 3H), 7.05 (s, 1H), 7.65 (s, 1H), 8.0 (br s, 2H), 8.35 (s, 1H), 10.0-11.0 (br s, 1H).

A portion (0.15 g) of the material so obtained and triphenylphosphine (0.31 g) were dissolved in DMF (3 ml). TBF (3 ml) was added causing partial precipitation of the starting material. A solution of N-(2-hydroxyethyl)piperidine (0.111 g) in THF (1 ml) was added followed by diethyl azodicarboxylate (0.186 ml) and the reaction mixture was stirred at ambient temperature for 30 minutes. Further portions of triphenylphosphine (0.105 g), N-(2-hydroxyethyl)piperidine (0.02 g) and diethyl azodicarboxylate (0.062 ml) were added and reaction mixture was stirred at ambient temperature for a further 30 minutes. The mixture was evaporated and the residue was purified by column chromatography on silica using increasingly polar mixtures of methylene chloride and methanol as eluent. There was thus obtained the required starting material (0.18 g); NMR Spectrum: (DMSOd$_6$ and CF$_3$COOD) 1.4 (m, 1H), 1.7 (m, 3H), 1.8 (m, 2H), 3.15 (m, 2H), 3.65 (m, 4H), 3.95 (s, 3H), 4.55 (t, 2H), 7.3 (s, 1H), 7.9 (s, 1H), 8.75 (s, 1H), 9.45 (br s, 1H); Mass Spectrum: M+H$^+$ 303.

[17] Acetonitrile was used as the reaction solvent and the reaction mixture was heated to 35° C. for 7 hours and then to 50° C. for 5 hours. The resultant precipitate was collected, washed in turn with acetonitrile and diethyl ether and dried. The product gave the following data: NMR Spectrum: (DMSOd$_6$ and CF$_3$COOD) 2.3 (m, 2H), 3.15 (m, 2H), 3.35 (m, 2H), 3.55 (m, 2H), 3.7 (t, 2H), 4.0 (s, 3H), 4.05 (m, 2H), 4.35 (t, 2H), 7.45 (t, 1H), 7.63 (d, 2H), 8.25 (s, 1H), 8.3 (s, 1H), 8.95 (s, 1H); Mass Spectrum: M+H$^{30}$ 506 and 508.

The 4-amino-6-methoxy-7-(3-morpholinopropoxy) quinazoline used as a starting material was prepared by the reaction of 4-amino-7-hydroxy-6-methoxyquinazoline and N(3-hydroxypropyl)morpholine using an analogous procedure to that described in the last paragraph of Note [16] above. There was thus obtained the required starting material; NMR Spectrum: (DMSOd$_6$ and CF$_3$COOD) 2.25 (m, 2H), 3.15 (m, 2H), 3.35 (m, 2H), 3.55 (m, 2H), 3.7 (t, 2H), 3.95 (s,3H), 4.05 (m, 2H), 4.3 (t, 2H), 7.35 (s, 1H), 7.85 (s, 1H), 8.75 (s, 1H), 9.4 (br s, 1H); Mass Spectrum: M+H$^+$ 319.

[18] Acetonitrile was used as the reaction solvent and the reaction mixture was heated to 35° C. for 7 hours and then to 50° C. for 5 hours. The resultant precipitate was collected, washed in turn with acetonitrile and diethyl ether and dried. The product gave the following data: NMR Spectrum: (DMSOd$_6$, and CF$_3$COOD) 2.3 (m, 2H), 2.95 (s, 3H), 3.2-3.8 (br s, 8H), 3.45 (m, 2H), 4.05 (s, 3H), 4.35 (t, 2H), 7.45 (t, 1H), 7.47 (s, 1H), 7.62 (d, 2H), 8.3 (s, 1H), 9.05 (s, 1H); Mass Spectrum: M+H$^+$ 519 and 521.

The 4-amino-6-methoxy-7-[3-(4-methylpiperazin-1-yl) propoxy]quinazoline used as a starting material was prepared by the reaction of 4-amino-7-hydroxy-6-methoxyquinazoline and 1-(3-hydroxypropyl)-4-methylpiperazine using an analogous procedure to that described in the last paragraph of Note [16] above. There was thus obtained the required starting material; NMR Spectrum: (DMSOd$_6$ and CF$_3$COOD) 2.3 (m, 2H), 2.95 (s, 3H), 3.2-3.8 (br s, 8H), 3.4 (m, 2H), 3.95 (s, 3H), 4.3 (t, 2H), 7.25 (s, 1H), 7.85 (s, 1H), 8.75 (s, 1H), 9.4 (br s, 1H); Mass Spectrum: M+H$^+$ 332.

[19] Acetonitrile was used as the reaction solvent and the reaction mixture was heated to 35° C. for 7 hours and then to 50° C. for 5 hours. The resultant precipitate was collected, washed in turn with acetonitrile and diethyl ether and dried. The product gave the following data: NMR Spectrum: (DMSOd$_6$ and CF$_3$COOD) 1.9 (m, 2H), 2.05 (m, 2H), 2.25 (m, 2H), 3.1 (m, 2H), 3.35 (m, 2H), 3.65 (m, 2H), 4.05 (s, 3H), 4.35 (t, 2H), 7.45 (t, 1H), 7.47 (s, 1H), 7.63 (d, 2H), 8.3 (s, 1H), 9.1 (s, 1H); Mass Spectrum: M+H$^+$ 490 and 492.

The 4-amino-6-methoxy-7-(3-pyrrolidin-1-ylpropoxy) quinazoline used as a starting material was prepared by the reaction of 4-amino-7-hydroxy-6-methoxyquinazoline and N-(3-hydroxypropyl)pyrrolidine using an analogous procedure to that described in the last paragraph of Note [16] above. There was thus obtained the required starting material; NMR Spectrum: (DMSOd$_6$ and CF$_3$COOD) 1.9 (m, 2H), 2.05 (m, 2H), 2.25 (m, 2H), 3.05 (m, (m, 2H), 3.35 (m, 2H), 3.65 (m, 2H), 3.95 (s, 3H), 4.3 (t, 2H), 7.25 (s, 1H), 7.85 (s, 1H), 8.75 (s, 1H), 9.4 (br s, 1H); Mass Spectrum: M+H$^+$ 303.

[20] Acetonitrile was used as the reaction solvent and the reaction mixture was heated to 35° C. for 7 hours and then to 50° C. for 5 hours. The resultant precipitate was collected, washed in turn with acetonitrile and diethyl ether and dried. The product gave the following data: NMR Spectrum: (DMSOd, and CF$_3$COOD) 2.3 (m, 2H), 3.5 (t, 2H), 3.65 (m, 4H), 3.85 (m, 4H), 4.05 (s, 3H), 4.35 (t, 2H), 7.43 (t, 1H), 7.46 (s, 1H), 7.65 (d, 2H), 8.3 (s, 1H), 9.05 (s, 1H); Mass Spectrum: M+H$^+$ 554 and 556.

The 4-amino-7-[3-(1,1-dioxotetrahydro-4 N-1,4-thiazin-4-yl)propoxy]-6-methoxyquinazoline used as a starting material was prepared by the reaction of 4-amino -7-hydroxy-6-methoxyquinazoline and N-(3-hydroxypropyl)-1,1-dioxotetrahydro -4H-1,4-thiazine using an analogous procedure to that described in the last paragraph of Note [16] above. There was thus obtained the required starting material; NMR Spectrum: DMSOd$_6$ and CF$_3$COOD) 2.3 (m, 2H), 3.5 (m, 2H), 3.65 (m, 4H), 3.85 (m, 4H), 3.95 (s, 3H), 4.25 (t, 2H), 7.25 (s, 1H), 7.85 (s, 1H), 8.75 (s, 1H), 9.4 Mass Spectrum: M+H$^+$ 367.

[21] Acetonitrile was used as the reaction solvent and the reaction mixture was heated to 35° C. for 7 hours and then to 50° C. for 5 hours. The resultant precipitate was collected, washed in turn with acetonitrile and diethyl ether and dried. The product gave the following data: NMR Spectrum: (DM- SOd$_6$, and CF$_3$COOD) 2.95 (s, 3H), 3.35 (s, 3H), 3.4 (m, 1H), 3.55 (m, 1H), 3.75 (m, 4H), 4.05 (s, 3H), 4.65 (t, 2H), 7.45 (t, 1H), 7.50 (s, 1H), 7.56 (d, 2H), 8.3 (s, 1H), 9.05 (s, 1H); Mass Spectrum: M+H$^+$ 494 and 496.

The 4-amino-6-methoxy-7-{2-[N-(2-methoxyethyl)-N-methylamino]ethoxy}-quinazoline used as a starting material was prepared by the reaction of 4-amino-7-hydroxy-6-methoxyquinazoline and 2-[N-(2-methoxyethyl)-N-methylamino]ethanol using an analogous procedure to that described in the last paragraph of Note [16] above. There was thus obtained the required starting material; NMR Spectrum: (DMSOd$_6$ and CF$_3$COOD) 2.95 (s, 3H), 3.35 (s, 3H), 3.4 (m, 1H), 3.55 (m, 1H), 3.75 (br m, 4H), 3.95 (s, 3H), (s, 4.55 (t, 2H), 7.25 (s, 1H), 7.85 (s, 1H), 8.75 (s, 1H), 9.45 (br s, 1H); Mass Spectrum: M+H307.

The 2-[N-(2-methoxyethyl)-N-methylamino]ethanol used as a starting material was prepared as follows:

A mixture of 2-methylaminoethanol (5.4 g), 2-bromoethyl methyl ether (10 g), triethylamine (10 ml) and acetonitrile (70 ml) was stirred and heated to reflux for 16 hours. The mixture was cooled to ambient temperature and filtered. The filtrate was evaporated and the residue was triturated under diethyl ether. The organic solution was separated and evaporated to give 2-[N-(2-methoxyethyl)-N-methylamino]ethanol (3 g, 31%); NMR Spectrum: (CDCl$_3$) 2.35 (s, 3H), 2.6 (t, 2H), 2.65 (t, 2H), 3.35 (s, 3H), 3.5 (t, 2H), 3.6 (t, 2H).

[22] Acetonitrile was used as the reaction solvent and the reaction mixture was heated to 35° C. for 7 hours and then to 50° C. for 5 hours. The resultant precipitate was collected, washed in turn with acetonitrile and diethyl ether and dried. The product gave the following data: NMR Spectrum: (DMSOd6, and CF$_3$COOD) 2.3 (m, 2H), 3.05 (s, 3H), 3.35 (t, 2H), 4.05 (s, 3H), 4.4 (t, 2H), 7.45 (m, 2H), 7.65 (d, 2H), 8.29 (s, 1H), 9.1 (s, 1H), Mass Spectrum: M+H$^+$ 499 and 501.

The 4-amino-6-methoxy-7-(3-mesylpropoxy)quinazoline used as a starting material was prepared by the reaction of 4-amino-7-hydroxy-6-methoxyquinazoliine and 3-mesylpropanol using an analogous procedure to that described in the last paragraph of Note [16] above. There was thus obtained the required starting material; NMR Spectrum: (DMSOd$_6$ and CF$_3$COOD) 2.3 (m, 2H), 3.05 (s, 3H), 3.3 (t, 2H), 3.95 (s, 3H), 4.3 (t, 2H), 7.2 (s, 1H), 7.85 (s, 1H), 8.75 (s, 1H), 9.45 (br s, 1H); Mass Spectrum: M+H$^+$ 312.

The 3-mesylpropanol used as a starting material was prepared as follows:

3-Chloroperoxybenzoic acid (25 g) was added in portions to a solution of 3-methylthiopropanol (5 ml) in methylene chloride (100 ml) while maintaining the reaction temperature at 25° C. The mixture was stirred at ambient temperature for 1 hour. The mixture was filtered and the filtrate was diluted with an aqueous solution of sodium sulphite (6.5 g) in water (200 ml). The organic layer was separated and evaporated. The white residue was triturated under acetone and the resultant solution was evaporated to give a solid which was dissolved in methylene chloride. Aluminum oxide (90 Å mesh) was added and the mixture was allowed to stand for 15 minutes. The mixture was filtered and the filtrate was evaporated to give 3-mesylpropanol as a colourless oil (4.46 g); NMR Spectrum: (CDCl$_3$) 1.9-2.1 (br s, 1H), 2.15 (m, 2H), 2.95 (s, 3H), 3.2 (t, 2H), 3.85 (t, 2H).

[23] Acetonitrile was used as the reaction solvent and the reaction mixture was heated to 35° C. for 7 hours and then to 50° C. for 5 hours. The resultant precipitate was collected, washed in turn with acetonitrile and diethyl ether and dried. The product gave the following data: NMR Spectrum: (DMSOd$_6$ and CF$_3$COOD) 2.45 (m, 2H), 4.0 (s, 3H), 4.25 (t, 2H), 4.6 (t, 2H), 7.38 (s, 1H), 7.43 (t, 1H), 7.63 (d, 2H), 7.77 (s, 1H), 8.22 (s, 1H), 8.26 (s, 1H), 9.03 (s, 1H); Mass Spectrum: M+H$^+$ 488 and 490.

The 4-amino-6-methoxy-7-[3-(1,2,3-triazol-1-yl)propoxy]quinazoline used as a starting material was prepared by the reaction of 4-amino-7-hydroxy-6-methoxyquinazoline and N$^1$-(3-hydroxypropyl)-1,2,3-triazole (see Note [106] hereinafter) using an analogous procedure to that described in the last paragraph of Note [16] above. There was thus obtained the required starting material; NMR Spectrum: (DMSOd$_6$ and CF$_3$COOD) 2.4 (m, 2H), 3.95 (s, 3H), 4.15 (t, 2H), 4.6 (t, 2H), 7.15 (s, 1H), 7.75 (s, 1H), 7.85 (s, 1H), 8.2 (s, 1H), 8.75 (s, 1H), 9.45 (br s, 1H); Mass Spectrum: M+H$^+$ 301.

[24] Acetonitrile was used as the reaction solvent and the reaction mixture was heated to 35° C. for 7 hours and then to 50° C. for 5 hours. The resultant precipitate was collected, washed in turn with acetonitrile and diethyl ether and dried. The product gave the following data: NMR Spectrum: (DMSOd$_6$ and CF$_3$COOD) 3.55 (t, 2H), 4.0 (s, 3H), 4.65 (t, 2H), 7.45 (t, 1H), 7.5 (s, 1H), 7.65 (d, 2H), 8.15 (d, 2H), 8.3 (s, 1H), 8.95 (d, 2H), 9.1 (s, 1H), Mass Spectrum: M+H$^+$ 484 and 486.

The 4-amino-6-methoxy-7-[2-(4-pyridyl)ethoxy]quinazoline used as a starting material was prepared by the reaction of 4-amino-7-hydroxy-6-methoxyquinazoline and 4-(2-hydroxyethyl)pyridine (*Zhur. Obshchei. Khim.* 1958, 28, 103-110) using an analogous procedure to that described in the last paragraph of Note [16] above. There was thus obtained the required starting material; NMR Spectrum: (DMSOd$_6$ and CF$_3$COOD) 3.5 (t, 2H), 3.9 (s, 3H), 4.6 (t, 2H), 7.3 (s, 1H), 7.85 (s, 1H), 8.15 (d, 2H), 8.75 (s, 1H), 8.95 (d, 2H), 9.4 (br s, 1H); Mass Spectrum: M+H$^+$ 297.

[25] The product gave the following data: NMR Spectrum: (CDCl$_3$+CD$_3$CO$_2$D) 1.78-1.9 (m, 2H), 2.05-2.3 (m, 3H), 2.64 (t, 2H), 2.7 (s, 3H), 3.59 (d, 2H), 4.04 (s, 3H), 4.1 (d, 2H), 7.25 (s, 1H), 7.44 (s, 2H), 7.74 (s, 1H), 8.2-8.6 (m, partially obscured by CD$_3$CO$_2$H), 8.71 (s, 1H), 12.4 (s, 1H); Mass Spectrum: M+H$^+$ 524 and 526.

[26] The product gave the following data: NMR Spectrum: (CDCl$_3$) 1.41-1.56 (m, 2H), 1.85-2.05 (m, 5H), 2.3 (s, 3H), 2.91 (d, 2H), 3.96 (s, 3H), 4.03 (d, 2H), 6.74 (m, 1H), 7.1 (m, 1H), 7.18 (s, 1H), 7.28 (s, 1H), 8.11 (m, 1H), 8.46 (s, 1H), 8.88 (s, 1H), 12.86 (s, 1H); Mass Spectrum: M+H$^+$ 458.

[27] The product gave the following data: NMR Spectrum: (CDCl$_3$) 1.42-1.58 (m, 2H), 1.87-2.08 (m, 5H), 2.31 (s, 3H), 2.93 (d, 2H), 3.84 (s, 3H), 4.02 (d, 2H), 6.9 (m, 2H), 7.28 (m, 2H), 8.16 (m, 1H), 8.76 (s, 1H), 8.86 (s, 1H), 12.65 (s, 1H); Mass Spectrum: M+H$^+$ 4.58.

[28] Methylene chloride was used as the reaction solvent. The product was obtained as a 1:1 adduct with DMF and gave the following data: NMR Spectrum: (CDCl$_3$) 1.4-1.55 (m, 2H), 1.9-2.1 (m, 5H), 2.3 (s, 3H), 2.88 (s, 3H), 2.93 (s, 3H), 2.9 (m, partially obscured by DMF signal), 3.72 (s, 3H), 3.85 (s, 3H), 3.91 (s, 3H), 4.01 (d, 2H), 6.6 (m, 1H) 6.86 (d, 1H), 7.28 (s, 1H), 7.36 (s, 1H), 7.98 (d, 1H), 8.02 (s, 1H), 8.55 (s, 1H), 8.87 (s, 1H), 12.75 (s, 1H); Mass Spectrum: M+H$^+$ 482 (relating to the parent ion).

[29] The product gave the following data: NMR Spectrum: (CDCl$_3$) 1.4-1.55 (m, 2H), 1.85-2.1 (m, 5H), 2.29 (s, 3H), 2.9 (d, 2H), 3.8 (s, 3H), 3.82 (s, 3H), 3,96 (s, 3H), 4.03 (d, 2H), 6.48 (m, 1H), 6.56 (d, 1H), 7.25 (s, 1H), 7.38 (s, 1H), 8.08 (d, 1H), 8.72 (s, 1H), 9.07 (s, 1H), 12.4 (s, 1H); Mass Spectrum: M+H$^+$ 482.

[30] Methylene chloride was used as the reaction solvent. The product gave the following data: NMR Spectrum: (CDCl$_3$) 1.17 (br s, 12H), 1.4-1.6 (m, 2H), 1.7 (br s, 2H), 1.85-2.1 (m, 5H), 2.3 (s, 3H), 2.91 (d, 2H), 3.3 (s, 3H), 4.01 (d, 2H), 7.2-7.22 (m, 3H), 7.3-7.4 (m, 1H), 7.5 (s, 1H), 8.62 (s, 1H), 9.7 (s, 1H), 11.4 (s, 1H); Mass Spectrum: M+H$^+$ 506.

[31] The product gave the following data: NMR Spectrum: (CDCl$_3$) 1.4-1.55 (m, 2H), 1.85-2.1 (m, 5H), 2.28 (s, 6H), 2.3 (s, 3H), 2.34 (s, 3H), 2.9 (d, 2H), 3,37 (s, 3H), 4.01 (d, 2H), 6.91 (s, 2H), 7.22 (s, 1H), 7.3 (s, 1H), 8.64 (s, 1H), 8.7 (s, 1H), 11.8 (s,1H); Mass Spectrum: M+H$^+$ 464.

[32] The product gave the following data: NMR Spectrum: (CDCl$_3$) 1.44-1.59 (m, 2H), 1.86-2.08 (m, 5H), 2.32 (d, 6H), 2.41 (s, 3H), 2.94 (d, 2H), 3.68 (s, 3H), 4.02 (d, 2H), 6.92 (d, 1H), 7.14 (d, 1H), 7.26 (m, 1H), 7.46 (s, 1H), 7.77 (s, 1H), 8.69 (s, 1H), 9.31 (s, 1H), 12.27 (s, 1H); Mass Spectrum: M+H$^+$ 450.

[33] The product gave the following data: NMR Spectrum: (CDCl$_3$) 1.18 (t, 6H), 1.4-1.55 (m, 2H), 1.85-2.06 (m, 5H), 2.3 (s, 3H),2.69 (q, 4H) 2.9 (d, 2H), 3.3 (s, 3H), 4.03 (d, 2H), 7.1-7.3 (m, 4H), 7.51 (s, 1H), 8.63 (s, 1H), 9.73 (s, 1H), 11.87 (s, 1H); Mass Spectrum: M+H$^+$ 478.

[34] The product gave the following data: NMR Spectrum: (CDCl$_3$) 1.2 (t, 3H), 1.4-1.6 (m, 2H), 1.85-2.06 (m, 5H), 2.3 (s, 6H), 2.7 (q, 2H), 2.92 (d, 2H), 3.32 (s, 3H), 4.02 (d, 2H), 7.1-7.3 (m, 4H), 7.51(s, 1H), 8.65 (s, 1H), 9.77 (s, 1H), 11.97 (s, 1H); Mass Spectrum: M+H$^+$ 464.

[35] The product gave the following data: NMR Spectrum: (CDCl$_3$) 1.51 (m, 2H), 1.9-2.1 (m, 5H), 2.3 (s, 9H), 2.95 (d, 2H), 3.52 (s, 3H), 4.02 (d, 2H), 7.23 (s, 1H), 7.25 (s, 2H), 7.37 (s, 1H), 8.67 (s, 1H), 9.32 (s, 1H), 11.82 (s, 1H); Mass Spectrum: M+H$^+$ 528 and 530.

[36] The product gave the following data: NMR Spectrum: (CDCl$_3$) 1.4-1.56 (m, 2H), 1.84-2.05 (m, 5H), 2.3 (s, 3H), 2.38 (s, 3H), 2.9 (d, 2H), 3.44 (s, 3H), 4.03 (d, 2H), 7.19 (d, 2H), 7.22 (s, 1H), 7.33 (t, 1H), 7.47 (s, 1H), 8.70 (s, 1H), 9.67 (s, 1H), 12.21 (s, 1H); Mass Spectrum: M+H$^+$ 470.

[37] The product gave the following data: N Spectrum: (CDCl$_3$) 1.81 (s, 4H), 2.17 (m, 2H), 2.57 (s, 4H), 2.7 (t, 2H), 3.77 (s, 3H), 4.26 (t, 2H), 7.23-7.45 (m, 2H), 7.38-7.45 (m, 2H), 8.7 (s, 1H), 8.96 (s, 1H), 12.23 (s, 1H); Mass Spectrum: M+H$^+$ 524 and 526.

The 4-amino-6-methoxy-7-(3-pyrrolidin-1-ylpropoxy)quinazoline used as a starting material was prepared as follows:

4-(4-Bromo-2-fluorophenoxy)-7-hydroxy-6-methoxyquinazoline was reacted with 3-pyrrolidin-1-ylpropyl chloride (Chemical Abstracts, volume 128, no. 227441; PCT Patent Application WO 98/13354) using an analogous procedure to that described in the second last paragraph of Note [38] below to give 4-(2-bromo4-fluorophenoxy)-6-methoxy-7-(3-pyrrolidin-1-ylpropoxy)quinazoline; NMR Spectrum: (CDCl$_3$) 1.8 (m, 4H), 2.18 (m, 2H), 2.57 (s, 4H), 2.69 (t, 2H), 4.05 (s, 3H), 4.3 (t, 2H), 7.16 (m, 1H), 7.28-7.36 (m, 2H), 7.44 (m, 1H), 7.57 (s, 1H), 8.6 (s, 1H); Mass Spectrum: M+H$^+$ 476 & 478.

The material so obtained was reacted with ammonia using an analogous procedure to that described in the last paragraph of Note [38] below to give the required starting material; NMR Spectrum: (CDCl$_3$) 1.8 (m, 4H), 2.14 (m, 2H), 2.54 (t, 4H), 2.67 (t, 2H), 3.96 (s, 3H), 4.23 (t, 2H), 5.54 (s, 2H), 6.91 (s, 1H), 7.23 (s, 1H), 8.52 (s, 1H); Mass Spectrum: M+H$^+$ 303.

[38] The product gave the following data: NMR Spectrum: (CDCl$_3$) 1.68. (s, 4H), 2.11 (m, 2H), 2.3 (s, 3H), 2.4-2.6 (m, 6H), 3.72 (s, 3H), 4.24 (t, 2H), 7.31 (s, 2H), 7.43 (s, 2H), 8.71 (s, 1H), 9.07 (s, 1H), 12.27 (s, 1H); Mass Spectrum: M+H$^+$ 553, 555 and 557.

The 4-amino-6-methoxy-7-[3-(4-methylpiperazin-1-yl)propoxy]quinazoline used as a starting material was prepared as follows:

A mixture of 7-acetoxy-6-methoxyquinazolin-4-one (International Patent Application WO 96/15118, Example 17 thereof; 15 g), thionyl chloride (225 ml) and DMF (5 ml) was stirred and heated to 90° C. for 4 hours. The mixture was cooled to ambient temperature and the thionyl chloride was evaporated. The material so obtained was dissolved in toluene and the solution was washed with a saturated aqueous sodium bicarbonate solution. The organic solution was dried over magnesium sulphate and evaporated. There was thus obtained 7-acetoxy-4-chloro-6-methoxyquinazoline (13.2 g) which was used without further purification.

A mixture of the material so obtained was reacted with 2-bromo-4-fluorophenol using an analogous procedure to that described in the second last paragraph of the portion of Example 1 above which is concerned with the preparation of starting materials. There was thus obtained 7-acetoxy-4-(2-bromo-4-fluorophenoxy)-6-methoxyquinazoline (14.7 g).

A mixture of a portion (3 g) of the material so obtained, concentrated ammonium hydroxide solution (0.88 g/ml, approximately 14M; 60 ml) and methanol (120 ml) was stirred at ambient temperature for 16 hours. The mixture was evaporated and the residue was triturated under diethyl ether. There was thus obtained 4-(2-bromo4-fluorophenoxy) -7-hydroxy-6-methoxyquinazoline (2.2 g); NMR Spectrum: (DMSOd$_6$) 3.99 (s, 3H), 7.25 (s, 1H), 7.39 (m, 1H), 7.54 (m, 2H), 7.78 (m, 1H), 8.47 (s, 1H), 10.82 (s, 1H); Mass Spectrum: M−R$^-$ 363 & 365.

A mixture of 4-(2-bromo-4-fluorophenoxy)-7-hydroxy-6-methoxyquinazoline (0.94 g), 3-(4-methylpiperazin-1-yl)propyl chloride (0.5 g), potassium carbonate (1.42 g) and DMF (20 ml) was stirred and heated to 65° C. for 16 hours. The mixture was filtered and evaporated. The resulting oil was purified by column chromatography on silica using increasingly polar mixtures of methylene chloride and a 2M methanolic ammonia solution as eluent. There was thus obtained 4-(2-bromo-4-fluorophenoxy)-6-methoxy-7-[3-(4-methylpiperazin-1-yl)propoxy]quinazoline (0.84 g); NMR Spectrum: (CDCl$_3$) 1.72 (s, 4H), 2.13 (m, 2H), 2.31 (s, 3H), 2.4-2.6 (m, 6H), 4.05 (s, 3H), 4.29 (t, 2H), 7.16 (m, 1H), 7.3 (s, 1H), 7.35 (s, 1H), 7.44 (m, 1H), 7.57 (s, 1H), 8.6 (s, 1H); Mass Spectrum: M+H$^{30}$ 505 & 507.

A mixture of the material so obtained, liquid ammonia (1 ml) and a 2M solution of ammonia in isopropanol (15 ml) was sealed in a Carius tube and heated to 120° C. for 16 hours. The mixture was cooled and evaporated. The residue was stirred under a 2N aqueous sodium hydroxide solution (200 ml) for 1 hour. The resultant solid was isolated and washed in turn with water (400 ml) and with methyl tert-butyl ether. There was thus obtained the required starting material (0.55 g); NMR Spectrum: (CDCl$_3$) 1.81 (s, 4H), 2.1 (m, 2H), 2.29 (s, 3H), 2.4-2.6 (m, 6H), 3.96 (s, 3H), 4.22 (t, 2H), 5.46 (s, 2H), 6.9 (s, 1H), 7.22 (s, 1H), 8.51 (s, 1H); Mass Spectrum: M+H$^+$ 332.

The 3-(4-methylpiperazin-1-yl)propyl chloride used as an intermediate was prepared by the reaction of 1-methylpiperazine with 1-bromo-3-chloropropane using an analogous procedure to that described in Note [42] hereinafter for the preparation of 3-morpholinopropyl chloride.

[39] The product gave the following data: NMR Spectrum: (CDCl$_3$) 1.42 (q, 2H), 1.58 (m, 4H), 2.09 (m, 2H), 2.38 (s, 4H), 2.49 (t, 2H), 3.63 (s, 3H), 4.23 (t, 2H), 7.18-7.27 (m, 2H), 7.37 (m, 2H), 7.41 (s, 1H), 8.71 (s, 1H), 9.3 (s, 1H), 12.34 (s, 1H); Mass Spectrum: M+H$^+$ 504 and 506.

[40] The product gave the following data: NMR Spectrum: (CDCl$_3$) 1.84 (m, 4H), 2.17 (m, 2H), 2.56 (s, 4H), 2.68 (t, 2H), 3.69 (s, 3H), 4.28 (t, 2H), 6.99 (t, 2H), 7.2-7.3 (m, 2H), 7.38 (s, 1H), 8.71 (s, 1H), 9.3 (s, 1H), 12.04 (s, 1H); Mass Spectrum: M+H+ 458.

[41] The product gave the following data: NMR Spectrum: (CDCl₃) 1.43 (m, 2H), 1.57-1.76 (m, 4H), 2.12 (m, 2H), 2.47 (s, 4H), 2.54 (t, 2H), 3.7 (s, 3H), 4.23 (t, 2H), 6.94-7.03 (m, 2H), 7.2-7.31 (m, 2H), 7.37 (s, 1H), 8.71 (s, 1H), 9.26 (s, 1H), 12.03 (s, 1H); Mass Spectrum: M+H+ 472.

[42] The product gave the following data: NMR Spectrum: (CDCl₃) 2.11 (m, 2H), 2.49 (br s, 4H), 2.57 (t, 2H), 3.73 (m, 7H), 4.26 (t, 2H), 7.0 (t, 2H), 7.27 (m, 1H), 7.3 (s, 1H), 7.38 (s, 1H), 8.73 (s, 1H), 9.24 (s, 1H), 12.04 (s, 1H); Mass Spectrum: M+H+ 474.

The 4-amino-6-methoxy-7-(3-morpholinopropoxy)quinazoline used as a starting material was prepared as follows:

4-(4-Bromo-2-fluorophenoxy)-7-hydroxy-6-methoxyquinazoline was reacted with 3-morpholinopropyl chloride using an analogous procedure to that described in the second last paragraph of Note [38] above to give 4-(2-bromo4-fluorophenoxy)-6-methoxy-7-(3-morpholinopropoxy)quinazoline; NMR Spectrum: (CDCl₃) 2.13 (m, 2H), 2.49 (t, 4H), 2.58 (t, 2H), 3.74 (t, 4H), 4.06 (s, 3H), 4.29 (t, 2H), 7.15 (m, 1H), 7.31 (m, 1H), 7.37 (s, 1H), 7.43 (m, 1H), 8.58 (s, 1H), 8.6 (s, 1H); Mass Spectrum: M+H+ 492 & 494.

The material so obtained was reacted with ammonia using an analogous procedure to that described in the last paragraph of Note [38] above to give the required starting material; NMR Spectrum: (CDCl₃) 2.09 (m, 2H), 2.48 (t, 4H), 2.55 (t, 2H), 3.61 (t, 4H), 3.96 (s, 3H), 4.24 (t, 2H), 5.44 (s, 2H), 6.9 (s, 1H), 7.24 (s, 1H), 8.52 (s, 1H).

The 3-morpholinopropyl chloride used as an intermediate was prepared as follows:

Morpholine (52.2 ml) and 1-bromo-3-chloropropane (30 ml) were taken up in dry toluene (180 ml) and stirred and heated to 70° C. for 3 hours. The resultant precipitate was filtered off and the filtrate was evaporated to give an orange oil which was purified by vacuum distillation collecting fractions at 62° C./5 mmHg and 58° C./2 mmHg. The required compound was obtained as an oil (37.9 g), NMR Spectrum: 1.85 (m, 2H), 2.3 (t, 4H), 2.38 (t, 2H), 3.53 (t, 4H), 3.65 (t, 2H); M/s: M+H+ 164.

[43] The product gave the following data: NMR Spectrum: (CDCl₃) 1.71 (s, 4H), 2.12 (m, 2H), 2.31 (s, 3H), 2.42-2.62 (m, 6H), 3.7 (s, 3H), 4.27 (t, 2H), 7.0 (m, 2H), 7.21-7.32 (m, 2H), 7.38 (s, 1H), 8.73 (s, 1H), 9.62 (s, 1H), 12.08 (s, 1H); Mass Spectrum: M+H+ 487.

[44] The product gave the following data: NMR Spectrum: (CDCl₃) 1.46 (m, 2H), 1.64 (m, 4H), 2.55 (t, 4H), 2.9 (t, 2H), 3.68 (s, 3H), 4.3 (t, 2H), 6.95-7.04 (m, 3H), 7.28 (M, 1H), 7.4 (s, 1H), 8.73 (s, 1H), 9.38 (s, 1H), 12.1 (s, 1H); Mass Spectrum: M+H+ 458.

[45] The product gave the following data: NMR Spectrum: (CDCl₃) 1.49 (m, 2H), 1.63 (m, 4H), 2.56 (t, 4H), 2.8 (t, 2H), 3.7 (s, 3H), 4.32 (t, 2H), 7.3 (s, 1H), 7.34 (s, 1H), 7.43 (s, 2H), 8.72 (s, 1H), 9.22 (s, 1H), 12.32 (s, 1H); Mass Spectrum: M+H+ 524 and 526.

[46] The product gave the following data: NMR Spectrum: (CDCl₃) 1.8 (m, 4H), 2.15 (m, 2H), 2.53 (s, 4H), 2.66 (t, 2H), 3.58 (s, 3H), 4.25 (t, 2H), 7.29 (s, 1H), 7.32-7.45 (m, 3H), 7.54 (d, 1H), 8.68 (s, 1H), 9.38 (s, 1H), 12.55 (s, 1H); Mass Spectrum: M+H+ 507.

[47] The product gave the following data: NMR Spectrum: (CDCl₃) 2.38 (s, 6H), 2.88 (t, 2H), 3.57 (s, 3H), 4.27 (t, 2H), 6.98 (t, 3H), 7.27 (s, 1H), 7.51 (s, 1H), 8.71 (s, 1H), 2.88 (s, 1H), 12.25 (s, 1H); Mass Spectrum: M+H+ 418.

The 4-amino-6-methoxy-7-(2-dimethylaminoethoxy)quinazoline used as a starting material was prepared as follows:

4-(4-Bromo2-fluorophenoxy)7-hydroxy-6-methoxyquinazoline was reacted with 2-dimethylaminoethyl chloride using an analogous procedure to that described in the second last paragraph of Note [38] above to give 4-(2-bromofluorophenoxy)-7-(2-dimethylaminoethoxy)-6-methoxyquinazoline; NMR Spectrum: (CDCl₃) 2.39 (s, 6H), 2.9 (t, 2H), 4.04 (s, 3H), 4.31 (t, 2H), 7.22 (t, 1H), 7.32 (s, 1H), 7.41 (m, 2H), 7.52 (s, 1H), 8.6 (s, 1H); Mass Spectrum: M+H+ 436 & 438.

The material so obtained was reacted with ammonia using an analogous procedure to that described in the last paragraph of Note [38] above to give the required starting material; NMR Spectrum: (DMSOd₆) 2.21 (s, 6H), 2.68 (t, 2H), 3.87 (s, 3H), 4.14 (t, 2H), 7.07 (s, 1H), 7.37 (s, 2H), 7.55 (s, 1H), 8.22 (s, 1H); Mass Spectrum: M+H+ 263.

[48] The product gave the following data: NMR Spectrum: (CDCl₃) 2.38 (s, 6H), 2.87 (t, 2H), 3.49 (s, 3H), 4.26 (t, 2H), 7.24 (s, 2H), 7.4 (d, 2H), 7.53 (s, 1H), 8.72 (s, 1H), 9.8 (s, 1H), 12.47 (s, 1H); Mass Spectrum: M+H+ 450 and 452.

[49] The product gave the following data: NMR Spectrum: (CDCl₃) 3.47 (t, 2H), 3.74 (m, 4H), 3.89 (s, 3H), 4.33 (t, 2H), 4.42 (s, 1H), 7.01 (t, 3H), 7.28 (m, 2H), 8.0 (s, 1H), 8.73 (s, 1H), 11.9 (s, 1H); Mass Spectrum: M+H+ 459.

The 4-amino-6-methoxy-7-[2-(2-oxoimidazolidin-1-yl)ethoxy]quinazoline used as a starting material was prepared as follows:

4-(4-Bromo-2-fluorophenoxy)-7-hydroxy-6-methoxyquinazoline was reacted with 2-(2-oxoimidazolidin-1-yl)ethyl chloride (*Indian J. Chem. Sect. B*, 1982, 21B, 928-940) using an analogous procedure to that described in the second last paragraph of Note [38] above to give 4-(2-bromo4fluorophenoxy)-6-methoxy-7-[2-(2-oxoimidazolidin-1-yl)ethoxy]quinazoline; NMR Spectrum: (CDCl₃) 3.47 (t, 2H), 3.75 (m, 4H), 4.05 (s, 3H), 4.35 (t, 2H), 4.47 (s, 1H), 7.21 (t, 1H), 7.30 (s, 1H), 7.41 (t, 2H), 7.54 (s, 1H), 8.6 (s, 1H); Mass Spectrum: M+H+ 477 & 479.

The material so obtained was reacted with ammonia using an analogous procedure to that described in the last paragraph of Note [38] above to give the required starting material; NMR Spectrum: (DMSOd₆) 3.23 (t, 2H), 3.48 (m, 4H), 3.87 (s, 3H), 4.2 (t, 2H), 6.4 (s, 1H), 7.1 (s, 1H), 7.4 (s, 2H), 7.58 (s, 1H), 8.23 (s, 1H); Mass Spectrum: M+H+ 304.

[50] The product gave the following data: NMR Spectrum: (CDCl₃) 3.48 (t, 2H), 3.73 (m, 7H), 4.32 (t, 2H), 4.48 (s, 1H), 7.13 (m, 2H), 7.44 (t, 3H), 8.74 (s, 1H), 9.1 (s, 1H), 12.27 (s, 1H); Mass Spectrum: M+H+ 491 and 493.

[51] The product gave the following data: NMR Spectrum: (CDCl₃) 1.87 (m, 4H), 2.71 (s, 4H), 3.06 (t, 2H), 3.58 (s, 3H), 4.33 (t, 2H), 7.1-7.27 (m, 2H), 7.36-7.46 (m, 3H), 8.73 (s, 1H), 9.5 (s, 1H), 12.37 (s, 1H); Mass Spectrum: M+H+ 476 and 478.

The 4-amino-6-methoxy-7-(2-pyrrolidin-1-ylethoxy)quinazoline used as a starting material was prepared as follows:

4-4-Bromo-2-fluorophenoxy)-7-hydroxy-6-methoxyquinazoline was reacted with 2-pyrrolidin-1-ylethyl chloride using an analogous procedure to that described in the second last paragraph of Note [38] above to give 4-(2-bromo4-fluorophenoxy)-6methoxy-7-(2-pyrrolidin-1-ylethoxy)quinazoline; NMR Spectrum: (CDCl₃) 1.83 (m, 4H), 2.69 (m, 4H), 3.06 (t, 2H), 4.04 (s, 3H), 4.34 (t, 2H), 7.21 (t, 1H), 7.31 (s, 1H), 7.4 (t, 2H), 7.53 (s, 1H), 8.6 (s, 1H); Mass Spectrum: M+H+ 462 & 464.

The material so obtained was reacted with ammonia using an analogous procedure to that described in the last paragraph of Note [38] above to give the required starting material; NMR Spectrum: (CDCl$_3$) 1.7 (s, 4H), 2.5 (m, 4H), 2.83 (t, 2H), 3.87 (s, 3H), 4.19 (t, 2H), 7.07 (s, 1H) 7.39 (s, 2H), 7.56 (s, 1H), 8.23 (s, 1H); Mass Spectrum: M+H$^+$ 289.

[52] The product gave the following data: NMR Spectrum: (CDCl$_3$) 1.87 (s, 4H), 2.73 (s, 4H), 3.07 (t, 2H), 3.65 (s, 3H), 4.34 (1, 2H), 6.99 (t, 3H), 7.28 (m, 1H), 7.43 (s, 1H), 8.75 (s, 1H), 9.47 (s, 1H), 12.11 (s, 1H); Mass Spectrum: M+H$^+$ 444.

[53] The product gave the following data: NMR Spectrum: (CDCl$_3$) 2.6 (t, 4H), 2.92 (t, 2H), 3.58 (s, 3H), 3.74 (t, 4H), 4.28 (t, 2H), 7.11-7.27 (m, 2H), 7.37-7.45 (m, 3H), 8.73 (s, 1H), 9.47 (s, 1H), 12.36 (s, 1H); Mass Spectrum: M+H$^+$ 492 and 494.

The 4-amino-6-methoxy-7-(2-morpholinoethoxy) quinazoline used as a starting material was prepared as follows:

4-(4-Bromo-2-fluorophenoxy)-7-hydroxy-6-methoxyquinazoline was reacted with 2-morpholinoethyl chloride using an analogous procedure to that described in the second last paragraph of Note [38] above to give 4-(2-bromo-4-fluorophenoxy)-6-methoxy-7-(2-morpholinoethoxy) quinazoline; NMR Spectrum: (CDCl$_3$) 2.63 (t, 4H), 2.98 (t, 2H), 3.76 (t, 4H), 4.06 (s, 3H), 4.34 (t, 2H), 7.22 (t, 1H), 7.32 (s, 1H), 7.41 (t, 2H), 7.52 (s, 1H), 8.2 (s, 1H); Mass Spectrum: M+H$^+$ 478 & 480.

The material so obtained was reacted with ammonia using an analogous procedure to that described in the last paragraph of Note [38] above to give the required starting material; NMR Spectrum: (DMSOd$_6$) 2.5 (m, 4H), 2.75 (t, 2H), 3.58 (t, 4H), 3.87 (s, 3H), 4.2 (t, 2H), 7.09 (s, 1H), 7.39 (s, 2H), 7.58 (s, 1H), 8.24 (s, 1H); Mass Spectrum: M+H$^+$ 305.

[54] The product gave the following data: NMR Spectrum: (CDCl$_3$) 2.63 (t, 4H), 3.04 (t, 2H), 3.61 (s, 3H), 3.76 (t, 4H), 4.33 (t, 2H), 6.99 (t, 2H), 7.27 (m, 2H), 7.45 (s, 1H), 8.74 (s, 1H), 9.57 (s, 1H), 12.15 (s, 1H); Mass Spectrum: M+H$^+$ 460.

[55] The product gave the following data: NMR Spectrum: (CDCl$_3$) 1.8 (m, 4H), 2.15 (m, 2H), 2.33 (s, 6H), 2.57 (br s, 4H), 2.69 (t, 2H), 3.41 (s, 3H), 4.26 (t, 2H), 7.14 (s, 3H), 7.28 (s, 1H), 7.5 (s, 1H), 8.66 (s, 1H), 9.66 (s, 1H), 11.95 (s, 1H); Mass Spectrum: M+H$^+$ 4.50.

[56] The product gave the following data: NMR Spectrum: (CDCl$_3$) 2.09 (m, 2H), 2.32 (s, 6H), 2.46 (t, 4H), 2.55 (t, 2H), 3.4 (s, 3H), 3.71 (t, 2H), 4.25 (t, 2H), 7.11 (m, 3H), 7.28 (s, 1H), 7.49 (s, 1H), 8.66 (s, 1H), 9.61 (s, 1H), 11.91 (s, 1H); Mass Spectrum: M+H$^+$ 466.

[57] The product gave the following data: NMR Spectrum: (CDCl$_3$) 1.72 (s, 4H), 2.1 (m, 2H), 2.3 (s, 3H), 2.33 (s, 6H), 2.4-2.6 (m, 6H), 3.4 (s, 3H), 4.23 (t, 2H), 7.16 (m, 3H), 7.28 (s, 1H), 7.49 (s, 1H), 8.66 (s, 1H), 9.64 (s, 1H), 11.91 (s, 1H); Mass Spectrum: M+H$^+$ 479.

[58] The product gave the following data: NMR Spectrum: (CDCl$_3$) 1.85 (m, 4H), 2.34 (s, 6H), 2.68 (s, 4H), 3.05 (t, 2H), 3.31 (s, 3H), 4.3 (t, 2H), 7.14 (m, 3H), 7.26 (s, 1H), 7.56 (s, 1H), 8.65 (s, 1H), 9.87 (s, 1H), 11.98 (s, 1H); Mass Spectrum: M+H$^+$ 436.

[59] The product gave the following data: N Spectrum: (CDCl$_3$) 1.47 (s, 2H), 1.64 (m, 4H), 2.32 (s, 6H), 2.55 (s, 4H), 2.91 (t, 2H), 3.36 (s, 3H), 4.32 (t, 2H), 7.14 (m, 3H), 7.26 (s, 1H), 7.54 (s, 1H), 8.66 (s, 1H), 9.79 (s, 1H), 11.98 (s, 1H); Mass Spectrum: M+H$^+$ 450.

[60] The product gave the following data: NMR Spectrum: (CDCl$_3$) 2.31 (s, 6H), 2.61 (m, 4H), 2.94 (t, 2H), 3.27 (s, 3H), 3.76 (t, 4H), 4.31 (t, 2H), 7.15 (m, 3H), 7.26 (s, 1H), 7.59 (s, 1H), 8.67 (s, 1H), 9.97 (s, 1H), 12.01 (s, 1H); Mass Spectrum: M+H$^+$ 452.

[61] The product gave the following data: NMR Spectrum: (CDCl$_3$) 2.33 (s, 6H), 3.35 (s, 3H), 3.46 (t, 2H), 3.72 (m, 4H), 4.28 (t, 2H), 4.67 (s, 1H), 7.14 (m, 3H), 7.25 (s, 1H), 7.61 (s, 1H), 8.67 (s, 1H), 9.91 (s, 1H), 11.98 (s, 1H); Mass Spectrum: M+H$^+$ 451.

[62] The product gave the following data: NMR Spectrum: (CDCl$_3$) 2.33 (s, 6H), 2.39 (s, 6H), 2.87 (t, 2H), 3.28 (s, 3H), 4.26 (t, 2H), 7.12 (m, 3H), 7.26 (s, 1H), 7.58 (s, 1H), 8.66 (s, 1H), 9.97 (s, 1H), 12.02 (s, 1H); Mass Spectrum: M+H$^+$ 410.

[63] The product gave the following data: NMR Spectrum: (CDCl$_3$) 1.81 (m, 4H), 2.16 (m, 2H), 2.31 (s, 6H), 2.59 (s, 4H), 2.7 (t, 2H), 3.52 (s, 3H), 4.26 (t, 2H), 7.27 (m, 3H), 7.39 (s, 1H), 8.67 (s, 1H), 9.34 (s, 1H), 11.83 (s, 1H); Mass Spectrum: M+H$^+$ 528 and 530.

[64] The product gave the following data: NMR Spectrum: (CDCl$_3$) 1.45 (q, 2H), 1.6 (m, 4H), 2.13 (m, 2H), 2.3 (s, 6H), 2.44 (s, 4H), 2.54 (t, 2H), 3.53 (s, 3H), 4.25 (t, 2H), 7.29 (m, 3H), 7.37 (s, 1H), 8.68 (s, 1H), 9.27 (s, 1H), 11.81 (s, 1H); Mass Spectrum: M+H$^+$ 542 and 544.

[65] The product gave the following data: NMR Spectrum: (CDCl$_3$) 2.12 (m, 2H), 2.3 (s, 6H), 2.5 (t, 4H), 2.58 (t, 2H), 3.5 (s, 3H), 3.5 (t, 4H), 4.27(t, 2H), 7.22-7.29 (m, 3H), 7.42 (s, 1H), 8.67 (s, 1H), 9.44 (s, 1H), 11.87 (s, 1H); Mass Spectrum: M+H$^+$ 544 and 546.

[66] The product gave the following data: NMR Spectrum: (CDCl$_3$) 1.66 (s, 10H), 2.11 (m, 2H), 2.3 (s, 3H), 2.4-2.6 (m, 6H), 3.58 (s, 3H), 4.24 (t, 2H), 7.25 (s, 3H), 7.34 (s, 1H), 8.67 (s, 1H), 9.2 (s, 1H), 11.79 (s, 1H); Mass Spectrum: M+H$^+$ 557 and 559.

[67] The product gave the following data: NMR Spectrum: (CDCl$_3$) 1.49 (m, 2H), 1.66 (m, 4H), 2.31 (s, 6H), 2.54 (t, 4H), 2.9 (t, 2H), 3.5 (s, 3H), 4.32 (t, 2H), 7.28 (m, 3H), 7.41 (s, 1H), 8.69 (s, 1H), 9.44 (s, 1H), 11.9 (s, 1H); Mass Spectrum: M+H$^+$ 528 and 530.

[68] The product gave the following data: NMR Spectrum: (CDCl$_3$) 2.3 (s, 6H), 2.64 (t, 4H), 2.95 (t, 2H), 3.41 (s, 3H), 3.77 (t, 4H), 4.33 (t, 2H), 7.27 (s, 3H), 7.48 (s, 1H), 8.69 (s, 1H), 9.71 (s, 1H), 11.97 (s, 1H); Mass Spectrum: M+H$^+$ 530 and 532.

[69] The product gave the following data: NMR Spectrum: (CDCl$_3$) 2.29 (s, 6H), 3.47 (t, 2H), 3.62 (s, 3H), 3.75 (m, 4H), 4.33 (t, 2H), 4.44 (s, 1H), 7.28 (m, 3H), 7.39 (s, 1H), 8.68 (s, 1H), 9.18 (s, 1H), 11.77 (s, 1H); Mass Spectrum: M+H$^+$ 529 and 531.

[70] The product gave the following data: NMR Spectrum: (CDCl$_3$) 3.39 (s, 3H), 3.54 (s, 3H), 3.6 (m, 2H), 3.75 (m, 2H), 3.98 (t, 2H), 4.33 (t, 2H), 7.24 (m, 2H), 7.41 (m, 2H), 7.48 (s, 1H), 8.73 (s, 1H), 9.68 (s, 1H), 12.46 (s, 1H); Mass Spectrum: M+H$^+$ 481 and 483.

The 4-amino-6-methoxy-7-[2-(2-methoxyethoxy)ethoxy] quinazoline used as a starting material was prepared as follows:

4-(4-Bromo-2-fluorophenoxy)-7-hydroxy-6-methoxyquinazoline was reacted with 2-(2-methoxy ethoxy) ethyl tosylate (prepared from 2-(2-methoxyethoxy)ethanol and tosyl chloride) using an analogous procedure to that described in the second last paragraph of Note [38] above to give 4-(2-bromo-4fluorophenoxy)-6-methoxy-7-[2-(2-methoxyethoxy)ethoxy]quinazoline; NMR Spectrum: (CDCl$_3$) 3.4 (s, 3H), 3.6 (m, 2H), 3.76 (m, 2H), 4.03 (m, 5H), 4.39 (t, 2H), 7.21 (m, 1H), 7.34 (s, 1H), 7.41 (t, 2H), 7.51 (s, 1H), 8.6 (s, 1H); Mass Spectrum: M+H$^+$ 467 & 469.

The material so obtained was reacted with ammonia using an analogous procedure to that described in the last paragraph of Note [38] above to give the required starting material; NMR Spectrum (DMSOd$_6$) 3.23 (s, 3H), 3.46 (m, 2H), 3.6

(m, 2H), 3.79 (t, 2H), 3.88 (s, 3H), 4.2 (t, 2H), 7.08 (s, 1H), 7.39 (s, 2H), 7.57 (s, 1H), 8.23 (s, 1H); Mass Spectrum: M+H$^+$ 294.

[71] The product gave the following data: NMR Spectrum: (CDCl$_3$) 3.39 (s, 3H), 3.6 (m, 5), 3.77 (m, 2H), 4.01 (t, 2H), 4.36 (s, 1H), 7.01 (t, 3H:), 7.26 (m, 2H), 7.46 (s, 1H), 8.72 (s, 1H), 9.58 (s, 1H), 12.16 (s, 1H); Mass Spectrum: M+H$^+$ 449.

[72] The product gave the following data: NMR Spectrum: (CDCl$_3$) 2.31 (s, 6H), 3.27 (s, 3H), 3.4 (s, 3H), 3.6 (m, 2H), 3.75 (m, 2H), 3.97 (t, 2H), 4.34 (t, 2H), 7.14 (m, 3H), 7.26 (s, 1H), 7.57 (s, 1H), 8.66 (s, 1H), 9.95 (s, 1H), 12.03 (s, 1H); Mass Spectrum: M+H$^+$ 4.41.

[73] The product gave the following data: NMR Spectrum: (CDCl$_3$) 1.4-1.54 (m, 2H), 1.82-2.03 (m, 5H), 2.3 (s, 3H), 2.91 (d, 2H), 3.53 (s, 3H), 4.02 (d, 2H), 7.26 (m, 1H), 7.31-7.47 (m, 3H), 7.55 (d, 1H), 8.68 (s, 1H), 9.49 (s, 1H), 12.6 (s, 1H), Mass Spectrum: M+H$^+$ 508.

[74] The product gave the following data: NMR Spectrum: (CDCl$_3$) 1.82 (m, 4H), 2.66 (m, 4H), 3.0 (t, 2H), 4.27 (t, 2H), 7.2-7.4 (m, 3H), 7.5 (d, 2H), 8.05 (d, 1H), 8.78 (s, 1H), 9.1 (br s, 1H), 12.07 (br s, 1H); Mass Spectrum: M+H$^+$ 446 and 448.

The 4-amino-7-(2-pyrrolidin-1-ylethoxy)quinazoline used as a starting material was prepared as follows:

A mixture of 7-hydroxy-4-methylthioquinazoline (6 g) and a saturated solution of ammonia gas in methanol (225 ml) was sealed in a pressure vessel and heated at 120° C. for 40 hours. The mixture was cooled to ambient temperature and evaporated. The residue was purified by column chromatography on silica using increasingly polar mixtures of methylene chloride and methanol as eluent. There was thus obtained 4-amino-7-hydroxyquinazoline (4.9 g); NMR Spectrum: (DMSOd$_6$) 6.9 (s, 1H), 6.9 (d, 1H), 9.5 (br s, 2H), 8.04 (d, 1H), 8.24 (s, 1H).

Diethyl azodicarboxylate (3.3 ml) was added dropwise to a stirred mixture of 4-amino-7-hydroxyquinazoline (5.16 g), triphenylphosphine (16.8 g) and methylene chloride (260 ml) which had been cooled to 0° C. The mixture was stirred at ambient temperature for 16 hours. The mixture was evaporated and the residue was purified by column chromatography on silica using a 50:45:5 mixture of methylene chloride, ethyl acetate and methanol as eluent. There was thus obtained triphenylphosphine N-(7-hydroxyquinazolin-4-yl)imide (9.7 g); NMR Spectrum: (DMSOd$_6$) 6.85 (s, 1H), 7.05 (m, 1H), 7.5-7.95 (m, 15H), 8.12 (s, 1H), 8.5 (d, 1H), 10.3 (br s, 1H).

3,3-Dimethyl-1,2,5-thiadiazolidine-1,1-dioxide (*J. Med. Chem.* 1994, 37, 3023; 0.39 g) was added portionwise to a stirred mixture of triphenylphosphine N-(7-hydroxyquinazolin-4-yl)imide (0.2 g), N-(2-hydroxyethyl)pyrrolidine (0.081 g) and methylene chloride (5 ml) and the mixture was stirred at ambient temperature for 1 hour. Diethyl ether (10 ml) was added and the mixture was filtered through diatomaceous earth. The filtrate was evaporated and the residue was purified by column chromatography on silica using as eluent a 48:50:2 mixture of methylene chloride, ethyl acetate and a saturated ammonia solution in methanol. There was thus obtained triphenylphosphine N-[7-(2-pyrrolidin-1-ylethoxy)quinazolin-4-yl]imide (0.084 g); NMR Spectrum: (DMSOd$_6$+CF$_3$CO$_2$D) 1.93 (m, 2H), 2.08 (m, 2H), 3.2 (m, 2H), 3.66 (m, 2H), 3.73 (m, 2H), 4.5 (m, 2H), 7.16 (s, 1H), 7.42 (m, 1H), 7.6-8.0 (m, 15H), 8.62 (s, 1H), 8.71 (d, 1H); Mass Spectrum: M+H$^+$ 519.

A mixture of a portion (0.42 g) of the material so obtained, a 1N aqueous acetic acid solution (2 ml) and ethanol (2 ml) was stirred and heated to 100° C. for 15 hours. The mixture was evaporated and the residue was dried under vacuum. There was thus obtained 4-amino-7-(2-pyrrolidin-1-ylethoxy)quinazoline in quantitative yield and this was used directly without future purification.

[75] The product gave the following data: Mass Spectrum: M+H$^+$ 426 and 428.

[76] The product gave the following data: Mass Spectrum: M+H$^+$ 412 and 414.

[77] The product gave the following data: Mass Spectrum: M+H$^+$ 480 and 482.

[78] The product gave the following data: NMR Spectrum: (CDCl$_3$) 1.4-1.7 (m, 6H), 2.55 (br s, 4H), 2.85 (t, 2H), 4.25 (t, 2H), 7.1-7.38 (m, 4H), 7.48 (d, 2H), 8.05 (d, 2H), 8.8 (s, 1H), 9.02 (br s, 1H); Mass Spectrum: M+H$^+$ 460 and 462.

The 4-amino-7-(2-piperidinoethoxy)quinazoline used as a starting material was prepared as follows:

Triphenylphosphine N-(7-hydroxyquinazolin-4-yl)imide was reacted with N-(2-hydroxyethyl)piperidine using an analogous procedure to that described in the second last paragraph of Note [74] above to give triphenylphosphine N-[7-(2-piperidinoethoxy)quinazolin-4-yl]imide in 21% yield; Mass Spectrum: M+H$^+$ 533. The material so obtained was reacted with aqueous acetic acid using an analogous Procedureto that described in the last paragraph of Note [74] above to give the required starting material; Mass Spectrum: M+H$^+$ 273.

[79] The product gave the following data: NMR Spectrum: (CDCl$_3$) 1.45 (br m, 2H), 1.55-1.75 (m, 4H), 2.55 (br s, 4H), 2.85 (t, 2H), 4.28 (t, 2H), 7.05 (m, 2H), 7.12-7.4 (m, 4H), 8.15 (d, 1H), 8.8 (s, 1H), 9.2 (s, 1H); Mass Spectrum: M+H$^+$ 428.

[80] The product gave the following data: NMR Spectrum: (CDCl$_3$) 1.4-1.72 (m, 6H), 2.42 (s, 3H), 2.55 (br s, 4H), 2.85 (t, 2H), 4.3 (t, 2H), 7.12-7.32 (m, 5H), 8.35 (d, 1H), 7.95 (d, 1H), 8.6 (s, 1H), 8.8 (s, 1H); Mass Spectrum: M+H$^+$ 440 and 442.

[81] The product gave the following data: Mass Spectrum: M+H$^+$ 426 and 428.

[82] The product gave the following data: Mass Spectrum: M+H$^+$ 494 and 496.

[83] The product gave the following data: NMR Spectrum: (CDCl$_3$) 2.32 (s, 3H), 2.5 (br s, 4H), 2.7 (br s, 4H), 2.9 (t, 2H), 4.3 (t, 2H), 7.2 (d, 1H), 7.25-7.4 (m, 3H), 7.47 (d, 2H), 8.05 (d, 1H), 8.8 (s, 1H), 9.05 (s, 1H); Mass Spectrum: M+H$^+$ 475 and 477.

The 4-amino-7-[2-(4-methylpiperazin-1-yl)ethoxy]quinazoline used as a starting material was prepared as follows:

Triphenylphosphine N-(7-hydroxyquinazolin-4-yl)imide was reacted with 1-(2-hydroxyethyl)-4-methylpiperazine using an analogous procedure to that described in the second last paragraph of Note [74] above to give triphenylphosphine N-{7-[2-(4-methylpiperazin-1-yl)ethoxy]quinazolin-4-yl}-imide in 30% yield; Mass Spectrum: M+H$^+$ 548. The material so obtained was reacted with aqueous acetic acid using an analogous procedure to that described in the last paragraph of Note [74] above to give the required starting material; Mass Spectrum: M+H$^+$ 288.

The 1-(2-hydroxyethyl)-4-methylpiperazine used as a starting material was prepared as follows:

A mixture of 2-bromoethanol (2.36 g), N-methylpiperazine (1.26 g), potassium carbonate (5.0 g) and ethanol (150 ml) was stirred and heated to reflux for 18 hours. The mixture was cooled to ambient temperature and filtered. The filtrate was evaporated and the residue was triturated under a mixture of methylene chloride and acetone. The resultant mixture was filtered and the filtrate was evaporated to give the required starting material as an oil (0.87 g); NMR Spectrum: (CDCl$_3$) 2.18 (s, 3H), 2.3-2.7 (br m, 81), 2.56 (t, 2H), 3.61 (t, 2H).

[84] The product gave the following data: Mass Spectrum: M+H+ 455 and 457.

[85] The product gave the following data: NMR Spectrum: (CDCl₃) 2.3 (s, 3H), 2.48 (br s, 4H), 2.65 (br s, 4H), 2.9 (t, 2H), 4.3 (t, 2H), 7.1 (m, 1H), 7.2-7.4 (m, 4H), 7.45 (d, 1H), 7.97 (d, 1H), 8.35 (br s, 1H), 8.45 (d, 1H), 8.85 (s, 1H); Mass Spectrum: M+H+ 441 and 443.

[86] The product gave the following data: Mass Spectrum: M+H+ 509 and 511.

[87] The product gave the following data: Mass Spectrum: M+H+ 460 and 462.

The 4-amino-7-(N-methylpiperidin-3-ylmethoxy)quinazoline used as a starting material was prepared as follows:

Triphenylphosphine N-(7-hydroxyquinazolin-4-yl)imide was reacted with 3-hydroxymethyl-N-methylpiperidine using an analogous procedure to that described in the second last paragraph of Note [74] above to give triphenylphosphine N-[7-(N-methylpiperidin-3-ylmethoxy)quinazolin-4-yl]imide in 49% yield; Mass Spectrum: M+H+ 533. The material so obtained was reacted with aqueous acetic acid using an analogous procedure to that described in the last paragraph of Note [74] above to give the required starting material; Mass Spectrum: M+H+ 273.

[88] The product gave the following data: Mass Spectrum: M+H+ 428.

[89] The product gave the following data: Mass Spectrum: M+H+ 440 and 442.

[90] The product gave the following data: Mass Spectrum: M+H+ 426 and 428.

[91] The product gave the following data: Mass Spectrum: M+H+ 494 and 496.

[92] The product gave the following data: NMR Spectrum: (CDCl₃) 1.85 (br s, 4H), 2.1 (m, 2H), 2.6 (br s, 4H), 2.7 (t, 2H), 4.2 (t, 2H), 7.15 (d, 1H), 7.2-7.4 (m, 3H), 7.5 (d, 2H), 8.1 (d, 1H), 8.8 (s, 1H), 9.2 (br s, 1H); Mass Spectrum: M+H+ 460 and 462.

The 4-amino-7-(3-pyrrolidin-1-ylpropoxy)quinazoline used as a starting material was prepared as follows:

Triphenylphosphine N-(7-hydroxyquinazolin-4-yl)imide was reacted with N-(3-hydroxypropyl)pyrrolidine using an analogous procedure to that described in the second last paragraph of Note [74] above to give triphenylphosphine N-[7-(3-pyrrolidin-1-ylpropoxy)quinazolin-4]imide in 42% yield; Mass Spectrum: M+H+ 533. The material so obtained was reacted with aqueous acetic acid using an analogous procedure to that described in the last paragraph of Note [74] above to give the required starting material; Mass Spectrum: M+H+ 273.

The N-(3-hydroxypropyl)pyrrolidine used as a starting material was prepared as follows:

A mixture of 3-chloropropanol (66 g), pyrrolidine (50 g), potassium carbonate (145 g) and acetonitrile (1 L) was stirred and heated to reflux for 20 hours. The mixture was cooled to ambient temperature and filtered. The filtrate was evaporated and the residue was purified by distillation to give the required starting material as an oil (62 g); NMR Spectrum: (CDCl₃) 1.6-1.8 (m, 6H), 2.55 (br s, 4H), 2.75 (t, 2H), 3.85 (t, 2H), 5.5 (br s, 1H).

[93] The product gave the following data: Mass Spectrum: M+H+ 428.

[94] The product gave the following data: Mass Spectrum: M+H+ 440 and 442.

[95] The product gave the following data: NMR Spectrum: (CDCl₃) 1.82 (br s, 4H), 2.1 (m, 2H), 2.55 (br s, 4H), 2.65 (t, 4H), 4.25 (t, 2H), 7.1 (m, 1H), 7.2-7.45 (m, 4H), 7.5 (d, 1H), 7.95 (d, 1H), 8.15 (s, 1H), 8.45 (d, 1H), 8.85 (s, 1H); Mass Spectrum: M+H+ 426 and 428.

[96] The product gave tie following data: NMR Spectrum: (CDCl₃) 7.2 (m, 1H), 7.25-7.4 (m, 3H), 7.5 (s, 1H), 8.0 (d, 1H), 8.8 (s, 1H), 8.95 (br s, 1H); Mass Spectrum: M+H+ 494 and 496.

[97] The product gave the following data: Mass Spectrum: M+H+ 444.

The 4-amino-7-(3-morpholinopropoxy)quinazoline used as a staring material was prepared as follows:

Triphenylphosphine N-(7-hydroxyquinazolin-4-yl)imide was reacted with N-(3-hydroxypropyl)morpholine using an analogous procedure to that described in the second last paragraph of Note [74] above to give triphenylphosphine N-[7-(3-morpholinopropoxy)quinazolin-4-yl]imide and the material so obtained was reacted with aqueous acetic acid using an analogous procedure to that described in the last paragraph of Note [74] above to give the required starting material; Mass Spectrum: M+H+ 289.

[98] The product gave the following data: Mass Spectrum: M+H+ 456 and 458.

[99] The product gave the following data: Mass Spectrum: M+H+ 510 and 512.

[100] The product gave the following data NMR Spectrum: (CDCl₃) 2.1 (m, 2H), 2.35 (s, 3H), 2.35-2.75 (m, 8H), 2.6 (t, 2H,) 4.22 (t, 2H), 7.12 (m, 1H), 7.2-7.38 (m, 3H), 7.5 (d, 2H), 8.15 (d, 1H), 8.8 (s, 1H;), 9.5 (br s, 1H); Mass Spectrum: M+H+ 489 and 491.

The 4-amino-7-[3-(4-methylpiperazin-1-yl)propoxy]quinazoline used as a starting material was prepared as follows:

Triphenylphosphine N-(7-hydroxyquinazolin-4-yl)imide was reacted with 1-(3-hydroxypropyl)-4-methylpiperazine using an analogous procedure to that described in the second last paragraph of Note [74] above to give triphenylphosphine N-{7-[3-(4-methylpiperazin-1-yl)propoxy]quinazolin-4-yl} imide in 44% yield; Mass Spectrum: M+H+ 562. The material so obtained was reacted with aqueous acetic acid using an analogous procedure to that described in the last paragraph of Note [74] above to give the required starting material; Mass Spectrum: M+H+ 302.

The 1-(3-hydroxypropyl)-4-methylpiperazine used as a starting material was prepared as follows:

A mixture of 3-bromopropanol (20 ml), N-methylpiperazine (29 ml), potassium carbonate (83 g) and ethanol (200 ml) was stirred and heated to reflux for 20 hours. The mixture was cooled to ambient temperature and filtered. The filtrate was evaporated and the residue was triturated under diethyl ether. The resultant mixture was filtered and the filtrate was evaporated. The residue was purified by distillation to give the required starting material as an oil; NMR Spectrum: (CDCl₃) 1.72 (m, 2H), 2.3 (s, 3H), 2.2-2.8 (m, 8H), 2.6 (t, 2H), 3.8 (t, 2H), 5.3 (br s, 1H).

[101] The product gave the following data: NMR Spectrum: (CDCl₃) 2.07 (t, 2H), 2.32 (s, 3H), 2.3-2.75 (m, 8H), 2.6 (t, 2H), 4.22 (t, 2H), 7.1 (m, 1H), 7.2-7.4 (m, 4H), 7.5 (d, 1H), 8.05 (d, 1H), 8.45 (d, 1H), 8.55 (s, 1H), 8.85 (s, 1H); Mass Spectrum: M+H+ 455 and 457.

[102] The product gave the following data: NMR Spectrum: (CDCl₃) 2.1 (m, 2H), 2.3 (s, 3H), 2.35-2.7 (m, 8H), 2.6 (t, 2H), 4.2 (t, 2H), 7.15 (m, 1H), 7.2-7.4 (m, 3H), 7.5 (s, 1H), 8.05 (d, 1H), 8.8 (s, 1H), 9.02 (br s, 1); Mass Spectrum: M+H+ 523 and 525.

[103] The product gave the following data: Mass Spectrum: M+H+ 492.

[104] The product gave the following data: Mass Spectrum: M+H+ 504 and 506.

[105] The product gave the following data: Mass Spectrum: M+H⁺ 558 and 560.

[106] The product gave the following data: NMR Spectrum: (CDCl₃) 2.55 (m, 2H), 4.15 (t, 2H), 4.7 (t, 2H), 7.2-7.4 (m, 4H), 7.5 (s, 1H), 7.58 (s, 1H), 7.65 (s, 1H), 7.95 (d, 1H), 8.55 (d, 1H), 8.8 (s, 1H); Mass Spectrum: M+H⁺ 492 and 494.

The 4-amino-7-[3-(1,2,3-triazol-1-yl)propoxy]quinazoline used as a starting material was prepared as follows:

Triphenylphosphine N-(7-hydroxyquinazolin-4-yl)imide was reacted with N¹-(3-hydroxypropyl)-1,2,3-triazole using an analogous procedure to that described in the second last paragraph of Note [74] above to give triphenylphosphine N-{7-[3-(1,2,3-triazol-1-yl)propoxy]quinazolin-4-yl}imide in 18% yield; Mass Spectrum: M+H⁺ 531. The material so obtained was reacted with aqueous acetic acid using an analogous procedure to that described in the last paragraph of Note [74] above to give the required starting material; Mass Spectrum: M+H⁺ 271.

The N¹-(3-hydroxypropyl)-1,2,3-triazole used as a starting material was prepared as follows:

A mixture of 1,2,3-triazole (5 g), ethyl acrylate (7.8 ml) and pyridine (50 drops) was stirred and heated to 90° C. for 4 hours. The mixture was cooled to ambient temperature and evaporated. The residue was purified by column chromatography on silica using increasingly polar mixtures of methylene chloride and diethyl ether as eluent. There was thus obtained ethyl 1,2,3-triazol-1-ylpropanoate (8.96 g); NMR Spectrum: (CDCl₃) 1.25 (t, 3H), 2.95 (t, 2H), 4.15 (q, 2H), 4.7 (t, 2H), 7.65 (s, 1H), 7.7 (s, 1H).

A solution of the material so obtained in THF (50 ml) was added dropwise to a suspension of lithium aluminium hydride (3 g) in THF (250 ml) which had been cooled to 0° C. The mixture was stirred at 5° C. for 1 hour and at ambient temperature for a further hour. The mixture was cooled to 0° C. and 4N aqueous sodium hydroxide solution (30 ml) was added dropwise. The mixture was filtered and the filtrate was dried over magnesium sulphate and evaporated. The residue was purified by column chromatography on silica using a 47:3 mixture of methylene chloride and methanol as eluent. There was thus obtained N¹-(3-hydroxypropyl)-1,2,3-triazole (6.2 g); NMR Spectrum: (CDCl₃) 2.1-2.2 (m, 3H), 3.65 (m, 2H), 4.6 (t, 2H), 7.6 (s, 1H), 7.72 (s, 1H).

[107] The product gave the following data: Mass Spectrum: M+H⁺ 440.

The 4-amino-7-[(E)4-pyrrolidin-1-ylbut-2-en-1-yloxy]quinazoline used as a starting material was prepared as follows:

Triphenylphosphine N-(7-hydroxyquinazolin4-yl)imide was reacted with (E)-4-pyrrolidin-1-ylbut-2-en-1-ol using an analogous procedure to that described in the second last paragraph of Note [74] above to give triphenylphosphine N-{7-[(E)-4-pyrrolidin-1-ylbut-2-en-1-yloxy]quinazolin-4-yl}imide in 38% yield; Mass Spectrum: M+H⁺ 545. The material so obtained was reacted with aqueous acetic acid using an analogous procedure to that described in the last paragraph of Note [74] above to give the required starting material; Mass Spectrum: M+H⁺ 285.

The (E)-4-pyrrolidin-1-ylbut-2-en-1-ol used as a starting material was prepared as follows:

Thionyl chloride (9.3 ml) was added portionwise to a stirred mixture of 2-butyne-1,4-diol (10 g), pyridine (10.3 ml) and toluene (15 ml) which had been cooled to 0° C. The mixture was stirred at ambient temperature for 3.5 hours and then poured onto a mixture of ice and water. The mixture was extracted with diethyl ether. The organic extract was washed with a saturated aqueous sodium bicarbonate solution and with brine, dried over magnesium sulphate and evaporated. The residue was purified by column chromatography on silica using a 7:3 mixture of petroleum ether (b.p. 40-60° C.) and diethyl ether as eluent. There was thus obtained 4-chlorobut-2-yn-1-ol (4.74 g); NMR Spectrum: (CDCl₃) 1.68 (t, 1H), 4.18 (d, 2H), 4.33 (d, 2H).

Pyrrolidine (7.8 ml) was added dropwise to a solution of 4-chlorobut-2-yn-1-ol (4.74 g) in toluene (40 ml) and the resultant mixture was stirred and heated to 60° C. for 1 hour. The mixture was evaporated and the residue was purified by column chromatography on silica using a 24:1 mixture of methylene chloride and methanol as eluent. There was thus obtained 4-pyrrolidin-1-ylbut-2-yn-1-ol (4.3 g); NMR Spectrum: (CDCl₃)1.82 (t, 4H), 2.63 (t, 4H), 3.44 (t, 2H), 4.29 (t, 2H).

A solution of the material so obtained in TBF (20 ml) was added dropwise to a suspension of lithium aluminium hydride (2.35 g) in THF (8 ml) and the mixture was stirred and heated to 60° C. for 2 hours. The mixture was cooled to 5° C. and 2N aqueous sodium hydroxide solution (28 ml) was slowly added. The resulting suspension was filtered and the filtrate was evaporated. The residue was dissolved in a mixture of methylene chloride and ethyl acetate, dried over magnesium sulphate and evaporated. The residue was purified by column chromatography on aluminium oxide using a 97:3 mixture of methylene chloride and methanol as eluent. There was thus obtained (E)-4-pyrrolidin-1-ylbut-2-en-1-ol (3.09 g); NMR Spectrum: (CDCl₃) 1.82 (m, 4H), 2.61 (m, 4H), 3.17 (m, 2H), 4.13 (s, 2H), 5.84 (m, 2H).

[108] The product gave the following data: Mass Spectrum: M+H⁺ 452 and 454.

[109] The product gave the following data: Mass Spectrum: M+H⁺ 438 and 440.

[110] DMF was used as the reaction solvent. The product gave the following data: NMR Spectrum: (DMSOd₆) 1.5-1.65 (m, 2H), 1.68-1.74 (m, 2H), 1.92 (t, 2H), 1.97 (t, 2H), 2.05 (m, 1H), 2.45 (t, 2H), 2.88 (d, 2H), 3.98 (s, 3H), 4.22 (t, 2H), 6.68 (s, 1H), 7.3 (s, 1H), 7.4 (t, 1H), 7.61 (d, 2H), 8.07 (s, 1H), 8.7 (s, 1H), 10.62 (s, 1H), 12.08 (s, 1H); Mass Spectrum: M+H⁺ 547 and 549.

The 4-amino-7-[3-(4-carbamoylpiperidin-1-yl)propoxy]-6-methoxyquinazoline used as a starting material was prepared as follows:

A mixture of 2-aminobenzyloxy-5-methoxybenzamide (*J. Med. Chem.*, 1977, 20, 146-149; 10 g) and Golds reagent (7.4 g) in dioxane (100 ml) was stirred and heated at reflux for 24 hours. Sodium acetate (3.02 g) and acetic acid (1.65 ml) were added to the reaction mixture and it was heated for a further 3 hours. The mixture was evaporated to dryness, water was added to the residue and the solid was filtered off, washed with water and dried. Recrystallisation of the solid from acetic acid gave 7-benzyloxy-6-methoxy-3,4-dihydroquinazolin-4-one (8.7 g, 84%).

7-Benzyloxy-6-methoxy-3,4-dihydroquinazol-4-one (20.3 g) was taken up in thionylchloride (440 ml) and DMF (1.75 ml) and heated to reflux for 4 hours. The thionyl chloride was evaporated under vacuum and the residue was azeotroped with toluene three times. There was thus obtained 7-benzyloxy-4-chloro-6-methoxyquinazoline which was used without further purification; NMR Spectrum: 4.88 (s, 3H), 5.25 (s, 2H), 7.44 (s, 1H), 7.49 (s, 1H), 7.32-7.52 (m, 5H), 8.83 (s, 1H).

A mixture of the crude 7-benzyloxy-4-chloro-6-methoxyquinazoline, potassium carbonate (50 g) and 4-bromo-2-fluorophenol (10 ml) in DMF (500 ml) was stirred and heated to 100° C. for. 5 hours. The mixture was allowed to cool to ambient temperature and was poured into water (2 L). The resultant solid was isolated and washed with water. The solid was dissolved in methylene chloride and filtered. The filtrate was treated with decolourising charcoal, boiled for a few minutes then filtered. The filtrate was evaporated to give a solid residue which was triturated under diethyl ether. There was thus obtained 7-benzyloxy-4-(4-bromo-2-fluorophenoxy)-6-methoxyquinazoline.

A mixture of the material so obtained and trifluoroacetic acid (15 ml) was stirred and heated to reflux for 3 hours. The reaction mixture was allowed to cool, toluene was added and the mixture was evaporated. The residue was triturated under diethyl ether. The precipitate was collected by filtration and dried to give 4-(4-bromo-2-fluorophenoxy)-7-hydroxy-6-methoxyquinazoline (20.3 g) which was used without further purification.

A mixture of 4-(4-bromo-2-fluorophenoxy)-7-hydroxy-6-methoxyquinazoline (18.2 g), 1,3-dibromopropane (80 ml), potassium carbonate (42 g) and DMF (1.2 L) was stirred and heated to 45° C. for 16 hours. The mixture was cooled to ambient temperature and filtered. The filtrate was evaporated and the residue was purified by column chromatography on silica using increasingly polar mixtures of methylene chloride and methanol as eluent. The product so obtained was stirred under diethyl ether (150 ml) and the resultant solid was isolated. There was thus obtained 4-(4-bromo-2-fluorophenoxy)-7-(3-bromopropoxy)-6-methoxyquinazoline (14.4 g); NMR Spectrum: (DMSOd$_6$) 2.35 (m, 2H), 3.69 (t, 2H), 3.98 (s, 3H), 4.31 (t, 2H), 7.4-7.6 (m, 4H), 7.78 (d, 1H), 8.78 (s, 1H); Mass Spectrum: M+H$^+$ 485, 487 and 489.

A mixture of a portion (2.4 g) of the material so obtained, piperidine-4-carboxamide (0.82 g), potassium carbonate (3.46 g) and DMF (40 ml) was stirred and heated to 45° C. for 20 hours. The resultant solid was isolated, washed in turn with DMF and with water and dried. There was thus obtained 4-(4-bromo-2-fluorophenoxy)-7-[3-(4-carbamoylpiperidin-1-yl)propoxy]-6-methoxyquinazoline (2.5 g); NMR Spectrum: (DMSOd$_6$) 1.45-1.7 (m, 4H), 1.82-2.1 (m, 5H), 2.22 (t, 2H), 2.86 (m, 2H), 3.96 (s, 3H), 4.03 (t, 2H), 6.65 (s, 1H), 7.14 (s, 1H), 7.38 (s, 1H), 7.42-7.55 (m, 3H), 7.78 (d, 1H), 8.53 (s, 1H); Mass Spectrum: M+H$^+$ 533 and 535.

A mixture of the material so obtained and a saturated solution of ammonia in isopropanol (100 ml) was sealed in a Carius tube and heated at 130° C. for 20 hours. The mixture was cooled and the solvent was evaporated. The residue was stirred with 2N aqueous sodium hydroxide solution (20 ml) for 1 hour. The solid was isolated and washed in turn with water and with methanol. There was thus obtained 4-amino-7-[3-(4-carbamoylpiperidin-1-yl)propoxy]-6-methoxyquinazoline (0.85 g); NMR Spectrum: (DMSOd$_6$) 1.4-1.7 (m, 4H), 1.8-2.1 (m, 5H), 2.4 (t, 2H), 2.68 (d, 2H), 3.86 (s, 3H), 4.1 (t, 2H), 6.66 (s, 1H), 7.03 (s, 1H), 7.15 (s, 1H), 7.33 (s, 2H), 7.53 (s, 1H), 8.23 (s, 1H); Mass Spectrum: M+H$^+$ 360.

[111] The product gave the following data: NMR Spectrum: (DMSOd$_6$) 1.5-1.7 (m, 4H), 1.8-2.1 (m, 5H), 2.4 (t, 2H), 2.88 (d, 2H), 2.94 (s, 3H), 4.0 (t, 2H), 6.65 (s, 1H), 7.1-7.5 (m, 5H), 8.05 (s, 1H), 8.66 (s, 1H), 10.6 (s, 1H), 11.8 (s, 1H); Mass Spectrum: M+H$^+$ 515.

[112] THF was added as a co-solvent. The product gave the following data: NMR Spectrum: (CDCl$_3$) 1.6-2.3 (m, 9H), 2.35 (s, 6H), 2.53 (t, 2H), 2.99 (d, 2H), 3.42 (s, 3H), 4.25 (t, 2H), 5.55 (s, 2H), 7.11 (s, 3H), 7.29 (s, 1H), 7.55 (s, 1H), 8.64 (s, 1H), 9.7 (s, 1H), 11.9 (s, 1H); Mass Spectrum: M+H$^+$ 507.

[113] DMF was used as the reaction solvent. The product was precipitated from the reaction mixture as a 1:1 adduct with DMF. This gave the following data: NMR Spectrum: (CDCl$_3$) 1.7-2.3 (m, 9H), 2.37 (s, 3H), 2.54 (t, 2H), 2.88 (s, 3H), 2.95 (s, 3H), 3.0 (m, partially obscured by DMF), 3.5 (s, 3H), 4.25 (t, 2H), 5.61 (broad d, 2H), 7.16-7.32 (m, 4H), 7.55 (s, 1H), 8.02 (s, 1H), 8.67 (s, 1H), 9.8 (s, 1H), 12.4 (s, 1H); Mass Spectrum: M+H$^+$ 527 and 529.

[114] Acetonitrile plus a few drops of DMF was used as the reaction solvent and the reaction mixture was heated to 45° C. for 3 hours. The product which was precipitated from the reaction mixture was isolated, washed with acetonitrile and diethyl ether and dried under vacuum. The. product gave the following data: Mass Spectrum: M+H$^+$ 440 and 442.

The 4-amino-7-[3-(pyrrolidin-1-yl)-1-propynyl]quinazoline used as a starting material was prepared as follows:

Trifluoromethanesulphonic anhydride (0.05 ml) was added dropwise to a stirred mixture of triphenylphosphine N-(7-hydroxyquinazolin-4-yl)imide (0.1 g), pyridine (0.5 ml) and methylene chloride (1 ml) which had been cooled to 0° C. The reaction mixture was stirred at 0° C. for 2 hours. A second portion (0.012 ml) of trifluoromethanesulphonic anhydride was added and the mixture was stirred at ambient temperature for 1.5 hours. The mixture was evaporated and the residue was partitioned between ethyl acetate and water. The organic solution was dried over magnesium sulphate and evaporated. The residue was purified by column chromatography on silica using increasingly polar mixtures of methylene chloride and ethyl acetate as eluent. There was thus obtained triphenylphosphine N-(7-trifluoromethanesulphonyloxyquinazolin-4-yl)imide (0.078 g).

A solution of 3-(pyrrolidin-1-yl)-1-propyne (J. Amer. Chem. Soc., 1958, 80, 4609; 0.08 g) in DMF (0.2 ml) was added to a mixture of triphenylphosphine N-(7-trifluoromethanesulphonyloxyquinazolin-4-yl)imide (0.2 g), cuprous iodide (0.004 g), tetrakis(triphenylphosphine)palladium(0) (0.02 g), triethylamine (0.201 ml) and DMF (8 ml). The mixture was degassed carefully and placed under an atomsphere of argon. The reaction mixture was stirred and heated to 60° C. for 2.5 hours. The mixture was cooled to ambient temperature and evaporated. The residue was partitioned between ethyl acetate and water. The organic phase was dried over magnesium sulphate and evaporated. The residue was purified by column chromatography on silica using a 9:1 mixture of methylene chloride and methanol as eluent. There was thus obtained triphenylphosphine N-{7-[3-(pyrrolidin-1-yl)-1-propynyl]quinazolin-4-yl}imide (0.18 g).

A mixture of the material so obtained, acetic acid (4 ml) and water (4 ml) was stirred and heated at 100° C. for 15 hours. The solvent was evaporated and the residue was partitioned between ethyl acetate and a saturated aqueous sodium bicarbonate solution. The organic solution was washed with water and brine, dried over magnesium sulphate and evaporated. The residue was purified by column chromatography on silica using initially a 9:1 mixture of methylene chloride and methanol and then a 19:1 mixture of methylene chloride and a saturated solution of ammonia in methanol as eluent. There was thus obtained 4-amino-7-[3-(pyrrolidin-1-yl)-1-propynyl]quinazoline (0.038 g); NMR Spectrum: (DMSOd$_6$) 1.75 (m, 4H), 2.6 (m, 4H), 3.65 (s, 2H), 7.45 (m, 1H), 7.25 (d, 1H), 7.85 (br s, 2H), 8.2 (d, 1H), 8.4 (s, 1H); Mass Spectrum: M+H$^+$ 253.

[115] DMF was used as the reaction solvent and 4-dimethylaminopyridine (0.1 equivalents) was added to catalyse the reaction. The product was precipitated from the reaction mixture by the addition of a mixture of diethyl ether and water. The product was isolated and dried under vaccuum and gave the following data: NMR Spectrum: (DMSOd$_6$) 1.72 (m, 4H), 2.6 (m, 4H), 3.69 (s, 2H), 3.97 (s, 3H), 7.4 (m, 1H), 7.58 (m, 2H), 7.9 (s, 1H), 8.15 (s, 1H), 8.75 (s, 1H), 10.8 (s, 1H), 11.95 (s, 1H); Mass Spectrum: M+H+ 470 and 472.

The 4-amino-6-methoxy-7-[3-(pyrrolidin-1-yl)-1-propynyl]quinazoline used as a starting material was prepared as follows:

Pyridine (1.13 ml) and a solution of trifluoromethanesulphonic anhydride (2.36 ml) in methylene chloride (10 ml) were added in turn to a stirred mixture of 4-(2-bromo-4-fluorophenoxy)-7-hydroxy-6-methoxyquinazoline (2.6 g) and methylene chloride (40 ml) which had been cooled in an ice bath to 0-5° C. The resultant mixture was stirred at ambient temperature for 4 hours. The mixture was washed in turn with dilute aqueous citric acid, water and a saturated aqueous sodium bicarbonate solution. The organic solution was dried over magnesium sulphate and evaporated. The residue was triturated under a 1:1 mixture of isohexane and diethyl ether. There was thus obtained 4-(2-bromo-4-fluorophenoxy)-6-methoxy-7-trifluoromethanesulphonyloxyquinazoline (2.58 g); NMR Spectrum: (CDCl$_3$) 4.13 (s, 3H), 7.14-7.5 (m, 3H), 7.81 (s, 1H), 7.91 (s, 1H), 8.7 (s, 1H); Mass Spectrum: M+H+ 497 and 499.

A mixture of a portion (0.8 g) of the material so obtained, 3-(pyrrolidin-1-yl)-1-propyne (0.57 g), triethylamine (0.8 ml), triphenylphosphine (0.03 g), bis(triphenylphosphine) palladium(II) chloride (0.06 g), cuprous iodide (0.06 g) and THF (5 ml) was stirred and heated to reflux for 3 hours. Dilute aqueous potassium carbonate solution was added and the mixture was extracted with ethyl acetate. The organic solution was dried over sodium sulphate and evaporated. The residue was purified by column chromatography on silica using a 10:1 mixture of methylene chloride and ethanol as eluent. There was thus obtained 4-(2-bromo-4-fluorophenoxy)-6-methoxy-7-[3-(pyrrolidin-1-yl)-1-propynyl]quinazoline (0.55 g); NMR Spectrum: (DMSOd$_6$) 1.75 (m, 4H), 2.64 (m, 4H), 3.71 (s, 2H), 4.01 (s, 3H), 7.38-7.81 (m, 3H), 7.66 (s, 1H), 8.0 (s, 1H), 8.62 (s, 1H); Mass Spectrum: M+H+ 456 & 458.

A mixture of the material so obtained and a 2M solution of ammonia in isopropanol (10 ml) was sealed in a Carius tube and heated to 130° C. for 18 hours. The reaction mixture was evaporated. The residue was partitioned between ethyl acetate and a 1N aqueous potassium carbonate solution. The organic solution was washed with brine, dried over anhydrous sodium sulphate and evaporated. The residue was triturated under a 1:1 mixture of isohexane and diethyl ether. The resultant solid was isolated and dried. There was thus obtained 4-amino-6-methoxy-7-[3-pyrrolidin-1-yl)-1-propynyl]quinazoline (0.24 g); Mass Spectrum: M+H+ 283.

[116] DMF was used as the reaction solvent and 4-dimethylaminopyridine (0.1 equivalents) was added to catalyse the reaction. The product gave the following data: NMR Spectrum: (DMSOd$_6$) 1.6 (m, 4H), 2.35 (m, 6H), 2.55 (m, 2H), 3.6 (m, 4H), 3.97 (s, 3H), 7.3-7.6 (m, 3H), 7.83 (s, 1H), 8.11 (s, 1H), 8.72 (s, 1H), 10.78 (s, 1H), 11.95 (s, 1H); Mass Spectrum: M+H+ 528 and 530.

The 4-amino-6-methoxy-7-(6-morpholino-1-hexynyl)quinazoline used as a starting material was prepared as follows:

Using an analogous procedure to that described in the second last paragraph of Note [115] above, 6-morpholino-1-hexyne was reacted with 4-(2-bromo-4-fluorophenoxy)-6-methoxy-7-trifluoromethanesulphonyloxyquinazoline to give 4-(2-bromo-4-fluorophenoxy)-6-methoxy-7-(6-morpholino-1-hexynyl)quinazoline, NMR Spectrum: (DMSOd$_6$) 1.63 (m, 4H), 2.33 (m, 6H), 2.55 (m, 2H), 3.56 (m, 4H), 4.0 (s, 3H), 7.35-7.8 (m, 3H), 7.65 (s, 1H), 7.96 (s, 1H), 8.6 (s, 1H); Mass Spectrum: M+H+ 514 and 516.

The material so obtained was reacted with ammonia using an analogous procedure to that described in the last paragraph of Note [115] above to give the required starting material.

6-Morpholino-1-hexyne was obtained by the reaction of 6-mesyloxy-1-hexyne with morpholine using an analogous procedure to that described in *J. Heterocyclic Chemistry* 1994, 31, 1421.

[171] DMF was used as the reaction solvent and 4-dimethylaminopyridine (0.1 equivalents) was added to catalyse the reaction. The product gave the following data: NMR Spectrum: (DMSOd$_6$) 1.6 (m, 4H), 2.32 (m, 6H), 2.55 (m, 2H), 3.55 (m, 4H), 3.98 (s, 3H), 7.1-7.4 (m, 3H), 7.82 (s, 1H), 8.11 (s, 1H), 8.7 (s, 1H), 10.78 (s, 1H), 11.68 (s, 1H), Mass Spectrum: M+H+ 496.

[118] DMF was used as the reaction solvent and 4-dimethylaminopyridine (0.1 equivalents) was added to catalyse the reaction. The product gave the following data: NMR Spectrum: (DMSOd$_6$) 1.55 (m, 2H), 1.85 (m, 2H), 2.28 (s, 3H), 2.56 (m, 2H), 3.9 (m, 2H), 3.96 (s, 3H), 6.7 (s, 1H), 7.07 (s, 1H), 7.36-7.62 (m, 3H), 7.85 (s, 1H), 8.13 (s, 1H), 8.71 (s, 1H) 10.8 (s, 1H), 11.95 (s, 1H); Mass Spectrum: M+H+ 523 and 525.

The 4-amino-6-methoxy-7-[6-(2-methylimidazol-1-yl)-1-hexynyl]quinazoline used as a starting material was prepared as follows:

Using an analogous procedure to that described in the second last paragraph of Note [115] above, 6-(2-methylimidazol-1-yl)-1-hexyne was reacted with 4-(2-bromo-4-fluorophenoxy)-6-methoxy-7-trifluoromethanesulphonyloxyquinazoline to give 4-(2-bromo-4-fluorophenoxy)-6-methoxy-7-[6-(2-methylimidazol-1-yl)-1-hexynyl]quinazoline; NMR Spectrum: (DMSOd$_6$) 1.56 (m, 2H), 1.85 (m, 2H), 2.28 (s, 3H), 2.56 (m, 2H), 3.9 (m, 2H), 3.98 (s, 3H), 6.75 (br m, 1H), 7.1 (br m, 1H), 7.36-7.82 (m, 3H), 7.63 (s, 1H), 8.61 (s, 1H); Mass Spectrum: M+H+ 509 and 511.

The material so obtained was reacted with ammonia using an analogous procedure to that described in the last paragraph of Note [115] above to give the required starting material.

6-(2-Methylimidazol-1-yl)-1-hexyne was obtained by the reaction of 6-mesyloxy-1-hexyne with 2-methylimidazole using an analogous procedure to that described in *J. Heterocyclic Chemistry*, 1994, 31, 1421.

[119] DMF was used as the reaction solvent and 4-dimethylaminopyridine (0.1 equivalents) was added to catalyse the reaction. The product gave the following data: NMR Spectrum: (DMSOd$_6$) 1.58 (m, 2H), 1.82 (m, 2H), 2.28 (s, 3H), 2.55 (m, 2H), 3.95 (m, 5H), 6.7 (s, 1H), 7.05 (s, 1H), 7.1-7.4 (m, 3H), 7.85 (s, 1H), 8.12 (s, 1H), 8.74 (s, 1H), 10.79 (s, 1H),; 11.69 (s, 1H); Mass Spectrum: M+H+ 491.

[120] DMF was used as the reaction solvent and 4-dimethylaminopyridine (0.1 equivalents) was added to catalyse the reaction. The product gave the following data: NMR Spectrum: (DMSOd$_6$) 2.28 (s, 6H), 3.54 (s, 2H), 3.98 (s, 3H), 7.18-7.47 (m, 3H), 7.92 (s, 1H), 8.15 (s, 1H), 8.74 (s, 1H), 10.8 (s, 1H), 11.68 (s, 1H); Mass Spectrum: M+H+ 412.

The 4-amino-6-methoxy-7-(3-dimethylamino-1-propynyl)quinazoline used as a starting material was prepared as follows:

Using an analogous procedure to that described in the second last paragraph of Note [115] above, 3-dimethylamino-1-propyne was reacted with 4-(2-bromo-4-fluorophenoxy)-6-methoxy-7-trifluoromethanesulphonyloxyquinazoline to give 4-(2-bromo-4-fluorophenoxy)-6-methoxy-7-(3-dimethylamino-1-propynyl)quinazoline; NMR Spectrum: (DMSOd$_6$) 2.29 (s, 6H), 3.55 (s, 2H), 4.0 (s, 3H), 7.38-7.83 (m, 3H), 7.67 (s, 1H), 8.05 (s, 1H), 8.63 (s, 1H); Mass Spectrum: M+H+ 430 and 432.

The material so obtained was reacted with ammonia using an analogous procedure to that described in the last paragraph of Note [115] above to give the required starting material.

[121] The product gave the following data: Mass Spectrum: M+H$^+$ 467.

[122] The product gave the following data: Mass Spectrum: M+H$^+$ 454.

[123] The product gave the following data: NMR Spectrum: (CDCl$_3$) 1.42-1.56 (m, 2H), 1.84-2.06 (m, 5H), 2.3 (s, 3H), 2.86-2.99 (m, 2H), 3.92 (s, 3H), 4.04 (d, 2H), 7.02 (m, 1H), 7.22 (s, 1H), 7.28 (s, 1H), 7.36 (d, 1H), 8.44 (d, 1H), 8.64 (s, 1H), 8.76 (s, 1H), 13.12 (s, 1H); Mass Spectrum: M+H$^+$ 490 and 492.

[124] The product gave the following data: NMR Spectrum: (CDCl$_3$) 1.42-1.58 (m, 2H), 1.84-2.06 (m, 5H), 2.3 (s, 3H), 2.58 (s, 3H), 2.86-2.96 (m, 2H), 3.86 (s, 3H), 4.04 (d, 2H), 7.22-7.28 (m, 2H), 7.36 (d, 1H), 7.92 (m, 1H), 8.6 (s, 1H), 8.76 (s, 1H), 9.06 (d, 1H), 12.62 (s, 1H); Mass Spectrum: M+H$^+$ 481.

[125] The product gave the following data: NMR Spectrum: (CDCl$_3$) 1.42-1.56 (m, 2H), 1.84-2.04 (m, 5H), 2.3 (s, 3H), 2.84-2.94 (m, 2H), 3.94 (s, 3H), 4.06 (d, 2H), 7.1 (s, 1H), 7.76-7.36 (m, 2H), 7.56 (d, 1H), 8.22 (s, 1H), 8.78 (m, 2H), 13.16 (s, 1H); Mass Spectrum: M+H$^+$ 524 and 526.

[126] The product gave the following data: NMR Spectrum: (CDCl$_3$) 1.42-1.56 (m, 2H), 1.86-2.06 (m, 5H), 2.3 (s, 3H), 2.84-2.96 (m, 2H), 3.94 (s, 3H), 3.98 (s, 3H), 4.04 (d, 2H), 6.84 (d, 1H), 7.04 (m, 1H), 7.2 (s, 1H), 7.28 (s, 1H), 8.3-8.38 (m, 2H), 8.76 (s, 1H), 12.74 (s, 1H); Mass Spectrum: M+H$^+$ 486 and 488.

[127]
The product gave the following data: NMR Spectrum: (CDCl$_3$) 1.44-1.56 (m, 2H), 1.86-2.06 (m, 5H), 2.3-2.34 (m, 6H), 2.84-2.96 (m, 2H), 3.86 (s, 3H), 3.98 (s, 4.04 (d, 2H), 6.82-6.9 (m, 2H), 7.24 (s, 1H), 7.36 (s, 1H), 8.06 (s, 1H), 8.76 (s, 1H), 8.9 (s, 1H), 12.64 (s, 1H); Mass Spectrum: M+H$^+$ 466.

[128] The product gave the following data: NMR Spectrum: (CDCl$_3$) 1.4-1.54 (m, 2H), 1.84-2.04 (m, 5H), 2.3 (s, 3H), 2.44 (s, 3H), 2.84-2.96 (m, 2H), 3.8 (s, 3H), 4.04 (d, 2H), 7.04 (m, 1H), 7.16 (d, 1H), 7.26 (s, 1H), 7.38. (s, 1H), 8.1 (s, 1H), 8.7 (s, 1H), 9.08 (s, 1H), 12.46 (s, 1H); Mass Spectrum: M+H$^+$ 470 and 472.

[129] The product gave the following data: NMR Spectrum: (CDCl$_3$) 1.42-1.56 (m, 2H), 1.84-2.04 (m, 5H), 2.3 (s, 3H), 2.44 (s, 3H), 2.86-2.96 (m, 2H), 3.86 (s, 3H), 4.04 (d, 2H), 6.8 (m, 1H), 7.18-7.22 (m, 1H), 7.24 (s, 1H), 7.28 (s, 1H), 7.96 (m, 1H), 8.58 (s, 1H), 8.72 (s, 1H), 12.4 (s, 1H); Mass Spectrum: M+H$^+$ 454.

[130] The product gave the following data: NMR Spectrum: (CDCl$_3$) 1.42-1.56 (m, 2H), 1,84-2.04 (m, 5H), 2.28 (s, 3H), 2.34 (s, 3H), 2.86-2.96 (m, 2H ), 3.86 (s, 3H), 4.04 (d, 2H), 6.88 (m, 1H), 7.22-7.32 (m, 3H), 8.12 (s, 1H), 8.76 (m, 2H), 12.78 (s, 1H); Mass Spectrum: M+H$^+$ 470 and 472.

[131] The product gave the following data: NMR Spectrum: (CDCl$_3$) 1.78-1.84 (m, 4H), 2.16 (m, 2H), 2.5-2.58 (m, 4H), 2.66 (t, 2H), 3.98 (s, 3H), 4.28 (t, 2H), 6.72-6.8 (m, 1H), 7.16-7.18 (m, 1H), 7.2 (s, 1H), 7.34 (s, 1H), 8.06-8.16 (m, 1H), 8.38 (s, 1H), 8.76 (s, 1H), 12.76 (s, 1H); Mass Spectrum: M+H$^+$ 458.

[132] The product gave the following data: NMR Spectrum: (CDCl$_3$) 1.78-1.84 (m, 4H), 2.16 (m, 2H), 2.48-2.58 (m, 4H), 2.66 (t, 2H), 3.96 (s, 3H), 4.28 (t, 2H), 7.02 (m, 1H), 7.14 (s, 1H), 7.32-7.4 (m, 2H), 8.3 (s, 1H), 8.46 (d, 1H), 8.78 (s, 1H), 13.06 (s, 1H); Mass Spectrum: M+H$^+$ 490 and 492.

[133] The product gave the following data: NMR Spectrum: (CDCl$_3$) 1.78-1.84 (m, 4H), 2.16 (m, 2H), 2.44 (s, 3H), 2.54-2.6 (m, 4H), 2.68 (t, 2H), 3.84 (s, 3H), 4.28 (t, 2H), 7.04 (m, 1H), 7.16 (d, 1H), 7.3 (s, 1H), 7.34 (s, 1H), 8.14 (d, 1H), 8.7 (s, 1H), 8.8 (s, 1H), 12.4 (s, 1H); Mass Spectrum: M+H$^+$ 470 and 472.

[134] The product gave the following data: NMR Spectrum: (CDCl$_3$) 1.78-1.84 (m, 4H), 2.16 (m, 2H), 2.44 (s, 3H), 2.5-2.6 (m, 4H), 2.66 (t, 2H), 3.86 (s, 3H), 4.28 (t, 2H), 6.72-6.8 (m, 1H), 7.16-7.2 (m, 2H), 7.34 (s, 1H), 7.96 (m, 1H), 8.46 (s, 1H), 8.72 (s, 1H), 12.4 (s, 1H); Mass Spectrum: M+H$^+$ 454.

[135] The product gave the following data: NMR Spectrum: (CDCl$_3$) 1.78-1.84 (m, 4H), 2.06-2.22 (m, 2H), 2.46-2.6 (m, 7H), 2.68 (t, 2H), 3.84 (s, 3H), 4.28 (t, 2H), 7.28 (m, 2H), 7.36 (d, 1H), 7.92 (d, 1H), 8.7 (s, 1H), 8.8 (s, 1H), 9.08 (s, 1H), 12.66 (s, 1H); Mass Spectrum: M+H$^+$ 481.

[136] The product gave tie following data: NMR Spectrum: (CDCl$_3$) 1.78-1.84 (m, 4H), 2.14 (m, 2H), 2.3 (s, 3H), 2.5-2.6 (m, 4H), 2.64 (t, 2H), 3.84 (s, 3), 4.28 (t, 2H), 6.88 (m, 1H), 7.28-7.36 (m, 3H), 8.14 (d, 1H), 8.78 (s, 1H), 8.88 (s, 1H), 12.9 (s, 1H); Mass Spectrum: M+H$^+$ 470 and 472.

[137] DMF was used as the reaction solvent. The product was obtained as a dihydrochloride salt and gave the following data: NMR Spectrum: (DMSOd$_6$) 1.6-1.7 (m, 2H), 1.82-1.96 (m, 2H), 2.58-2.62 (t, 2H), 2.8 (s, 3H), 3.3-3.9 (m, 10H), 4.02 (s, 3H), 7.4-7.6 (m, 3H), 7.95 (s, 1H), 8.21 (s, 1H), 8.8 (s, 1H), 11.6-12.0 (m, 2H); Mass Spectrum: M+H$^+$ 541 and 543.

The 4-amino-6-methoxy-7-[6-(N-methylpiperazin-1-yl)-1-hexynyl]quinazoline used as a starting material was prepared as follows:

Using an analogous procedure to that described in the second last paragraph of Note [115] above, 6-(N-methylpiperazin-1-yl)-1-hexyne was reacted with 4-(2-bromo-4-fluorophenoxy)-6-methoxy-7-trifluoromethane-sulphonyloxyquinazoline to give 4-(2-bromo-4-fluorophenoxy)-6-methoxy-7-[6-(N-methylpiperazin-1-yl)-1-hexynyl]quinazoline; NMR Spectrum: (DMSOd$_6$) 1.55-1.65 (m, 4H), 2.16 (s, 3H), 2.3-2.45 (m, 10H), 2.5-2.6 (m, 2H), 4.0 (s, 3H), 7.4-7.8 (m, 3H), 7.65 (s, 1H), 7.98 (s, 1H), 8.6 (s, 1H); Mass Spectrum: M+H$^+$ 527 and 529.

The material so obtained was reacted with ammonia using an analogous procedure to that described in the last paragraph of Note [115] above to give the required starting material. 6-(N-Methylpiperazin-1-yl)-1-hexyne was obtained by the reaction of 6-mesyloxy-1-hexyne with N-methylpiperazine using an analogous procedure to that described in *J. Heterocyclic Chemistry*, 1994, 31, 1421.

[138] The reactants were heated to 45° C. for 20 hours. The product gave the following data: NMR Spectrum: (CDCl$_3$) 2.24 (s, 3H), 2.34 (s, 3H), 2.78 (s, 3H), 3.08 (s, 3H), 3.58 (s, 3H), 5.3 (s, 2H), 7.06 (d, 1H), 7.18 (d, 1H), 7.3-7.52 (m, 7H), 8.64 (s, 1H), 9.4 (s, 1H), 11.87 (s, 1H); Mass Spectrum: M+H$^+$ 500.

The 3-(N,N-dimethylcarbamoyl)-2,6-dimethylphenylisocyanate used as a starting material was prepared as follows:

A solution of di-tert-butyl dicarbonate (0.081 g) in methylene chloride (1.6 ml) and a solution of 3-amino-N,N,2,4-tetramethylbenzamide (*J. Chem. Soc., Perkin Trans. I*, 1973, 1-4; 0.072 g) in methylene chloride (1.0 ml) were added in turn to a solution of 4-dimethylaminopyridine (0.004 g) in methylene chloride (0.4 ml). The resultant mixture was stirred at ambient temperature for 20 minutes. There was thus obtained a solution of 3-(N,N-dimethylcarbamoyl)-2,6-dimethylphenylisocyanate which was used without further purification.

[139] The product gave the following data: NMR Spectrum: (DMSOd$_6$) 0.37 (m, 2H), 0.62 (m, 2H), 1.32 (m, 1H), 2.25 (s, 6H), 3.94 (s, 3H), 4.03 (d, 2H), 7.12 (s, 3H), 7.22 (s, 1H), 8.07 (s, 1H), 8.66 (s, 1H), 10.38 (s, 1H), 11.68 (s, 1H); Mass Spectrum: M+H$^+$ 393.

The 4-amino-7-cyclopropylmethoxy-6-methoxyquinazoline used as a starting material was prepared as follows:

A mixture of 4-(4-bromo-2-fluorophenoxy)-7-hydroxy-6-methoxyquinazoline (6.99 g), cyclopropylmethyl chloride (2.16 g), potassium iodide (0.043 g), potassium carbonate (12 g) and DMF (200 ml) was stirred and heated to 45° C. for 16 hours. The mixture was cooled to ambient temperature and filtered. The filtrate was evaporated and the residue was purified by column chromatography on silica using increasingly polar mixtures of methylene chloride and methanol as eluent. There was thus obtained 4-(4-bromo-2-fluorophenoxy)-7-cyclopropylmethoxy-6-methoxyquinazoline (7.6 g); NMR Spectrum: (DMSOd$_6$) 0.43 (m, 2H), 0.68 (m, 2H), 1.37 (m, 1H), 4.0 (s, 3H), 4.1 (d, 2H), 7.4 (s, 1H), 7.45 (m, 1H), 7.57 (m, 2H), 7.82 (m, 1H), 8.58 (s, 1H); Mass Spectrum: M+H$^+$ 421 and 423.

Using an analogous procedure to that described in the last paragraph of the portion of Example 1 that is concerned with starting materials, 4-(4-bromo-2-fluorophenoxy)-7-cyclopropylmethoxy-6-methoxyquinazoline (1.75 g) was reacted with ammonia in isopropanol. There was thus obtained 4-amino-7-cyclopropylmethoxy-6-methoxyquinazoline (1.75 g); NMR Spectrum: (DMSOd$_6$) 0.36 (m, 2H), 0.58 (m, 2H), 1.3 (m, 1H), 3.88 (s, 3H), 3.94 (d, 2H), 6.97 (s, 1H), 7.39 (br s, 2H), 7.55 (s, 1H), 8.25 (s, 1H); Mass Spectrum: M+H$^+$ 246.

[140] The product gave the following data: NMR Spectrum: (DMSOd$_6$) 1.23-1.46 (m, 6H), 1.55-1.69 (m, 2H), 2.1 (s, 3H), 2.1-2.4 (m, 10H), 2.7-2.8 (m, 2H), 3.97 (s, 3H), 7.3-7.6 (m, 3H), 7.65 (s, 1H), 8.05 (s, 1H), 8.7 (s, 1H), 10.7 (s, 1H), 12.05 (s, 1H); Mass Spectrum: M+H$^+$ 545 and 547.

The 4-amino-6-methoxy-7-[6-(N-methylpiperazin-1-yl)hexyl]quinazoline used as a staring material was prepared as follows:

A mixture of 4-amino-6-methoxy-7-[6-(N-methylpiperazin-1-yl)-1-hexynyl]quinazoline (0.145 g), 10% palladium-on-charcoal catalyst (0.02 g) and ethanol (10 ml) was stirred at ambient temperature under 5 atmospheres pressure of hydrogen until uptake of hydrogen ceased. The reaction mixture was filtered and the filtrate was evaporated. There was thus obtained the title compound as a solid (0.142 g); Mass Spectrum: M+H$^+$ 358.

[141] The product gave the following data: NMR Spectrum: (CDCl$_3$) 1.8-2.0 (m, 6H), 2.5-2.7 (m, 6H), 2.79-2.85 (t, 2H), 3.6 (s, 3H), 7.2-7.4 (m, 3H), 7.4 (s, 1H), 7.73 (s, 1H), 8.72 (s, 1H), 9.3-9.45 (s, 1H), 12.3 (s, 1H); Mass Spectrum: M+H$^+$ 474 and 476.

The 4-amino-6-methoxy-7-[3-(pyrrolidin-1-yl)propyl]quinazoline used as a starting material was prepared by the hydrogenation of 4-amino-6-methoxy-7-[3-(pyrrolidin-1-yl)-1-propynyl]quinazoline using an analogous procedure to that described in Note [139] above.

[142] The product gave the following data: NMR Spectrum: DMSOd$_6$) 1.6-1.75 (m, 2H), 2.1 (s, 3H), 2.2-2.4 (m, 10H), 3.3 (m, 2H), 4.0 (s, 3H), 7.25-7.6 (m, 3H), 7.94 (s, 1H), 8.19 (s, 1H), 8.5 (br t, 1H), 8.77 (s, 1H), 10.87 (s, 1H), 11.96 (s, 1H); Mass Spectrum: M+H$^+$ 546 and 548.

The 4-amino-6-methoxy-7-{N-[3-(N-methylpiperazin-1-yl)propyl]carbamoyl}quinazoline used as a starting material was prepared as follows:

A mixture of 4-(2-bromo-4-fluorophenoxy)-6-methoxy-7-trifluoromethanesulphonyloxyquinazoline (9.7 g), palladium acetate (0.137 g), 1,3-bis(diphenylphosphino)propane (0.402 g), triethylamine (5.5 ml), DMF (60 ml) and methanol (1.2 L) was stirred and heated to 70° C. under 10 atmospheres pressure of carbon monoxide for 2 hours. The reaction mixture was cooled to ambient temperature and the solid was isolated, washed with methanol and dried under vacuum. There was thus obtained 4-(2-bromo-4-fluorophenoxy)-6-methoxy-7-methoxycarbonylquinazoline (5.96 g); NMR Spectrum: (DMSOd$_6$) 3.91 (s, 3H), 4.02 (s, 3H), 7.4-7.8 (m, 3H), 7.8 (s, 1H), 8.2 (s, 1H), 8.69 (s, 1H); Mass Spectrum: M+H$^+$ 407 & 409.

A mixture of a portion (2 g) of the product so obtained, 2,4,6-trimethoxybenzylamine hydrochloride (2.34 g), anhydrous potassium carbonate (2.76 g) and DMF (20 ml) was stirred and heated to 70° C. for 2 hours. The mixture was cooled to ambient temperature and diluted with water. The resultant solid was isolated, washed in turn with water and diethyl ether and dried under vacuum at 80° C. There was thus obtained 6-methoxy-7-methoxycarbonyl-4-(2,4,6-trimethoxybenzylamino)quinazoline (1.9 g); NMR Spectrum: (DMSOd$_6$) 3.75-3.85 (m, 15H), 4.55 (d, 2H), 6.3 (s, 2H), 7.8 (m, 2H), 7.9 (m, 1H), 8.45 (s, 1H); Mass Spectrum: M+H$^+$ 414.

A portion (1.8 g) of the material so obtained was suspended in a mixture of THF (27 ml), methanol (14 ml) and water (14 ml) and lithium hydroxide (0.945 g) was added portionwise. The resultant mixture was stirred at ambient temperature for 2 hours. The mixture was concentrated by evaporation and acidified to pH4 by the addition of 2N aqueous hydrochloride acid. The resultant solid was isolated, washed in turn with water and diethyl ether and dried at 80° C. There was thus obtained 7-carboxy-6-methoxy-4-(2,4,6-trimethoxybenzylamino)quinazoline (1.68 g); NMR Spectrum: (DMSOd$_6$) 3.7-3.9 (m, 12H), 4.55 (s, 2H), 6.28 (s, 2H), 7.7-7.9 (m, 3H), 8.42 (s, 1H); Mass Spectrum: M+H$^{30}$ 400.

A mixture of a portion (0.3 g) of the material so obtained, 3-(N-methylpiperazin-1-yl)propylamine (0.33 g), N-hydroxybenzotriazole (0.13 g), 1-(3-dimethylaminopropyl)-3-ethylcarbodiimide hydrochloride (0.287 g) and DMF (3 ml) was stirred at ambient temperature for 16 hours. Dilute aqueous potassium carbonate solution was added and the resultant solid was isolated, washed in turn with water and diethyl ether and dried at 60° C. under vacuum. There was thus obtained 6-methoxy-7-{N-[3-(N-methylpiperazin-1-yl)propyl]carbamoyl)4(2,4,6-trimethoxybenzylamino)quinazoline (0.285 g); NMR Spectrum: (DMSOd$_6$) 1.58-1.7 (m, 2H), 2.11 (s, 3H), 2.2-2.4 (m, 10H), 3.2-3.4 (m, 2H), 3.7-3.92 (m, 12H), 4.51 (m, 2H), 6.3 (s, 2H), 7.7-7.86 (m, 3H), 8.3-8.4 (br t, 1H), 8.42 (s, 1H); Mass Spectrum: M+H$^+$ 539.

A mixture of the material so obtained, trifluoroacetic acid (2 ml), anisole (0.2 ml) and concentrated sulphuric acid (0.2 ml) was stirred at ambient temperature for 2 hours. The mixture was evaporated and the residue was partitioned between diethyl ether and a 2M aqueous potassium carbonate solution. The aqueous solution was evaporated and the residue was extracted with methanol. The methanolic extracts were evaporated and the resultant solid was dried under vacuum. There was thus obtained 4-amino-6-methoxy-7-{N-[3-(N-methylpiperazin-1-yl)propyl]carbamoyl}quinazoline (0.086 g), Mass Spectrum: M+H$^+$ 359.

[143] The product gave the following data: NMR Spectrum: (DMSOd$_6$) 1.88-2.02 (m, 2H), 3.18-3.25 (m, 2H), 4.0 (s, 3H), 4.0-4.08 (m, 2H), 6.88 (s, 1H), 7.22 (s, 1H), 7.3-7.6 (m, 4H), 7.98 (s, 1H), 8.22 (s, 1H), 8.55-8.6 (br t, 1H), 8.8 (s, 1H), 10.9 (s, 1H), 11.98 (s, 1H); Mass Spectrum: M+H$^+$ 514 and 516.

The 4-amino-6-methoxy-7-{N-[3-(N-methylpiperazin-1-yl)propyl]carbamoyl}quinazoline used as a starting material was prepared by the reaction of 7-carboxy-6-methoxy-4-(2,4,6-trimethoxybenzylamino)quinazoline and 3-(1-imidazolyl)propylamine and subsequent cleavage of the 2,4,6-trimethoxybenzyl group using analogous procedures to those described in Note [142] above.

[144] The product gave the following data: NMR Spectrum: (DMSOd$_6$) 2.2 (s, 3H), 3.18-3.24 (m, 4H), 3.3-3.4 (m, 4H), 3.97 (s, 3H), 7.18 (s, 1H), 7.3-7.6 (m, 3H), 7.98 (s, 1H), 8.65 (s, 1H), 10.6 (s, 1H), 12.12 (s, 1H); Mass Spectrum: M+H$^+$ 461 and 463.

The 4-amino-6-methoxy-7-(N-methylpiperazin-1-yl)quinazoline used as a starting material was prepared as follows:

A mixture of 4-(2-bromo-4-fluorophenoxy)-6-methoxy-7-trifluoromethanesulphonyloxyquinazoline (0.8 g), 1-methylpiperazine (0.35 ml), caesium carbonate (0.78 g), 1,1'-bis(diphenylphosphino)ferrocene (0.088 g), bis(dibenzylideneacetone)palladium (0.046 g) and toluene (12 ml) was stirred and heated to 100° C. for 6 hours. The mixture was cooled to ambient temperature and partitioned between ethyl acetate and water. The organic extract was washed with a saturated aqueous sodium chloride solution, dried over anhydrous sodiumsulphate and evaporated. The residue was purified by column chromatography on silica using increasingly polar mixtures of methylene chloride and methanol as eluent. There was thus obtained 4-(2-bromofluorophenoxy)-6-methoxy-7-(N-methylpiperazin-1-yl)quinazoline (0.26 g); NMR Spectrum: (CDCl$_3$) 2.4 (s, 3H), 2.66-2.68 (m, 4H), 3.34-3.38 (m, 4H), 4.05 (s, 3H), 7.1-7.44 (m, 3H), 7.38 (s, 1H), 7.55 (s, 1H), 8.58 (s, 1H); Mass Spectrum: M+H$^+$ 447 and 449.

The material so obtained was reacted with ammonia using an analogous procedure to that described in the last paragraph of Note [115] above to give the required starting material.

[145] The product gave the following data: NMR Spectrum: (DMSOd$_6$) 1.43 (s, 9H), 3.13-3.19 (m, 4H), 3.45-3.55 (m, 4H), 4.0 (s, 3H), 7.2 (s, 1H), 7.35-7.6 (m, 3H), 8.02 (s, 1H), 8.65 (s, 1H), 10.65 (s, 1H), 12.1 (s, 1H); Mass Spectrum: M+H$^+$ 547 and 549.

The 4-amino-7-[N-(tert-butoxycarbonyl)piperazin-1-yl]-6-methoxyquinazoline used as a starting material was prepared from as follows:

The procedure described in the first paragraph of the portion of Note [144] above which is concerned with the preparation of starting materials was repeated except that 1-(tert-butoxycarbonyl)piperazine was used in place of 1-methylpiperazine. There was thus obtained 4-(2-bromo-4-fluorophenoxy)-6-methoxy-7-[N-(tert-butoxycarbonyl)piperazin-1-yl]quinazoline; NMR Spectrum: (CDCl$_3$) 1.5 (s, 9H), 3.22 (m, 4H), 3.66 (m, 4H), 4.08 (s, 3H), 7.1-7.46 (m, 3H), 7.35 (s, 1H), 7.57 (s, 1H), 8.58 (s, 1H); Mass Spectrum: M+H$^+$ 533 and 535.

The material so obtained was reacted with ammonia using an analogous procedure to that described in the last paragraph of Note [115] above to give the required starting material.

[146] The product gave the following data: NMR Spectrum: (DMSOd$_6$) 1.75-1.85 (m, 2H), 2.3-2.45 (m, 6H), 3.25-3.35 (m, 2H), 3.6-3.68 (m, 4H), 4.0 (s, 3H), 6.7 (s, 1H), 6.89 (t, 1H), 7.35-7.6 (m, 3H), 7.88 (s, 1H), 8.51 (s, 1H), 10.3 (s, 1H), 12.25 (s, 1H); Mass Spectrum: M+H$^+$ 505 and 507.

The 4-amino-6-methoxy-7-(3-morpholinopropylamino)quinazoline used as a starting material was prepared as follows:

The procedure described in the first paragraph of the portion of Note [144] above which is concerned with the preparation of starting materials was repeated except that 3-morpholinopropylamine was used in place of 1-methylpiperazine. There was thus obtained 4-(2-bromofluorophenoxy)-6-methoxy-7-)3-morpholinopropylamino)quinazoline; NMR Spectrum: (CDCl$_3$) 1.9-2.0 (m, 2H), 2.48-2.6 (m, 6H), 3.35-3.42 (m, 2H), 3.78-3.82 (m, 4H), 4.07 (s, 3H), 6.4-648 (t, 1H), 6.86 (s, 1H), 7.1-7.42 (m, 3H), 7.43 (s, 1H) 8.5 (s, 1H); Mass Spectrum: M+H$^+$ 491 and 493.

The material so obtained was reacted with ammonia using an analogous procedure to that described in the last paragraph of Note [115] above to give the required starting material.

[147] The product gave the following data: NMR Spectrum: (DMSOd$_6$) 2.0-2.12 (m, 2H), 3.15-3.25 (m, 2H), 4.0 (s, 3H), 4.05-4.12 (m, 2H), 6.45-6.5 (t, 1H), 6.68 (s, 1H), 6.9 (s, 1H), 7.22 (s, 1H), 7.35-7.6 (m, 3H), 7.65 (s, 1H), 7.88 (s, 1H), 8.55 (s, 1H), 10.35 (s, 1H), 12.22 (s, 1H); Mass Spectrum: M+H$^+$ 486 and 488.

The 4-amino-7-(3-imidazol-1-ylpropylamino)-6-methoxyquinazoline used as a starting material was prepared from as follows:

The procedure described in the first paragraph of the portion of Note [144] above which is concerned with the preparation of starting materials was repeated except that 3-imidazol-1-ylpropylamine was used in place of 1-methylpiperazine. There was thus obtained 4-(2-bromo-4-fluorophenoxy)-7-(3-imidazol-1-ylpropylamino)-6-methoxyquinazoline; NMR Spectrum: (CDCl$_3$) 2.2-2.3 (m, 2H), 3.3-3.4 (m, 2H), 4.05 (s, 3H), 4.1-4.15 (m, 2H), 5.04-5.13 (br t, 1H), 6.88 (s, 1H), 6.96 (s, 1H), 7.1 (s, 1H), 7.15-7.5 (m, 3H), 7.45 (s, 1H), 7.52 (s, 1H), 8.55 (s, 1H); Mass Spectrum: M+H$^+$ 472 and 474.

The material so obtained was reacted with ammonia using an analogous procedure to that described in the last paragraph of Note [115] above to give the required starting material.

[148] The reactants were heated to 45° C. for 20 hours. The product gave the following data: NMR Spectrum: (CDCl$_3$) 1.2-1.4 (m, 2H), 1.66-1.94 (m, 5H), 2.14 (s, 3H), 2.16 (s, 3H), 2.26 (s, 3H), 2.7 (m, 2H), 2.78 (s, 3H), 2.98 (s, 3H), 3.94 (s, 3H), 4.04 (d, 2H), 7.0 (d, 1H), 7.18 (d, 1H), 7.24 (s, 1H), 8.02 (s, 1H), 8.64 (s, 1H), 10.36 (s, 1H), 11.72 (s, 1H); Mass Spectrum: M+H$^+$ 521.

[149] The product gave the following data: NMR Spectrum: (CDCl$_3$) 1.73 (m, 4H), 2.09 (m, 2H), 2.28 (s, 3H), 2.48 (br m, 4H), 2.57 (t, 2H), 3.35 (s, 3H), 4.18 (t, 2H), 5.24 (s, 1H), 7.08 (d, 2H), 7.19 (s, 1H), 7.27 (t, 1H), 7.42 (s, 1H), 8.61 (s, 1H), 9.72 (s, 1H), 12.19 (s, 1H), Mass Spectrum: M+H$^+$ 470 and 472.

[150] The product gave the following data: Mass Spectrum: M+H$^+$ 450 and 452.

The 4-amino-7-(3-methoxypropylamino)-6-methoxyquinazoline used as a starting material was prepared from as follows:

The procedure described in the first paragraph of the portion of Note [144] above which is concerned with the preparation of starting materials was repeated except that 3-methoxypropylamine was used in place of 1-methylpiperazine. There was thus obtained 4-(2-bromofluorophenoxy)-7-(3-methoxypropylamino)-6-methoxyquinazoline.

The material so obtained was reacted with ammonia using an analogous procedure to that described in the last paragraph of Note [115] above to give the required starting material.

[151] The product gave the following data: Mass Spectrum: M+H$^+$ 421 and 423.

The 4-amino-7-(2-aminoethylamino)-6-methoxyquinazoline used as a starting material was prepared from as follows:

The procedure described in the first paragraph of the portion of Note [144] above which is concerned with the preparation of starting materials was repeated except that ethylenediamine was used in place of 1-methylpiperazine. There was thus obtained 7-(2-aminoethylamino)-4-(2-bromo-4-fluorophenoxy)-6-methoxyquinazoline.

The material so obtained was reacted with ammonia using an analogous procedure to that described in the last paragraph of Note [115] above to give the required starting material.

[152] The product gave the following data: Mass Spectrum: M+H$^+$ 491 and 493.

The 4-amino-7-[N-(2-diethylaminoethyl)-N-methylamino]-6-methoxyquinazoline used as a starting material was prepared from as follows:

The procedure described in the first paragraph of the portion of Note [144] above which is concerned with the preparation of starting materials was repeated except that N-(2-diethylaminoethyl)-N-methylamine was used in place of 1-methylpiperazine. There was thus obtained 4-(2-bromo-4-fluorophenoxy)-7-[N-(2-diethylaminoethyl)-N-methylamino]-6-methoxyquinazoline.

The material so obtained was reacted with ammonia using an analogous procedure to that described in the last paragraph of Note [115] above to give the required starting material.

EXAMPLE 3

1-(7-benzyloxy-6-methoxyquinazolin-4-yl)-3-(2,6-dichlorophenyl)urea 2,6-Dichlorophenyl isocyanate (0.745 g) was added to a solution of 4-amino-7-benzyloxy-6-methoxyquinazoline (0.279 g) in chloroform (10 ml) and the reaction mixture was stirred at ambient temperature for 16 hours. The resultant precipitate was isolated by filtration. There was thus obtained the title compound (0.343 g); NMR Spectrum: (DMSOd$_6$) 3.96 (s, 3H), 5,32 (s, 2H), 7.35-7.60 (m, 10H), 8.1 (s, 1H), 8.69 (s, 1H), 10.65 (s, 1H), 12.09 (s, 1H); Mass Spectrum: M+H$^+$ 467 & 469.

EXAMPLE 4

1-(2,6-dichlorophenyl)-3-(6,7-dimethoxyquinazolin-4-yl)urea

Using an analogous procedure to that described in Example 3, 2,6-dichlorophenyl isocyanate was reacted with 4-amino-6,7-dimethoxyquinazoline (European Patent Application No. 30156, Chemical Abstract volume 95, abstract 187290) to give the title compound; NMR Spectrum: (DMSOd$_6$) 3.96 (s, 3H), 7.31 (m, 2H), 7.38 (t, 1H), 7.5 (d, 2H), 7.6 (d, 2H), 8.43 (s, 1H), 8.7 (s, 1H), 10.61 (s, 1H), 12.09 (s, 1H); Mass Spectrum M+H$^+$ 393 & 395.

EXAMPLE 5

1-(2,6-dichlorophenyl)-3-[6-methoxy-7-(N-methylpiperidin-4-ylmethoxy)quinazolin-4-yl]-3-methylurea 6-Methoxymethylamino-7-(N-methylpiperidin-4-ylmethoxy)quinazoline (0.195 g) was added to 2,6-dichlorophenyl isocyanate (0.3 g) under argon and the solids were mixed together using a spatula. The mixture was heated to 85° C. with gentle mixing for 40 minutes. The mixture was cooled to ambient temperature, dissolved in a mixture of chloroform (15 ml) and methanol (5 ml) and purified by column chromatography on silica using increasingly polar mixtures of methylene chloride and a 1% aqueous ammonium hydroxide solution as eluent. There was thus obtained the title compound (0.016 g); NMR Spectrum: (CDCl$_3$) 1.5 (m, 2H), 1.98 (m, 5H), 2.3 (s, 3H), 2.91 (d, 2H), 3.6 (s, 3H), 4.02 (s, 3H), 4.03 (d, 2H), 7.1 (t, 1H), 7.28 (s, 2H), 7.37 (d, 2H), 8.61 (s, 1H), 8.96 (s, 1H); Mass Spectrum: M+H$^+$ 504.

The 6-methoxy-4-methylamino-7-(N-metylpiperidin-4-ylmethoxy)quinazoline used as a starting material was obtained as follows:

A mixture of 4-chloro-6-methoxy-7-(N-methylpiperidin-4-ylmethoxy)quinazoline (1 g) and methylamine (1M solution in THF; 20 ml) was heated with agitation in a Carius tube at 120° C. for 16 hours. The Carius tube was cooled and opened and the reaction mixture was evaporated. The residue was partitioned between chloroform and a 2N aqueous. sodium hydroxide solution. The chloroform solution was dried over magnesium sulphate and evaporated and the resultant solid was washed with methyl tert-butyl ether (20 ml). There was thus obtained the required starting material (0.48 g); NMR Spectrum: (DMSOd$_6$) 1.33 (m, 2H), 1.8 (m, 5H), 2.14 (s, 3H), 2.76 (d, 2H), 2.96 (d, 3H), 3.85 (s, 3H), 3.92 (d, 2H), 7.03 (s, 1H), 7.51 (s, 1H), 7.84 (q, 1H), 8.31 (s, 1H).

EXAMPLE 6

1-16-methoxy-7-(N-methylpiperidin-4-ylmethoxy)quinazolin-4-yl]-3-(2-methylbenzyl)urea Using an analogous procedure to that described in Example 3, 2-methylbenzyl isocyanate was reacted with 4-amino-6-methoxy-7-(N-methylpiperidin-4-ylmethoxy)quinazoline. The resultant solid was purified by column chromatography on silica using increasingly polar mixtures of methylene chloride, methanol and a 1% aqueous ammonium hydroxide solution as eluent There was thus obtained the title compound; NMR Spectrum: (CDCl$_3$) 1.39-1.56 (m, 2H), 1.84-2.04 (m, 5H), 2.29 (s, 3H), 2.39 (s, 3H), 2.9 (d, 2H), 3.92 (s, 3H), 4.03 (d, 2H), 4.66 (d, 2H), 7.21 (m, 4H), 7.34 (m, 2H), (m, 2H), 8.6 (s, 1H), 8.74 (s, 1H), 10.44 (t, 1H); Mass Spectrum: M+H$^+$ 450.

EXAMPLE 7

1-(2,6-dichlorophenyl)-3-(thieno[3,2-d]pyrimidin-4-yl)urea 2,6-Dichlorophenyl isocyanate (0.075 g) was added to a mixture of 4-aminothieno[3,2-d]pyrimidine (*Tetrahedron,* 1971, 27, 487; 0.201 g) and acetonitrile (16 ml) and the resultant mixture was stirred at ambient temperature for 16 hours. The precipitate was isolated and washed in turn with diethyl ether and methanol. There was thus obtained the title compound (0.31 g); NMR Spectrum: (DMSOd$_6$) 7.25 (t, 1H), 7.45 (d, 1H), 7.55 (d, 1H), 7.95 (d, 1H), 8.4 (s, 1H), 8.8 (s, 1H), 11.7 (br s, 1H); Mass Spectrum: M+H$^+$ 339 and 341; Elemental Analysis: Found C, 45.8; H 2.4; N, 16.5; $C_{13}H_8Cl_2N_4OS$ requires C, 46.03; H, 2.38; N, 16.52%.

EXAMPLE 8

(E)-3-{4-[3-(2,6-dichlorophenyl)ureido]thieno[3,2-d]pyrimidin-6-yl}acrylic acid Hydrogen chloride gas was bubbled during 3 hours through a stirred solution of tert-butyl (E)-3-{4-[3-(2,6-dichlorophenyl)ureido]thieno[3,2-d]pyrimidin-6-yl}acrylate (1.4 g) in methylene chloride (200 ml) which had been cooled in an ice-bath to 0° C. The mixture was evaporated and there was thus obtained the title compound as its hydrochloride salt; (1.3 g); NMR Spectrum: (DMSOd$_6$ and CF$_3$COOD) 6.6 (d, 1H, J=16 Hz), 7.4 (t, 1H), 7.65 (d, 2H), 7.95 (d, 1H), 7.96 (s, 1H), 8.9 (s, 1H), Mass Spectrum: M+H$^+$ 409, 411 and 413.

The tert-butyl (E)-3- {4-[3-(2,6-dichlorophenyl)ureido] thieno[3,2-d]pyrimidin-6-yl}acrylate used as a starting material was obtained as follows:

A mixture of methyl 3-aminothiophene-2-carboxylate (94 g), formamidine acetic acid salt (187 g) and 2-hydroxyethyl methyl ether (1 L) was stirred and heated to reflux for 3 hours. The mixture was cooled to ambient temperature and water (400 ml) was added. The resultant solid was isolated, washed thoroughly with water and with diethyl ether and dried under vacuum. There was thus obtained 3,4dihydrothieno[3,2-d]-pyrimidin-4-one (65 g); NMR Spectrum: (DMSOd$_6$) 7.4 (d, 1H), 8.15 (s, 1H), 8.18 (d, 2H); Mass Spectrum: M+Na$^+$ 175.

A mixture of a portion (20 g) of the material so obtained, thionyl chloride (250 ml) and DMF (1 ml) was heated to reflux for 2 hours. The mixture was evaporated. Toluene was added and the mixture was evaporated. The residual solid was partitioned between ethyl acetate and a saturated aqueous sodium bicarbonate solution. The organic layer was washed in turn with water and brine, dried over magnesium sulphate and evaporated. The solid so obtained was triturated under petroleum ether (b.p. 60-80° C.), re-isolated and dried under vacuum. There was thus obtained 4-chlorothieno[3,2,-d]pyrimidine (18.5 g); NMR Spectrum: (CDCl$_3$) 7.65 (d, 1H), 8.1 (d, 1H), 9.0 (s, 1H); Mass Spectrum: M$^{30}$ 170 and 172.

A portion (17 g) of the material so obtained was dissolved in DMF (100 ml). Sodium methylthiolate (9.1 g) was added and the mixture was stirred at ambient temperature for 1.5 hours. The mixture was partitioned between ethyl acetate and water. The organic layer was washed with brine, dried over magnesium sulphate and purified by column chromatography on silica using a 9:1 mixture of methylene chloride and ethyl acetate as eluent. There was thus obtained 4-methylthiothieno [3,2-d]pyrimidine (16.5 g); NMR Spectrum: (CDCl$_3$) 2.76 (s, 3H), 7.5 (d, 1H), 7.85 (d, 1H), 8.97 (s, 1H).

A portion (5.5 g) of the material so obtained was dissolved in THF (20 ml) and cooled to −78° C. A solution of lithium diisopropylamide [prepared using diisopropylamine (10.5 ml) and n-butyllithium (2.5M in THF; 30 ml)] was added and the mixture was stirred at −78° C. for 1 hour. DMF (7 ml) was added and the mixture was allowed to warm to ambient temperature and was stirred for 16 hours. The resultant mixture was partitioned between ethyl acetate and a saturated aqueous ammonium chloride solution. The organic layer was evaporated and the residue was purified by column chromatography on silica using a 9:1 mixture of methylene chloride and ethyl acetate as eluent. There was thus obtained 6-formyl-4-methylthiothieno[3,2-d]pyrimidine (4.1 g); NMR Spectrum: (CDCl$_3$) 2.78 (s, 3H), 8.13 (s, 1H), 9.04 (s, 1H), 10.23 (s, 1H); Mass Spectrum: M+H$^+$ 211.

tert-Butoxycarbonylmethylenetriphenylphosphorane (20.6 g) was added portionwise to a solution of 6-formyl-4-methylthiothieno[3,2-d]pyrimidine (9.6 g) in methylene chloride (500 ml) and the mixture was stirred at ambient temperature for 16 hours. The mixture was concentrated to half of its original volume and poured onto a column of silica. The column was eluted initially with methylene chloride followed by a 19:1 mixture of methylene chloride and ethyl acetate. The material so obtained was triturated under petroleum ether (b.p. 60-80° C.), re-isolated and dried under vacuum. There was thus obtained tert-butyl (E)-3-(4-methylthiothieno[3,2-d]pyrimidin-6-yl)acrylate (12 g); NMR Spectrum: (CDCl$_3$) 1.54 (s, 9H), 2.76 (s, 3H), 6.42 (d, 1H, J=15 Hz), 7.53 (s, 1H), 7.8 (d, 1H); Mass Spectrum: M+H$^+$ 308.

A portion (2.9 g) of the material so obtained was dissolved in methylene chloride (200 ml) and m-chloroperoxybenzoic acid (70%; 9.25 g) was added. The resultant mixture was stirred at ambient temperature for 2 hours. The mixture was washed with an aqueous sodium bisulphite solution. The organic layer was washed with a dilute (5%) aqueous sodium bicarbonate solution and with brine, dried over magnesium sulphate and evaporated. There was thus obtained tert-butyl (E)-3-(4-methylsulphonylthieno[3,2-d]pyrimidin-6-yl)acrylate (3.1 g); NMR Spectrum: (CDCl$_3$) 1.55 (s, 9H), 3.39 (s, 3H), 6.6 (d, 1H, J=16 Hz), 7.71 (s, 1H), 7.85 (d, 1H), 9.3 (s, 1H).

A solution of the sulphone so obtained (3 g) in THF (100 ml) was cooled at 0° C. and gaseous ammonia was bubbled through the solution for 2 hours. The mixture was evaporated and the residue was triturated under diethyl ether. The solid so obtained was purified by column chromatography on silica using a 49:1 mixture of methylene chloride and methanol as eluent. There was thus obtained tert-butyl (E)-3-(4-aminothieno[3,2-d]pyrimidin-6-yl)acrylate (1.7 g); NMR Spectrum: (CDCl$_3$) 1.55 (s, 9H), 5.25 (br s, 2H), 6.38 (d, 1H, J=16 Hz), 7.51 (s, 1H), 7.76 (d, 1H), 8.6 (s, 1H); Mass Spectrum: M+H$^+$ 277.

A mixture of the material so obtained, 2,6-dichlorophenyl isocyanate (1.41 g) and methylene chloride (250 ml) was stirred at ambient temperature for 3 hours. Water was added and the organic layer was separated, washed with water and brine, dried over magnesium sulphate and evaporated. The residue was purified by column chromatography on silica using a 49:1 mixture of methylene chloride and methanol as eluent. There was thus obtained tert-butyl (E)-3-(4-[3-(2,6-dichlorophenyl)ureido]thieno[3,2-d]pyrimidin-6-yl}acrylate (1.5 g); NMR Spectrum: (CDCl$_3$) 1.57 (s, 9H), 6.29 (d, 1H, J=16 Hz), 7.3 (t, 1H), 7.53 (d, 2H), 7.55 (s, 1H), 7.74 (d, 1H), 8.8 (s, 1H), 9.95 (br s, 1H), 11.8 (br s, 1H), Mass Spectrum: M+H$^+$ 465, 467 & 469.

EXAMPLE 9

(E)-3-{4-[3-(2,6-dichlorophenyl)ureido]thieno[3,2-d]pyrimidin-6-yl}-N-(2-piperidinoethyl)acrylamide Diphenylphosphoryl azide (0.085 ml) was added to a mixture of (E)-3-{4-[3-(2,6-dichlorophenyl)ureido]thieno[3,2-d]pyrimidin-6-yl)acrylic acid hydrochloride salt (0.11 g), 2-piperidinoethylamine (0.064 g), triethylamine (0.07 ml) and DMF (1.5 ml). The mixture was stirred at ambient temperature for 16 hours. The mixture was evaporated and the residue was purified by column chromatography on silica using increasingly polar mixtures of methylene chloride and methanol as eluent. The material so obtained was triturated under diethyl ether, isolated, washed with diethyl ether and dried under vacuum. There was thus obtained the title compound (0.087 g); NMR Spectrum: (DMSOd$_6$ and CF$_3$COOD) 1.3-1.5 (m, 1H), 1.6-1.8 (m, 4H), 1.85 (d, 2H), 2.95 (t, 2H), 3.2 (t, 2H), 3.55 (d, 2H), 3.6 (t, 2H), 6.82 (d, 1H, J=16 Hz), 7.4 (t, 1H), 7.6 (d, 1H), 7.86 (s, 1H), 7.86 (d, 1H), 8.95 (s, 1H); Mass Spectrum: M+H$^+$ 519 and 521.

EXAMPLE 10

Using an analogous procedure to that described in Example 9, the appropriate amine was reacted with (E)-3-(4-[3-(2,6-dichlorophenyl)ureido]thieno[3,2-d]pyrimidin-6-yl}acrylic acid to give the compounds described in Table II.

TABLE II

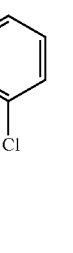

| No. | $R^a$ | $R^b$ | Note |
|---|---|---|---|
| 1 | 2-dimethylaminoethyl | hydrogen | (a) |
| 2 | 3-dimethylaminopropyl | hydrogen | (b) |
| 3 | 2-pyrrolidin-1-ylethyl | hydrogen | (c) |
| 4 | 3-(2-oxopyrrolidin-1-yl)propyl | hydrogen | (d) |
| 5 | 3-morpholinopropyl | hydrogen | (e) |
| 6 | 3-(4-methylpiperazin-1-yl)propyl | hydrogen | (f) |
| 7 | 3-imidazol-1-ylpropyl | hydrogen | (g) |
| 8 | 4-pyridylmethyl | hydrogen | (h) |
| 9 | 2-(2-pyridyl)ethyl | hydrogen | (i) |
| 10 | 2-(2-pyridyl)ethyl | methyl | (j) |

Notes
(a) The product gave the following data: NMR Spectrum: (DMSOd$_6$ and CF$_3$COOD) 2.9(s, 6H), 3.25(t, 2H), 3.6(t, 2H), 6.9(d, 1H, J=16 Hz), 7.42(t, 1H), 7.65(d, 2H), 7.85(d, 1H), 7.88(s, 1H), 9.05(s, 1H); Mass Spectrum: M+H$^+$ 479 and 481.
(b) The product gave the following data: NMR Spectrum: (DMSOd$_6$ and CF$_3$COOD) 1.8-1.9(m, 2H), 2.81(s, 3H), 3.15(m, 2H), 3.3(t, 2H), 6.84(d, 1H, J=19 Hz), 7.45(t, 1H), 7.6(d, 2H), 7.81(d, 1H), 7.85(s, 1H), 9.02(s, 1H); Mass Spectrum: M+H$^+$ 493 and 495.
(c) The product gave the following data: NMR Spectrum: (DMSOd$_6$ and CF$_3$COOD) 1.8-1.95(m, 2H), 1.95-2.1(m, 2H), 3.0-3.15(m, 2H), 3.3(t, 2H), 3.55(t, 2H), 3.55-3.7(m, 2H), 6.8(d, 1H), 7.42(t, 1H), 7.6(d, 2H), 7.82(d, 1H), 7.84(s, 1H), 8.9(s, 1H); Mass Spectrum: M+H$^+$ 505 and 507.
(d) The product gave the following data: NMR Spectrum: (DMSOd$_6$ and CF$_3$COOD) 1.65-1.75(m, 2H), 1.9-2.0(m, 2H), 2.3(t, 2H), 3.25(t, 2H), 3.3(t, 2H), 3.4(t, 2H), 6.25(d, 1H, J=16 Hz), 7.42(t, 1H), 7.62(d, 2H), 7.81(d, 1H), 7.85(s, 1H), 9.12(s, 1H); Mass Spectrum: M+H$^+$ 533 and 535.
(e) The product gave the following data: NMR Spectrum: (DMSOd$_6$ and CF$_3$COOD) 1.85-2.0(m, 2H), 3.0-3.25(m, 4H), 3.3(t, 2H), 3.5(d, 2H), 3.7(1, 2H), 4.0(d, 2H), 6.9(d, 1H, J=16 Hz), 7.45(t, 1H), 7.61(d, 2H), 7.85(d, 1H), 7.87(s, 1H), 9.08(s, 1H); Mass Spectrum: M+H$^+$ 535 and 537.
(f) The product gave the following data: NMR Spectrum: (DMSOd$_6$ and CF$_3$COOD) 1.85-2.0(m, 2H), 2.95(s, 3H), 3.2-3.4(m, 6H), 3.4-4.0(br m, 6H), 6.85(d, 1H, J=14 Hz), 7.42 (t, 1H), 7.65(d, 2H), 7.82(d, 1H), 7.85(s, 1H), 9.0(s, 1H); Mass Spectrum: M+H$^+$ 548 and 550.
(g) The product gave the following data: NMR Spectrum: (DMSOd$_6$ and CF$_3$COOD) 2.0-2.1(m, 2H), 3.25(t, 2H), 4.25(t, 2H), 6.75(d, 1H, J=15 Hz), 7.2-7.3(d, 1H), 7.4(t, 2H), 7.6(d, 2H), 7.85(m, 2H), 8.9(s, 1H), 9.2(s, 1H); Mass Spectrum: M+H$^+$ 516.
(h) The product gave the following data: NMR Spectrum: (DMSOd$_6$ and CF$_3$COOD) 4.75(br s, 2H), 6.95(d, 1H, J=15 Hz), 7.4(1, 1H), 7.6(d, 1H), 7.85(s, 1H), 7.87(d, 1H), 8.05(d, 2H), 8.9(d, 2H), 8.93(s, 1H); Mass Spectrum: M+H$^+$ 499 and 501.
(i) The product gave the following data: NMR Spectrum: (DMSOd$_6$ and CF$_3$COOD) 3.25(t, 2H), 3.7(1, 2H), 6.8(d, 1H, J=15 Hz), 7.42(t, 1H), 7.62(d, 2H), 7.75(d, 1H), 7.83(s, 1H), 8.0(1, 1H), 8.05(d, 1H), 8.58(1, 1H), 8.9(d, 1H), 9.0(s, 1H); Mass Spectrum: M+H$^+$ 513 and 515.
(j) The product gave the following data: NMR Spectrum: (DMSOd$_6$ and CF$_3$COOD) 3.4(s, 3H), 5.0(s, 2H), 7.35-7.5(m, 2H), 7.61(d, 1H), 7.8(d, 1H), 7.98(s, 1H), 7.85-8.1(m, 2H), 8.6(t, 1H), 8.9(d, 1H), 9.0(s, 1H); Mass Spectrum: M+H$^+$ 513 and 515.

EXAMPLE 11

1-benzyl-3-[6-methoxy-7-(N-methylpiperidin-4-ylmethoxy)quinazolin-4-yl]urea

Using an analogous procedure to that described in Example 1 except that the reaction mixture was heated to 35° C. for 16 hours, benzyl isocyanate was reacted within 4-amino-6-methoxy-7-(N-methylpiperidin-4-ylmethoxy)quinazoline to give the title compound; NMR Spectrum: (DMSOd$_6$): 1.3-1.5 (m, 2H), 1.8-1.9 (m, 4H), 1.95 (t, 1H), 2.2 (s, 3H), 2.8 (br, d 2H), 3.9 (br s, 3H), 4.0 (br d, 2H), 4.5 (br d, 2H), 7.2-7.3 (m, 2H), 7.3-7.4 (m, 4H), 8.0 (br s, 1H), 8.55 (br s, 1H), 10.2-10.5 (br s, 1H), 10.4 (t, 1H); Mass Spectrum: M+H$^+$ 436.

EXAMPLE 12

1-[6-methoxy-7-(N-methylpiperidin-4-ylmethoxy)quinazolin-4-yl]-3-phenethylurea

Using an analogous procedure to that described in Example 3, phenethyl isocyanate was reacted with 4-amino-6methoxy-7-(N-methylpiperidin4ylmethoxy)quinazoline to give the title compound; NMR Spectrum: (CDCl$_3$) 1.48 (m, 2H), 1.98 (m, 5H), 2.29 (s, 3H), 2.91 (m, 4H), 3.7 (q, 2H), 4.02 (d, 5H), 7.28 (m, partially obscured by CHCl$_3$ peak), 8.47 (s, 1H), 8.65 (s, 1H), 10.1 (s, 1H); Mass Spectrum: M+H$^+$ 450.

EXAMPLE 13

Using an analogous procedure to that described in Example 1 except that, unless otherwise stated, chloroform was used in place of methylene chloride as the reaction solvent, the appropriate 4aminoquinazoline was reacted with the appropriate isocyanate to give the compounds described in Table III.

TABLE III

| No. | $R^6$ | $R^7$ | $(R^2)_n$ | Note |
|---|---|---|---|---|
| 1 | methoxy | N-methylpiperidin-4-ylmethoxy | 4-chloro | (a) |
| 2 | methoxy | N-methylpiperidin-4-ylmethoxy | 3,4-dichloro | (b) |
| 3 | methoxy | N-methylpiperidin-4-ylmethoxy | 3,5-dichloro | (c) |
| 4 | methoxy | N-methylpiperidin-4-ylmethoxy | 4-bromo | (d) |
| 5 | methoxy | N-methylpiperidin-4-ylmethoxy | 4-nitro | (e) |

Notes
(a) DMF was used in place of methylene chloride as the reaction solvent. The product gave the following data: NMR Spectrum: (CDCl$_3$) 1.48(m, 2H), 1.97(m, 5H), 2.29(s, 3H), 2.91(m, 2H), 3.81(s, 3H), 4.04(d, 2H), 7.25(s, 2H), 7.3(d, 2H), 7.57(d, 2H), 8.73(s, 1H), 8.91(s, 1H), 12.5(s, 1H); Mass Spectrum: M+H$^+$ 456 and 458.
(b) The product gave the following data: NMR Spectrum: (CDCl$_3$) 1.51(m, 2H), 1.92(m, 5H), 2.3(s, 3H), 2.92(d, 2H), 3.9(s, 3H), 4.03(d, 2H), 7.2(s, 1H), 7.24(s, partially obscured by CHCl$_3$ peak), 7.41(m, 2H), 7.82 (s, 1H), 8.55(s, 1H), 8.74(s, 1H), 12.55(s, 1H); Mass Spectrum: M+H$^+$ 490 and 492.
(c) DMF was used in place of methylene chloride as the reaction solvent. The product gave the following data: NMR Spectrum: (CDCl$_3$) 1.48(m, 2H), 1.95(m, 5H), 2.28(s, 3H), 2.95(d, 2H), 3.91(s, 3H), 4.03(d, 2H), 7.11(s, 1H), 7.26(s, 2H), 7.58(s, 2H), 8.63(s, 1H), 8.75(s, 1H), 12.7(s, 1H); Mass Spectrum: M+H$^+$ 490 and 492.
(d) Methylene chloride was used as the reaction solvent and the reaction mixture was heated to 35° C. for 16 hours. The product gave the following data: NMR Spectrum: (DMSOd$_6$) 1.2-1.4(m, 2H), 1.7-1.8(m, 4H), 1.85(t, 1H), 2.1(s, 3H), 2.8(d, 2H), 3.9(br s, 3H), 4.0(br d, 2H), 7.2(s, 1H), 7.4-7.45 (m, 2H), 7.5-7.55(m, 2H), 7.6-7.7(m, 2H), 8.0(br s, 1H), 8.7(br s, 1H); Mass Spectrum: M+H$^+$ 500 and 502.
(e) Methylene chloride was used as the reaction solvent and the reaction mixture was heated to 35° C. for 16 hours. The product gave the following data: NMR Spectrum: (DMSOd$_6$) 1.3-1.4(m, 2H), 1.7-1.8(m, 4H), 1.85(t, 1H), 2.1(s, 3H), 2.7(d, 2H), 3.9(s, 3H), 4.0(br d, 2H), 7.2(s, 1H), 7.8(d, 2H), 7.9(s, 1H), 8.1(d, 2H), 8.6(br s, 1H), 10.2-10.5(br s, 1H), 12.3-12.7(br s, 1H); Mass Spectrum: M+H$^+$ 467.

EXAMPLE 14

1-[6-methoxy-7-(N-methylpiperidin-4-ylmethoxy)quinazolin-4-yl]-3-(traits-2-phenylcyclopropyl)urea Trans-2-Phenylcyclopropyl isocyanate (0.2 ml) was added to a stirred mixture of 4-amino-6methoxy-7-(1-methylpiperidin-4-ylmethoxy)quinazoline (0.1 g) and chloroform (3 ml) and the resultant mixture was stirred at ambient temperature for 20 hours. The reaction mixture was diluted with chloroform (3 ml) and tris-(2-aminoethyl)amine polystyrene resin (0.5 g) was added. The mixture was stirred at ambient temperature for 1 hour. The mixture was filtered and the filtrate was evaporated. The residue was purified by column chromatography on silica using increasingly polar mixtures of methylene chloride and 2M methanolic ammonia as eluent. There was thus obtained the title compound (0.11 g); NMR Spectrum: (CDCl$_3$) 1.24-1.38 (m, 2H), 1.41-1.57 (m, 2H), 1.87-2.05 (m, 5H), 2.21 (m, 1H), 2.3 (s, 3H), 2.91 (d, 2H), 3.05 (m, 1H), 3.97 (s, 3H), 4.04 (d, 2H), 7.1-7.26 (m, 6H partially obscured by CHCl$_3$ peak), 7.34 (m, 1H), 8.66 (s, 1H), 8.72 (s, 1H), 10.31 (s, 1H), Mass Spectrum: M+H$^+$ 462.

EXAMPLE 15

1-16-methoxy-7(N-methylpiperidin-4-ylmethoxy)quinazolin-4-yl]-3-[(S)-(−)-α-methylbenzyl]urea Using an analogous procedure to that described in Example 14, (S)-(−)-α-methylbenzyl isocyanate was reacted with 4-amino-6-methoxy-7-(N-methylpiperidin-4-ylmethoxy)quinazoline to give the title compound; NMR Spectrum: (CDCl$_3$) 1.4-1.56 (m, 2H), 1.61 (d, 3H), 1.84-2.05 (m, 5H), 2.31 (s, 3H), 2.91 (d, 2H), 3.88 (s, 3H), 4.04 (d, 2H), 5.2 (m, 1H), 7.23 (d, 2H), 7.3-7.41 (m, 5H), 8.66 (s, 1H), 8.7 (s, 1H), 10.58 (s, 1H); Mass Spectrum: M+H$^+$ 450.

EXAMPLE 16

1-16-methoxy-7-(N-methylpiperidin-4-ylmethoxy)quinazolin-4-yl]-3-1(R)-(+)-α-methylbenzyl]urea Using an analogous procedure to that described in Example 14, (R)-(+)-α-methylbenzyl isocyanate was reacted with 4-amino-6-methoxy-7-(N-methylpiperidin-4-ylmethoxy)quinazoline to give the title compound; NMR Spectrum: (CDCl$_3$) 1.39-1.56 (m, 2H), 1.64 (d, 3H), 1.862.05 (m, 5H), 2.3 (s, 3H), 2.9 (d, 2H), 3.9 (s, 3H), 4.01 (d, 2H), 5.19 (m, 1H), 7.24 (d, 2H), 7.32-7.41 (m, 5H), 8.44 (s, 1H), 8.67 (s, 1H), 10.5 (s, 1H); Mass Spectrum: M+H$^+$ 450.

EXAMPLE 17

1-[6-methoxy-7-N-methylpiperidin-4-ylmethoxy)quinazolin-4-yl]-3-[1-(1-naphthyl)ethyl]urea Using an analogous procedure to that described in Example 14, 1-(1-naphthyl)ethyl isocyanate was reacted with 4amino6-methoxy-7-(N-methylpiperidin-4-ylmethoxy)quinazoline to give the title compound; NMR Spectrum: (CDCl$_3$) 1.41-1.57 (m, 2H), 1.76 (m, partially obscured by water peak), 1.86-2.05 (m, 5H), 2.02 (s, 3H), 2.91 (s, 2H), 3.87 (s, 3H), 4.02 (d, 2H), 5.95 (s, 1H), 7.19 (s, 1H), 7.23 (s, 1H), 7.39-7.52 (m, 3H), 7.6 (d, 1H), 7.71 (d, 1H), 7.84 (m, 1H), 8.12 (m, 1H), 8.57 (s, 1H), 8.64 (s, 1H), 10.67 (t, 1H); Mass Spectrum: M+H$^+$ 500.

There is no Example 18

EXAMPLE 19

Using an analogous procedure to that described in Example 14, the appropriate 4-aminoquinazoline was, unless otherwise stated, reacted with (R)-(+)-α-methylbenzyl isocyanate to give the compounds described in Table IV.

TABLE IV

| No. | R$^6$ | R$^7$ | Z | Note |
|---|---|---|---|---|
| 1 | methoxy | 2-pyrrolidin-1-ylethoxy | O | (a) |
| 2 | methoxy | 2-piperidinoethoxy | O | (b) |
| 3 | methoxy | 2-piperidinoethoxy | O | (c) |
| 4 | methoxy | 2-morpholinoethoxy | O | (d) |
| 5 | methoxy | 2-(2-oxoimidazolidin-1-yl)ethoxy | O | (e) |
| 6 | methoxy | 3-pyrrolidin-1-ylpropoxy | O | (f) |
| 7 | methoxy | 3-piperidinopropoxy | O | (g) |
| 8 | methoxy | 3-morpholinopropoxy | O | (h) |
| 9 | methoxy | 3-(4-methylpiperazin-1-yl)propoxy | O | (i) |
| 10 | methoxy | 2-(2-methoxyethoxy)ethoxy | O | (j) |
| 11 | 3-piperidinopropoxy | methoxy | O | (k) |
| 12 | methoxy | N-methylpiperidin-4-ylmethoxy | S | (l) |

Notes
(a) The product gave the following data: NMR Spectrum: (CDCl$_3$) 1.63(d, 3H), 1.87(s, 4H), 2.74(s, 4H), 3.07(t, 2H), 3.98(s, 3H), 4.34(t, 2H), 5.18(m, 1H), 7.19-7.4(m, 7H), 8.68(d, 2H), 10.54(d, 1H); Mass Spectrum: M+H$^+$ 436.
(b) The product gave the following data: NMR Spectrum: (CDCl$_3$) 1.47(m, 2H), 1.66(d, 7H), 2.54(t, 4H), 2.9(t, 2H), 3.89(s, 3H), 4.3(t, 2H), 5.19(m, 1H), 7.2-7.4(m, 7H), 8.68(s, 1H), 8.8(s, 1H), 10.55(d, 1H); Mass Spectrum: M+H$^+$ 450.
(c) (S)-(−)-α-Methylbenzyl isocyanate was used in place of (R)-(+)-α-methylbenzyl isocyanate. The product gave the following data: NMR Spectrum: (CDCl$_3$) 1.47(m, 2H), 1.62(m, 7H), 2.56(s, 4H), 2.9(t, 2H), 3.88(s, 3H), 4.31(t, 2H), 5.17(m, 1H), 7.19-7.41(m, 7H), 8.68(s, 1H), 8.8(s, 1H), 10.55(d, 1H); Mass Spectrum: M+H$^+$ 450.
(d) The product gave the following data: NMR Spectrum: (CDCl$_3$) 1.4(d, 3H), 2.65(t, 4H), 3.05(t, 2H), 3.75(t, 4H), 3.87(s, 3H), 4.31(t, 2H), 5.18(m, 1H), 7.14(d, 2H), 7.19-7.41(m, 5H), 8.68(s, 1H), 8.85(s, 1H), 10.54(d, 1H); Mass Spectrum: M+H$^+$ 452.
(e) The product gave the following data: NMR Spectrum: (CDCl$_3$) 1.63(d, 3H), 3.46(t, 2H), 3.75(m, 4H), 3.93(s, 3H), 4.29(t, 2H), 4.61(s, 1H), 5.17(m, 1H), 7.2-7.41(m, 7H), 8.57(s, 1H), 8.67(s, 1H), 10.5(d, 1H); Mass Spectrum: M+H$^+$ 451.
(f) The product gave the following data: NMR Spectrum: (CDCl$_3$) 1.62(d, 3H), 1.87(s, 4H), 2.2(m, 2H), 2.7(s, 4H), 2.8(t, 2H), 3.91(s, 3H), 4.24(t, 2H), 5.18(m, 1H), 7.2-7.27(m, 2H), 7.29-7.32(m, 5H), 8.44(s, 1H), 8.67(s, 1H), 10.47(d, 1H); Mass Spectrum: M+H$^+$ 450.
(g) The product gave the following data: NMR Spectrum: (CDCl$_3$) 1.39(m, 2H), 1.62(d,3H), 1.9(s, 4H), 2.39(t, 2H), 2.8-3.01(br m, 6H), 3.9(s, 3H), 4.24(t, 2H), 5.14(m, 1H),7.1-7.44(m, 7H), 8.45(s, 1H), 8.65(s, 1H), 10.45(d, 1H); Mass Spectrum: M+H$^+$ 464.
(h) The product gave the following data: NMR Spectrum: (CDCl$_3$) 1.62(d, 3H), 2.13(m, 2H), 2.59(m, 6H), 3.85(t, 4H), 3.91(s, 3H), 4.26(t, 2H), 5.18(m, 1H), 7.2-7.4(m, 7H), 8.5(s, 1H), 8.77(s, 1H), 10.5(d, 1H); Mass Spectrum: M+H$^+$ 466.
(i) The product gave the following data: NMR Spectrum: (CDCl$_3$) 1.62(d, 3H), 1.76(s, 4H), 2.1(m, 2H), 2.31(s, 3H), 2.4-2.6(m, 6H), 3.92(s, 3H), 4.24(t, 2H), 5.19(m, 1H), 7.21-7.41(m, 7H), 8.49(s, 1H), 8.68(s, 1H), 10.5(d, 1H); Mass Spectrum: M+H$^+$ 479.

TABLE IV-continued

[Structure: quinazoline with R6, R7 substituents and Z=thiourea/urea linked to HN-C(Z)-NH-CH(Me)-phenyl]

| No. | R⁶ | R⁷ | Z | Note |
|---|---|---|---|---|

(j) The product gave the following data: NMR Spectrum: (CDCl₃) 1.59(d, 3H), 3.39(s, 3H), 3.6(m, 2H), 3.76(m, 2H), 3.87(s, 3H), 4.0(t, 2H), 4.36(t, 2H), 5.21(m, 1H), 7.19-7.39(m, 7H), 8.69(s, 1H), 8.97(s, 1H), 10.58(d, 1H); Mass Spectrum: M+H⁺ 441.

(k) The product gave the following data: NMR Spectrum: (DMSOd₆) 1.38 (br s, 2H), 1.53(m, 6H), 2.0(m, 2H), 3.3-3.53(br s, 6H), 3.95(s, 3H), 4.17(t, 2H), 5.04(m, 1H), 7.25(s, 1H), 7.37(br m, 5H), 8.02(s, 1H), 8.65(s, 1H), 10.1 (s, 1H), 10.5(d, 1H); Mass Spectrum: M+H⁺ 464.

TABLE IV-continued

[Structure]

| No. | R⁶ | R⁷ | Z | Note |
|---|---|---|---|---|

(l) The 4-aminoquinazoline was reacted with (R)-(+)-α-methylbenzyl isothiocyanate. The product gave the following data: NMR Spectrum: (CDCl₃) 1.42-1.57(m, 2H), 1.71(d, 3H), 1.86-2.06(m, 5H), 2.31(s, 3H), 2.92 (d, 2H), 4.02(m, 5H), 5.69(m, 1H), 6.98(s, 1H),7.24-7.31(m, 2H), 7.34-7.47 (m, 4H), 8.54(s, 1H), 8.65(s, 1H), 12.57(d, 1H); Mass Spectrum: M+H⁺ 466.

EXAMPLE 20

Using an analogous procedure to that described in Example 5, the appropriate 4-aminoquinazoline was reacted with the appropriate isocyanate to give the compounds described in Table V.

TABLE V

[Structure: quinazoline with R6, R7 substituents; 4-position linked through HN-C(O)-NH to phenyl bearing (R²)ₙ]

| No. | R⁶ | R⁷ | (R²)ₙ | Note |
|---|---|---|---|---|
| 1 | methoxy | 3-(4-tert-butoxycarbonylaminomethylpiperidin-1-yl)propoxy | 2,6-dichloro | (a) |
| 2 | methoxy | 3-(4-tert-butoxycarbonylaminomethylpiperidin-1-yl)propoxy | 2,6-difluoro | (b) |
| 3 | methoxy | 3-(4-tert-butoxycarbonylaminomethylpiperidin-1-yl)propoxy | 2,6-dimethyl | (c) |
| 4 | methoxy | 3-(4-tert-butoxycarbonylaminomethylpiperidin-1-yl)propoxy | 2-chloro-6-methyl | (d) |

Notes (a) The product gave the following data: NMR Spectrum: (DMSOd₆) 1.2-1.35(m, 2H),1.43(s, 9H), 1.6-1.72(m,, 3H), 1.94(t, 2H), 2.0-2.15(m, 2H), 2.52(t, 2H), 2.9(d, 2H), 3.02(t, 2H), 3.6(s, 3H), 4.23(t, 2H), 4.6(s, 1H), 7.1-7.3(m, 3H), 7.38-7.43(m, 2H), 8.7(s, 1H), 9.38(s, 1H), 12.38 (s, 1H); Mass Spectrum: M+H⁺ 633 and 635.

The 4-amino-7-[3-(4-tert-butoxycarbonylaminomethylpiperidin-1-yl)propoxyl]-6-methoxyquinazoline used as a starting material was prepared as follows A mixture of 4-(4-bromo-2-fluorophenoxy)-7-(3-bromopropoxy)-6-methoxyquinazoline (0.486 g), 4-(tert-butoxycarbonylaminomethyl)piperidine (Chemical Abstracts Registry No. 135632-53-0, for example U.S. Pat. No. 5,864,039; 0.252 g), potassium carbonate (0.7 g) and DMF (10 ml) was stirred at 45° C. for 20 hours. The solvent was evaporated and the residue was stirred with water (20 ml). The resultant solid was isolated and purified by column chromatography on silica using increasingly polar mixtures of methylene chloride and a 2N solution of ammonia in methanol as eluent. There was thus obtained 4-(4-bromo-2-fluorophenoxy)-7-[3-(4-tert-butoxycarbonylaminomethylpiperidin-1-yl)propoxyl]-6-methoxyquinazoline as a resinous solid (0.4 g); NMR Spectrum: (CDCl₃) 1.22-1.4(m, 2H), 1.44(s, 9H), 1.69(m, 3H), 1.98(t, 2H), 2.12(m, 2H), 2.56(t, 2H), 2.9-3.1(m, 4H), 4.04(s, 3H), 4.26(t, 2H), 4.6(br s, 1H), 7.22(m, 1H), 7.3-7.45(m, 3H), 7.51(s, 1H), 8.67(s, 1H); Mass Spectrum: M+H⁺ 619 and 621.

TABLE V-continued

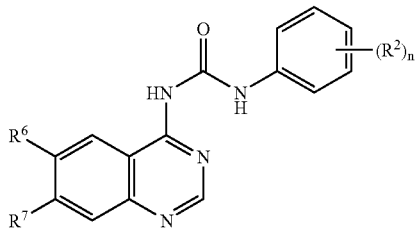

| No. | R⁶ | R⁷ | (R²)ₙ | Note |
|-----|----|----|-------|------|

A mixture of a portion (0.2 g) of the material so obtained and a saturated solution of ammonia in isopropanol (32 ml) was sealed in a Carius tube and heated at 110° C. for 20 hours. The mixture was cooled to ambient temperature and the solvent was evaporated. The residue was stirred with a mixture of a 2N aqueous sodium hydroxide solution (5 ml), methylene chloride (18 ml) and methanol (2 ml) for 1 hour. The solid was isolated and dried. There was thus obtained the required starting material (0.046 g); NMR Spectrum: (DMSOd$_6$) 1.0-1.15(m, 2H), 1.4(m, 1H), 1.45(s, 9H), 1.56(d, 2H), 1.75-1.85(m, 4H), 2.39(d, 2H), 2.74-2.9(m, 4H), 3.85(s, 3H), 4.09(t, 2H), 6.75(br s, 1H), 7.02(s, 1H), 7.32(s, 2H), 7.54(s, 1H), 8.24(s,.1H); Mass Spectrum: M+H⁺ 446.

(b) The product gave the following data: NMR Spectrum: (DMSOd$_6$) 1.0-1.2(m, 2H), 1.25-1.3 (m, 1H), 1.35(s, 9H), 1.58(d, 2H), 1.8-2.0(m, 4H), 2.42(t, 2H), 2.7-2.9(m, 4H), 3.95(s, 3H), 4.21(t, 2H), 6.76(t, 1H), 7.1-7.5(m, 4H), 8.04(s, 1H), 8.67(s, 1H), 10.6(s, 1H), 11.8(s, 1H); Mass Spectrum: M+H⁺ 601.

(c) The product gave the following data: NMR Spectrum: (CDCl$_3$) 1.2-1.4(m, 3H), 1.43(s, 9H), 1.9-2.15(m, 4H), 2.33(s, 6H), 2.52(t, 2H), 2.92(d, 4H), 3.02(t, 2H), 3.38(s, 3H), 4.21(t, 2H), 4.6(s, 1H), 7.05-7.15(m, 4H), 7.48(s, 1H), 8.66(s, 1H), 9.64(s, 1H), 11.9(s, 1H); Mass Spectrum: M+H⁺ 593.

(d) The product gave the following data: NMR Spectrum: (CDCl$_3$) 1.22-1.35(m, 3H), 1.42(s, 9H), 1.7(m, 2H), 1.95(t, 2H), 2.09(m, 2H), 2.35(s, 3H), 2.52(t, 2H), 2.91(d, 2H), 3.02(t, 2H), 3.5(s, 3H), 4.22(t, 2H), 4.6(s, 1H), 7.17(m, 2H), 7.25-7.35(m, 2H), 7.46(s, 1H), 8.69(s, 1H), 9.54(s, 1H), 12.2(s, 1H); Mass Spectrum: M+H⁺ 613 and 615.

EXAMPLE 21

1-{7-[3-(4-aminomethylpiperidin-1-yl)propoxy]-6-methoxyquinazolin-4-yl}-3-(2,6dichlorophenyl)urea A mixture of 1-{7-[3-(4-tert-butoxycarbonylaminomethylpiperidin-1-yl)propoxy]-6-methoxyquinazolin-4-yl}-3-(2,6-dichlorophenyl)urea (0.075 g), trifluoroacetic acid (0.35 ml) and chloroform (1.5 ml) was stirred at ambient temperature for 40 minutes. The mixture was evaporated and the residue was stirred under a 1N aqueous sodium hydroxide solution (3 ml) for 1 hour. The resultant solid was isolated and dried. There was thus obtained the title compound (0.037 g); NMR Spectrum: (DMSOd$_6$) 1:12 (m, 3H), 1.62-1.7 (m, 2H), 1.9 (t, 2H), 2.0 (m, 4H), 2.38-2.54 (m, 4H), 2.92 (m, 2H), 3.3 (m, partially obscured by a water signal), 3.95 (s, 3H), 4.26 (t, 2H), 7.28 (s, 1H), 7.41 (t, 1H), 7.62 (d, 2H), 8.06 (s, 1H), 8.66 (s, 1H); Mass Spectrum: M+H⁺ 533 and 535.

EXAMPLE 22

1-{7-[3-(4-aminomethylpiperidin-1-yl)propoxy]-6-methoxyquinazolin-4-yl}-3(2,6difluorophenyl)urea Using an analogous procedure to that described in Example 21, 1-{7-[3-(4-tert-butoxycarbonylaminomethylpiperidin-1-yl)propoxyl-6-methoxyquinazolin-4-yl}-3-(2,6-difluorophenyl) urea was reacted with trifluoroacetic acid to give the title compound; NMR Spectrum: (DMSOd$_6$) 1.0-1.4 (m, 3H), 1.7 (d, 2H), 1.9-2.1 (m, 6H), 2.4 (m, 2H), 2.9 (d, 2H), 3.3 (s, partially obscured by a water signal), 4.0 (s, 3H), 4.24 (t, 3H) 5.0-7.0 (br m, 1H), 7.2-7.4 (m, 4H), 8.05 (s, 1H), 8.68 (s, 11H), 11.75 (s, 3H), 4.24 (t, 3H), M+H⁺ 501.

EXAMPLE 23

1-{7-[3-(4-aminomethylpiperidin-1-yl)propoxy]-6-methoxyquinazolin-4-yl}-3-(2,6-dimethylphenyl) urea Using an analogous procedure to that described in Example 21, 1-{7-[3-(4 tert-butoxycarbonylaminomethylpiperidin-1-yl)propoxy]-6-methoxyquinazolin-4-yl}-3-(2,6-dimethylphenyl)urea was reacted with trifluoroacetic acid to give the title compound; NMR Spectrum: (DMSOd$_6$) 1.0-2.0 (m, 9H), 2.23 (s, 6H), 2.4 (m, 2H), 2.7-2.9 (m, 4H), 3.1-3.5 (partially obscured by a water signal), 3.93 (s, 3H), 4.18 (t, 2H), 6.9-7.15 (m, 4H), 7.23 (s, 1H), 8.03 (s, 1H), 8.62 (s, 1H), 11.7 (s, 1H); Mass Spectrum: M+H⁺ 493.

EXAMPLE 24

1-{7-[3-(4-aminomethylpiperidin-1-yl)propoxy]-6-methoxyquinazolin-4-yl}-3-(2-chloro-6-methylphenyl)urea Using an analogous procedure to that described in Example 21, 1-{7-[3-(4-tert-butoxycarbonylaminomethylpiperidin-1-yl)propoxy]-6-methoxyquinazolin-4-yl}-3-(2-chloro-6-methylphenyl)urea was reacted with trifluoroacetic acid to give the title compound; NMR Spectrum: (DMSOd$_6$) 1.0-1.3 (m, 3H), 1.63 (d, 2H), 1.7-2.0 (m, 4H), 2.28 (s, 3H), 2.4 (m, 2H), 2.86 (d, 2H), 3.1-3.5 (partially obscured by a water signal) 3.94 (s, 3H), 4.19 (t, 2H), 7.1-7.4 (m, 4H), 8.06 (s, 1H), 8.66 (s, 1H), 11.85 (s, 1H); Mass Spectrum: M+H⁺ 513 and 515.

EXAMPLE 25

Using an analogous procedure to that described in Example 1, the appropriate 4aminoquinazoline was reacted with the appropriate isocyanate to give the compounds described in Table VI.

TABLE VI

| No. | $R^6$ | $R^7$ | $(R^2)_n$ | Note |
|---|---|---|---|---|
| 1 | 3-morpholinopropoxy | methoxy | 2-methyl | (a) |
| 2 | 3-morpholinopropoxy | methoxy | 2,6-dichloro | (b) |
| 3 | 3-morpholinopropoxy | methoxy | 2,6-difluoro | (c) |
| 4 | 3-morpholinopropoxy | methoxy | 2,6-dimethyl | (d) |
| 5 | 3-piperidinopropoxy | methoxy | 2,6-dichloro | (e) |
| 6 | 3-piperidinopropoxy | methoxy | 2,6-difluoro | (f) |
| 7 | 3-piperidinopropoxy | methoxy | 2,6-dimethyl | (g) |
| 8 | 2-pyrrolidin-1-ylethoxy | methoxy | 2,6-dichloro | (h) |
| 9 | N-(3-morpholinopropyl)carbamoyl | methoxy | 2,6-dimethyl | (i) |
| 10 | 2-(2-methoxyethoxy)ethoxy | methoxy | 2,6-dichloro | (j) |
| 11 | 2-(2-methoxyethoxy)ethoxy | methoxy | 2,6-dimethyl | (k) |

Notes (a) The reaction product was dissolved in methylene chloride and treated with a saturated solution of hydrogen chloride gas in diethyl ether. The hydrochloride salt so obtained gave the following data: NMR Spectrum: (DMSOd$_6$+CF$_3$CO$_2$D) 2.35(m, 2H), 2.45(s, 3H), 3.15(m, 2H), 3.35(m, 2H), 3.55(d, 2H), 3.75(t, 2H), 4.0(m, 2H), 4.05(s, 3H), 4.4(m, 2H), 7.1(m, H), 7.3(m, 2H), 7.5(s, H), 7.95(d, 1H), 8.45(s, H), 9.15(s, 1H); Mass Spectrum: M+H$^+$ 452.

The 4-amino-7-methoxy-6-(3-morpholinopropoxy)quinazoline used as a starting material was prepared as follows:

A mixture of 4-(3-chloro-4-fluoroanhino)-7-inethoxy-6-(3-morpholinopropoxy)quinazoline(International Patent Application WO 96/33 980, Example 1 therein; 6 g) and 6N aqueous hydrochloric acid solution(120 ml) was stirred and heated to reflux for 6 hours. The mixture was cooled to 0° C. and carefully, with cooling, was neutralised by the addition of concentrated aqueous ammonium hydroxide solution. The resultant precipitate was isolated, washed in turn with a dilute aqueous amimonium hydroxide solution and with water and dried under vacuum. There was thus obtained 7-methoxy-6-(3-morpholinopropoxy)-3,4-dihydroquinazolin-4-one (4.2 g); NMR Spectrum: (DMSOd$_6$) 2.4(m, 6H), 3.59(t, 4H), 3.75(t, 2H), 3.9(s, 3H), 4.12 (t, 2H), 7.12(s, 1H), 7.43(s, 1H), 7.98(s, 1H), 12.0(br s, 1H); Mass Spectrum: M+H$^+$ 320.

A mixture of a portion (0.99 g) of the material so obtained, thionyl chloride(10 ml) and DMF(0.1 ml) was stirred and heated to 80° C. for 1.5 hours. The mixture was cooled to ambient temperature, toluene (10 ml) was added and the mixture was evaporated. The residue was partitioned between ethyl acetate and water (the acidity of the aqueous layer being adjusted to pH 7.5 by the addition of 2N aqueous sodium hydroxide solution). The organic layer was washed with brine, dried over magnesium sulphate and evaporated. The residue was purified by column chromatography on silica using a 9:1 mixture of methylene chloride and methanol as eluent. The solid so obtained was triturated under hexane, re-isolated and washed with diethyl ether. There was thus obtained 4-chloro-7-methoxy-6-(3-morpholinopropoxy)quinazoline(0.614 g); NMR Spectrum: (CDC$_3$) 2.12(m, 2H), 2.5(br s, 4H), 2.59(t, 2H), 3.73(t, 4H), 4.05(s, 3H), 4.27(t, 2H), 7.33(s, 1H), 7.4(s, 1H), 8.86(s, 1H).

TABLE VI-continued

| No. | $R^6$ | $R^7$ | $(R^2)_n$ | Note |
|---|---|---|---|---|

A mixture of 4-chloro-7-methoxy-6-(3-morpholinopropoxy)quinazoline (1.6 g) and isopropanol(50 ml) was placed in a Carius tube which was cooled to −78° C. prior to the addition of liquid ammonia(10 ml). The Carius tube was sealed and heated to 130 ° C. for 20 hours. The Carius tube was cooled to ambient temperature, opened and the mixture was evaporated. The residue was triturated under diethyl ether. There was thus obtained 4-amino-7-methoxy-6-(3-morpholinopropoxy)quinazoline(containing 2.9 equivalents of ammonium chloride; 1.54 g) which was used without further purification. A portion of the material was purified by column chromatography on silica using a 19:1 mixture of methylene chloride and methanol as eluent. The purified product gave the following data: -NMR Spectrum: (DMSOd$^+$ 319.

(b) The product gave the following data: NMR Spectrum: 2.35(m, 2H), 3.15 (m, 2H), 3.35(m, 2H), 3.55(d, 2H), 3.7(t, 2H), 4.0(m, 2H), 4.05(s, 3H), 4.35 (m, 2H), 7.45(m, 2H), 7.65(m, 2H), 8.3(s, 1H), 9.05(s, 1H); Mass Spectrum: M+H$^+$ 506 and 508.

(c) The product gave the following data: NMR Specirum: (DMSOd$_6$+ CF$_3$CO$_2$D) 2.3(m, 2H), 3.15(m, 2H), 3.35(m, 2H), 3.55(d, 2H), 3.7(t, 2H), 4.0(m, 2H), 4.05(m, 5H), 4.3(m, 2H), 7.25(m, 2H), 7.4(m, 2H), 8.25(s, 1H), 9.0(s, 1H); Mass Spectrum: M+H$^+$ 474.

(d) The product gave the following data: NMR Spectrum: (DMSOd$_6$+ CF$_3$CO$_2$D) 2.35(m, 8H), 3.15(m, 2H), 3.35(m, 2H), 3.55(d, 2H), 3.7(t, 2H), 4.0(m, 2H), 4.05(s, 3H), 4.35(m, 2H), 7.2(m, 2H), 7.5(s, 1H), 8.3(s, 1H), 9.05(s, 1H); Mass Spectrum: M+H$^+$ 466.

(e) The product gave the following data: NMR Spectrum: (DMSOd$_6$) 1.4(br s, 2H), 1.55(br s, 4H), 2.04(hr s, 2H), 3.26-3.48(m, 6H), 3.95(s, 3H), 4.20(t, 2H), 7.32(s, 1H), 7.39(t, 1H), 7.56(m, 2H), 8.08(s, 1H), 8.69(s, 1H), 10.64(s, 1H), 12.08(s, 1H); Mass Spectrum: M+H$^+$ 504 and 506.

The 4-amino-7-methoxy-6-(3-piperidinopropoxy)quinazoline used as a starting material was prepared as follows:

A mixture of 6-acetoxy-7-methoxyquinazolin-4-one(International Patent Application WO 96/15118, Example 39 thereof; 15 g), thionyl chloride(215 ml) and DMF(4.3 ml) was stirred and heated to 90° C. for 4 hours. The mixture was cooled to ambient temperature and the thionyl chloride was evaporated. The material so obtained was dissolved in toluene and the solution was washed with a saturated aqueous sodium bicarbonate solution. The organic solution was dried over magnesium sulphate and evaporated. There was thus obtained 6-acetoxy-4-chloro-7-methoxyquinazoline(14.8 g) which was used without further purification.

A mixture of a portion(5 g) of the material so obtained, diphenylmethyleneamine(3.75 g), caesium carbonate(25.67 g) and xylene(200 ml) was stirred at ambient temperature for 30 minutes. Racemic 2,2'-bis(diphenylphosphino)-1,1'-binaphthyl (1.227 g) and palladium diacetate(0.221 g) were added and the mixture was stirred and heated to 135° C. for 16 hours. The mixture was cooled to ambient temperature and diethyl ether(600 ml) was added. The mixture was filtered and the filtrate was evaporated. There was thus obtained N-diphenylmethylene-6-acetoxy-7-methoxyquinazolin-4-amine(7.12 g); Mass Spectrum: M+H$^+$ 398.

A mixture of a portion(3.09 g) of the material so obtained, concentrated ammonium hydroxide solution(0.88 g/ml, approximately 14M 60 ml) and methanol(120 ml) was stirred at ambient temperature for 16 hours. The mixture was evaporated. Toluene(200 ml) was added and the mixture was evaporated again. The residue was triturated under diethyl ether(50 ml). There was thus obtained N-diphenylmethylene-6-hydroxy-7-methoxyquinazolin-4-amine(0.938 g); Mass Spectrum: M+H$^+$ 356.

TABLE VI-continued

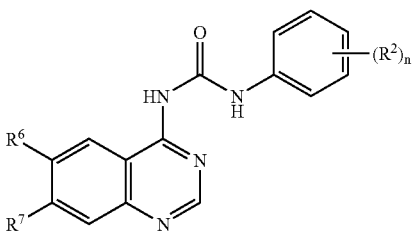

| No. | R⁶ | R⁷ | (R²)ₙ | Note |
|---|---|---|---|---|

A mixture of the material so obtained, 3-piperidinopropyl chloride(0.55 g), potassium carbonate(1.46 g) and DMF(50 ml) was stirred and heated to 65° C. for 16 hours. The resultant mixture was evaporated and the residue was partitioned between ethyl acetate and water. The organic solution was washed with a saturated aqueous sodium chloride solution, dried over magnesium sulphate and evaporated The residue was purified by column chromatographyon silica using increasingly polar mixtures of me methanol as eluent. There was thus obtained N-dphenylinethylene-6-(3-piperidinopropoxy)-7-methoxyquinazolin-4-amine (0.277 g); NMR Spectrum: (DMSOd$_6$) 1.3(br s, 2H), 1.42(hr s, 4H), 1.88(t, 2H), 2.28(br s, 4H), 2.38(t, 2H), 3.92(s, 3H), 4.07(t, 2H), 7.0(s, 1H), 7.23(s, 1H), 7.2-7.65(br m, 10H), 8.62(s, 1H); Mass Spectrum: M+H⁺ 481.

A mixture of the material so obtained, 3N aqueous hydrochloric acid solution(2 ml) and THF(14 ml) was stirred at ambient temperature for 3 hours. The mixture was evaporated and the residue was treated with a 2N aqueous sodium hydroxide solution(10 ml). The resultant precipitate was isolated, washed with water(10 ml) and dried under vacuum. There was thus obtained 4-amino-7-methoxy-6-(3-piperidinopropoxy)quinazoline (0.202 g); NMR Spectrum: (DMSOd$_6$) 1.36(br s, 2H), 1.47(br s, 4H), 1.93(t, 2H), 2.25-2.43 (br m, 6H), 3.88(s, 3H), 4.05(t, 2H), 7.04(s, 1H), 7.35(br s, 2H), 7.55(s, 1H), 8.23(s, 1H); Mass Spectrum: M+H⁺ 317.

(f) The product gave the following data: NMR Spectrum: (DMSOd$_6$) 1.4(br s, 2H), 1.53(br s, 4H), 2.02(br s, 2H), 3.24-3.47(br s, 6H), 3.97(s, 3H), 4.23 (t, 2H), 7.22(m, 2H), 7.31(s, 1H), 7.4(m, 1H), 8.05(s, 1H), 8.69(s, 1H), 10.67 (s, 1H), 11.82(s, 1H); Mass Spectrum: M+H⁺ 472.

(g) The product gave the following data: NMR Spectrum: (DMSOd$_6$) 1.38 (br s, 2H), 1.5(br s, 4H), 1.96(m, 2H), 2.25(s, 6H), 2.3-2.48(br m, 6H), 3.96 (s, 3H), 4.15(t, 2H), 7.14(m, 3H), 7.3(s, 1H), 8.07(s, 1H), 8.67(s, 1H), 10.38 (s, 1H), 11.69(s, 1H); Mass Spectrum: M+H⁺ 464.

(h) The product gave the following data: NMR Spectrum: (DMSOd$_6$) 1.72 (br s, 4H), 2.67(br s, 4H), 2.97(br s,2H), 3.99(s, 3H), 4.3(t, 2H), 7.31(s, 1H), 7.37(t, 1H), 7.59(d, 2H), 8.07(s, 1H), 8.72(s, 1H), 10.52(s, 1H), 12.06(s, 1H); Mass Spectrum: M+H⁺ 476 and 478.

The 4-amino-7-methoxy-6-(2-pyrrolidin-1-ylethoxy)quinazoline used as a starting material was prepared from N-diphenylmethylene-6-hydroxy-7-methoxyquinazolin-4-amine and 2-pyrrolidin-1-ylethyl chloride using analogous procedures to those described in the last two paragraphs of Note (e) above. The material so obtained gave the following data:- NMR Spectrum: (DMSOd$_6$) 1.68(m, 4H), 2.58(m, 6H), 3.86(s, 3H), 4.15(t, 2H), 7.05(s, 1H), 7.33(s, 1H), 8.24(s, 1H); Mass Spectrum: M+H⁺ 289.

(i) Chloroform was used as the reaction solvent. Triethylamine (1 equivalent) was also added. The product gave the following data: NMR Spectrum: (CDCl$_3$) 1.99(t, 2H), 2.37(s, 6H), 2.7(m, 4H), 3.63(q, 2H), 3.79(m, 6H), 4.15 (s, 3H), 7.13(s, 3H), 7.4(s, 1H), 8.0(t, 1H), 8.2(s, 1H), 8.79(s, 1H), 8.9(s, 1H), 11.2(s, 1H); Mass Spectrum: M+H⁺ 493.

The 4-amino-7-methoxy-6-[N-(3-morpholinopropyl)carbamoyl]quinazoline used as a starting material was prepared as follows:-

Methyl 4-amino-5-cyano-2-hydroxybenzoate(J. Chem. Soc. Perkin I, 1979, 677; 4 g) was added to stirred concentrated sulphuric acid(6 ml) and the mixture was heated to 80° C. for 30 minutes. The mixture was cooled to ambient temperature and poured onto crushed ice. The resultant solid was filtered off, washed well with water and dried to give methyl 4-amino-5-carbamoyl-2-hydroxybenzoate(2.8 g); NMR Spectrum: (DMSOd$_6$) 3.83(s, 3H), 6.1(s, 1H), 6.75(br m, 2H), 8.08 (s, 1H).

A mixture of methyl 4-amino-5-carbamoyl-2-hydroxybenzoate(5.4 g) and formic acid(5.0 ml) was heated to reflux for 1 hour. The mixture was evaporated. Toluene (75 ml) was added and the mixture was evaporated. The solid residue was washed with methanol and diethyl ether and dried to give methyl 7-hydroxy-4-oxo-3,4-dihydroquinazoline-6-carboxylate(5.2 g); NMR Spectrum: (DMSOd$_6$) 4.9(s, 3H), 7.09(s, 1H), 7.39(s, 1H), 8.5(s, 1H).

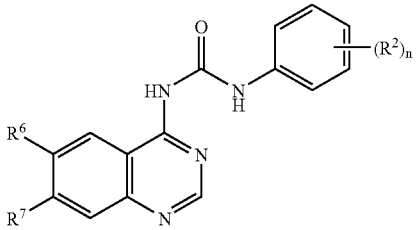

| No. | R⁶ | R⁷ | (R²)ₙ | Note |
|---|---|---|---|---|

A mixture of methyl 7-hydroxy-4-oxo-3,4-dihydroquinazoline-6-carboxylate(17.7 g) and acetic anhydride(200 ml) was heated to 120° C. for 1.5 hours. The mixture was evaporated. Toluene(75 ml) was added and the mixture was re-evaporated. There was thus obtained methyl 7-acetoxy-4-oxo-3, 4-dihydroquinazoline-6-carboxylate(20.7 g); NMR Spectrum: (DMSOd$_6$) 2.33(s, 3H), 3.86(s, 3H), 7.5(s, 1H), 8.28(s, 1H), 8.68(s, 1H); Mass Spectrum: M+H⁺ 263.

A mixture of a portion(7.2 g) of the material so obtained and thionyl chloride(75 ml) was heated to reflux for 1 hour. The excess thionyl chloride was evaporated. Toluene(50 ml) was added and the mixture was re-evaporated. The residue was dissolved in methylene chloride and treated with triethylamine(3.34 g). The mixture was passed through a silica gel column(40 g) using increasingly polar mixtures of methylene chloride and methanol as eluent. There was thus obtained methyl 7-acetoxy-4-chloroquinazoline-6-carboxylate(6.88 g); NMR Spectrum: (CDCl$_3$) 2.43(s, 3H), 4.0(s, 3H), 7.8(s, 1H), 8.99(s, 1H), 9.12(s, 1H).

A mixture of a portion(2.74 g) of the material so obtained, 2,4,6-trimethoxybenzylamine(3.86 g) and methylene chloride(90 ml) was allowed to stand at ambient temperature for 16 hours. The mixture was filtered and the filtrate was evaporated. The residue was triturated under diethyl ether. The resultant solid was purified by column chromatography on silica using increasingly polar mixtures of methylene chloride and methanol as eluent. There was thus obtained methyl 7-hydroxy-4-(2,4,6-trimethoxybenzylamino)quinazoline-6-carboxylate(3.25 g); NMR Spectrum: (DMSOd$_6$) 3.85 (s, 9H), 3.98(s, 3H), 4.82(d, 2H), 6.2(s, 1H), 7.25(s, 1H), 7.27(s, 1H), 8.27(s, 1H), 8.67(s, 1H), 10.73(s, 1H); Mass Spectrum: M+H⁺ 400.

(Trimethylsilyl)diazomethane(2M in hexane, 10 ml) was added to a mixture of the material so obtained, di-isopropylethylamine(1.26 g), methanol (10 ml) and methylene chloride(30 ml) and the resultant mixture was stirred at ambient temperature for 3 hours. The reaction mixture was treated with a second alliquot of (trimethylsilyl)diazomethane solution(10 ml) and stirred for a further 18 hours. Silica gel(2 g) was added cautiously and the mixture was stirred for 5 minutes. The mixture was evaporated and the reaction product (adsorbed onto silica) was purified by column chromatography on silica using increasingly polar mixtures of methylene chloride and methanol as eluent. There was thus obtained methyl 7-methoxy-4-(2,4,6-trimethoxybenzylamino)quinazoline-6-carboxylate(1.244 g); Mass Spectrum: M+H⁺ 414.

A mixture of a portion(0.295 g) of the material so obtained and N-(3-aminopropyl)morpholine(0.5 ml) was stirred and heated to 150° C. for 1 hour. The mixture was partitioned between methylene chloride and water. The organic solution was dried over magnesium sulphate and evaporated. The residue was purified by column chromatography on silica using increasingly polar mixtures of methylene chloride and methanol as eluent. There was thus obtained 4-(2,4,6-trimethoxybenzylamino)-7-methoxy-6-[N-(3-morpholinopropyl)carbamoyl]quinazoline(0.144 g) Mass Spectrum: M+H⁺ 526.

Trifluoroacetic acid(1 ml) was added to a mixture of the material so obtained, triethylsilane(0.093 g) and methylene chloride(0.15 ml) and the reaction mixture was stirred and heated to reflux for 2 minutes. The mixture was evaporated and the residue was partitioned between methylene chloride and water. The organic solution was evaporated to give 4-amino-7-methoxy-6-[N-(3-morpholinopropyl)carbamoyl]quinazoline(0.129 g); Mass Spectrum:M+H⁺ 346.

(j) The product gave the following data: NMR Spectrum: (CDCl$_3$) 3.39(s, 3H), 3.6(m, 2H), 3.75(m, 2H), 3.86(m. 2H), 4.02(s, 3H), 4.07(m, 2H), 7.21(t, 1H), 7.29(s, 1H), 7.39(d, 2H), 7.51(s, 1H), 8.73(s, 1H), 9.14(s, 1H), 12.19(s, 1H); Mass Spectrum: M+H⁺ 481 and 483.

The 4-amino-7-methoxy-6-[2-(2-methoxyethoxy)ethoxy]quinazoline used as a starting material was prepared from N-diphenyhnethylene-6-hydroxy-7-methoxyquinazolin-4-amine and 2-(2-methoxyethoxy)ethyl chloride using analogous procedures to those described in the last two paragraphs of Note (e) above. In a further preparation, 2-(2-methoxyethoxy)ethyl 4-toluenesulphonate was used. The required starting material gave the following data: NMR Spectrum: (CDCl$_3$) 3.4(s, 3H), 3.61(m, 2H), 3.7(m, 2H), 5.67(br s, 2H), 7.2(s, 1H), 7.32(s, 1H), 8.5(s, 1H); Mass SDectrum: M+H⁺ 294.

TABLE VI-continued

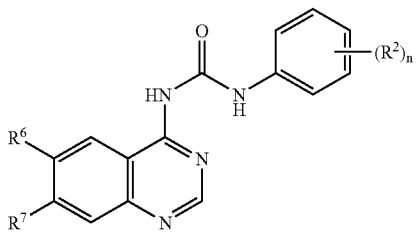

| No. | R⁶ | R⁷ | (R²)ₙ | Note |

(k) The product gave the following data: NMR Spectrum: (CDCl₃) 2.31(s, 6H), 3.38(s, 3H), 3.6(m, 2H), 3.69(m, 4H), 3.85(m, 2H), 4.14(s, 3H), 7.12 (m, 4H), 7.58(s, 1H), 8.68(s, 1H), 9.44(s, 1H), 11.77(s, 1H); Mass Spectrum: M+H⁺ 441.

EXAMPLE 26

1-(2,6-dichlorophenyl)-3-[6-methoxy-7-(6-methylamino-1-hexynyl)quinazolin-4-yl]urea A mixture of 1-(2,6dichlorophenyl}3-{7-[6-(4-tert-butoxycarbonylamino-N-methylamino)1-hexynyl ]-6-methoxyquinazolinyl}urea (0.1 g), trifluoroacetic acid (1 ml) and methylene chloride (1 ml) was stirred at ambient temperature for 1.5 hours. The mixture was evaporated and a solution of hydrogen chloride gas in ethyl acetate was added. Toluene was added and the mixture was evaporated. The residue was triturated under diethyl ether and the resultant solid was isolated. There was thus obtained the title compound as the hydrochloride salt (0.095 g); NMR Spectrum: (DMSOd₆) 1.65 (m, 2H), 1.78 (s, 2H), 2.55 (m, 5H), 2.95 (m, 2H), 4.0 (s, 3H), 7.38 (t, 1H), 7.6 (d, 2H), 7.89 (s, 1H) 6.16 (s, 1H), 8.7 (m, 3H), 10.9 (br, 1H), 11.8 (s, 1H); Mass Spectrum: M+H⁺ 472 and 474.

The 1-(2,6-dichlorophenyl)-3-{7-[6-in-tert-butoxycarbonylamino)-N-methylamino-1-hexynyl]-6-methoxyquinazolin-4-yl}urea used as a starting material was prepared as follows:

Using an analogous procedure to that described in the second last paragraph of Note [115] in Example 2 above, 6-(N- tert-butoxycarbonylamino-N-methylamino)-1-hexyne was reacted with 4-(2-bromo-4-fluorophenoxy)-6-methoxy-7-trifluoromethanesulphonyloxyquinazoline to give 4-(2-bromo-4-fluorophenoxy)-6-methoxy-7-[6-(N-tert-butoxycarbonylamino)N-methylamino-1-hexynyl]quinazoline; NMR Spectrum: (DMSOd₆) 1.4 (s, 9H), 1.55 (s, 2H), 1.65 (m, 2H), 2.57 (t, 2H), 2.79 (s, 3H), 3.24 (t, 2H), 4.0.(s, 3H), 7.35-7.82 (m, 3H), 7.65 (s, 1H), 7.95 (s, 1H), 8.6 (s, 1H); Mass Spectrum: M+H⁺ 558 and 560.

The material so obtained was reacted with ammonia using an analogous procedure to that described in the last paragraph of Note [115] in Example 2 above, except that the ammonia reaction was carried out at 110° C rather than at 130° C. There was thus obtained 4-amino-6-methoxy-7-[6-(N-tert-butoxycarbonylamino)-N-methylamino-1-hexynyl]quinazoline.

The material so obtained was reacted with 2,6-dichlorophenyl isocyanate using an analogous procedure to that described in Example 1. There was thus obtained the required starting material; NMR Spectrum: (DMSOd₆) 1.39 (s, 9H), 1.55 (m, 2H), 1.67 (m, 2H), 2.56 (s, 2H), 2.79 (s, 3H), 3.2 (s, 2H), 3.97 (s, 3H), 7.4 (m, 1H), 7.6 (m, 2H), 7.84 (s, 1H), 8.14 (s, 1H), 8.75 (s, 1H), 10.8 (s, 1H), 11.95 (s, 1H).

The 6-N-tert-butoxycarbonylamino-N-methylamino)-1-hexyne used as a starting material was prepared as follows:

6Mesyloxy-1-hexyne was reacted with methylamine using an analogous procedure to that described in J. Heterocyclic Chemistry, 1994, 31, 1421 to give 6-methylamino-1-hexyne which was reacted di-tert-butyl dicarbonate using a conventional procedure.

EXAMPLE 27

1-(2,6-dimethylphenyl)-3-[6-methoxy-7-(N-methylpiperidin-4-ylmethoxy)quinazolin-4-yl]thiourea A solution of 4-amino-6-methoxy-7-(1-methylpiperidin-4-ylmethoxy)quinazoline (150 mg) in DMF (4.5 ml) was added to sodium hydride (60% dispersion in mineral oil, 0.03 g) and the reaction mixture was stirred at ambient temperature for 20 minutes. 2,6-Dimethylphenyl isothiocyanate (0.162 g) was added and the mixture was stirred at ambient temperature for 20 hours. The reaction mixture was evaporated and the residual solid-was purified by column chromatography on silica using increasingly polar mixtures of methylene chloride and a 2M solution of ammonia in methanol as eluent. There was thus obtained the title compound (0.112 g); NM Spectrum: (CDCl₃) 1.44-1.61 (m, 2H), 1.87-2.08 (m, 5H), 2.32 (s, 3H), 2.36 (s, 6H), 2.94 (d, 2H), 4.04 (m, 5H), 7.1 (s, 1H), 7.19 (m, 3H), 7.29 (s, 1H), 8.69 (s, 1H), 8.9 (s, 1H), 13.37 (s, 1H); Mass Spectrum: M+H⁺ 466.

EXAMPLE 28

Using an analogous procedure to that described in Example 27, the appropriate 4-aminoquinazoline was reacted with the appropriate isothiocyanate to give the compounds described in Table VII.

TABLE VII

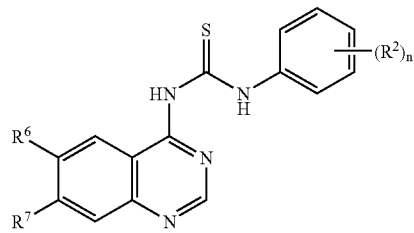

| No. | R⁶ | R⁷ | (R²)ₙ | Note |
|---|---|---|---|---|
| 1 | methoxy | N-methylpiperidin-4-ylmethoxy | 2,6-dichloro | (a) |
| 2 | methoxy | N-methylpiperidin-4-ylmethoxy | 2,6-difluoro | (b) |
| 3 | methoxy | N-methylpiperidin-4-ylmethoxy | 2-chloro-6-methyl | (c) |
| 4 | methoxy | N-methylpiperidin-4-ylmethoxy | 2,4,6-trichloro | (d) |
| 5 | methoxy | N-methylpiperidin-4-ylmethoxy | 2,6-dimethyl-4-bromo | (e) |
| 6 | methoxy | N-methylpiperidin-4-ylmethoxy | 2,5-dimethyl | (f) |
| 7 | methoxy | 3-pyrrolidin-1-ylpropoxy | 2,6-dichloro | (g) |
| 8 | methoxy | 3-pyrrolidin-1-ylpropoxy | 2,6-difluoro | (h) |
| 9 | methoxy | 3-pyrrolidin-1-ylpropoxy | 2-chloro-6-methyl | (i) |
| 10 | methoxy | 2-(2-methoxyethoxy)ethoxy | 2,6-dimethyl | (j) |
| 11 | methoxy | 2-morpholinoethoxy | 2,6-dimethyl | (k) |
| 12 | methoxy | 3-morpholinopropoxy | 2,6-dimethyl | (l) |
| 13 | methoxy | cyclopropylmethoxy | 2,6-dimethyl | (m) |
| 14 | methoxy | 2-morpholinoethoxy | 2-chloro-6-methyl | (n) |

TABLE VII-continued

![structure: quinazoline with R6, R7 and thiourea-NH-C(=S)-NH-phenyl(R2)n]

| No. | R⁶ | R⁷ | (R²)ₙ | Note |
|-----|------|------|------|------|
| 15 | methoxy | 3-morpholinopropoxy | 2-chloro-6-methyl | (o) |
| 16 | methoxy | N-methylpiperidin-4-ylmethoxy | 2-methyl | (p) |
| 17 | methoxy | 2-pyrrolidin-1-ylethoxy | 2,6-dimethyl | (q) |

Notes (a) The product gave the following data: Mass Spectrum: M+H⁺ 506 and 508.
(b) The product gave the following data: NMR Spectrum: (CDCl₃) 1.43-1.6 (m, 2H), 1.83-2.09(m, 5H), 2.33(s, 3H), 2.94(d, 2H), 4.04(m, 5H), 7.0-7.14 (m, 4H), 7.27(m, 1H), 7.35(m, 1H), 8.7(s, 1H), 13.49(s, 1H); Mass Spectrum: M+H⁺ 474.
(c) The product gave the following data: NMR Spectrum: (CDCl₃) 1.45-1.61 (m, 2H), 1.87-2.11(m, 5H), 2.31(s, 3H), 2.42(s, 2H), 3.97(d, 2H), 4.02(m, 5H), 7.07(s, 1H), 7.2-7.3(m, 3H), 7.38(t, 1H), 8.7(s, 1H), 8.9(s, 1H) 13.51(s, 1H); Mass Spectrum: M+H⁺ 486 and 488.
(d) The product gave the following data: NMR Spectrum: (CDCl₃) 1.48-1.61 (m, 2H), 1.88-2.16(m, 5H), 2.36(s, 3H), 3.0(d, 2H), 4.07(m, 5H), 7.11(s, 1H), 7.3(d, 2H), 7.43(s, 1H), 7.49(s, 1H), 8.72(s, 1H) 13.71(s, 1H); Mass Spectrum: M+H⁺ 540 and 543.
(e) The product gave the following data: NMR Spectrum: (CDCl₃) 1.47-1.61 (m, 2H), 1.87-2.11(m, 5H), 2.32(d, 9H), 2.99(d, 2H), 4.04(m, 5H), 7.1(s, 1H), 7.3(s, 1H), 7.32(s, 1H), 8.7(s, 1H), 8.9(s, 1H), 13.31(s, 1H); Mass Spectrum: M+H⁺ 544 and 546.
(f) The product gave the following data: NMR Spectrum: (CDCl₃) 1.44-1.59 (m, 2H), 1.88-2.07(m, 5H), 2.31(s, 3H), 2.35(d, 6H), 2.94(d, 2H), 4.04(m, 5H), 7.08(d, 1H), 7.2(d, 1H), 7.29(s, 1H), 7.55(s, 1H), 8.68(s, 1H), 8.77(s, 1H), 13.63(s, 1H); Mass Spectrum: M+H⁺ 466.
(g) The product gave the following data: NMR Spectrum: (CDCl₃) 1.83(s, 4H), 2.21(m, 2H), 2.63(s, 4H), 2.76(t, 2H), 4.03(s, 3H), 4.29(t, 2H), 7.08(t, 1H), 7.27-7.33(s, 2H), 7.44(m, 3H), 8.73(s, 1H), 13.7(s, 1H); Mass Spectrum: M+H⁺ 506 and 508.
(h) The product gave the following data: NMR Spectrum: (CDCl₃) 1.83(s, 4H), 2.2(m, 2H), 2.61(s, 4H), 2.74(t, 2H), 4.04(s, 3H), 4.48(t, 2H), 6.98-7.11 (m, 3H), 7.27-7.41(m, 3H), 8.71(s, 1H), 13.48(s, 1H); Mass Spectrum: M+H⁺ 474.
(i) The product gave the following data: NMR Spectrum: (CDCl₃) 1.8(m, 4H), 2.18(m, 2H), 2.4(s, 3H), 2.55(m, 4H), 2.68(t, 2H), 4.02(s, 3H), 4.3(t, 2H), 7.07(s, 1H), 7.26(m, 1H), 7.31(s, 1H), 7.37(m, 1H), 8.7(s, 1H), 8.94(br s, 1H), 13.51(s, 1H); Mass Spectrum: M+H⁺ 486 and 488.
(j) The product gave the following data: NMR Spectrum: (CDCl₃) 2.35(s, 6H), 3.4(s, 3H), 3.6(m, 2H), 3.87(m, 2H), 4.03(t, 2H), 4.05(s, 3H), 4.37(t, 2H), 7.09(s, 1H), 7.14-7.21(m, 3H), 7.33(s, 1H), 8.68(s, 1H), 8.84(s, 1H), 13.32(s, 1H); Mass Spectrum: M+H⁺ 457.
(k) The product gave the following data: NMR Spectrum: (CDCl₃) 2.36(s, 6H), 2.61(t, 4H), 2.95(t, 2H), 3.77(t, 4H), 4.04(s, 3H), 4.34(1, 2H), 7.11(s, 1H), 7.2(m, 3H), 7.31(s, 1H), 8.69(s, 1H), 8.9(s, 1H), 13.36(s, 1H); Mass Spectrum: M+H⁺ 468.
(l) The product gave the following data: NMR Spectrum: (DMSOd₆) 2.0(m, 2H), 2.4(s, 4H), 2.45(t, 2H), 3.58(t, 4H), 4.03(s, 3H), 4.21(t, 2H), 7.18(m, 3H), 7.33(s, 1H), 8.19(s, 1H), 8.71(s, 1H), 11.09(s, 1H), 13.7(s, 1H); Mass Spectrum: M+H⁺ 482.
(m) The product gave the following data: NMR Spectrum: (DMSOd₆) 0.39 (m, 2H), 0.61(m, 2H), 1.32(m, 1H), 2.25(s, 6H), 4.0(m, 5H), 7.17(s, 3H), 7.25(s, 1H), 8.17(s, 1H), 8.72(s, 1H), 11.08(br s, 1H), 13.67(s, 1H); Mass Spectrum: M+H⁺ 409.
(n) The product gave the following data: Mass Spectrum: M+H⁺ 488 and 490.
(o) The product gave the following data: Mass Spectrum: M+H⁺ 502 and 504.
(p) The product gave the following data: Mass Spectrum: M+H⁺ 452.
(q) The product gave the following data: Mass Spectrum: M+H⁺ 452.

EXAMPLE 29

1-(2,6-dimethylphenyl)-3-[6-methoxy-7-(N-methylpiperidin-4-ylmethoxy)quinazolin-4-yl] guanidine Mercuric(II) oxide (0.059 g) was added to a mixture of 1-(2,6-dimethylphenyl)-3-[6-methoxy-7-(N-methylpiperidin-4-ylmethoxy)quinazolin-4-yl]thiourea (0.105 g), a 2M solution of ammonia in methanol (3 ml) and chloroform (1 ml) and the reaction mixture was stirred at ambient temperature for 2 hours. The mixture was evaporated and the residue was purified by column chromatography on silica using increasingly polar mixtures of methylene chloride and a 2M solution of ammonia in methanol as eluent. There was thus obtained the title compound (0.074 g); NMR Spectrum: (CDCl₃) 1.39-1.53 (m, 2H), 1.87-2.02 (q, 5H), 2.29 (s, 3H), 2.36 (s, 6H), 2.9 (d, 2H), 4.01 (m, 5H), 5.79 (br s, 1H), 7.16 (s, 1H), 7.19 (m, 3H), 7.87 (s, 1H), 8.57 (s, 1H); Mass Spectrum: M+H⁺ 449.

EXAMPLE 30

Using an analogous procedure to that described in Example 29, the appropriate quinazoline-4-thiourea was reacted with ammonia to give the guanidines described in Table VIII.

TABLE VIII

![structure: quinazoline with R6, R7 and guanidine -NH-C(=NH)-NH-phenyl(R2)n]

| No. | R⁶ | R⁷ | (R²)ₙ | Note |
|-----|------|------|------|------|
| 1 | methoxy | N-methylpiperidin-4-ylmethoxy | 2,6-dichloro | (a) |
| 2 | methoxy | N-methylpiperidin-4-ylmethoxy | 2,6-difluoro | (b) |
| 3 | methoxy | N-methylpiperidin-4-ylmethoxy | 2-chloro-6-methyl | (c) |
| 4 | methoxy | N-methylpiperidin-4-ylmethoxy | 2,6-dimethyl-4-bromo | (d) |
| 5 | methoxy | N-methylpiperidin-4-ylmethoxy | 2,5-dimethyl | (e) |
| 6 | methoxy | 3-pyrrolidin-1-ylpropoxy | 2,6-dichloro | (f) |
| 7 | methoxy | 3-pyrrolidin-1-ylpropoxy | 2,6-difluoro | (g) |
| 8 | methoxy | 3-pyrrolidin-1-ylpropoxy | 2-chloro-6-methyl | (h) |
| 9 | methoxy | 2-(2-methoxyethoxy)ethoxy | 2,6-dimethyl | (i) |
| 10 | methoxy | 2-morpholinoethoxy | 2,6-dimethyl | (j) |
| 11 | methoxy | cyclopropylmethoxy | 2,6-dimethyl | (k) |
| 12 | methoxy | 2-pyrrolidin-1-ylethoxy | 2,6-dimethyl | (l) |
| 13 | methoxy | N-methylpiperidin-4-ylmethoxy | 2-methyl | (m) |

Notes
(a) The product gave the following data: NMR Spectrum: (DMSOd₆, 100° C.) 1.4(m, 2H), 1.78(m, 3H), 1.96(t, 2H), 2.2(s, 3H), 2.8(m, 2H), 3.76(s, 3H), 4.0(d, 2H), 7.11(s, 1H), 7.28(t, 2H), 7.47(s, 1H), 7.54(d, 2H). 7.98(s, 1H), 8.5(s, 1H). 9.0(br s, 1H); Mass Spectrum: M+H⁺ 489 and 491.
(b) The product gave the following data: NMR Spectrum: (DMSOd₆) 1.34 (m, 2H), 1.73(d, 3H), 1.88(t, 2H), 2.16(s, 3H), 2.79(d, 2H), 3.3(s, 2H), 3.69 (s, 3H), 3.95(d, 2H), 7.07(s, 1H), 7.2(t, 2H), 7.34(br s, 1H), 8.49(s, 1H), 8.74 (s, 1H); Mass Spectrum: M+H⁺ 457.
(c) The product gave the following data: NMR Spectrum: (CDCl₃) 1.4-1.56 (m, 2H), 1.87-2.05(q, 5H), 2.3(s, 3H), 2.4(s, 3H), 2.9(d, 2H), 3.98-4.05(m, 5H), 7.13-7.27(m, 3H), 7.38(m, 1H), 7.81(s, 1H), 8.59(s, 1H); Mass Spectrum: M+H⁺ 469 and 471.

TABLE VIII-continued

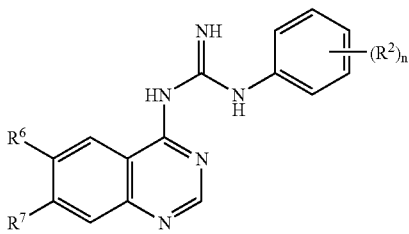

| No. | R⁶ | R⁷ | (R²)ₙ | Note |
|---|---|---|---|---|

(d) The product gave the following data: NMR Spectrum: (CDCl₃) 1.38-1.54 (m, 2H), 1.82-2.02(q, 5H), 2.28(s, 3H), 2,32(s, 6H), 2.89(d, 2H): 4.0(m, 5H), 5.7(br s, 1H), 7.03-7.27(m, 3H), 7.32(s, 2H), 7.81(s, 1H), 8.57(s, 1H); Mass Spectrum: M+H⁺ 526 and 528.
(e) The product gave the following data: NMR Spectrum: (CDCl₃) 1.39-1.44 (m, 2H), 1.87-2.04(q, 5H), 2.29(s, 3H), 2.34(d, 6H), 2,89(d, 2H), 4.02(m, 5H), 6.19(br s, 1H), 7.05(d, 1H), 7.14(s, 2H), 7.2(d, 1H), 7.84(s, 1H), 8.57(s, 1H); Mass Spectrum: M+H⁺ 449.
(f) The product gave the following data: NMR Spectrum: (CDCl₃) 1.8(m, 4H), 2.17(m, 2H), 2.53(s, 4H), 2.67(t, 2H), 3.99(s, 3H), 4.25(t, 2H), 7.1(t, 1H), 7.2(s, 1H), 7.41(d, 1H), 7.51(s, 1H), 8.57(s, 1H); Mass Spectrum: M+H⁺ 489 and 491.
(g) The product gave the following data: NMR Spectrum: (CDCl₃) 1.79(m, 4H), 2.14(m, 2H), 2.53(m, 4H), 2.67(t, 2H), 3.97(s, 3H), 4.24(t, 2H), 7.03(t, 2H), 7.2(m, 2H), 7.63(s, 1H), 8.59(s, 1H); Mass Spectrum: M+H⁺ 457.
(h) The product gave the following data: NMR Spectrum: (CDCl₃) 1.79(m, 4H), 2.15(m, 2H), 2.4(s, 3H), 2.56(s, 4H), 2.68(t, 2H), 3.98(s, 3H), 4.26(t, 2H), 6.13(br s, 1H), 7.14-7.26(m, 3H), 7.37(m, 1H), 7.82(s, 1H), 8.58(s, 1H); Mass Spectrum: M+H⁺ 469 and 471.
(i) The product gave the following data: NMR Spectrum: (CDCl₃) 2.35(s, 6H), 3.4(s, 3H), 3.61(m, 2H), 3.77(m, 2H), 3.99(m, 5H), 4.34(t, 2H), 5.76(br s, 1H), 7.17(m, 4H), 7.87(s, 1H), 8.56(s, 1H); Mass Spectrum: M+H⁺ 440.
(j) The product gave the following data: NMR Spectrum: (DMSOd₆, 100° C.) 2.29(s, 6H), 2.53(m, 4H), 2.79(t, 2H), 3.6(t, 4H), 3.74(s, 3H), 4.22(t 2H), 7.09(s, 1H), 7.16(s, 3H), 7.51(s, 1H), 7.7(s, 2H), 8.45(s, 1H), 8.88(br s, 1H); Mass Spectrum: M+H⁺ 451.
(k) The product gave the following data: NMR Spectrum: (CDCl₃) 0.34(m, 2H), 0.63(m, 2H), 1.37(m, 1H), 2,28(s, 6H), 3.93(d, 2H), 3.97(s, 3H), 5.9(br m, 1H), 7.07(s, 1H), 7.12(m, 4H), 7.79(s, 1H), 8.48(s, 1H); Mass Spectrum: M+H⁺ 392.
(l) The product gave the following data: Mass Spectrum: M+H⁺ 435.
(m) The product gave the following data: Mass Spectrum: M+H⁺ 435.

EXAMPLE 31

1-[6-methoxy-7-(N-methylpiperidin-4-ylmethoxy)quinazolin-4-yl]-3-[(R)-(+)-α-methylbenzyl]guanidine Using an analogous procedure to that described in Example 29, 1 [6-methoxy-7-(N-methylpiperidin-4-ylmethoxy)quinazolin-4-yl]-3-[(R)-(+)-α-methylbenzyl]thiourea was reacted with ammonia to give the title compound; NMR Spectrum: (CDCl₃)1.38-1.42 (m, 2H), 1.61 (d, 3H), 1.86-2.01 (q, 5H), 2.29 (s, 3H), 2.89 (d, 2H), 3.95 (m, 3H), 4.0 (d, 2H), 4.7 (q, 1H), 6.5 (br s, 1H), 7.12 (s, 1H), 7.29-7.31 (m, 5H), 7.79 (s, 1H), 8.53 (s, 1H); Mass spectrum: M+H⁺ 449.

EXAMPLE 32

1-(2-aminophenyl)-3-(6,7-dimethoxyquinazolin-4-yl)urea

A mixture of 1-(6,7dimethoxyquinazolin-4-yl)-3-(2-nitrophenyl)urea (0.18 g), 10% palladium charcoal catalyst (0.023 g) and DMF (10 ml) was stirred at ambient temperature under an atmosphere of hydrogen for 16 hours. The reaction mixture was filtered and the filtrate was evaporated. The resultant gum was triturated under ethyl acetate and there was thus obtained the title compound as a solid (0.137 g); NMR Spectrum: (DMSOd₆) 3.95-3.95 (br s, 8H), 6.63 (t, 1H), 6.81 (d, 1H), 6.91 (t, 1H), 7.25 (s, 1H), 7.47 (d, 1H), 8.05 (s, 1H), 8.64 (s, 1H), 10.28 (br, s, 1H), 11.74 (br, s, 1H); Mass spectrum M+H⁺340.

The 1-(6,7-dimethoxyquinazolin-4-yl)-3-(2-nitrophenyl)urea used as a starting material was prepared by the reaction of 2-nitrophenylisocyanate and 4amino-6,7-dimethoxyquinazoline using an analogous procedure to that described in Example 1. There was thus obtained the required starting material in 62% yield; NMR Spectrum: (DMSOd₆) 3.95 (s, 6H), 7.3 (s, 1H:), 7.28-7.35 (t, 1H), 7.74 (t, 1H), 8.05 (s, 1H), 8.13 (m, 1H), 8.51 (m, 1H), 8.72 (s, 1H), 10.61 (s, 1H), 13.67 (br s, 1H); Mass Spectrum: M+H⁺ 370.

EXAMPLE 33

1-(2,6-dichlorophenyl)-3-(6-methoxy-7-piperazin-1-ylquinazolin-4-yl)urea

A mixture of 1-(2,6-dichlorophenyl)-3-{6-methoxy-7-[N-(tert-butoxycarbonyl)piperazin-1-yl]quinazolin-4-yl} urea (0.075 g), trifluoroacetic acid (1 ml) and methylene chloride (1 ml) was stirred at ambient temperature for 1 hour. The resultant mixture was evaporated. A saturated solution of hydrogen chloride gas in ethyl acetate was added and the mixture was evaporated. The resultant solid was triturated under diethyl ether, isolated and dried. There was thus obtained the title compound, as a dihydrochloride salt (0.042 g); NMR Spectrum: (DMSOd₆) 3.25-3.3 (m, 4H), 3.45-3.5 (m, 4H), 4.03 (s, 3H), 7.3 (s, 1H), 7.36-7.63 (m, 3H), 8.16 (s, 1H), 8.78 (s, 1H), 9.15-9.27 (br s, 2H), 10.9-11.3 (br s, 1H), 10.8 (s, 1H); Mass Spectrum: M+H⁺ 447 and 449.

EXAMPLE 34

Using an analogous procedure to that described in Example 29, except that the appropriate quinazoline-4-thiourea was reacted with ethylamine rather than with ammonia, there were obtained the 2-ethylguanidines described in Table IX

TABLE IX

| No. | R⁶ | R⁷ | (R²)ₙ | Note |
|---|---|---|---|---|
| 1 | methoxy | N-methylpiperidin-4-ylmethoxy | 2-chloro-6-methyl | (a) |
| 2 | methoxy | N-methylpiperidin-4-ylmethoxy | 2,6-dimethyl | (b) |
| 3 | methoxy | 2-morpholinoethoxy | 2,6-dimethyl | (c) |
| 4 | methoxy | cyclopropylmethoxy | 2,6-dimethyl | (d) |

Notes
(a) The product gave the following data: NMR Spectrum: (DMSOd₆, 100° C.) 1.31(t, 3H), 1.36-1.47(m, 2H), 1.71-1.84(m, 3H), 1.95(t, 2H), 2.2(s, 3H), 2.33(s, 3H), 2.79(d, 2H), 3.57(m, 2H), 3.72(s, 3H), 3.99(t, 2H), 7.06(s, 1H), 7.29(m, 2H), 7.41(m, 2H), 8.35(br s, 1H), 8.45(s, 1H), 10.11(br s, 1H); Mass Spectrum: M+H⁺ 497 and 499.
(b) The product gave the following data: NMR Spectrum: (DMSOd₆, 100° C.) 1.28(t, 3H), 1.4(m, 2H), 1.76(m, 3H), 1.95(m, 2H), 2.19(s, 3H), 2.26(s, 6H), 2.78(m, 2H), 3.53(q, 2H), 3.76(s, 3H), 3.99(d, 2H), 7.04(s, 1H), 7.16(s, 3H), 7.55(s, 1H), 8.41(s, 1H), 10.41(br s, 1H); Mass Spectrum: M+H⁺ 477.

TABLE IX-continued

![Structure showing quinazoline with NEt, HN, NH, phenyl(R²)ₙ, R⁶, R⁷ substituents]

| No. | R⁶ | R⁷ | (R²)ₙ | Note |
|---|---|---|---|---|

(c) The product gave the following data: NMR Spectrum: (DMSOd₆, 100° C.) 1.27(t, 3H), 2.27(s, 6H), 2.54(m, 4H), 2.8(t, 2H), 3.54(m, 2H), 3.61(t, 4H), 3.78(s, 3H), 4.26(t, 2H), 7.11(s, 1H), 7.19(s, 3H), 7.59(s, 1H), 8.42(s, 1H), 10.42(br s, 1h); Mass Spectrum: M+H⁺ 479.

(d) The product gave the following data: NMR Spectrum: (DMSOd₆) 0.38 (m, 2H), 0.6(m, 2H), 1.27(m, 4H), 2.25(s, 6H), 3.21(m), 3.5(m, 2H), 3.73(s, 3H), 3.95(d, 2H), 6.99(s, 1H), 7.17(s, 3H), 7.55(br s, 1H), 8.42(s, 1H); Mass Spectrum: M+H⁺ 420.

EXAMPLE 35

Pharmaceutical Compositions

The following illustrate representative pharmaceutical dosage forms of the invention as deemed herein (the active ingredient being termed "Compound X"), for therapeutic or prophylactic use in humans:

| | mg/tablet |
|---|---|
| (a) Tablet I | |
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |
| (b) Tablet II | |
| Compound X | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| (c) Tablet III | |
| Compound X | 1.0 |
| Lactose Ph. Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph. Eur | 488.5 |
| Magnesium | 1.5 |

| (e) Injection I | (50 mg/ml) |
|---|---|
| Compound X | 5.0% w/v |
| 1M Sodium hydroxide solution | 15.0% v/v |
| 0.1 M Hydrochloric acid (to adjust pH to 7.6) | |
| Polyethylene glycol 400 | 4.5% w/v |
| Water for injection to 100% | |

| (f) Injection II | (10 mg/ml) |
|---|---|
| Compound X | 1.0% w/v |
| Sodium phosphate BP | 3.6% w/v |
| 0.1 M Sodium hydroxide solution | 15.0% v/v |
| Water for injection to 100% | |

| (g) Injection III | (1 mg/ml, buffered to pH 6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

| | mg/ml |
|---|---|
| (h) Aerosol I | |
| Compound X | 10.0 |
| Sorbitan trioleate | 13.5 |
| Trichlorofluoromethane | 910.0 |
| Dichlorodifluoromethane | 490.0 |
| (i) Aerosol II | |
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |
| (j) Aerosol III | |
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |
| (k) Aerosol IV | |
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

| (l) Ointment | ml |
|---|---|
| Compound X | 40 mg |
| Ethanol | 300 μl |
| Water | 300 μl |
| 1-Dodecylazacycloheptan-2-one | 50 μl |
| Propylene glycol | to 1 ml |

The invention claimed is:

1. A method of producing an antiangiogenic or vascular permeability reducing effect in a warm-blooded animal in need of such treatment which comprises administering to the animal an effective amount of a compound of the formula (I):

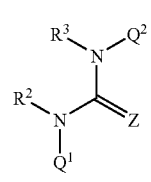

I wherein
Q¹ is a quinazoline ring of the formula Ia

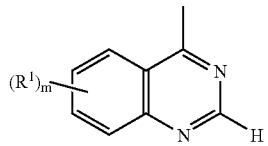

Ia wherein:
m is 0, 1, 2, 3 or 4;
each R¹ group, which may be the same or different, is selected from halogeno, trifluoromethyl, cyano, isocyano, nitro, hydroxy, mercapto, amino, formyl, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

Q³—X¹— wherein X¹ is a direct bond or is selected from O, S, SO, SO₂, N(R⁴), CO, CH(OR⁴), CON(R⁴), N(R⁴)CO, SO₂N(R⁴), N(R⁴)SO₂, OC(R⁴)₂, SC(R⁴)₂ and N(R⁴)C(R⁴)₂, wherein R⁴ is hydrogen or (1-6C)alkyl, and Q³ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, or (R¹)ₘ is (1-3C)alkylenedioxy,
and wherein adjacent carbon atoms in any (2-6C)alkylene chain within a R¹ substituent are optionally separated by the insertion into the chain of a group selected from O, S, SO, SO₂, N(R⁵), CO, CH(OR⁵), CON(R⁵), N(R⁵)CO, SO₂N(R⁵), N(R⁵)SO₂, CH=CH and C≡C wherein R⁵ is hydrogen or (1-6C)alkyl,
and wherein any CH₂=CH— or HC≡C— group within a R¹ substituent optionally bears at the terminal CH₂= or HC≡ position a substituent selected from halogeno, carboxy, carbamoyl, (1-6C)alkoxycarbonyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

Q⁴—X²— wherein X² is a direct bond or is selected from CO and N(R⁶)CO, wherein R⁶ is hydrogen or (1-6C)alkyl, and Q⁴ is aryl, aryl-(1-6C)alkyl, heteroaryl, heteroaryl-(1-6C)alkyl, heterocyclyl or heterocyclyl-(1-6C)alkyl,
and wherein any CH₂ or CH₃ group within a R¹ substituent optionally bears on each said CH₂ or CH₃ group one or more halogeno substituents or a substituent selected from hydroxy, cyano, amino, carboxy, carbamoyl, (1-6C)alkyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—X³—Q⁵ wherein X³ is a direct bond or is selected from O, S, SO, SO₂, N(R⁷), CO, CH(OR⁷), CON(R⁷), N(R⁷)CO, SO₂N(R⁷), N(R⁷)SO₂, C(R⁷)₂O, C(R⁷)₂S and N(R⁷)C(R⁷)₂, wherein R⁷ is hydrogen or (1-6C)alkyl, and Q⁵ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl,
and wherein any aryl, heteroaryl or heterocyclyl group within a substituent on R¹ optionally bears 1, 2 or 3 substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—X⁴—R⁸ wherein X⁴ is a direct bond or is selected from O and N(R⁹), wherein R⁹ is hydrogen or (1-6C)alkyl, and R⁸ is halogeno-(1-6C)alkyl, hydroxyl-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl, (2-6C)alkanoylamino-(1-6C)alkyl or (1-6C)alkoxycarbonylamino-(1-6C)alkyl, or from a group of the formula:

—X⁵—Q⁶ wherein X⁵ is a direct bond or is selected from O and N(R¹⁰), wherein R¹⁰ is hydrogen or (1-6C)alkyl, and Q⁶ is aryl, aryl-(1-6C)alkyl, heteroaryl, heteroaryl-(1-6C)alkyl, heterocyclyl or heterocyclyl-(1-6C)alkyl, and any Q⁶ group optionally bears 1 or 2 substituents, which may be the same or different, selected from halogeno, (1-6C)alkyl and (1-6C)alkoxy,
and wherein any heterocyclyl group within a substituent on R¹ optionally bears 1 or 2 oxo or thioxo substituents;
R² is hydrogen or (1-6C)alkyl and R³ is hydrogen or (1-6C) alkyl, or R² and R³ together form a CH₂, (CH)₂ or (CH₂)₃ group;
Z is O, S, N(C≡N) or N(R¹¹), wherein R¹¹ is hydrogen or (1-6C)alkyl; and
Q² is aryl, aryl-(1-3C)alkyl, aryl-(3-7C)cycloalkyl, heteroaryl, heteroaryl-(1-3C)alkyl or heteroaryl-(3-7C)cycloalkyl wherein each aryl group is phenyl or naphthyl and each heteroaryl group is a 5- or 6-membered monocyclic or a 9- or 10-membered bicyclic heteroaryl ring containing 1 or 2 nitrogen heteroatoms and optionally containing a further heteroatom selected from nitrogen, oxygen and sulphur, and $Q^2$ is optionally substituted with 1, 2, 3 or 4 substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-1-[(1-6C)allyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—X⁶—R¹² wherein $X^6$ is a direct bond or is selected from O and N($R^{13}$), wherein $R^{13}$ is hydrogen or (1-6C)alkyl, and $R^{12}$ is halogeno(1-6C)alkyl, hydroxy(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino(1-6C)alkyl, or from a group of the formula:

—X⁷—Q⁷ wherein $X^7$ is a direct bond or is selected from O, S, SO, $SO_2$, N($R^{14}$), CO, CH(O$R^{14}$), CON($R^{14}$), N($R^{14}$)CO, $SO_2$N($R^{14}$), N($R^{14}$)$SO_2$, C($R^{14}$)$_2$O, C($R^{14}$)$_2$S and C($R^{14}$), wherein each $R^{14}$ is hydrogen or (1-6C)alkyl, and $Q^7$ is aryl, aryl-(1-6C)alkyl, heteroaryl, heteroaryl-(1-6C)alkyl, heterocyclyl or heterocyclyl-(1-6C)alkyl, or $Q^2$ is optionally substituted with a (1-3C)alkylenedioxy group, and wherein any aryl, heteroaryl or heterocyclyl group within a substituent on $Q^2$ optionally bears 1, 2 or 3 substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)allyl]carbamoyl, (2-6C)alkanoyl, (2-6C)alkanoyloxy, (2-6C)alkanoylamino, N-(1-6C)alkyl2-6C)alkanoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—X⁸—R¹⁵ wherein $X^8$ is a direct bond or is selected from O and N($R^{16}$), wherein $R^{16}$ is hydrogen or (1-6C)alkyl, and $R^{15}$ is halogeno-(1-6C)alkyl, hydroxyl-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6)alkyl]amino-(1-6C)alkyl, and wherein any heterocyclyl group within a substituent on $Q^2$ optionally bears 1 or 2 oxo or thioxo substituents;

or a pharmaceutically acceptable salt thereof.

2. The method according to claim 1 wherein the compound of formula I is a compound of formual II:

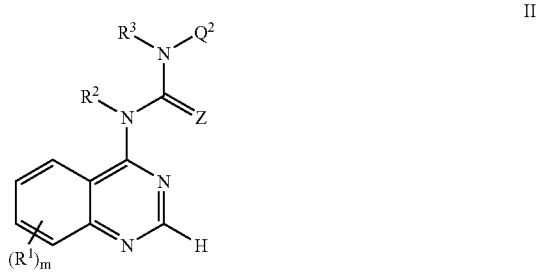

II wherein each of $R^1$, $R^2$, $R^3$, Z and $Q^2$ is as defined in claim 1, or a pharmaceutically acceptable salt thereof.

3. The method according to claim 2 of a compound of formula II, as defined in claim 2, or a pharmaceutically acceptable acid addition salt thereof, wherein m is 1 and the $R^1$ group is located at the 6- or 7-position and is selected from methoxy, benzyloxy, cyclopropylmethoxy, 2-aminoethylamino, 3-methoxypropylamino, 2-dimethylaminoethoxy, 2-diethylaminoethoxy, 3-dimethylaminopropoxy, 3-diethylaminopropoxy, 2-(1,2,3-triazol-1-yl)ethoxy, 3-(1,2,3-triazol-1-yl)propoxy, pyrid-2-ylmethoxy, pyrid-3-ylmethoxy, 2-pyrid-2-ylethoxy, 2-pyrid-3-ylethoxy, 2-pyrid4-ylethoxy, 3-pyrid-2-ylpropoxy, 3-pyrid-3-ylpropoxy, 3-pyrid4-ylpropoxy, N-[3-(imidazol-1-yl)propyl]carbamoyl, 2-pyrrolidin-1-ylethoxy, 3-pyrrolidin-1-ylpropoxy, 3-pyrrolidin-1-ylpropyl, 3-(pyrrolidin-1-yl)-1-propenyl, pyrrolidin-3-yloxy, N-methylpyrrolidin-3-yloxy, pyrrolidin-2-ylmethoxy, N-methylpyrrolidin-2-ylmethoxy, 2-pyrrolidin-2-ylethoxy, 2-(N-methylpyrrolidin-2-yl)ethoxy, 3-pyrrolidin-2-ylpropoxy, 3-(N-methylpyrrolidin-2-yl)propoxy, 4-(pyrrolidin-1-yl)but-2-en-1-yloxy, 2-(2-oxoimidazolidin-1-yl)ethoxy, 2-morpholinoethoxy, 3-morpholinopropoxy, 2-(1,1-dioxotetrahydro-4H-1,4thiazin-4-yl)ethoxy, 3-(1,1-dioxotetrahydro-4H-1,4thiazin-4-yl)propoxy, 2-piperidinoethoxy, 3-piperidinopropoxy, piperidin-3-yloxy, piperidin-4-yloxy, N-methylpiperidin-4-yloxy, piperidin-3-ylmethoxy, N-methylpiperidin-3-ylmethoxy, 2-piperidin-3-ylethoxy, 2-(N-methylpiperidin-3-yl)ethoxy, piperidin-4-ylmethoxy, N-methylpiperidin-4-ylmethoxy, 2-piperidin-4-ylethoxy, 2-(N-methylpiperidinyl-4-yl)ethoxy, 3-(4-aminomethylpiperidin-1-yl)propoxy, 3-(4tert-butoxycarbonylaminopiperidin-1-yl)propoxy, 3-(4-tert-butoxycarbonylaminomethylpiperidin-1-yl)propoxy, 4-tert-butoxycarbonylpiperazin-1-yl, 3-(4-carbamoylpiperidin-1-yl)propoxy, 2-piperazin-1-ylethoxy, 3-piperazin-1-ylpropoxy, 2-(4-methylpiperazin-1-yl)ethoxy, 3-(4-methylpiperazin-1-yl)propoxy, N-[3-(4-methylpiperazin-1-yl)propyl]carbamoyl, 4-morpholinobut-2-en-1-yloxy, 4-morpholinobut-2-yn-1-yloxy, 2-(2-morpholinoethoxy)ethoxy, 3-morpholinopropylcarbamoyl, 2-methylsulphonylethoxy, 3-methylsulphonylpropoxy, N-(2-diethylaminoethyl)-N-methylamino, -[N-(2-methoxyethyl)-N-methylamino]ethoxy, 3-[N2-methoxyethyl)-N-methylamino]propoxy, 2-(2-methoxyethoxy)ethoxy, 3-methylamino-1-propynyl, 3-dimethylamino-1-propynyl, 3-diethylamino-1-propynyl, 6-methylamino-1-hexynyl, 6-dimethylamino-1-hexynyl, 3-(pyrrolidin-1-yl)-1-propynyl, 3-(piperidino)-1-propynyl, 3-(morpholino)-1-propynyl, 3-(4-methylpiperazin-1-yl)-1-propynyl, 6-(2-methylimidazol-1-yl)-1-hexynyl, 6-(pyrrolidin-1-yl)-1-hexynyl, 6-(piperidino)-1-hexynyl, 6-(morpholino)-1-hexynyl, 6-(4-methylpiperazin-1-yl)-1-hexynyl, piperazin-1-yl, 4-methylpiperazin-1-yl, 3-imidazol-1-ylpropylamino, 3-pyrrolidin-1-ylpropylamino, 3-morpholinopropylamino, 3-piperidinopropylamino and 3-piperazin-1-ylpropylamino, 6-(4-methylpiperazin-1-yl)hexyl, or m is 2 and the $R^1$ groups are located at the 6- and 7-positions, one $R^1$ group is located at the 6- or 7-position and is selected from the groups defined immediately hereinbefore and the other $R^1$ group is a methoxy group;

$R^2$ is hydrogen or methyl;

$R^3$ is hydrogen;

Z is O, S, NH or N(Et); and $Q^2$ is phenyl, benzyl or phenethyl which optionally bears 1, 2 or 3 substituents, which may be the same or different, selected from fluoro, chloro, bromo, trifluoromethyl, nitro, methyl, ethyl and methoxy provided that at least one substituent is located at an ortho position.

4. The method according to claim 2 of a compound of formula II, as defined in claim 2, or a pharmaceutically acceptable acid addition salt thereof, wherein m is 1 and the $R^1$ group is located at the 6- or 7-position and is selected from methoxy, cyclopropylmethoxy, 2-aminoethylamino, 2-dimethylaminoethoxy, 3-(1,2,3-triazol-1-yl)propoxy, 2-pyrid-4-ylethoxy, N-[3-(imidazol-1-yl)propyl]carbamoyl, 2-pyrrolidin-1-ylethoxy, 3-pyrrolidin-1-ylpropoxy, 3-pyrrolidin-1-ylpropyl, 3-(pyrrolidin-1-yl)-1-propenyl, 4-(pyrrolidin-1-yl)but-2-en-1-yloxy, 2-(2-oxoimidazolidin-1-yl)ethoxy, 2-morpholinoethoxy, 3-morpholinopropoxy, 3-(1,1-dioxotetrahydro4H-1,4-thiazin-4-yl)propoxy, 2-piperidinoethoxy, 3-piperidinopropoxy, N-methylpiperidin-3-ylmethoxy, N-methylpiperidin-4-ylmethoxy, 3-(4-aminomethylpiperidin-1-yl)propoxy, 3-(4-tert-butoxycarbonylaminomethylpiperidin-1-yl)propoxy, 4-tert-butoxycarbonylpiperazin-1-yl, 3-(4-carbamoylpiperidin-1-yl)propoxy, 2-(4-methylpiperazin-1-yl)ethoxy, 3-(4-methylpiperazin-1-yl)propoxy, N-[3-(4-methylpiperazin-1-yl)propyl]carbamoyl, 4-morpholinobut-2-en-1-yloxy, 4-morpholinobut-2-yn-1-yloxy, 3-methylsulphonylpropoxy, N-(2-diethylaminoethyl)-N-methylamino, 2-[N-(2-methoxyethyl)-N-methylamino]ethoxy, 2-(2-methoxyethoxy)ethoxy, 6-methylamino-1-hexynyl, 3-(pyrrolidin-1-yl)-1-propynyl, 6-(2-methylimidazol-1-yl)-1-hexynyl, 6-(morpholino)-1-hexynyl, 4methylpiperazin-1-yl, 3-imidazol-1-ylpropylamino, 3-morpholinopropylamino, and 6-(4methylpiperazin-1-yl)hexyl, or m is 2 and the $R^1$ groups are located at the 6- and 7-positions, one $R^1$ group is located at the 6- or 7-position and is selected from the groups defined immediately hereinbefore and the other $R^1$ group is a methoxy group;

$R^2$ is hydrogen;

$R^3$ is hydrogen;

Z is O, S, NH or N(t); and $Q^2$ is phenyl, benzyl or phenethyl which optionally bears 1, 2 or 3 substituents, which may be the same or different, selected from fluoro, chloro, bromo, methyl and ethyl provided that at least one substituent is located at an ortho position.

* * * * *